US010266896B2

(12) United States Patent
Hakonarson et al.

(10) Patent No.: US 10,266,896 B2
(45) Date of Patent: Apr. 23, 2019

(54) GENETIC ALTERATIONS ON CHROMOSOME 16 AND METHODS OF USE THEREOF FOR THE DIAGNOSIS AND TREATMENT OF TYPE 1 DIABETES

(71) Applicant: The Children's Hospital of Philadelphia, Philadelphia, PA (US)

(72) Inventors: Hakon Hakonarson, Malvern, PA (US); Struan F. A. Grant, Philadelphia, PA (US); Jonathan P. Bradfield, Philadelphia, PA (US); Constantin Polychronakos, Quebec (CA)

(73) Assignee: The Children's Hospital of Philadelphia, Philadelphia, PA (US)

( * ) Notice: Subject to any disclaimer, the term of this patent is extended or adjusted under 35 U.S.C. 154(b) by 41 days.

(21) Appl. No.: 15/265,197

(22) Filed: Sep. 14, 2016

(65) Prior Publication Data
US 2017/0044611 A1 Feb. 16, 2017

Related U.S. Application Data

(63) Continuation of application No. 12/531,272, filed as application No. PCT/US2008/056869 on Mar. 13, 2008.

(60) Provisional application No. 60/894,649, filed on Mar. 13, 2007, provisional application No. 60/910,019, filed on Apr. 4, 2007, provisional application No. 60/940,274, filed on May 25, 2007.

(51) Int. Cl.
*C12Q 1/68* (2018.01)
*C12Q 1/6883* (2018.01)
*C12N 15/113* (2010.01)
*C07H 21/02* (2006.01)

(52) U.S. Cl.
CPC .......... *C12Q 1/6883* (2013.01); *C12N 15/113* (2013.01); *C12N 15/1137* (2013.01); *C12N 15/1138* (2013.01); *C12Y 207/11022* (2013.01); *C12N 2310/14* (2013.01); *C12Q 2600/136* (2013.01); *C12Q 2600/156* (2013.01)

(58) Field of Classification Search
CPC ............ C12Q 1/6883; C12Q 2600/136; C12Q 2600/156; C12N 15/113; C12N 15/1137; C12N 15/1138; C12N 2310/14
See application file for complete search history.

(56) References Cited

U.S. PATENT DOCUMENTS

2009/0155230 A1* 6/2009 Salonen ............... C12Q 1/6883
514/1.1

OTHER PUBLICATIONS

Kwok, P-Y., Methods for Genotyping Single Nucleotide Polymorphisms, Ann. Rev. Genomics Hum. Genet., vol. 2, pp. 235-258 (Year: 2001).*
Nakajima, D. et al., Preparation of a Set of Expression-Ready Clones of Mammalian Long cDNAs Encoding Large Proteins by the ORF Trap Cloning Method, DNA Res., vol. 12, pp. 257-267 (Year: 2005).*
Nakajima, D. et al., Preparation of a Set of Expression-Ready Clones of Mammalian Long cDNAs Encoding Large Proteins by the ORF Trap Cloning Method, DNA Res., vol. 12, supplemental Table I, pp. 1-16 (Year: 2005).*
Myakishev, M.V. et al., High-Throughput SNP Genotyping by Allele-Specific PCR with Universal Energy-Transfer-Labeled Primers, Genome Res., vol. 11, pp. 163-169 (Year: 2001).*
GenBank Accession No. AB002348, *Homo sapiens* mRNA for KIAA0350 protein, partial cds (May 2002).*
Bekris, L.M., et al. "Glutahione-s-transferase M1 and T1 polymorphisms and associations with type 1 diabetes age-at-onset." Autoimmunity, 38(8): 567-575 (Dec. 2005).
Soleimanpour, Scott A, et al. "The diabetes susceptibility gene Clec16a regulates mitophagy." Cell 157.7 (2014): 1577-1590.
Soleimanpour, Scott A, and Doris A. Staffers. "The pancreatic β cell and type 1 diabetes: innocent bystander or active participant?." Trends in Endocrinology & Metabolism 24.7 (2013): 324-331.
Herold, Kaven C., and Lesley Taylor. "Treatment of type 1 diabetes with anti-CD3 monoclonal antibody." Immunologic Research 28.2 (2003): 141-150.
Kantarova, D., and M. Buc. "Genetic susceptibility to type 1 diabetes mellitus in humans." Physiological research 56.3 2007): 255.
Bartsocas, C. S., and a Gerasimidi-Vazeou. "Genetics of type 1 diabetes mellitus." Pediatric endocrinology reviews: PER 3 (2006): 508-513.
Lee, Y. H., et al."The PTPN22 C1858T functional polymorphism and autoimmune diseases—a meta-analysis." Rheumatalogy 46.1 (2006): 49-56.
Smyth, Deborah J., et al. "A genome-wide association study of nonsynonymous SNPs identifies a type 1 diabetes locus in the interferon-induced helicase (IFIH1) region." Nature genetics 38.6 (2006): 617-619.
Osterholm, A-M., et al. "Genome-wide scan for type 1 diabetic nephropathy in the Finnish population reveals suggestive linkage to a single locus on chromosome 3q." Kidney international 71.2 (2007): 140-145.
Hakonarson, Hakon, et al. "A genome-wide association study identifies KIAA0350 as a type 1 diabetes gene." Nature 448.7153 (2007): 591-594.

(Continued)

*Primary Examiner* — Teresa E Strzelecka
(74) *Attorney, Agent, or Firm* — Kathleen D. Rigaut; Howson & Howson LLP

(57) ABSTRACT

Compositions and methods for the detection and treatment of T1D are provided.

3 Claims, 4 Drawing Sheets
Specification includes a Sequence Listing.

(56) References Cited

OTHER PUBLICATIONS

Hakonarson, Hakon, et al. "A novel susceptibility locus for type 1 diabetes on Chr12q13 identified by a genome-wide association study." Diabetes 57.4 (2008): 1143-1146.

Iyengar, Sudha K., Barry I. Freedman, and John R. Sedor. "Mining the genome for susceptibility to diabetic hephropathy: the role of large-scale studies and consortia." Seminars in nephrology. vol. 27 No. 2. WB Saunders, (2007): 208-22.

Mehers, K. L., & Gillespie, K. M. "The genetic basis of type 1 diabetes." British Medical Bulletin, 88(1) (2008): 115-129.

Barker, Jennifer M., et al. "Prediction of autoantibody positivity and progression to type 1 diabetes: Diabetes Autoimmunity Study in the Young (DAISY)." The Journal of Clinical Endocrinology & Metabolism 89.8 (2004): 3896-3902.

"Guidance for Industry. Diabetes Mellitus: Developing Drugs and Therapeutic Biologics for Treatment and Prevention", US Department of Health and Human Services, FDA, CDR, pp. 1-30 (Feb. 2008).

Márquez, Ana, et al. "Specific association of a CLEC16A/KIAA0350 polymorphism with NOD2/CARD15—Crohn's disease patients." European Journal of Human Genetics 17.10 (2009): 1304-1308.

Swanberg, Maria, et al. "Polymorphisms in the inflammatory genes CIITA, CLEC16A and IFNG influence BMD, bone loss and fracture in elderly women." PloS one 7.10 (2012): e47964.

Fredericksen, B. N. et al., "Evidence of Stage- and Age-Related Heterogeneity of Non-HLA SNPs and Risk of Islet Autoimmunity and Type I Diabetes: The Diabetes Autoimmunity Study in the Young " Clin. Dev. Immunol., ID 417657, pp. 108 (2013).

Berge, T. et al., "From Identification to Characterization of the Multiple Sclerosis Susceptibility Gene CLE CI 6A" Int. J. Mol. Sci., vol. 14, pp. 4476-4497 (2013).

Stratagene Catalog, p. 39 (1988).

\* cited by examiner

Figure 2A: Nucleic Acid (SEQ ID NO: 583); coding region 13-3295)

```
   1 gaggaaggcg gctcgcggtt cctccaccgc ctccgccgcc gcatcctccg cttgtgctac
  61 cgccgcgggc gctgggccgc tctgctggtc cggcatgaga ccgtgagacg agagacgggt
 121 cggggccgcc gacatgtttg gccgctcgcg gagctgggtg ggcggggcc atggcaagac
 181 ttcccgcaac atccactcct tggaccacct caagtatctg taccacgttt tgaccaaaaa
 241 caccacagtc acagaacaga accggaacct gctagtggag accatccgtt ccatcactga
 301 gatcctgatc tggggagatc aaaatgacag ctctgtattt gacttcttcc tggagaagaa
 361 tatgtttgtt ttcttcttga acatcttgcg gcaaaagtcg ggccgttacg tgtgcgttca
 421 gctgctgcag accttgaaca tcctctttga gaacatcagt cacgagacct cactttatta
 481 tttgctctca aataactacg taaattctat catcgttcat aaatttgact tttctgatga
 541 ggagattatg gcctattata tatcgttcct gaaaacactt tcgttaaaac tcaacaacca
 601 cactgtccat ttctttata atgagcacac caatgacttt gccctgtaca cagaagccat
 661 caagttttc aaccaccctg aaagcatggt tagaattgct gtaagaacca taactttgaa
 721 tgtctataaa gtgtcattgg ataaccaggc catgctgcac tacatccgag ataaaactgc
 781 tgttccttac ttctccaatt tggtctggtt cattgggagc catgtgatcg aactcgatga
 841 ctgcgtgcag actgatgagg agcatcggaa tcggggtaaa ctgagtgatc tggtggcaga
 901 gcacctagac cacctgcact atctcaatga catcctgatc atcaactgtg agttcctcaa
 961 cgatgtgctc actgaccacc tgctcaacag gctcttcctg cccctctacg tgtactcact
1021 ggagaaccag gacaagggag gagaacggcc gaaaattagc ctgccggtgt ctctttatct
1081 tctgtcacag gtcttcttaa ttatacatca tgcaccgctg gtgaactcgt tagctgaagt
1141 cattctgaat ggtgatctgt ctgagatgta cgctaagact gaacaggata ttcagagaag
1201 ttctgccaag cccagcattc ggtgcttcat taaacccacc gagacactcg agcggtccct
1261 tgagatgaac aagcacaagg gcaagaggcg ggtgcaaaag agacccaact acaaaaacgt
1321 tggggaagaa gaagatgagg agaaagggcc caccgaggat gcccaagaag acgccgagaa
1381 ggctaaaggt acagagggtg gttcaaaagg catcaagacg agtggggaga gtgaagagat
1441 cgagatggtg atcatggagc gtagcaagct ctcagagctg gccgccagca cctccgtgca
1501 ggagcagaac accacggacg aggagaaaag cgccgccgcc acctgctctg agagcacgca
1561 atggagcaga cccttcctgg atatggtgta ccacgcgctg gacagcccgg atgatgatta
1621 ccatgccctg ttcgtgctct gcctcctcta tgccatgtct cataataaag gcatggatcc
1681 tgaaaaatta gagcgaatcc agctccccgt gccaaatgcg gccgagaaga ccacctacaa
1741 ccacccgcta gctgaaagac tcatccaggat catgaacaac gctgcccagc cagatgggaa
1801 gatccggctg gcgacgctgg agctgagctg cctgcttctg aagcagcaag tcctgatgag
1861 tgctggctgc atcatgaagg acgtgcacct ggcctgcctg gagggtgcga gagaagaaag
1921 tgttcacctt gtacgacatt tttataaggg agaagacatt ttttggaca tgtttgaaga
1981 tgagtatagg agcatgacaa tgaagcccat gaacgtggaa tatctcatga tggacgcctc
2041 catcctgctg cccccaacag gcacgccact gacgggcatt gacttcgtga agcggctgcc
2101 gtgtggcgat gtggagaaga cccggcgggc catccgggtg ttcttcatgc tgcgttccct
2161 gtcactgcaa ttgcgagggg agcctgagac acagttgccg ctgactcggg aggaggacct
2221 gatcaagact gatgatgtcc tggatctgaa taacagcgac ttgattgcat gtacagtgat
2281 caccaaggat ggcggcatgg tccagcgatt cctggctgtg gatatttacc agatgagttt
2341 ggtggagcct gatgtgtcca gcttggctg gggagtggtc aagtttgcag cctattgca
2401 ggacatgcag gtgactggcg tggaggacga cagccgtgcc ctgaacatca ccatccacaa
2461 gcctgcgtcc agccccatt ccaagccctt ccccatcctc caggccacct tcatcttctc
2521 agaccacatc cgctgcatca tcgccaagca gcgcctggcc aaaggccgca tccaggcaag
2581 gcgcatgaag atgcagagaa tagctgccct cctggacctc caatccagc ccaccactga
2641 agtcctgggg tttggactcg gctcctccac ctccactcag cacctgcctt tccgcttcta
2701 cgaccagggg cgccggggca gcagcgaccc cacagtgcag cgctccgtgt ttgcatcggt
2761 ggacaaggtg ccaggcttcg ccgtggccca gtgcataaac cagcacagct cccgtccct
2821 gtcctcacag tcgccaccct ccgccagcgg gagccccagc ggcagcggga gcaccagcca
2881 ctgcgactct ggaggcacca gctcgtcctc caccccctcc acagcccaga gtccagcaga
2941 tgccccatg agtccagaac tgcctaagcc tcaccttcct gaccagttgg taatcgtcaa
```

Fig. 2B

```
3001 cgaaacggaa gcagactcta agcccagcaa gaacgtggcc aggagcgcag ccgtggagac
3061 agccagcctg tcccccagcc tcgtccctgc ccggcagccc accatttccc tgctctgcga
3121 ggacacggct gacacgctga gcgtcgaatc gctgacccttgtcccccag ttgaccccca
3181 cagcctccgc agcctcaccg gcatgccccc gctgtccacg ccggctgccg cctgcacaga
3241 gcccgtgggc gaagaggctg catgtgctga gcctgtgggc accgctgagg actgagtcag
3301 tgccggggcc tcccttttgtg tgtgtggccc cgctggtagg gaccccagtg ccgctgactg
3361 gcaagacaca ctgggagcac ccaccattct gtgcggcccc cagcagccat ctcaaccacc
3421 tatccctgcg ctcccttgaa tgggaagaag ccccacgttg tccttgaatt ccttttttcac
3481 tttgcatctc ttcacgtgca ggctgggacc agcggagaca ccgcggcgaa tgcagatgac
3541 tgcaccggcc actcagggag ctgcctgggc tccgtgtctc tgagccccgg gtggcaggac
3601 ccaccggcac ctctttcttc ctctgtcata tggctcctct gtcaccagcc cagtgtgca
3661 cagaagaatt ggaccaggtc actgtacgta gaaatttgta gaaaagcaga cttagataaa
3721 catctccttt ggatatttat ttccgcttttggcagcaggt gaacatttat ttttaaaact
3781 tctatttaaa agaagtccaa aaacatcaac actaaggttt gatgtcatgt gaaaagtgta
3841 ataataacag ttaagatttc atgatcattt tcactggacc tttcctgata ttttgtttca
3901 gagttcttag tgtggctttt tccatttatt taagtgattc tttgttactc actaactctg
3961 caagcctgtg gaataatgaa gtaccttcct ggaaagtttg gattattttt taaacaaaaa
4021 caagggagat acatgtattc tcaggtacac acagagctga gagggctgaa tggttttctg
4081 ctatagcagc cgagaggcct cccatcatgg aaagatttct ccaggaaaag gaggaatgta
4141 gccagctccc cactcaggac gcttcctcat ttctcttcac caaaaccaaa cagagacagc
4201 ttccagcacc ttcttcagtg ttaccatctc taagaaggaa ccagttggga ccgtgaagac
4261 tcccgaccct gtggccatga tggaaatcaa aggaagacac cctctacgtc acctgccctc
4321 gactgtgtgt gcccacatgt gccgagagat ggcccagagc cagttcccct ccagctgcaa
4381 gggcatggtg tccccagagc tctgagtctg tcactctccc tctgctactg ctgctgatct
4441 gaatatggaa accccatggt tcccttcccc attcggactg ggtgtgtaca agcaaggacc
4501 cagatgcatc agacacagcc cccaagatgt tcctttctac tcggccagct cgggagccag
4561 acacagcact cacagcccag gccgtgatcc accctcccca agtccaccag gccagcggc
4621 ccctcacctc tctggtcact ggtgagacct tccacaactt tcctccagac ctgccagcag
4681 atgtgcccac caggggcatt aggtatccgc cggagcctgg ccatagggta gtctcgggag
4741 ccgcgctgag atcttttgcc acctgcattt tagaagaaca tggtctctgt ctcctcggcc
4801 cagccagctg tcccggcaag gcctgccgag ggcagttttc aacctcatga aggaaacaca
4861 gtcctgccaa ggaggggag tggcgcccat ggggacaggc ctcagtcctt agaagccctc
4921 tgggtagctg tgcccaccca gccttcatgg ctgcaggtac aaggacctttgcttccatag
4981 agaaaacgca cagctcagaa aggggggccac atgggcagaa acccaaagga aggacaaacc
5041 acgaccaccg tggccatctg cagaatccct ggaagagaag gaaggcaggg tggagcgggg
5101 ggaagaccat catggagaga aggaccacag catcaggaga cgggacacgc cacacccagc
5161 aggcagcctg tgtgttgctt aattttttaa gagcagagg ggtagagagg atcaagctgg
5221 ccctggctgg agatggctag cccctgagac atgcacttct ggttttgaaa tgactctgtc
5281 tgtggggcag cagaaactag agaaggcaag tggctgcccc accccaaggc gtgaccagga
5341 ggaacagcct gcagctcact ccatgccaca cgggtgggcc accagcctgc tgtcagaagt
5401 ctctgggctc caactggtct tgtaaccact gagcactgaa ggagagaggt cttggtcagg
5461 gctggacagc atgcccggga ggaccagcag aggattaaag gtgactggga ggaccagcgg
5521 aggataaaag acactgctca gggcagggct tctaccctgc atccctggcc aagaaaaggg
5581 cagtccccat gtgggcttgc agggtcactc tcagggcct ctttcagctg ggctggcaa
5641 cttgcgtctg ggggacacct ccaggtgtgt gggtgagga tttcctataa ccagggctcc
5701 cagaagcttt gcttatgtaa ggaggtctgg gagccagccc attggaggcc accagccatt
5761 ttggcttcaa aggaccccac ctcacccagg tctcagcggc agtgggcaca gctatgtctt
5821 caggagctcc cgtcaaacct catagctggg gcgctcccag acaggccagt ccagacagga
5881 cacgctgggc cctggcatcc agaggaaga ccaggagtg tgggaaggcc cacagtgggg
5941 gctgtggctt ctgacactca ggtcatagcc tcagaggtct gaggtcagcc cccacagacc
6001 catccggccc gccccccaag tcctgcaga gagcacttag agttatggcc caggccctgg
6061 tccaccttc ccctgtgcac ctccggctgg gtttgccaag tcagggagca gggctggccg
6121 caggaactcc caaaccttgg ctttgaatat tgttgtggag gtgtgctcgt cccttctgg
6181 acgtgcaagg tacctgtccc agcaggtcag atgggccag ctgaggcgct ccccaggca
6241 ggaagggcca gccttcacca tcgcgtggga ttgggaggag gggcctccgt gagcagcccc
6301 tcctctgccg ctgtcccagc ccagtccctc tcccggagcc ttggcagcct cccacaaccc
6361 agacacttgc gttcacaagc aacctaaggg gcaggtgaag aagcgcagcc ctgccagacg
```

Fig. 2C
```
6421 cgctagattc ctctaaggtc tctgagatgc accgtttttt aaaaaggcgt ggggtgaact
6481 gattttgatc ttcttgtcta gatgcaataa ataaatctga agcatttaat gtagtcatct
6541 tgacattggg cctacactgt acgagttcct tatgtttcct tgagctaaaa atatgtaaat
6601 aattttgtc ccagtgagaa ccgagggtta gaaaacctcg atgcctctga gcctcgggac
6661 cgctctaggg aagtacctgc tttcgccagc atgactcatg cttcgtgggt actgaacacg
6721 agggtggaaa tgaaaactgg aacttccttg taaatttaaa cttggcaata aagagaaaa
6781 aaagtt
```

Fig. 2D Protein (SEQ ID NO: 584)

MFGRSRSWVGGGHGKTSRNIHSLDHLKYLYHVLTKNTTVTEQNR

NLLVETIRSITEILIWGDQNDSSVFDFFLEKNMFVFFLNILRQKSGRYVCVQLLQTLN

ILFENISHETSLYYLLSNNYVNSIIVHKFDFSDEEIMAYYISFLKTLSLKLNNHTVHF

FYNEHTNDFALYTEAIKFFNHPESMVRIAVRTITLNVYKVSLDNQAMLHYIRDKTAVP

YFSNLVWFIGSHVIELDDCVQTDEEHRNRGKLSDLVAEHLDHLHYLNDILIINCEFLN

DVLTDHLLNRLFLPLYVYSLENQDKGGERPKISLPVSLYLLSQVFLIIHHAPLVNSLA

EVILNGDLSEMYAKTEQDIQRSSAKPSIRCFIKPTETLERSLEMNKHKGKRRVQKRPN

YKNVGEEEDEEKGPTEDAQEDAEKAKGTEGGSKGIKTSGESEEIEMVIMERSKLSELA

ASTSVQEQNTTDEEKSAAATCSESTQWSRPFLDMVYHALDSPDDDYHALFVLCLLYAM

SHNKGMDPEKLERIQLPVPNAAEKTTYNHPLAERLIRIMNNAAQPDGKIRLATLELSC

LLLKQQVLMSAGCIMKDVHLACLEGAREESVHLVRHFYKGEDIFLDMFEDEYRSMTMK

PMNVEYLMMDASILLPPTGTPLTGIDFVKRLPCGDVEKTRRAIRVFFMLRSLSLQLRG

EPETQLPLTREEDLIKTDDVLDLNNSDLIACTVITKDGGMVQRFLAVDIYQMSLVEPD

VSRLGWGVVKFAGLLQDMQVTGVEDDSRALNITIHKPASSPHSKPFPILQATFIFSDH

IRCIIAKQRLAKGRIQARRMKMQRIAALLDLPIQPTTEVLGFGLGSSTSTQHLPFRFY

DQGRRGSSDPTVQRSVFASVDKVPGFAVAQCINQHSSPSLSSQSPPSASGSPSGSGST

SHCDSGGTSSSSTPSTAQSPADAPMSPELPKPHLPDQLVIVNETEADSKPSKNVARSA

AVETASLSPSLVPARQPTISLLCEDTADTLSVESLTLVPPVDPHSLRSLTGMPPLSTP

AACTEPVGEEAACAEPVGTAED

SEQUENCE LISTING

```
<160> NUMBER OF SEQ ID NOS: 584

<210> SEQ ID NO 1
<211> LENGTH: 21
<212> TYPE: DNA
<213> ORGANISM: Artificial Sequence
<220> FEATURE:
<223> OTHER INFORMATION: siRNA

<400> SEQUENCE: 1
caaaaaaaug ucuucuccct t                                             21

<210> SEQ ID NO 2
<211> LENGTH: 21
<212> TYPE: DNA
<213> ORGANISM: Artificial Sequence
<220> FEATURE:
<223> OTHER INFORMATION: siRNA

<400> SEQUENCE: 2
aaauauccaa aggagaugut t                                             21

<210> SEQ ID NO 3
<211> LENGTH: 21
<212> TYPE: DNA
<213> ORGANISM: Artificial Sequence
<220> FEATURE:
<223> OTHER INFORMATION: siRNA

<400> SEQUENCE: 3
cugcuauagc agaaaaccat t                                             21
```

<210> SEQ ID NO 4
<211> LENGTH: 21
<212> TYPE: DNA
<213> ORGANISM: Artificial Sequence
<220> FEATURE:
<223> OTHER INFORMATION: siRNA

<400> SEQUENCE: 4
uucucuuuua uugccaagut t                                              21

<210> SEQ ID NO 5
<211> LENGTH: 21
<212> TYPE: DNA
<213> ORGANISM: Artificial Sequence
<220> FEATURE:
<223> OTHER INFORMATION: siRNA

<400> SEQUENCE: 5
gagguuuucu aacccucggt t                                              21

<210> SEQ ID NO 6
<211> LENGTH: 21
<212> TYPE: DNA
<213> ORGANISM: Artificial Sequence
<220> FEATURE:
<223> OTHER INFORMATION: siRNA

<400> SEQUENCE: 6
caaaacgugg uacagauact t                                              21

<210> SEQ ID NO 7
<211> LENGTH: 21
<212> TYPE: DNA
<213> ORGANISM: Artificial Sequence
<220> FEATURE:
<223> OTHER INFORMATION: siRNA

<400> SEQUENCE: 7
uucugugacu gugguguuut t                                              21

<210> SEQ ID NO 8
<211> LENGTH: 21
<212> TYPE: DNA
<213> ORGANISM: Artificial Sequence
<220> FEATURE:
<223> OTHER INFORMATION: siRNA

<400> SEQUENCE: 8
cuagcagguu ccgguucugt t                                              21

<210> SEQ ID NO 9
<211> LENGTH: 21
<212> TYPE: DNA
<213> ORGANISM: Artificial Sequence
<220> FEATURE:
<223> OTHER INFORMATION: siRNA

<400> SEQUENCE: 9
cuccacuagc agguuccggt t                                              21

<210> SEQ ID NO 10
<211> LENGTH: 21
<212> TYPE: DNA
<213> ORGANISM: Artificial Sequence
<220> FEATURE:

```
<223> OTHER INFORMATION: siRNA

<400> SEQUENCE: 10
gauggucucc acuagcaggt t                                              21

<210> SEQ ID NO 11
<211> LENGTH: 21
<212> TYPE: DNA
<213> ORGANISM: Artificial Sequence
<220> FEATURE:
<223> OTHER INFORMATION: siRNA

<400> SEQUENCE: 11
caagaagaaa acaaacauat t                                              21

<210> SEQ ID NO 12
<211> LENGTH: 21
<212> TYPE: DNA
<213> ORGANISM: Artificial Sequence
<220> FEATURE:
<223> OTHER INFORMATION: siRNA

<400> SEQUENCE: 12
acacguaacg gcccgacuut t                                              21

<210> SEQ ID NO 13
<211> LENGTH: 21
<212> TYPE: DNA
<213> ORGANISM: Artificial Sequence
<220> FEATURE:
<223> OTHER INFORMATION: siRNA

<400> SEQUENCE: 13
ugaggucucg ugacugaugt t                                              21

<210> SEQ ID NO 14
<211> LENGTH: 21
<212> TYPE: DNA
<213> ORGANISM: Artificial Sequence
<220> FEATURE:
<223> OTHER INFORMATION: siRNA

<400> SEQUENCE: 14
cucaucagaa aagucaaaut t                                              21

<210> SEQ ID NO 15
<211> LENGTH: 19
<212> TYPE: DNA
<213> ORGANISM: Artificial Sequence
<220> FEATURE:
<223> OTHER INFORMATION: siRNA

<400> SEQUENCE: 15
gaguuuuaac gaaaguguu                                                 19

<210> SEQ ID NO 16
<211> LENGTH: 21
<212> TYPE: DNA
<213> ORGANISM: Artificial Sequence
<220> FEATURE:
<223> OTHER INFORMATION: siRNA

<400> SEQUENCE: 16
aaagaaaugg acaguguggt t                                              21
```

```
<210> SEQ ID NO 17
<211> LENGTH: 21
<212> TYPE: DNA
<213> ORGANISM: Artificial Sequence
<220> FEATURE:
<223> OTHER INFORMATION: siRNA

<400> SEQUENCE: 17
uguguacagg gcaaagucat t                                              21

<210> SEQ ID NO 18
<211> LENGTH: 21
<212> TYPE: DNA
<213> ORGANISM: Artificial Sequence
<220> FEATURE:
<223> OTHER INFORMATION: siRNA

<400> SEQUENCE: 18
gguugaaaaa cuugauggct t                                              21

<210> SEQ ID NO 19
<211> LENGTH: 21
<212> TYPE: DNA
<213> ORGANISM: Artificial Sequence
<220> FEATURE:
<223> OTHER INFORMATION: siRNA

<400> SEQUENCE: 19
uucagggugg uugaaaaact t                                              21

<210> SEQ ID NO 20
<211> LENGTH: 21
<212> TYPE: DNA
<213> ORGANISM: Artificial Sequence
<220> FEATURE:
<223> OTHER INFORMATION: siRNA

<400> SEQUENCE: 20
acuuuauaga cauucaaagt t                                              21

<210> SEQ ID NO 21
<211> LENGTH: 21
<212> TYPE: DNA
<213> ORGANISM: Artificial Sequence
<220> FEATURE:
<223> OTHER INFORMATION: siRNA

<400> SEQUENCE: 21
cccaaugaac cagaccaaat t                                              21

<210> SEQ ID NO 22
<211> LENGTH: 21
<212> TYPE: DNA
<213> ORGANISM: Artificial Sequence
<220> FEATURE:
<223> OTHER INFORMATION: siRNA

<400> SEQUENCE: 22
ucugcacgca gucaucgagt t                                              21

<210> SEQ ID NO 23
<211> LENGTH: 21
<212> TYPE: DNA
<213> ORGANISM: Artificial Sequence
<220> FEATURE:
<223> OTHER INFORMATION: siRNA
```

```
<400> SEQUENCE: 23
guugaugauc aggaugucat t                                              21

<210> SEQ ID NO 24
<211> LENGTH: 21
<212> TYPE: DNA
<213> ORGANISM: Artificial Sequence
<220> FEATURE:
<223> OTHER INFORMATION: siRNA

<400> SEQUENCE: 24
aucguugagg aacucacagt t                                              21

<210> SEQ ID NO 25
<211> LENGTH: 21
<212> TYPE: DNA
<213> ORGANISM: Artificial Sequence
<220> FEATURE:
<223> OTHER INFORMATION: siRNA

<400> SEQUENCE: 25
guggucagug agcacaucgt t                                              21

<210> SEQ ID NO 26
<211> LENGTH: 21
<212> TYPE: DNA
<213> ORGANISM: Artificial Sequence
<220> FEATURE:
<223> OTHER INFORMATION: siRNA

<400> SEQUENCE: 26
agcggugcau gauguauaat t                                              21

<210> SEQ ID NO 27
<211> LENGTH: 21
<212> TYPE: DNA
<213> ORGANISM: Artificial Sequence
<220> FEATURE:
<223> OTHER INFORMATION: siRNA

<400> SEQUENCE: 27
aaugacuuca gcuaacgagt t                                              21

<210> SEQ ID NO 28
<211> LENGTH: 21
<212> TYPE: DNA
<213> ORGANISM: Artificial Sequence
<220> FEATURE:
<223> OTHER INFORMATION: siRNA

<400> SEQUENCE: 28
gaucaccauu cagaaugact t                                              21

<210> SEQ ID NO 29
<211> LENGTH: 21
<212> TYPE: DNA
<213> ORGANISM: Artificial Sequence
<220> FEATURE:
<223> OTHER INFORMATION: siRNA

<400> SEQUENCE: 29
caucucagac agaucaccat t                                              21

<210> SEQ ID NO 30
<211> LENGTH: 21
```

```
<212> TYPE: DNA
<213> ORGANISM: Artificial Sequence
<220> FEATURE:
<223> OTHER INFORMATION: siRNA

<400> SEQUENCE: 30
cugaauaucc uguucaguct t                                              21

<210> SEQ ID NO 31
<211> LENGTH: 21
<212> TYPE: DNA
<213> ORGANISM: Artificial Sequence
<220> FEATURE:
<223> OTHER INFORMATION: siRNA

<400> SEQUENCE: 31
aacuucucug aauauccugt t                                              21

<210> SEQ ID NO 32
<211> LENGTH: 21
<212> TYPE: DNA
<213> ORGANISM: Artificial Sequence
<220> FEATURE:
<223> OTHER INFORMATION: siRNA

<400> SEQUENCE: 32
ccucuugccc uugugcuugt t                                              21

<210> SEQ ID NO 33
<211> LENGTH: 21
<212> TYPE: DNA
<213> ORGANISM: Artificial Sequence
<220> FEATURE:
<223> OTHER INFORMATION: siRNA

<400> SEQUENCE: 33
ugggcccuuu cuccucauct t                                              21

<210> SEQ ID NO 34
<211> LENGTH: 21
<212> TYPE: DNA
<213> ORGANISM: Artificial Sequence
<220> FEATURE:
<223> OTHER INFORMATION: siRNA

<400> SEQUENCE: 34
ggcauccucg gugggcccut t                                              21

<210> SEQ ID NO 35
<211> LENGTH: 21
<212> TYPE: DNA
<213> ORGANISM: Artificial Sequence
<220> FEATURE:
<223> OTHER INFORMATION: siRNA

<400> SEQUENCE: 35
gcuggauucg cucuaauuut t                                              21

<210> SEQ ID NO 36
<211> LENGTH: 21
<212> TYPE: DNA
<213> ORGANISM: Artificial Sequence
<220> FEATURE:
<223> OTHER INFORMATION: siRNA

<400> SEQUENCE: 36
```
aucuggcugg gcagcguugt t                                    21

<210> SEQ ID NO 37
<211> LENGTH: 21
<212> TYPE: DNA
<213> ORGANISM: Artificial Sequence
<220> FEATURE:
<223> OTHER INFORMATION: siRNA

<400> SEQUENCE: 37
cagcgucgcc agccggaucu t                                    21

<210> SEQ ID NO 38
<211> LENGTH: 21
<212> TYPE: DNA
<213> ORGANISM: Artificial Sequence
<220> FEATURE:
<223> OTHER INFORMATION: siRNA

<400> SEQUENCE: 38
acucaucagg acuugcugct t                                    21

<210> SEQ ID NO 39
<211> LENGTH: 21
<212> TYPE: DNA
<213> ORGANISM: Artificial Sequence
<220> FEATURE:
<223> OTHER INFORMATION: siRNA

<400> SEQUENCE: 39
agccagcacu caucaggact t                                    21

<210> SEQ ID NO 40
<211> LENGTH: 21
<212> TYPE: DNA
<213> ORGANISM: Artificial Sequence
<220> FEATURE:
<223> OTHER INFORMATION: siRNA

<400> SEQUENCE: 40
gcaggccagg ugcacgucct t                                    21

<210> SEQ ID NO 41
<211> LENGTH: 19
<212> TYPE: DNA
<213> ORGANISM: Artificial Sequence
<220> FEATURE:
<223> OTHER INFORMATION: siRNA

<400> SEQUENCE: 41
acauguccaa aaaauguc                                        19

<210> SEQ ID NO 42
<211> LENGTH: 21
<212> TYPE: DNA
<213> ORGANISM: Artificial Sequence
<220> FEATURE:
<223> OTHER INFORMATION: siRNA

<400> SEQUENCE: 42
ucaugcuccu auacucauct t                                    21

<210> SEQ ID NO 43
<211> LENGTH: 21
<212> TYPE: DNA
<213> ORGANISM: Artificial Sequence

```
<220> FEATURE:
<223> OTHER INFORMATION: siRNA

<400> SEQUENCE: 43
aggcuugugg auggugaugt t                                              21

<210> SEQ ID NO 44
<211> LENGTH: 21
<212> TYPE: DNA
<213> ORGANISM: Artificial Sequence
<220> FEATURE:
<223> OTHER INFORMATION: siRNA

<400> SEQUENCE: 44
cuggucagga aggugaggct t                                              21

<210> SEQ ID NO 45
<211> LENGTH: 21
<212> TYPE: DNA
<213> ORGANISM: Artificial Sequence
<220> FEATURE:
<223> OTHER INFORMATION: siRNA

<400> SEQUENCE: 45
ugcgcuccug gccacguuct t                                              21

<210> SEQ ID NO 46
<211> LENGTH: 21
<212> TYPE: DNA
<213> ORGANISM: Artificial Sequence
<220> FEATURE:
<223> OTHER INFORMATION: siRNA

<400> SEQUENCE: 46
ggcugcgcuc cuggccacgt t                                              21

<210> SEQ ID NO 47
<211> LENGTH: 21
<212> TYPE: DNA
<213> ORGANISM: Artificial Sequence
<220> FEATURE:
<223> OTHER INFORMATION: siRNA

<400> SEQUENCE: 47
ugggugcucc cagugugtct t                                              21

<210> SEQ ID NO 48
<211> LENGTH: 21
<212> TYPE: DNA
<213> ORGANISM: Artificial Sequence
<220> FEATURE:
<223> OTHER INFORMATION: siRNA

<400> SEQUENCE: 48
ggagcgcagg gauagguggt t                                              21

<210> SEQ ID NO 49
<211> LENGTH: 21
<212> TYPE: DNA
<213> ORGANISM: Artificial Sequence
<220> FEATURE:
<223> OTHER INFORMATION: siRNA

<400> SEQUENCE: 49
ugauguuuuu ggacuucuut t                                              21
```

<210> SEQ ID NO 50
<211> LENGTH: 21
<212> TYPE: DNA
<213> ORGANISM: Artificial Sequence
<220> FEATURE:
<223> OTHER INFORMATION: siRNA

<400> SEQUENCE: 50
guugauguuu uuggacuuct t                                              21

<210> SEQ ID NO 51
<211> LENGTH: 21
<212> TYPE: DNA
<213> ORGANISM: Artificial Sequence
<220> FEATURE:
<223> OTHER INFORMATION: siRNA

<400> SEQUENCE: 51
aguguugaug uuuuuggact t                                              21

<210> SEQ ID NO 52
<211> LENGTH: 21
<212> TYPE: DNA
<213> ORGANISM: Artificial Sequence
<220> FEATURE:
<223> OTHER INFORMATION: siRNA

<400> SEQUENCE: 52
aaccuuagug uugauguuut t                                              21

<210> SEQ ID NO 53
<211> LENGTH: 21
<212> TYPE: DNA
<213> ORGANISM: Artificial Sequence
<220> FEATURE:
<223> OTHER INFORMATION: siRNA

<400> SEQUENCE: 53
caaaccuuag uguugaugut t                                              21

<210> SEQ ID NO 54
<211> LENGTH: 21
<212> TYPE: DNA
<213> ORGANISM: Artificial Sequence
<220> FEATURE:
<223> OTHER INFORMATION: siRNA

<400> SEQUENCE: 54
acuucauuau uccacaggct t                                              21

<210> SEQ ID NO 55
<211> LENGTH: 21
<212> TYPE: DNA
<213> ORGANISM: Artificial Sequence
<220> FEATURE:
<223> OTHER INFORMATION: siRNA

<400> SEQUENCE: 55
uuuccaggaa gguacuucat t                                              21

<210> SEQ ID NO 56
<211> LENGTH: 19
<212> TYPE: DNA
<213> ORGANISM: Artificial Sequence
<220> FEATURE:
<223> OTHER INFORMATION: siRNA

<400> SEQUENCE: 56
guaucucccu uguuuuugu                                                19

<210> SEQ ID NO 57
<211> LENGTH: 21
<212> TYPE: DNA
<213> ORGANISM: Artificial Sequence
<220> FEATURE:
<223> OTHER INFORMATION: siRNA

<400> SEQUENCE: 57
ggaagcuguc ucuguuuggt t                                             21

<210> SEQ ID NO 58
<211> LENGTH: 21
<212> TYPE: DNA
<213> ORGANISM: Artificial Sequence
<220> FEATURE:
<223> OTHER INFORMATION: siRNA

<400> SEQUENCE: 58
ucuucacggu cccaacuggt t                                             21

<210> SEQ ID NO 59
<211> LENGTH: 21
<212> TYPE: DNA
<213> ORGANISM: Artificial Sequence
<220> FEATURE:
<223> OTHER INFORMATION: siRNA

<400> SEQUENCE: 59
ggccacaggg ucgggaguct t                                             21

<210> SEQ ID NO 60
<211> LENGTH: 21
<212> TYPE: DNA
<213> ORGANISM: Artificial Sequence
<220> FEATURE:
<223> OTHER INFORMATION: siRNA

<400> SEQUENCE: 60
gucugaugca ucugggucct t                                             21

<210> SEQ ID NO 61
<211> LENGTH: 21
<212> TYPE: DNA
<213> ORGANISM: Artificial Sequence
<220> FEATURE:
<223> OTHER INFORMATION: siRNA

<400> SEQUENCE: 61
ccgaguagaa aggaacauct t                                             21

<210> SEQ ID NO 62
<211> LENGTH: 21
<212> TYPE: DNA
<213> ORGANISM: Artificial Sequence
<220> FEATURE:
<223> OTHER INFORMATION: siRNA

<400> SEQUENCE: 62
uggcaggucu ggaggaaagt t                                             21

<210> SEQ ID NO 63

```
<211> LENGTH: 21
<212> TYPE: DNA
<213> ORGANISM: Artificial Sequence
<220> FEATURE:
<223> OTHER INFORMATION: siRNA

<400> SEQUENCE: 63
ggagacagag accauguuct t                                              21

<210> SEQ ID NO 64
<211> LENGTH: 21
<212> TYPE: DNA
<213> ORGANISM: Artificial Sequence
<220> FEATURE:
<223> OTHER INFORMATION: siRNA

<400> SEQUENCE: 64
cgaggagaca gagaccaugt t                                              21

<210> SEQ ID NO 65
<211> LENGTH: 21
<212> TYPE: DNA
<213> ORGANISM: Artificial Sequence
<220> FEATURE:
<223> OTHER INFORMATION: siRNA

<400> SEQUENCE: 65
aaacugcccu cggcaggcct t                                              21

<210> SEQ ID NO 66
<211> LENGTH: 21
<212> TYPE: DNA
<213> ORGANISM: Artificial Sequence
<220> FEATURE:
<223> OTHER INFORMATION: siRNA

<400> SEQUENCE: 66
uuggcaggac uguguuucct t                                              21

<210> SEQ ID NO 67
<211> LENGTH: 19
<212> TYPE: DNA
<213> ORGANISM: Artificial Sequence
<220> FEATURE:
<223> OTHER INFORMATION: siRNA

<400> SEQUENCE: 67
cuccuuggca ggacugugu                                                 19

<210> SEQ ID NO 68
<211> LENGTH: 21
<212> TYPE: DNA
<213> ORGANISM: Artificial Sequence
<220> FEATURE:
<223> OTHER INFORMATION: siRNA

<400> SEQUENCE: 68
ugggcgccac uccccctucct t                                             21

<210> SEQ ID NO 69
<211> LENGTH: 19
<212> TYPE: DNA
<213> ORGANISM: Artificial Sequence
<220> FEATURE:
<223> OTHER INFORMATION: siRNA

<400> SEQUENCE: 69
```

```
ccuuucugag cugugcguu                                             19

<210> SEQ ID NO 70
<211> LENGTH: 21
<212> TYPE: DNA
<213> ORGANISM: Artificial Sequence
<220> FEATURE:
<223> OTHER INFORMATION: siRNA

<400> SEQUENCE: 70
guugguccuu ccuuggguu t                                           21

<210> SEQ ID NO 71
<211> LENGTH: 21
<212> TYPE: DNA
<213> ORGANISM: Artificial Sequence
<220> FEATURE:
<223> OTHER INFORMATION: siRNA

<400> SEQUENCE: 71 cuggggugg ggcagccact t                                           21

<210> SEQ ID NO 72
<211> LENGTH: 21
<212> TYPE: DNA
<213> ORGANISM: Artificial Sequence
<220> FEATURE:
<223> OTHER INFORMATION: siRNA

<400> SEQUENCE: 72
cugggugagg uggggucccu t                                          21

<210> SEQ ID NO 73
<211> LENGTH: 21
<212> TYPE: DNA
<213> ORGANISM: Artificial Sequence
<220> FEATURE:
<223> OTHER INFORMATION: siRNA

<400> SEQUENCE: 73
acaaaaauua uuuacauaut t                                          21

<210> SEQ ID NO 74
<211> LENGTH: 21
<212> TYPE: DNA
<213> ORGANISM: Artificial Sequence
<220> FEATURE:
<223> OTHER INFORMATION: siRNA

<400> SEQUENCE: 74
ucacugggac aaaaauuaut t                                          21

<210> SEQ ID NO 75
<211> LENGTH: 21
<212> TYPE: DNA
<213> ORGANISM: Artificial Sequence
<220> FEATURE:
<223> OTHER INFORMATION: siRNA

<400> SEQUENCE: 75
guucucacug ggacaaaaat t                                          21

<210> SEQ ID NO 76
<211> LENGTH: 21
<212> TYPE: DNA
```

```
<213> ORGANISM: Artificial Sequence
<220> FEATURE:
<223> OTHER INFORMATION: siRNA

<400> SEQUENCE: 76
gcucagaggc aucgagguut t                                              21

<210> SEQ ID NO 77
<211> LENGTH: 21
<212> TYPE: DNA
<213> ORGANISM: Artificial Sequence
<220> FEATURE:
<223> OTHER INFORMATION: siRNA

<400> SEQUENCE: 77
aggcucagag gcaucgaggt t                                              21

<210> SEQ ID NO 78
<211> LENGTH: 20
<212> TYPE: DNA
<213> ORGANISM: Artificial Sequence
<220> FEATURE:
<223> OTHER INFORMATION: siRNA

<400> SEQUENCE: 78
ucacucaguu uaccccgatt                                                20

<210> SEQ ID NO 79
<211> LENGTH: 21
<212> TYPE: DNA
<213> ORGANISM: Artificial Sequence
<220> FEATURE:
<223> OTHER INFORMATION: siRNA

<400> SEQUENCE: 79
ggaggaaccg cgagccgcct t                                              21

<210> SEQ ID NO 80
<211> LENGTH: 21
<212> TYPE: DNA
<213> ORGANISM: Artificial Sequence
<220> FEATURE:
<223> OTHER INFORMATION: siRNA

<400> SEQUENCE: 80
guggauguug cgggaaguct t                                              21

<210> SEQ ID NO 81
<211> LENGTH: 21
<212> TYPE: DNA
<213> ORGANISM: Artificial Sequence
<220> FEATURE:
<223> OTHER INFORMATION: siRNA

<400> SEQUENCE: 81
gugguccaag gaguggaugt t                                              21

<210> SEQ ID NO 82
<211> LENGTH: 21
<212> TYPE: DNA
<213> ORGANISM: Artificial Sequence
<220> FEATURE:
<223> OTHER INFORMATION: siRNA

<400> SEQUENCE: 82
uguucuguga cuguggugut t                                              21
```

<210> SEQ ID NO 83
<211> LENGTH: 21
<212> TYPE: DNA
<213> ORGANISM: Artificial Sequence
<220> FEATURE:
<223> OTHER INFORMATION: siRNA

<400> SEQUENCE: 83
caaauacaga gcugucauut t                                          21

<210> SEQ ID NO 84
<211> LENGTH: 21
<212> TYPE: DNA
<213> ORGANISM: Artificial Sequence
<220> FEATURE:
<223> OTHER INFORMATION: siRNA

<400> SEQUENCE: 84
gucaaauaca gagcugucat t                                          21

<210> SEQ ID NO 85
<211> LENGTH: 21
<212> TYPE: DNA
<213> ORGANISM: Artificial Sequence
<220> FEATURE:
<223> OTHER INFORMATION: siRNA

<400> SEQUENCE: 85
gaagaaaaca aacauauuct t                                          21

<210> SEQ ID NO 86
<211> LENGTH: 21
<212> TYPE: DNA
<213> ORGANISM: Artificial Sequence
<220> FEATURE:
<223> OTHER INFORMATION: siRNA

<400> SEQUENCE: 86
cgacuuuugc cgcaagaugt t                                          21

<210> SEQ ID NO 87
<211> LENGTH: 21
<212> TYPE: DNA
<213> ORGANISM: Artificial Sequence
<220> FEATURE:
<223> OTHER INFORMATION: siRNA

<400> SEQUENCE: 87
gcacacguaa cggcccgact t                                          21

<210> SEQ ID NO 88
<211> LENGTH: 21
<212> TYPE: DNA
<213> ORGANISM: Artificial Sequence
<220> FEATURE:
<223> OTHER INFORMATION: siRNA

<400> SEQUENCE: 88
gauguucuca aagaggaugt t                                          21

<210> SEQ ID NO 89
<211> LENGTH: 21
<212> TYPE: DNA
<213> ORGANISM: Artificial Sequence
<220> FEATURE:

```
<223> OTHER INFORMATION: siRNA

<400> SEQUENCE: 89
auagaauuua cguaguuaut t                                              21

<210> SEQ ID NO 90
<211> LENGTH: 19
<212> TYPE: DNA
<213> ORGANISM: Artificial Sequence
<220> FEATURE:
<223> OTHER INFORMATION: siRNA

<400> SEQUENCE: 90
gaugauagaa uuuacguag                                                 19

<210> SEQ ID NO 91
<211> LENGTH: 21
<212> TYPE: DNA
<213> ORGANISM: Artificial Sequence
<220> FEATURE:
<223> OTHER INFORMATION: siRNA

<400> SEQUENCE: 91
uuaugaacga ugauagaaut t                                              21

<210> SEQ ID NO 92
<211> LENGTH: 19
<212> TYPE: DNA
<213> ORGANISM: Artificial Sequence
<220> FEATURE:
<223> OTHER INFORMATION: siRNA

<400> SEQUENCE: 92
uugaguuuua acgaaagug                                                 19

<210> SEQ ID NO 93
<211> LENGTH: 21
<212> TYPE: DNA
<213> ORGANISM: Artificial Sequence
<220> FEATURE:
<223> OTHER INFORMATION: siRNA

<400> SEQUENCE: 93
ggacagugug guuguugagt t                                              21

<210> SEQ ID NO 94
<211> LENGTH: 21
<212> TYPE: DNA
<213> ORGANISM: Artificial Sequence
<220> FEATURE:
<223> OTHER INFORMATION: siRNA

<400> SEQUENCE: 94
gaaauggaca guggguugt t                                               21

<210> SEQ ID NO 95
<211> LENGTH: 21
<212> TYPE: DNA
<213> ORGANISM: Artificial Sequence
<220> FEATURE:
<223> OTHER INFORMATION: siRNA

<400> SEQUENCE: 95
aaagucauug gugugcucat t                                              21
```

```
<210> SEQ ID NO 96
<211> LENGTH: 19
<212> TYPE: DNA
<213> ORGANISM: Artificial Sequence
<220> FEATURE:
<223> OTHER INFORMATION: siRNA

<400> SEQUENCE: 96
aaccaugcuu ucagggugg                                                    19

<210> SEQ ID NO 97
<211> LENGTH: 21
<212> TYPE: DNA
<213> ORGANISM: Artificial Sequence
<220> FEATURE:
<223> OTHER INFORMATION: siRNA

<400> SEQUENCE: 97
cagcaauucu aaccaugcut t                                                 21

<210> SEQ ID NO 98
<211> LENGTH: 21
<212> TYPE: DNA
<213> ORGANISM: Artificial Sequence
<220> FEATURE:
<223> OTHER INFORMATION: siRNA

<400> SEQUENCE: 98
guuaugguuc uuacagcaat t                                                 21

<210> SEQ ID NO 99
<211> LENGTH: 21
<212> TYPE: DNA
<213> ORGANISM: Artificial Sequence
<220> FEATURE:
<223> OTHER INFORMATION: siRNA

<400> SEQUENCE: 99
acauucaaag uuaugguuct t                                                 21

<210> SEQ ID NO 100
<211> LENGTH: 21
<212> TYPE: DNA
<213> ORGANISM: Artificial Sequence
<220> FEATURE:
<223> OTHER INFORMATION: siRNA

<400> SEQUENCE: 100
uagacauuca aguuauggt t                                                  21

<210> SEQ ID NO 101
<211> LENGTH: 21
<212> TYPE: DNA
<213> ORGANISM: Artificial Sequence
<220> FEATURE:
<223> OTHER INFORMATION: siRNA

<400> SEQUENCE: 101
caaugacacu uuauagacat t                                                 21

<210> SEQ ID NO 102
<211> LENGTH: 21
<212> TYPE: DNA
<213> ORGANISM: Artificial Sequence
<220> FEATURE:
<223> OTHER INFORMATION: siRNA
```

```
<400> SEQUENCE: 102
cugguuaucc aaugacacut t                                              21

<210> SEQ ID NO 103
<211> LENGTH: 19
<212> TYPE: DNA
<213> ORGANISM: Artificial Sequence
<220> FEATURE:
<223> OTHER INFORMATION: siRNA

<400> SEQUENCE: 103
guagugcagc auggccugg                                                 19

<210> SEQ ID NO 104
<211> LENGTH: 21
<212> TYPE: DNA
<213> ORGANISM: Artificial Sequence
<220> FEATURE:
<223> OTHER INFORMATION: siRNA

<400> SEQUENCE: 104
gaaguaagga acagcaguut t                                              21

<210> SEQ ID NO 105
<211> LENGTH: 21
<212> TYPE: DNA
<213> ORGANISM: Artificial Sequence
<220> FEATURE:
<223> OTHER INFORMATION: siRNA

<400> SEQUENCE: 105
gagaaguaag gaacagcagt t                                              21

<210> SEQ ID NO 106
<211> LENGTH: 21
<212> TYPE: DNA
<213> ORGANISM: Artificial Sequence
<220> FEATURE:
<223> OTHER INFORMATION: siRNA

<400> SEQUENCE: 106
ugccaccaga ucacucagut t                                              21

<210> SEQ ID NO 107
<211> LENGTH: 21
<212> TYPE: DNA
<213> ORGANISM: Artificial Sequence
<220> FEATURE:
<223> OTHER INFORMATION: siRNA

<400> SEQUENCE: 107
gaggggcagg aagagccugt t                                              21

<210> SEQ ID NO 108
<211> LENGTH: 21
<212> TYPE: DNA
<213> ORGANISM: Artificial Sequence
<220> FEATURE:
<223> OTHER INFORMATION: siRNA

<400> SEQUENCE: 108
uucuccuccc uuguccuggt t                                              21

<210> SEQ ID NO 109
<211> LENGTH: 21
```

```
<212> TYPE: DNA
<213> ORGANISM: Artificial Sequence
<220> FEATURE:
<223> OTHER INFORMATION: siRNA

<400> SEQUENCE: 109
uuucggccgu ucuccuccct t                                              21

<210> SEQ ID NO 110
<211> LENGTH: 19
<212> TYPE: DNA
<213> ORGANISM: Artificial Sequence
<220> FEATURE:
<223> OTHER INFORMATION: siRNA

<400> SEQUENCE: 110
gcaggcuaau uuucggccg                                                 19

<210> SEQ ID NO 111
<211> LENGTH: 19
<212> TYPE: DNA
<213> ORGANISM: Artificial Sequence
<220> FEATURE:
<223> OTHER INFORMATION: siRNA

<400> SEQUENCE: 111
agacaccggc aggcuaauu                                                 19

<210> SEQ ID NO 112
<211> LENGTH: 21
<212> TYPE: DNA
<213> ORGANISM: Artificial Sequence
<220> FEATURE:
<223> OTHER INFORMATION: siRNA

<400> SEQUENCE: 112
agagacaccg gcaggcuaat t                                              21

<210> SEQ ID NO 113
<211> LENGTH: 21
<212> TYPE: DNA
<213> ORGANISM: Artificial Sequence
<220> FEATURE:
<223> OTHER INFORMATION: siRNA

<400> SEQUENCE: 113
augcugggcu uggcagaact t                                              21

<210> SEQ ID NO 114
<211> LENGTH: 21
<212> TYPE: DNA
<213> ORGANISM: Artificial Sequence
<220> FEATURE:
<223> OTHER INFORMATION: siRNA

<400> SEQUENCE: 114
gaagcaccga augcugggct t                                              21

<210> SEQ ID NO 115
<211> LENGTH: 21
<212> TYPE: DNA
<213> ORGANISM: Artificial Sequence
<220> FEATURE:
<223> OTHER INFORMATION: siRNA

<400> SEQUENCE: 115
```
cucgaguguc ucgguggggut t                                             21

<210> SEQ ID NO 116
<211> LENGTH: 21
<212> TYPE: DNA
<213> ORGANISM: Artificial Sequence
<220> FEATURE:
<223> OTHER INFORMATION: siRNA

<400> SEQUENCE: 116
ccgccucuug cccuugugct t                                              21

<210> SEQ ID NO 117
<211> LENGTH: 21
<212> TYPE: DNA
<213> ORGANISM: Artificial Sequence
<220> FEATURE:
<223> OTHER INFORMATION: siRNA

<400> SEQUENCE: 117
uugcacccgc cucuugccct t                                              21

<210> SEQ ID NO 118
<211> LENGTH: 21
<212> TYPE: DNA
<213> ORGANISM: Artificial Sequence
<220> FEATURE:
<223> OTHER INFORMATION: siRNA

<400> SEQUENCE: 118
ucucuuuugc acccgccuct t                                              21

<210> SEQ ID NO 119
<211> LENGTH: 21
<212> TYPE: DNA
<213> ORGANISM: Artificial Sequence
<220> FEATURE:
<223> OTHER INFORMATION: siRNA

<400> SEQUENCE: 119
uuuuguaguu gggucucuut t                                              21

<210> SEQ ID NO 120
<211> LENGTH: 21
<212> TYPE: DNA
<213> ORGANISM: Artificial Sequence
<220> FEATURE:
<223> OTHER INFORMATION: siRNA

<400> SEQUENCE: 120 guuuuguag uugggucuct t                                               21

<210> SEQ ID NO 121
<211> LENGTH: 21
<212> TYPE: DNA
<213> ORGANISM: Artificial Sequence
<220> FEATURE:
<223> OTHER INFORMATION: siRNA

<400> SEQUENCE: 121
uuccccaacg uuuuuguagt t                                              21

<210> SEQ ID NO 122
<211> LENGTH: 21
<212> TYPE: DNA
<213> ORGANISM: Artificial Sequence

```
<220> FEATURE:
<223> OTHER INFORMATION: siRNA

<400> SEQUENCE: 122
uucuucuucc ccaacguuut t                                              21

<210> SEQ ID NO 123
<211> LENGTH: 21
<212> TYPE: DNA
<213> ORGANISM: Artificial Sequence
<220> FEATURE:
<223> OTHER INFORMATION: siRNA

<400> SEQUENCE: 123
ucuucuucuu ccccaacgut t                                              21

<210> SEQ ID NO 124
<211> LENGTH: 21
<212> TYPE: DNA
<213> ORGANISM: Artificial Sequence
<220> FEATURE:
<223> OTHER INFORMATION: siRNA

<400> SEQUENCE: 124
cuuucuccuc aucuucuuct t                                              21

<210> SEQ ID NO 125
<211> LENGTH: 21
<212> TYPE: DNA
<213> ORGANISM: Artificial Sequence
<220> FEATURE:
<223> OTHER INFORMATION: siRNA

<400> SEQUENCE: 125
gcccuuucuc cucaucuuct t                                              21

<210> SEQ ID NO 126
<211> LENGTH: 21
<212> TYPE: DNA
<213> ORGANISM: Artificial Sequence
<220> FEATURE:
<223> OTHER INFORMATION: siRNA

<400> SEQUENCE: 126
uagccuucuc ggcgucuuct t                                              21

<210> SEQ ID NO 127
<211> LENGTH: 21
<212> TYPE: DNA
<213> ORGANISM: Artificial Sequence
<220> FEATURE:
<223> OTHER INFORMATION: siRNA

<400> SEQUENCE: 127
cuuuagccuu cucggcguct t                                              21

<210> SEQ ID NO 128
<211> LENGTH: 21
<212> TYPE: DNA
<213> ORGANISM: Artificial Sequence
<220> FEATURE:
<223> OTHER INFORMATION: siRNA

<400> SEQUENCE: 128
acccucugua ccuuuagcct t                                              21
```

<210> SEQ ID NO 129
<211> LENGTH: 21
<212> TYPE: DNA
<213> ORGANISM: Artificial Sequence
<220> FEATURE:
<223> OTHER INFORMATION: siRNA

<400> SEQUENCE: 129
ugaaccaccc ucuguaccut t                                         21

<210> SEQ ID NO 130
<211> LENGTH: 21
<212> TYPE: DNA
<213> ORGANISM: Artificial Sequence
<220> FEATURE:
<223> OTHER INFORMATION: siRNA

<400> SEQUENCE: 130
ccacucgucu ugaugccuut t                                         21

<210> SEQ ID NO 131
<211> LENGTH: 21
<212> TYPE: DNA
<213> ORGANISM: Artificial Sequence
<220> FEATURE:
<223> OTHER INFORMATION: siRNA

<400> SEQUENCE: 131
ccccacucgu cuugaugcct t                                         21

<210> SEQ ID NO 132
<211> LENGTH: 21
<212> TYPE: DNA
<213> ORGANISM: Artificial Sequence
<220> FEATURE:
<223> OTHER INFORMATION: siRNA

<400> SEQUENCE: 132
uucacucucc ccacucguct t                                         21

<210> SEQ ID NO 133
<211> LENGTH: 21
<212> TYPE: DNA
<213> ORGANISM: Artificial Sequence
<220> FEATURE:
<223> OTHER INFORMATION: siRNA

<400> SEQUENCE: 133
ugaucaccau cucgaucuct t                                         21

<210> SEQ ID NO 134
<211> LENGTH: 21
<212> TYPE: DNA
<213> ORGANISM: Artificial Sequence
<220> FEATURE:
<223> OTHER INFORMATION: siRNA

<400> SEQUENCE: 134
ggcggccagc ucugagagct t                                         21

<210> SEQ ID NO 135
<211> LENGTH: 21
<212> TYPE: DNA
<213> ORGANISM: Artificial Sequence
<220> FEATURE:
<223> OTHER INFORMATION: siRNA

```
<400> SEQUENCE: 135
uuucuccucg uccguggugt t                                              21

<210> SEQ ID NO 136
<211> LENGTH: 21
<212> TYPE: DNA
<213> ORGANISM: Artificial Sequence
<220> FEATURE:
<223> OTHER INFORMATION: siRNA

<400> SEQUENCE: 136
gcagguggcg gcggcgcuut t                                              21

<210> SEQ ID NO 137
<211> LENGTH: 21
<212> TYPE: DNA
<213> ORGANISM: Artificial Sequence
<220> FEATURE:
<223> OTHER INFORMATION: siRNA

<400> SEQUENCE: 137
gagcaggugg cggcggcgct t                                              21

<210> SEQ ID NO 138
<211> LENGTH: 21
<212> TYPE: DNA
<213> ORGANISM: Artificial Sequence
<220> FEATURE:
<223> OTHER INFORMATION: siRNA

<400> SEQUENCE: 138
ccaggaaggg ucugcuccat t                                              21

<210> SEQ ID NO 139
<211> LENGTH: 21
<212> TYPE: DNA
<213> ORGANISM: Artificial Sequence
<220> FEATURE:
<223> OTHER INFORMATION: siRNA

<400> SEQUENCE: 139
uucaggaucc augccuuuat t                                              21

<210> SEQ ID NO 140
<211> LENGTH: 19
<212> TYPE: DNA
<213> ORGANISM: Artificial Sequence
<220> FEATURE:
<223> OTHER INFORMATION: siRNA

<400> SEQUENCE: 140
uuuuucagga uccaugccu                                                 19

<210> SEQ ID NO 141
<211> LENGTH: 21
<212> TYPE: DNA
<213> ORGANISM: Artificial Sequence
<220> FEATURE:
<223> OTHER INFORMATION: siRNA

<400> SEQUENCE: 141
gagcuggauu cgcucuaaut t                                              21

<210> SEQ ID NO 142
```

```
<211> LENGTH: 21
<212> TYPE: DNA
<213> ORGANISM: Artificial Sequence
<220> FEATURE:
<223> OTHER INFORMATION: siRNA

<400> SEQUENCE: 142
uuuggcacgg ggagcuggat t                                              21

<210> SEQ ID NO 143
<211> LENGTH: 21
<212> TYPE: DNA
<213> ORGANISM: Artificial Sequence
<220> FEATURE:
<223> OTHER INFORMATION: siRNA

<400> SEQUENCE: 143
guggucuucu cggccgcaut t                                              21

<210> SEQ ID NO 144
<211> LENGTH: 21
<212> TYPE: DNA
<213> ORGANISM: Artificial Sequence
<220> FEATURE:
<223> OTHER INFORMATION: siRNA

<400> SEQUENCE: 144
cgggugguug uaggugguct t                                              21

<210> SEQ ID NO 145
<211> LENGTH: 21
<212> TYPE: DNA
<213> ORGANISM: Artificial Sequence
<220> FEATURE:
<223> OTHER INFORMATION: siRNA

<400> SEQUENCE: 145
ucuuucagcu agcggguggt t                                              21

<210> SEQ ID NO 146
<211> LENGTH: 21
<212> TYPE: DNA
<213> ORGANISM: Artificial Sequence
<220> FEATURE:
<223> OTHER INFORMATION: siRNA

<400> SEQUENCE: 146
ucaugauccu gaugagucut t                                              21

<210> SEQ ID NO 147
<211> LENGTH: 21
<212> TYPE: DNA
<213> ORGANISM: Artificial Sequence
<220> FEATURE:
<223> OTHER INFORMATION: siRNA

<400> SEQUENCE: 147
guacaaggug aacacuuuct t                                              21

<210> SEQ ID NO 148
<211> LENGTH: 19
<212> TYPE: DNA
<213> ORGANISM: Artificial Sequence
<220> FEATURE:
<223> OTHER INFORMATION: siRNA

<400> SEQUENCE: 148
```
gucguacaag gugaacacu                                            19

<210> SEQ ID NO 149
<211> LENGTH: 21
<212> TYPE: DNA
<213> ORGANISM: Artificial Sequence
<220> FEATURE:
<223> OTHER INFORMATION: siRNA

<400> SEQUENCE: 149
uccacguuca ugggcuucat t                                         21

<210> SEQ ID NO 150
<211> LENGTH: 21
<212> TYPE: DNA
<213> ORGANISM: Artificial Sequence
<220> FEATURE:
<223> OTHER INFORMATION: siRNA

<400> SEQUENCE: 150
auauuccacg uucaugggct t                                         21

<210> SEQ ID NO 151
<211> LENGTH: 21
<212> TYPE: DNA
<213> ORGANISM: Artificial Sequence
<220> FEATURE:
<223> OTHER INFORMATION: siRNA

<400> SEQUENCE: 151
caucaugaga uauuccacgt t                                         21

<210> SEQ ID NO 152
<211> LENGTH: 19
<212> TYPE: DNA
<213> ORGANISM: Artificial Sequence
<220> FEATURE:
<223> OTHER INFORMATION: siRNA

<400> SEQUENCE: 152
aggcguccau caugagaua                                            19

<210> SEQ ID NO 153
<211> LENGTH: 21
<212> TYPE: DNA
<213> ORGANISM: Artificial Sequence
<220> FEATURE:
<223> OTHER INFORMATION: siRNA

<400> SEQUENCE: 153
cccgucagug gcgugccugt t                                         21

<210> SEQ ID NO 154
<211> LENGTH: 21
<212> TYPE: DNA
<213> ORGANISM: Artificial Sequence
<220> FEATURE:
<223> OTHER INFORMATION: siRNA

<400> SEQUENCE: 154
aucgccacac ggcagccgct t                                         21

<210> SEQ ID NO 155
<211> LENGTH: 21
<212> TYPE: DNA

```
<213> ORGANISM: Artificial Sequence
<220> FEATURE:
<223> OTHER INFORMATION: siRNA

<400> SEQUENCE: 155
ccggauggcc cgccggguct t                                               21

<210> SEQ ID NO 156
<211> LENGTH: 21
<212> TYPE: DNA
<213> ORGANISM: Artificial Sequence
<220> FEATURE:
<223> OTHER INFORMATION: siRNA

<400> SEQUENCE: 156
ucucaggcuc cccucgcaat t                                               21

<210> SEQ ID NO 157
<211> LENGTH: 21
<212> TYPE: DNA
<213> ORGANISM: Artificial Sequence
<220> FEATURE:
<223> OTHER INFORMATION: siRNA

<400> SEQUENCE: 157
auccaggaca ucaucaguct t                                               21

<210> SEQ ID NO 158
<211> LENGTH: 21
<212> TYPE: DNA
<213> ORGANISM: Artificial Sequence
<220> FEATURE:
<223> OTHER INFORMATION: siRNA

<400> SEQUENCE: 158
ugcaaucaag ucgcuguuat t                                               21

<210> SEQ ID NO 159
<211> LENGTH: 21
<212> TYPE: DNA
<213> ORGANISM: Artificial Sequence
<220> FEATURE:
<223> OTHER INFORMATION: siRNA

<400> SEQUENCE: 159
acaugcaauc aagucgcugt t                                               21

<210> SEQ ID NO 160
<211> LENGTH: 21
<212> TYPE: DNA
<213> ORGANISM: Artificial Sequence
<220> FEATURE:
<223> OTHER INFORMATION: siRNA

<400> SEQUENCE: 160
cuggaccaug ccgccaucct t                                               21

<210> SEQ ID NO 161
<211> LENGTH: 21
<212> TYPE: DNA
<213> ORGANISM: Artificial Sequence
<220> FEATURE:
<223> OTHER INFORMATION: siRNA

<400> SEQUENCE: 161
cugcaauagg ccugcaaact t                                               21
```

<210> SEQ ID NO 162
<211> LENGTH: 21
<212> TYPE: DNA
<213> ORGANISM: Artificial Sequence
<220> FEATURE:
<223> OTHER INFORMATION: siRNA

<400> SEQUENCE: 162
cuggaggaug gggaagggct t                                              21

<210> SEQ ID NO 163
<211> LENGTH: 21
<212> TYPE: DNA
<213> ORGANISM: Artificial Sequence
<220> FEATURE:
<223> OTHER INFORMATION: siRNA

<400> SEQUENCE: 163
gccuuuggcc aggcgcugct t                                              21

<210> SEQ ID NO 164
<211> LENGTH: 21
<212> TYPE: DNA
<213> ORGANISM: Artificial Sequence
<220> FEATURE:
<223> OTHER INFORMATION: siRNA

<400> SEQUENCE: 164
ccuugccugg augcggccut t                                              21

<210> SEQ ID NO 165
<211> LENGTH: 21
<212> TYPE: DNA
<213> ORGANISM: Artificial Sequence
<220> FEATURE:
<223> OTHER INFORMATION: siRNA

<400> SEQUENCE: 165
cucugcaucu ucaugcgcct t                                              21

<210> SEQ ID NO 166
<211> LENGTH: 21
<212> TYPE: DNA
<213> ORGANISM: Artificial Sequence
<220> FEATURE:
<223> OTHER INFORMATION: siRNA

<400> SEQUENCE: 166
ggcagcuauu cucugcauct t                                              21

<210> SEQ ID NO 167
<211> LENGTH: 21
<212> TYPE: DNA
<213> ORGANISM: Artificial Sequence
<220> FEATURE:
<223> OTHER INFORMATION: siRNA

<400> SEQUENCE: 167
agguccagga gggcagcuat t                                              21

<210> SEQ ID NO 168
<211> LENGTH: 21
<212> TYPE: DNA
<213> ORGANISM: Artificial Sequence
<220> FEATURE:

<223> OTHER INFORMATION: siRNA

<400> SEQUENCE: 168
acuucagugg ugggcuggat t                                              21

<210> SEQ ID NO 169
<211> LENGTH: 21
<212> TYPE: DNA
<213> ORGANISM: Artificial Sequence
<220> FEATURE:
<223> OTHER INFORMATION: siRNA

<400> SEQUENCE: 169
cgaguccaaa ccccaggact t                                              21

<210> SEQ ID NO 170
<211> LENGTH: 21
<212> TYPE: DNA
<213> ORGANISM: Artificial Sequence
<220> FEATURE:
<223> OTHER INFORMATION: siRNA

<400> SEQUENCE: 170
cacggcgaag ccuggcacct t                                              21

<210> SEQ ID NO 171
<211> LENGTH: 19
<212> TYPE: DNA
<213> ORGANISM: Artificial Sequence
<220> FEATURE:
<223> OTHER INFORMATION: siRNA

<400> SEQUENCE: 171
gacggggagc ugugcuggu                                                 19

<210> SEQ ID NO 172
<211> LENGTH: 21
<212> TYPE: DNA
<213> ORGANISM: Artificial Sequence
<220> FEATURE:
<223> OTHER INFORMATION: siRNA

<400> SEQUENCE: 172
gaaggugagg cuuaggcagt t                                              21

<210> SEQ ID NO 173
<211> LENGTH: 21
<212> TYPE: DNA
<213> ORGANISM: Artificial Sequence
<220> FEATURE:
<223> OTHER INFORMATION: siRNA

<400> SEQUENCE: 173
gcuuccguuu cguugacgat t                                              21

<210> SEQ ID NO 174
<211> LENGTH: 21
<212> TYPE: DNA
<213> ORGANISM: Artificial Sequence
<220> FEATURE:
<223> OTHER INFORMATION: siRNA

<400> SEQUENCE: 174
agagucugcu uccguuucgt t                                              21

```
<210> SEQ ID NO 175
<211> LENGTH: 21
<212> TYPE: DNA
<213> ORGANISM: Artificial Sequence
<220> FEATURE:
<223> OTHER INFORMATION: siRNA

<400> SEQUENCE: 175
gcuuagaguc ugcuuccgut t                                              21

<210> SEQ ID NO 176
<211> LENGTH: 21
<212> TYPE: DNA
<213> ORGANISM: Artificial Sequence
<220> FEATURE:
<223> OTHER INFORMATION: siRNA

<400> SEQUENCE: 176
ugcugggcuu agagucugct t                                              21

<210> SEQ ID NO 177
<211> LENGTH: 21
<212> TYPE: DNA
<213> ORGANISM: Artificial Sequence
<220> FEATURE:
<223> OTHER INFORMATION: siRNA

<400> SEQUENCE: 177
ggccacguuc uugcugggct t                                              21

<210> SEQ ID NO 178
<211> LENGTH: 21
<212> TYPE: DNA
<213> ORGANISM: Artificial Sequence
<220> FEATURE:
<223> OTHER INFORMATION: siRNA

<400> SEQUENCE: 178
gggggacaag ggucagcgat t                                              21

<210> SEQ ID NO 179
<211> LENGTH: 21
<212> TYPE: DNA
<213> ORGANISM: Artificial Sequence
<220> FEATURE:
<223> OTHER INFORMATION: siRNA

<400> SEQUENCE: 179
gcucagcaca ugcagccuct t                                              21

<210> SEQ ID NO 180
<211> LENGTH: 21
<212> TYPE: DNA
<213> ORGANISM: Artificial Sequence
<220> FEATURE:
<223> OTHER INFORMATION: siRNA

<400> SEQUENCE: 180 aacgugggc uucuucccat t                                               21

<210> SEQ ID NO 181
<211> LENGTH: 21
<212> TYPE: DNA
<213> ORGANISM: Artificial Sequence
<220> FEATURE:
<223> OTHER INFORMATION: siRNA
```

```
<400> SEQUENCE: 181
uucaaggaca acgugggct t                                               21

<210> SEQ ID NO 182
<211> LENGTH: 21
<212> TYPE: DNA
<213> ORGANISM: Artificial Sequence
<220> FEATURE:
<223> OTHER INFORMATION: siRNA

<400> SEQUENCE: 182
augcaaagug aaaaggaat t                                               21

<210> SEQ ID NO 183
<211> LENGTH: 21
<212> TYPE: DNA
<213> ORGANISM: Artificial Sequence
<220> FEATURE:
<223> OTHER INFORMATION: siRNA

<400> SEQUENCE: 183
gccggugcag ucaucugcat t                                              21

<210> SEQ ID NO 184
<211> LENGTH: 21
<212> TYPE: DNA
<213> ORGANISM: Artificial Sequence
<220> FEATURE:
<223> OTHER INFORMATION: siRNA

<400> SEQUENCE: 184
cagugaccug guccaauuct t                                              21

<210> SEQ ID NO 185
<211> LENGTH: 21
<212> TYPE: DNA
<213> ORGANISM: Artificial Sequence
<220> FEATURE:
<223> OTHER INFORMATION: siRNA

<400> SEQUENCE: 185
agucugcuuu ucuacaaaut t                                              21

<210> SEQ ID NO 186
<211> LENGTH: 21
<212> TYPE: DNA
<213> ORGANISM: Artificial Sequence
<220> FEATURE:
<223> OTHER INFORMATION: siRNA

<400> SEQUENCE: 186
uguuuaucua agucugcuut t                                              21

<210> SEQ ID NO 187
<211> LENGTH: 21
<212> TYPE: DNA
<213> ORGANISM: Artificial Sequence
<220> FEATURE:
<223> OTHER INFORMATION: siRNA

<400> SEQUENCE: 187
gauguuuauc uaagucugct t                                              21

<210> SEQ ID NO 188
<211> LENGTH: 21
```

```
<212> TYPE: DNA
<213> ORGANISM: Artificial Sequence
<220> FEATURE:
<223> OTHER INFORMATION: siRNA

<400> SEQUENCE: 188
gaaguuuuaa aaauaaaugt t                                              21

<210> SEQ ID NO 189
<211> LENGTH: 21
<212> TYPE: DNA
<213> ORGANISM: Artificial Sequence
<220> FEATURE:
<223> OTHER INFORMATION: siRNA

<400> SEQUENCE: 189
cuucuuuuaa auagaaguut t                                              21

<210> SEQ ID NO 190
<211> LENGTH: 21
<212> TYPE: DNA
<213> ORGANISM: Artificial Sequence
<220> FEATURE:
<223> OTHER INFORMATION: siRNA

<400> SEQUENCE: 190
gacuucuuuu aaauagaagt t                                              21

<210> SEQ ID NO 191
<211> LENGTH: 21
<212> TYPE: DNA
<213> ORGANISM: Artificial Sequence
<220> FEATURE:
<223> OTHER INFORMATION: siRNA

<400> SEQUENCE: 191
augacaucaa accuuagugt t                                              21

<210> SEQ ID NO 192
<211> LENGTH: 21
<212> TYPE: DNA
<213> ORGANISM: Artificial Sequence
<220> FEATURE:
<223> OTHER INFORMATION: siRNA

<400> SEQUENCE: 192
uuucacauga caucaaacct t                                              21

<210> SEQ ID NO 193
<211> LENGTH: 21
<212> TYPE: DNA
<213> ORGANISM: Artificial Sequence
<220> FEATURE:
<223> OTHER INFORMATION: siRNA

<400> SEQUENCE: 193
aacuguuauu auuacacuut t                                              21

<210> SEQ ID NO 194
<211> LENGTH: 21
<212> TYPE: DNA
<213> ORGANISM: Artificial Sequence
<220> FEATURE:
<223> OTHER INFORMATION: siRNA

<400> SEQUENCE: 194
```
uuaacuguua uuauuacact t                                              21

<210> SEQ ID NO 195
<211> LENGTH: 21
<212> TYPE: DNA
<213> ORGANISM: Artificial Sequence
<220> FEATURE:
<223> OTHER INFORMATION: siRNA

<400> SEQUENCE: 195
gaaaucuuaa cuguuauuat t                                              21

<210> SEQ ID NO 196
<211> LENGTH: 21
<212> TYPE: DNA
<213> ORGANISM: Artificial Sequence
<220> FEATURE:
<223> OTHER INFORMATION: siRNA

<400> SEQUENCE: 196
caugaaaucu uaacuguuat t                                              21

<210> SEQ ID NO 197
<211> LENGTH: 21
<212> TYPE: DNA
<213> ORGANISM: Artificial Sequence
<220> FEATURE:
<223> OTHER INFORMATION: siRNA

<400> SEQUENCE: 197
gaucaugaaa ucuuaacugt t                                              21

<210> SEQ ID NO 198
<211> LENGTH: 19
<212> TYPE: DNA
<213> ORGANISM: Artificial Sequence
<220> FEATURE:
<223> OTHER INFORMATION: siRNA

<400> SEQUENCE: 198
ugaaaaugau caugaaauc                                                 19

<210> SEQ ID NO 199
<211> LENGTH: 21
<212> TYPE: DNA
<213> ORGANISM: Artificial Sequence
<220> FEATURE:
<223> OTHER INFORMATION: siRNA

<400> SEQUENCE: 199
gugaguaaca aagaaucact t                                              21

<210> SEQ ID NO 200
<211> LENGTH: 21
<212> TYPE: DNA
<213> ORGANISM: Artificial Sequence
<220> FEATURE:
<223> OTHER INFORMATION: siRNA

<400> SEQUENCE: 200
auuccacagg cuugcagagt t                                              21

<210> SEQ ID NO 201
<211> LENGTH: 21
<212> TYPE: DNA
<213> ORGANISM: Artificial Sequence
<220> FEATURE:
<223> OTHER INFORMATION: siRNA

<400> SEQUENCE: 201
ccaggaaggu acuucauuat t          21

<210> SEQ ID NO 202
<211> LENGTH: 21
<212> TYPE: DNA
<213> ORGANISM: Artificial Sequence
<220> FEATURE:
<223> OTHER INFORMATION: siRNA

<400> SEQUENCE: 202
aaacuuucca ggaagguact t          21

<210> SEQ ID NO 203
<211> LENGTH: 21
<212> TYPE: DNA
<213> ORGANISM: Artificial Sequence
<220> FEATURE:
<223> OTHER INFORMATION: siRNA

<400> SEQUENCE: 203
uuaaaaaaua auccaaacut t          21

<210> SEQ ID NO 204
<211> LENGTH: 21
<212> TYPE: DNA
<213> ORGANISM: Artificial Sequence
<220> FEATURE:
<223> OTHER INFORMATION: siRNA

<400> SEQUENCE: 204
acauguaucu cccuuguuut t          21

<210> SEQ ID NO 205
<211> LENGTH: 21
<212> TYPE: DNA
<213> ORGANISM: Artificial Sequence
<220> FEATURE:
<223> OTHER INFORMATION: siRNA

<400> SEQUENCE: 205
auacauguau cucccuugut t          21

<210> SEQ ID NO 206
<211> LENGTH: 19
<212> TYPE: DNA
<213> ORGANISM: Artificial Sequence
<220> FEATURE:
<223> OTHER INFORMATION: siRNA

<400> SEQUENCE: 206
gagaauacau guaucuccc             19

<210> SEQ ID NO 207
<211> LENGTH: 21
<212> TYPE: DNA
<213> ORGANISM: Artificial Sequence
<220> FEATURE:
<223> OTHER INFORMATION: siRNA

<400> SEQUENCE: 207 ccuuuccug gagaaaucut t           21

```
<210> SEQ ID NO 208
<211> LENGTH: 19
<212> TYPE: DNA
<213> ORGANISM: Artificial Sequence
<220> FEATURE:
<223> OTHER INFORMATION: siRNA

<400> SEQUENCE: 208
gcuggcuaca uuccuccuu                                                19

<210> SEQ ID NO 209
<211> LENGTH: 21
<212> TYPE: DNA
<213> ORGANISM: Artificial Sequence
<220> FEATURE:
<223> OTHER INFORMATION: siRNA

<400> SEQUENCE: 209
gagcuggcua cauuccucct t                                             21

<210> SEQ ID NO 210
<211> LENGTH: 21
<212> TYPE: DNA
<213> ORGANISM: Artificial Sequence
<220> FEATURE:
<223> OTHER INFORMATION: siRNA

<400> SEQUENCE: 210 gagugggag cuggcuacat t                                              21

<210> SEQ ID NO 211
<211> LENGTH: 21
<212> TYPE: DNA
<213> ORGANISM: Artificial Sequence
<220> FEATURE:
<223> OTHER INFORMATION: siRNA

<400> SEQUENCE: 211
aagcugucuc uguuugguut t                                             21

<210> SEQ ID NO 212
<211> LENGTH: 19
<212> TYPE: DNA
<213> ORGANISM: Artificial Sequence
<220> FEATURE:
<223> OTHER INFORMATION: siRNA

<400> SEQUENCE: 212
ugcuggaagc ugucucugu                                                19

<210> SEQ ID NO 213
<211> LENGTH: 21
<212> TYPE: DNA
<213> ORGANISM: Artificial Sequence
<220> FEATURE:
<223> OTHER INFORMATION: siRNA

<400> SEQUENCE: 213
ggucccaacu gguuccuuct t                                             21

<210> SEQ ID NO 214
<211> LENGTH: 21
<212> TYPE: DNA
<213> ORGANISM: Artificial Sequence
<220> FEATURE:
<223> OTHER INFORMATION: siRNA
```

<400> SEQUENCE: 214
cacgguccca acugguucct t                                              21

<210> SEQ ID NO 215
<211> LENGTH: 21
<212> TYPE: DNA
<213> ORGANISM: Artificial Sequence
<220> FEATURE:
<223> OTHER INFORMATION: siRNA

<400> SEQUENCE: 215 gaggugucu uccuuugaut t                                               21

<210> SEQ ID NO 216
<211> LENGTH: 21
<212> TYPE: DNA
<213> ORGANISM: Artificial Sequence
<220> FEATURE:
<223> OTHER INFORMATION: siRNA

<400> SEQUENCE: 216
acguagaggg ugucuuccut t                                              21

<210> SEQ ID NO 217
<211> LENGTH: 21
<212> TYPE: DNA
<213> ORGANISM: Artificial Sequence
<220> FEATURE:
<223> OTHER INFORMATION: siRNA

<400> SEQUENCE: 217
aggugacgua gaggguguct t                                              21

<210> SEQ ID NO 218
<211> LENGTH: 21
<212> TYPE: DNA
<213> ORGANISM: Artificial Sequence
<220> FEATURE:
<223> OTHER INFORMATION: siRNA

<400> SEQUENCE: 218 cucugggac accaugccct t                                               21

<210> SEQ ID NO 219
<211> LENGTH: 21
<212> TYPE: DNA
<213> ORGANISM: Artificial Sequence
<220> FEATURE:
<223> OTHER INFORMATION: siRNA

<400> SEQUENCE: 219
gaaccauggg guuuccauat t                                              21

<210> SEQ ID NO 220
<211> LENGTH: 21
<212> TYPE: DNA
<213> ORGANISM: Artificial Sequence
<220> FEATURE:
<223> OTHER INFORMATION: siRNA

<400> SEQUENCE: 220
gaugcaucug gguccuugct t                                              21

<210> SEQ ID NO 221

```
<211> LENGTH: 21
<212> TYPE: DNA
<213> ORGANISM: Artificial Sequence
<220> FEATURE:
<223> OTHER INFORMATION: siRNA

<400> SEQUENCE: 221
cuguguuucc uucaugaggt t                                                    21

<210> SEQ ID NO 222
<211> LENGTH: 19
<212> TYPE: DNA
<213> ORGANISM: Artificial Sequence
<220> FEATURE:
<223> OTHER INFORMATION: siRNA

<400> SEQUENCE: 222
gcacagcuac ccagagggc                                                       19

<210> SEQ ID NO 223
<211> LENGTH: 19
<212> TYPE: DNA
<213> ORGANISM: Artificial Sequence
<220> FEATURE:
<223> OTHER INFORMATION: siRNA

<400> SEQUENCE: 223
ucuauggaag caaaggucc                                                       19

<210> SEQ ID NO 224
<211> LENGTH: 21
<212> TYPE: DNA
<213> ORGANISM: Artificial Sequence
<220> FEATURE:
<223> OTHER INFORMATION: siRNA

<400> SEQUENCE: 224
ccccuuucug agcugugcgt t                                                    21

<210> SEQ ID NO 225
<211> LENGTH: 21
<212> TYPE: DNA
<213> ORGANISM: Artificial Sequence
<220> FEATURE:
<223> OTHER INFORMATION: siRNA

<400> SEQUENCE: 225
ucugcccaug uggcccccut t                                                    21

<210> SEQ ID NO 226
<211> LENGTH: 21
<212> TYPE: DNA
<213> ORGANISM: Artificial Sequence
<220> FEATURE:
<223> OTHER INFORMATION: siRNA

<400> SEQUENCE: 226
gucgugguuu guccuuccut t                                                    21

<210> SEQ ID NO 227
<211> LENGTH: 19
<212> TYPE: DNA
<213> ORGANISM: Artificial Sequence
<220> FEATURE:
<223> OTHER INFORMATION: siRNA

<400> SEQUENCE: 227
```
cgguggucgu gguuugucc                                                19

<210> SEQ ID NO 228
<211> LENGTH: 21
<212> TYPE: DNA
<213> ORGANISM: Artificial Sequence
<220> FEATURE:
<223> OTHER INFORMATION: siRNA

<400> SEQUENCE: 228
uggccacggu ggucgugguu t                                             21

<210> SEQ ID NO 229
<211> LENGTH: 21
<212> TYPE: DNA
<213> ORGANISM: Artificial Sequence
<220> FEATURE:
<223> OTHER INFORMATION: siRNA

<400> SEQUENCE: 229
cuuccuucuc uuccagggau t                                             21

<210> SEQ ID NO 230
<211> LENGTH: 21
<212> TYPE: DNA
<213> ORGANISM: Artificial Sequence
<220> FEATURE:
<223> OTHER INFORMATION: siRNA

<400> SEQUENCE: 230
ccacccugcc uuccuucucu t                                             21

<210> SEQ ID NO 231
<211> LENGTH: 21
<212> TYPE: DNA
<213> ORGANISM: Artificial Sequence
<220> FEATURE:
<223> OTHER INFORMATION: siRNA

<400> SEQUENCE: 231
ccgcuccacc cugccuuccu t                                             21

<210> SEQ ID NO 232
<211> LENGTH: 21
<212> TYPE: DNA
<213> ORGANISM: Artificial Sequence
<220> FEATURE:
<223> OTHER INFORMATION: siRNA

<400> SEQUENCE: 232 cccccgcuc cacccugcct t                                              21

<210> SEQ ID NO 233
<211> LENGTH: 21
<212> TYPE: DNA
<213> ORGANISM: Artificial Sequence
<220> FEATURE:
<223> OTHER INFORMATION: siRNA

<400> SEQUENCE: 233
ccuucucucc augauggcu t                                              21

<210> SEQ ID NO 234
<211> LENGTH: 21
<212> TYPE: DNA

<210> SEQ ID NO 235
<211> LENGTH: 21
<212> TYPE: DNA
<213> ORGANISM: Artificial Sequence
<220> FEATURE:
<223> OTHER INFORMATION: siRNA

<400> SEQUENCE: 234
ucuccugaug cguggucct t                                              21

<210> SEQ ID NO 235
<211> LENGTH: 21
<212> TYPE: DNA
<213> ORGANISM: Artificial Sequence
<220> FEATURE:
<223> OTHER INFORMATION: siRNA

<400> SEQUENCE: 235
cccucuugcu cuuaaaaaat t                                             21

<210> SEQ ID NO 236
<211> LENGTH: 21
<212> TYPE: DNA
<213> ORGANISM: Artificial Sequence
<220> FEATURE:
<223> OTHER INFORMATION: siRNA

<400> SEQUENCE: 236
cucucuaccc cucuugcuct t                                             21

<210> SEQ ID NO 237
<211> LENGTH: 21
<212> TYPE: DNA
<213> ORGANISM: Artificial Sequence
<220> FEATURE:
<223> OTHER INFORMATION: siRNA

<400> SEQUENCE: 237
uugauccucu cuaccccuct t                                             21

<210> SEQ ID NO 238
<211> LENGTH: 19
<212> TYPE: DNA
<213> ORGANISM: Artificial Sequence
<220> FEATURE:
<223> OTHER INFORMATION: siRNA

<400> SEQUENCE: 238
aucuccagcc agggccagc                                                19

<210> SEQ ID NO 239
<211> LENGTH: 21
<212> TYPE: DNA
<213> ORGANISM: Artificial Sequence
<220> FEATURE:
<223> OTHER INFORMATION: siRNA

<400> SEQUENCE: 239
gccccacaga cagagucaut t                                             21

<210> SEQ ID NO 240
<211> LENGTH: 21
<212> TYPE: DNA
<213> ORGANISM: Artificial Sequence
<220> FEATURE:
<223> OTHER INFORMATION: siRNA

<400> SEQUENCE: 240
gccacuugcc uucucuagut t                                             21

<210> SEQ ID NO 241
<211> LENGTH: 21
<212> TYPE: DNA
<213> ORGANISM: Artificial Sequence
<220> FEATURE:
<223> OTHER INFORMATION: siRNA

<400> SEQUENCE: 241 ggugggggcag ccacuugcct t                                              21

<210> SEQ ID NO 242
<211> LENGTH: 21
<212> TYPE: DNA
<213> ORGANISM: Artificial Sequence
<220> FEATURE:
<223> OTHER INFORMATION: siRNA

<400> SEQUENCE: 242
uguuccuccu ggucacgcct t                                               21

<210> SEQ ID NO 243
<211> LENGTH: 21
<212> TYPE: DNA
<213> ORGANISM: Artificial Sequence
<220> FEATURE:
<223> OTHER INFORMATION: siRNA

<400> SEQUENCE: 243
uggagugagc ugcaggcugt t                                               21

<210> SEQ ID NO 244
<211> LENGTH: 21
<212> TYPE: DNA
<213> ORGANISM: Artificial Sequence
<220> FEATURE:
<223> OTHER INFORMATION: siRNA

<400> SEQUENCE: 244
ccaguuggag cccagagact t                                               21

<210> SEQ ID NO 245
<211> LENGTH: 21
<212> TYPE: DNA
<213> ORGANISM: Artificial Sequence
<220> FEATURE:
<223> OTHER INFORMATION: siRNA

<400> SEQUENCE: 245
ucagugguua caagaccagt t                                               21

<210> SEQ ID NO 246
<211> LENGTH: 21
<212> TYPE: DNA
<213> ORGANISM: Artificial Sequence
<220> FEATURE:
<223> OTHER INFORMATION: siRNA

<400> SEQUENCE: 246
cuccuucagu gcucaguggt t                                               21

<210> SEQ ID NO 247
<211> LENGTH: 21
<212> TYPE: DNA
<213> ORGANISM: Artificial Sequence
<220> FEATURE:

```
<223> OTHER INFORMATION: siRNA

<400> SEQUENCE: 247
cugaccaaga ccucucucct t                                              21

<210> SEQ ID NO 248
<211> LENGTH: 21
<212> TYPE: DNA
<213> ORGANISM: Artificial Sequence
<220> FEATURE:
<223> OTHER INFORMATION: siRNA

<400> SEQUENCE: 248
cugguccucc cagucaccut t                                              21

<210> SEQ ID NO 249
<211> LENGTH: 21
<212> TYPE: DNA
<213> ORGANISM: Artificial Sequence
<220> FEATURE:
<223> OTHER INFORMATION: siRNA

<400> SEQUENCE: 249
cugcccugag cagugucuut t                                              21

<210> SEQ ID NO 250
<211> LENGTH: 21
<212> TYPE: DNA
<213> ORGANISM: Artificial Sequence
<220> FEATURE:
<223> OTHER INFORMATION: siRNA

<400> SEQUENCE: 250
cccugcccug agcaguguct t                                              21

<210> SEQ ID NO 251
<211> LENGTH: 21
<212> TYPE: DNA
<213> ORGANISM: Artificial Sequence
<220> FEATURE:
<223> OTHER INFORMATION: siRNA

<400> SEQUENCE: 251 caugggacu gcccuuuuct t                                               21

<210> SEQ ID NO 252
<211> LENGTH: 21
<212> TYPE: DNA
<213> ORGANISM: Artificial Sequence
<220> FEATURE:
<223> OTHER INFORMATION: siRNA

<400> SEQUENCE: 252
ccacaugggg acugcccuut t                                              21

<210> SEQ ID NO 253
<211> LENGTH: 19
<212> TYPE: DNA
<213> ORGANISM: Artificial Sequence
<220> FEATURE:
<223> OTHER INFORMATION: siRNA

<400> SEQUENCE: 253
gcccacaugg ggacugccc                                                 19
```

```
<210> SEQ ID NO 254
<211> LENGTH: 21
<212> TYPE: DNA
<213> ORGANISM: Artificial Sequence
<220> FEATURE:
<223> OTHER INFORMATION: siRNA

<400> SEQUENCE: 254
gguguccccc agacgcaagt t                                             21

<210> SEQ ID NO 255
<211> LENGTH: 21
<212> TYPE: DNA
<213> ORGANISM: Artificial Sequence
<220> FEATURE:
<223> OTHER INFORMATION: siRNA

<400> SEQUENCE: 255
cuccuuacau aagcaaagct t                                             21

<210> SEQ ID NO 256
<211> LENGTH: 21
<212> TYPE: DNA
<213> ORGANISM: Artificial Sequence
<220> FEATURE:
<223> OTHER INFORMATION: siRNA

<400> SEQUENCE: 256
ggcuggcucc cagaccucct t                                             21

<210> SEQ ID NO 257
<211> LENGTH: 21
<212> TYPE: DNA
<213> ORGANISM: Artificial Sequence
<220> FEATURE:
<223> OTHER INFORMATION: siRNA

<400> SEQUENCE: 257
agcgccccag cuaugaggut t                                             21

<210> SEQ ID NO 258
<211> LENGTH: 21
<212> TYPE: DNA
<213> ORGANISM: Artificial Sequence
<220> FEATURE:
<223> OTHER INFORMATION: siRNA

<400> SEQUENCE: 258
cuucccacac uccuggcuct t                                             21

<210> SEQ ID NO 259
<211> LENGTH: 21
<212> TYPE: DNA
<213> ORGANISM: Artificial Sequence
<220> FEATURE:
<223> OTHER INFORMATION: siRNA

<400> SEQUENCE: 259
acagccccca cugugggcct t                                             21

<210> SEQ ID NO 260
<211> LENGTH: 21
<212> TYPE: DNA
<213> ORGANISM: Artificial Sequence
<220> FEATURE:
<223> OTHER INFORMATION: siRNA
```

```
<400> SEQUENCE: 260
aagugcucuc ugcagggact t                                              21

<210> SEQ ID NO 261
<211> LENGTH: 21
<212> TYPE: DNA
<213> ORGANISM: Artificial Sequence
<220> FEATURE:
<223> OTHER INFORMATION: siRNA

<400> SEQUENCE: 261
gccagcccug cucccugact t                                              21

<210> SEQ ID NO 262
<211> LENGTH: 21
<212> TYPE: DNA
<213> ORGANISM: Artificial Sequence
<220> FEATURE:
<223> OTHER INFORMATION: siRNA

<400> SEQUENCE: 262
caaagccaag guuugggagt t                                              21

<210> SEQ ID NO 263
<211> LENGTH: 21
<212> TYPE: DNA
<213> ORGANISM: Artificial Sequence
<220> FEATURE:
<223> OTHER INFORMATION: siRNA

<400> SEQUENCE: 263
caauauucaa agccaaggut t                                              21

<210> SEQ ID NO 264
<211> LENGTH: 19
<212> TYPE: DNA
<213> ORGANISM: Artificial Sequence
<220> FEATURE:
<223> OTHER INFORMATION: siRNA

<400> SEQUENCE: 264
gcacaccucc acaacaaua                                                 19

<210> SEQ ID NO 265
<211> LENGTH: 21
<212> TYPE: DNA
<213> ORGANISM: Artificial Sequence
<220> FEATURE:
<223> OTHER INFORMATION: siRNA

<400> SEQUENCE: 265
accugcuggg acagguacct t                                              21

<210> SEQ ID NO 266
<211> LENGTH: 21
<212> TYPE: DNA
<213> ORGANISM: Artificial Sequence
<220> FEATURE:
<223> OTHER INFORMATION: siRNA

<400> SEQUENCE: 266
cgauggugaa ggcuggccct t                                              21

<210> SEQ ID NO 267
<211> LENGTH: 19
```

```
<212> TYPE: DNA
<213> ORGANISM: Artificial Sequence
<220> FEATURE:
<223> OTHER INFORMATION: siRNA

<400> SEQUENCE: 267
gugaacgcaa gugucuggg                                                    19

<210> SEQ ID NO 268
<211> LENGTH: 21
<212> TYPE: DNA
<213> ORGANISM: Artificial Sequence
<220> FEATURE:
<223> OTHER INFORMATION: siRNA

<400> SEQUENCE: 268
caccugcccc uuagguugct t                                                 21

<210> SEQ ID NO 269
<211> LENGTH: 21
<212> TYPE: DNA
<213> ORGANISM: Artificial Sequence
<220> FEATURE:
<223> OTHER INFORMATION: siRNA

<400> SEQUENCE: 269
ucuucaccug ccccuuaggt t                                                 21

<210> SEQ ID NO 270
<211> LENGTH: 21
<212> TYPE: DNA
<213> ORGANISM: Artificial Sequence
<220> FEATURE:
<223> OTHER INFORMATION: siRNA

<400> SEQUENCE: 270
gcgucuggca gggcugcgct t                                                 21

<210> SEQ ID NO 271
<211> LENGTH: 21
<212> TYPE: DNA
<213> ORGANISM: Artificial Sequence
<220> FEATURE:
<223> OTHER INFORMATION: siRNA

<400> SEQUENCE: 271
acggugcauc ucagagacct t                                                 21

<210> SEQ ID NO 272
<211> LENGTH: 21
<212> TYPE: DNA
<213> ORGANISM: Artificial Sequence
<220> FEATURE:
<223> OTHER INFORMATION: siRNA

<400> SEQUENCE: 272
aucaguucac cccacgccut t                                                 21

<210> SEQ ID NO 273
<211> LENGTH: 21
<212> TYPE: DNA
<213> ORGANISM: Artificial Sequence
<220> FEATURE:
<223> OTHER INFORMATION: siRNA

<400> SEQUENCE: 273
```
acaagaagau caaaaucagt t                                              21

<210> SEQ ID NO 274
<211> LENGTH: 21
<212> TYPE: DNA
<213> ORGANISM: Artificial Sequence
<220> FEATURE:
<223> OTHER INFORMATION: siRNA

<400> SEQUENCE: 274
aaugcuucag auuuauuuat t                                              21

<210> SEQ ID NO 275
<211> LENGTH: 21
<212> TYPE: DNA
<213> ORGANISM: Artificial Sequence
<220> FEATURE:
<223> OTHER INFORMATION: siRNA

<400> SEQUENCE: 275
uuaaaugcuu cagauuuaut t                                              21

<210> SEQ ID NO 276
<211> LENGTH: 21
<212> TYPE: DNA
<213> ORGANISM: Artificial Sequence
<220> FEATURE:
<223> OTHER INFORMATION: siRNA

<400> SEQUENCE: 276
uacauuaaau gcuucagaut t                                              21

<210> SEQ ID NO 277
<211> LENGTH: 21
<212> TYPE: DNA
<213> ORGANISM: Artificial Sequence
<220> FEATURE:
<223> OTHER INFORMATION: siRNA

<400> SEQUENCE: 277
agaugacuac auuaaaugct t                                              21

<210> SEQ ID NO 278
<211> LENGTH: 21
<212> TYPE: DNA
<213> ORGANISM: Artificial Sequence
<220> FEATURE:
<223> OTHER INFORMATION: siRNA

<400> SEQUENCE: 278
caaugucaag augacuacat t                                              21

<210> SEQ ID NO 279
<211> LENGTH: 21
<212> TYPE: DNA
<213> ORGANISM: Artificial Sequence
<220> FEATURE:
<223> OTHER INFORMATION: siRNA

<400> SEQUENCE: 279
aaaaauuauu uacauauuut t                                              21

<210> SEQ ID NO 280
<211> LENGTH: 21
<212> TYPE: DNA
<213> ORGANISM: Artificial Sequence

```
<220> FEATURE:
<223> OTHER INFORMATION: siRNA

<400> SEQUENCE: 280
ugcuggcgaa agcagguact t                                              21

<210> SEQ ID NO 281
<211> LENGTH: 21
<212> TYPE: DNA
<213> ORGANISM: Artificial Sequence
<220> FEATURE:
<223> OTHER INFORMATION: siRNA

<400> SEQUENCE: 281
uuucauuucc acccucgugt t                                              21

<210> SEQ ID NO 282
<211> LENGTH: 21
<212> TYPE: DNA
<213> ORGANISM: Artificial Sequence
<220> FEATURE:
<223> OTHER INFORMATION: siRNA

<400> SEQUENCE: 282
aggaaguucc aguuuucaut t                                              21

<210> SEQ ID NO 283
<211> LENGTH: 21
<212> TYPE: DNA
<213> ORGANISM: Artificial Sequence
<220> FEATURE:
<223> OTHER INFORMATION: siRNA

<400> SEQUENCE: 283
uuacaaggaa guuccaguut t                                              21

<210> SEQ ID NO 284
<211> LENGTH: 21
<212> TYPE: DNA
<213> ORGANISM: Artificial Sequence
<220> FEATURE:
<223> OTHER INFORMATION: siRNA

<400> SEQUENCE: 284
auuuacaagg aaguuccagt t                                              21

<210> SEQ ID NO 285
<211> LENGTH: 21
<212> TYPE: DNA
<213> ORGANISM: Artificial Sequence
<220> FEATURE:
<223> OTHER INFORMATION: siRNA

<400> SEQUENCE: 285
guuuaaauuu acaaggaagt t                                              21

<210> SEQ ID NO 286
<211> LENGTH: 21
<212> TYPE: DNA
<213> ORGANISM: Artificial Sequence
<220> FEATURE:
<223> OTHER INFORMATION: siRNA

<400> SEQUENCE: 286
auuuaaacuu ggcaauaaat t                                              21
```

```
<210> SEQ ID NO 287
<211> LENGTH: 21
<212> TYPE: DNA
<213> ORGANISM: Artificial Sequence
<220> FEATURE:
<223> OTHER INFORMATION: siRNA

<400> SEQUENCE: 287
acuuggcaau aaaagagaat t                                              21

<210> SEQ ID NO 288
<211> LENGTH: 21
<212> TYPE: DNA
<213> ORGANISM: Artificial Sequence
<220> FEATURE:
<223> OTHER INFORMATION: siRNA

<400> SEQUENCE: 288
cuucuauuua aaagaaguct t                                              21

<210> SEQ ID NO 289
<211> LENGTH: 21
<212> TYPE: DNA
<213> ORGANISM: Artificial Sequence
<220> FEATURE:
<223> OTHER INFORMATION: siRNA

<400> SEQUENCE: 289
acaccacagu cacagaacat t                                              21

<210> SEQ ID NO 290
<211> LENGTH: 21
<212> TYPE: DNA
<213> ORGANISM: Artificial Sequence
<220> FEATURE:
<223> OTHER INFORMATION: siRNA

<400> SEQUENCE: 290
uauguuuguu uucuucuugt t                                              21

<210> SEQ ID NO 291
<211> LENGTH: 21
<212> TYPE: DNA
<213> ORGANISM: Artificial Sequence
<220> FEATURE:
<223> OTHER INFORMATION: siRNA

<400> SEQUENCE: 291
cauccucuuu gagaacauct t                                              21

<210> SEQ ID NO 292
<211> LENGTH: 19
<212> TYPE: DNA
<213> ORGANISM: Artificial Sequence
<220> FEATURE:
<223> OTHER INFORMATION: siRNA

<400> SEQUENCE: 292
auucuaucau cguucauaa                                                 19

<210> SEQ ID NO 293
<211> LENGTH: 19
<212> TYPE: DNA
<213> ORGANISM: Artificial Sequence
<220> FEATURE:
<223> OTHER INFORMATION: siRNA
```

```
<400> SEQUENCE: 293
cacuuucguu aaaacucaa                                                    19

<210> SEQ ID NO 294
<211> LENGTH: 21
<212> TYPE: DNA
<213> ORGANISM: Artificial Sequence
<220> FEATURE:
<223> OTHER INFORMATION: siRNA

<400> SEQUENCE: 294
aacucaacaa ccacacugut t                                                 21

<210> SEQ ID NO 295
<211> LENGTH: 21
<212> TYPE: DNA
<213> ORGANISM: Artificial Sequence
<220> FEATURE:
<223> OTHER INFORMATION: siRNA

<400> SEQUENCE: 295
cucaacaacc acacugcct t                                                  21

<210> SEQ ID NO 296
<211> LENGTH: 21
<212> TYPE: DNA
<213> ORGANISM: Artificial Sequence
<220> FEATURE:
<223> OTHER INFORMATION: siRNA

<400> SEQUENCE: 296
agcaugguua gaauugcugt t                                                 21

<210> SEQ ID NO 297
<211> LENGTH: 21
<212> TYPE: DNA
<213> ORGANISM: Artificial Sequence
<220> FEATURE:
<223> OTHER INFORMATION: siRNA

<400> SEQUENCE: 297
ccauaacuuu gaaugucuat t                                                 21

<210> SEQ ID NO 298
<211> LENGTH: 21
<212> TYPE: DNA
<213> ORGANISM: Artificial Sequence
<220> FEATURE:
<223> OTHER INFORMATION: siRNA

<400> SEQUENCE: 298
aacugcuguu ccuuacuuct t                                                 21

<210> SEQ ID NO 299
<211> LENGTH: 21
<212> TYPE: DNA
<213> ORGANISM: Artificial Sequence
<220> FEATURE:
<223> OTHER INFORMATION: siRNA

<400> SEQUENCE: 299
ccaggacaag ggaggagaat t                                                 21

<210> SEQ ID NO 300
```

```
<211> LENGTH: 19
<212> TYPE: DNA
<213> ORGANISM: Artificial Sequence
<220> FEATURE:
<223> OTHER INFORMATION: siRNA

<400> SEQUENCE: 300
uuagccugcc ggugucucu                                                  19

<210> SEQ ID NO 301
<211> LENGTH: 21
<212> TYPE: DNA
<213> ORGANISM: Artificial Sequence
<220> FEATURE:
<223> OTHER INFORMATION: siRNA

<400> SEQUENCE: 301
gaggcgggug caaaagagat t                                               21

<210> SEQ ID NO 302
<211> LENGTH: 21
<212> TYPE: DNA
<213> ORGANISM: Artificial Sequence
<220> FEATURE:
<223> OTHER INFORMATION: siRNA

<400> SEQUENCE: 302
aagagaccca acuacaaaat t                                               21

<210> SEQ ID NO 303
<211> LENGTH: 21
<212> TYPE: DNA
<213> ORGANISM: Artificial Sequence
<220> FEATURE:
<223> OTHER INFORMATION: siRNA

<400> SEQUENCE: 303
gaagaagaug aggagaaagt t                                               21

<210> SEQ ID NO 304
<211> LENGTH: 21
<212> TYPE: DNA
<213> ORGANISM: Artificial Sequence
<220> FEATURE:
<223> OTHER INFORMATION: siRNA

<400> SEQUENCE: 304
gaagaugagg agaaagggct t                                               21

<210> SEQ ID NO 305
<211> LENGTH: 21
<212> TYPE: DNA
<213> ORGANISM: Artificial Sequence
<220> FEATURE:
<223> OTHER INFORMATION: siRNA

<400> SEQUENCE: 305
ggcuaaaggu acagagggut t                                               21

<210> SEQ ID NO 306
<211> LENGTH: 21
<212> TYPE: DNA
<213> ORGANISM: Artificial Sequence
<220> FEATURE:
<223> OTHER INFORMATION: siRNA

<400> SEQUENCE: 306
```
agguacagag ggugguucat t                                              21

<210> SEQ ID NO 307
<211> LENGTH: 21
<212> TYPE: DNA
<213> ORGANISM: Artificial Sequence
<220> FEATURE:
<223> OTHER INFORMATION: siRNA

<400> SEQUENCE: 307
gagaucgaga uggugaucat t                                              21

<210> SEQ ID NO 308
<211> LENGTH: 21
<212> TYPE: DNA
<213> ORGANISM: Artificial Sequence
<220> FEATURE:
<223> OTHER INFORMATION: siRNA

<400> SEQUENCE: 308
uggagcagac ccuuccuggt t                                              21

<210> SEQ ID NO 309
<211> LENGTH: 21
<212> TYPE: DNA
<213> ORGANISM: Artificial Sequence
<220> FEATURE:
<223> OTHER INFORMATION: siRNA

<400> SEQUENCE: 309
agacucauca ggaucaugat t                                              21

<210> SEQ ID NO 310
<211> LENGTH: 21
<212> TYPE: DNA
<213> ORGANISM: Artificial Sequence
<220> FEATURE:
<223> OTHER INFORMATION: siRNA

<400> SEQUENCE: 310
caacgcugcc cagccagaut t                                              21

<210> SEQ ID NO 311
<211> LENGTH: 21
<212> TYPE: DNA
<213> ORGANISM: Artificial Sequence
<220> FEATURE:
<223> OTHER INFORMATION: siRNA

<400> SEQUENCE: 311
ugaagcccau gaacguggat t                                              21

<210> SEQ ID NO 312
<211> LENGTH: 21
<212> TYPE: DNA
<213> ORGANISM: Artificial Sequence
<220> FEATURE:
<223> OTHER INFORMATION: siRNA

<400> SEQUENCE: 312
cguggaauau cucaugaugt t                                              21

<210> SEQ ID NO 313
<211> LENGTH: 21
<212> TYPE: DNA

```
<213> ORGANISM: Artificial Sequence
<220> FEATURE:
<223> OTHER INFORMATION: siRNA

<400> SEQUENCE: 313
caggcacgcc acugacgggt t                                              21

<210> SEQ ID NO 314
<211> LENGTH: 21
<212> TYPE: DNA
<213> ORGANISM: Artificial Sequence
<220> FEATURE:
<223> OTHER INFORMATION: siRNA

<400> SEQUENCE: 314
gcggcugccg uguggcgaut t                                              21

<210> SEQ ID NO 315
<211> LENGTH: 21
<212> TYPE: DNA
<213> ORGANISM: Artificial Sequence
<220> FEATURE:
<223> OTHER INFORMATION: siRNA

<400> SEQUENCE: 315
gacccggcgg gccauccggt t                                              21

<210> SEQ ID NO 316
<211> LENGTH: 21
<212> TYPE: DNA
<213> ORGANISM: Artificial Sequence
<220> FEATURE:
<223> OTHER INFORMATION: siRNA

<400> SEQUENCE: 316
uugcgagggg agccugagat t                                              21

<210> SEQ ID NO 317
<211> LENGTH: 21
<212> TYPE: DNA
<213> ORGANISM: Artificial Sequence
<220> FEATURE:
<223> OTHER INFORMATION: siRNA

<400> SEQUENCE: 317
ucgucaacga aacggaagct t                                              21

<210> SEQ ID NO 318
<211> LENGTH: 21
<212> TYPE: DNA
<213> ORGANISM: Artificial Sequence
<220> FEATURE:
<223> OTHER INFORMATION: siRNA

<400> SEQUENCE: 318
cgaaacggaa gcagacucut t                                              21

<210> SEQ ID NO 319
<211> LENGTH: 21
<212> TYPE: DNA
<213> ORGANISM: Artificial Sequence
<220> FEATURE:
<223> OTHER INFORMATION: siRNA

<400> SEQUENCE: 319
acggaagcag acucuaagct t                                              21
```

<210> SEQ ID NO 320
<211> LENGTH: 19
<212> TYPE: DNA
<213> ORGANISM: Artificial Sequence
<220> FEATURE:
<223> OTHER INFORMATION: siRNA

<400> SEQUENCE: 320
cguggccagg agcgcagcc                                                  19

<210> SEQ ID NO 321
<211> LENGTH: 21
<212> TYPE: DNA
<213> ORGANISM: Artificial Sequence
<220> FEATURE:
<223> OTHER INFORMATION: siRNA

<400> SEQUENCE: 321
gaggcugcau gugcugagct t                                               21

<210> SEQ ID NO 322
<211> LENGTH: 21
<212> TYPE: DNA
<213> ORGANISM: Artificial Sequence
<220> FEATURE:
<223> OTHER INFORMATION: siRNA

<400> SEQUENCE: 322
gccccacguu guccuugaat t                                               21

<210> SEQ ID NO 323
<211> LENGTH: 21
<212> TYPE: DNA
<213> ORGANISM: Artificial Sequence
<220> FEATURE:
<223> OTHER INFORMATION: siRNA

<400> SEQUENCE: 323
gcagacuuag auaaacauct t                                               21

<210> SEQ ID NO 324
<211> LENGTH: 21
<212> TYPE: DNA
<213> ORGANISM: Artificial Sequence
<220> FEATURE:
<223> OTHER INFORMATION: siRNA

<400> SEQUENCE: 324
acaucuccuu uggauauuut t                                               21

<210> SEQ ID NO 325
<211> LENGTH: 19
<212> TYPE: DNA
<213> ORGANISM: Artificial Sequence
<220> FEATURE:
<223> OTHER INFORMATION: siRNA

<400> SEQUENCE: 325
cauuuauuuu uaaaacuuc                                                  19

<210> SEQ ID NO 326
<211> LENGTH: 21
<212> TYPE: DNA
<213> ORGANISM: Artificial Sequence
<220> FEATURE:

```
<223> OTHER INFORMATION: siRNA

<400> SEQUENCE: 326
aacuucuauu uaaaagaagt t                                           21

<210> SEQ ID NO 327
<211> LENGTH: 21
<212> TYPE: DNA
<213> ORGANISM: Artificial Sequence
<220> FEATURE:
<223> OTHER INFORMATION: siRNA

<400> SEQUENCE: 327
guccaaaaac aucaacacut t                                           21

<210> SEQ ID NO 328
<211> LENGTH: 21
<212> TYPE: DNA
<213> ORGANISM: Artificial Sequence
<220> FEATURE:
<223> OTHER INFORMATION: siRNA

<400> SEQUENCE: 328
gguuugaugu caugugaaat t                                           21

<210> SEQ ID NO 329
<211> LENGTH: 19
<212> TYPE: DNA
<213> ORGANISM: Artificial Sequence
<220> FEATURE:
<223> OTHER INFORMATION: siRNA

<400> SEQUENCE: 329
aaguguaaua auaacaguu                                              19

<210> SEQ ID NO 330
<211> LENGTH: 21
<212> TYPE: DNA
<213> ORGANISM: Artificial Sequence
<220> FEATURE:
<223> OTHER INFORMATION: siRNA

<400> SEQUENCE: 330
guguaauaau aacaguuaat t                                           21

<210> SEQ ID NO 331
<211> LENGTH: 21
<212> TYPE: DNA
<213> ORGANISM: Artificial Sequence
<220> FEATURE:
<223> OTHER INFORMATION: siRNA

<400> SEQUENCE: 331
uaauaacagu uaagauuuct t                                           21

<210> SEQ ID NO 332
<211> LENGTH: 21
<212> TYPE: DNA
<213> ORGANISM: Artificial Sequence
<220> FEATURE:
<223> OTHER INFORMATION: siRNA

<400> SEQUENCE: 332
uaacaguuaa gauuucaugt t                                           21
```

```
<210> SEQ ID NO 333
<211> LENGTH: 21
<212> TYPE: DNA
<213> ORGANISM: Artificial Sequence
<220> FEATURE:
<223> OTHER INFORMATION: siRNA

<400> SEQUENCE: 333
caguuaagau uucaugauct t                                              21

<210> SEQ ID NO 334
<211> LENGTH: 21
<212> TYPE: DNA
<213> ORGANISM: Artificial Sequence
<220> FEATURE:
<223> OTHER INFORMATION: siRNA

<400> SEQUENCE: 334
gauuucauga ucauuucat t                                               21

<210> SEQ ID NO 335
<211> LENGTH: 21
<212> TYPE: DNA
<213> ORGANISM: Artificial Sequence
<220> FEATURE:
<223> OTHER INFORMATION: siRNA

<400> SEQUENCE: 335
guaccuuccu ggaaaguuut t                                              21

<210> SEQ ID NO 336
<211> LENGTH: 19
<212> TYPE: DNA
<213> ORGANISM: Artificial Sequence
<220> FEATURE:
<223> OTHER INFORMATION: siRNA

<400> SEQUENCE: 336
agauuucucc aggaaaagg                                                 19

<210> SEQ ID NO 337
<211> LENGTH: 21
<212> TYPE: DNA
<213> ORGANISM: Artificial Sequence
<220> FEATURE:
<223> OTHER INFORMATION: siRNA

<400> SEQUENCE: 337
aaggaggaau guagccagct t                                              21

<210> SEQ ID NO 338
<211> LENGTH: 21
<212> TYPE: DNA
<213> ORGANISM: Artificial Sequence
<220> FEATURE:
<223> OTHER INFORMATION: siRNA

<400> SEQUENCE: 338
ggaggaaugu agccagcuct t                                              21

<210> SEQ ID NO 339
<211> LENGTH: 21
<212> TYPE: DNA
<213> ORGANISM: Artificial Sequence
<220> FEATURE:
<223> OTHER INFORMATION: siRNA
```

```
<400> SEQUENCE: 339
uguagccagc uccccacuct t                                              21

<210> SEQ ID NO 340
<211> LENGTH: 21
<212> TYPE: DNA
<213> ORGANISM: Artificial Sequence
<220> FEATURE:
<223> OTHER INFORMATION: siRNA

<400> SEQUENCE: 340
aaccaaacag agacagcuut t                                              21

<210> SEQ ID NO 341
<211> LENGTH: 21
<212> TYPE: DNA
<213> ORGANISM: Artificial Sequence
<220> FEATURE:
<223> OTHER INFORMATION: siRNA

<400> SEQUENCE: 341
ccaaacagag acagcuucct t                                              21

<210> SEQ ID NO 342
<211> LENGTH: 21
<212> TYPE: DNA
<213> ORGANISM: Artificial Sequence
<220> FEATURE:
<223> OTHER INFORMATION: siRNA

<400> SEQUENCE: 342
acagagacag cuuccagcat t                                              21

<210> SEQ ID NO 343
<211> LENGTH: 21
<212> TYPE: DNA
<213> ORGANISM: Artificial Sequence
<220> FEATURE:
<223> OTHER INFORMATION: siRNA

<400> SEQUENCE: 343
aucaaaggaa gacacccuct t                                              21

<210> SEQ ID NO 344
<211> LENGTH: 21
<212> TYPE: DNA
<213> ORGANISM: Artificial Sequence
<220> FEATURE:
<223> OTHER INFORMATION: siRNA

<400> SEQUENCE: 344
cgcacagcuc agaaaggggt t                                              21

<210> SEQ ID NO 345
<211> LENGTH: 21
<212> TYPE: DNA
<213> ORGANISM: Artificial Sequence
<220> FEATURE:
<223> OTHER INFORMATION: siRNA

<400> SEQUENCE: 345 aggggggccac augggcagat t                                             21

<210> SEQ ID NO 346
<211> LENGTH: 21
```

<212> TYPE: DNA
<213> ORGANISM: Artificial Sequence
<220> FEATURE:
<223> OTHER INFORMATION: siRNA

<400> SEQUENCE: 346
acccaaagga aggacaaact t     21

<210> SEQ ID NO 347
<211> LENGTH: 19
<212> TYPE: DNA
<213> ORGANISM: Artificial Sequence
<220> FEATURE:
<223> OTHER INFORMATION: siRNA

<400> SEQUENCE: 347
aggaaggaca aaccacgac     19

<210> SEQ ID NO 348
<211> LENGTH: 19
<212> TYPE: DNA
<213> ORGANISM: Artificial Sequence
<220> FEATURE:
<223> OTHER INFORMATION: siRNA

<400> SEQUENCE: 348
ggacaaacca cgaccaccg     19

<210> SEQ ID NO 349
<211> LENGTH: 21
<212> TYPE: DNA
<213> ORGANISM: Artificial Sequence
<220> FEATURE:
<223> OTHER INFORMATION: siRNA

<400> SEQUENCE: 349
accacgacca ccguggccat t     21

<210> SEQ ID NO 350
<211> LENGTH: 21
<212> TYPE: DNA
<213> ORGANISM: Artificial Sequence
<220> FEATURE:
<223> OTHER INFORMATION: siRNA

<400> SEQUENCE: 350
acuagagaag gcaaguggct t     21

<210> SEQ ID NO 351
<211> LENGTH: 21
<212> TYPE: DNA
<213> ORGANISM: Artificial Sequence
<220> FEATURE:
<223> OTHER INFORMATION: siRNA

<400> SEQUENCE: 351
ggcgugacca ggaggaacat t     21

<210> SEQ ID NO 352
<211> LENGTH: 21
<212> TYPE: DNA
<213> ORGANISM: Artificial Sequence
<220> FEATURE:
<223> OTHER INFORMATION: siRNA

<400> SEQUENCE: 352
gcuuugcuua uguaaggagt t                                                    21

<210> SEQ ID NO 353
<211> LENGTH: 21
<212> TYPE: DNA
<213> ORGANISM: Artificial Sequence
<220> FEATURE:
<223> OTHER INFORMATION: siRNA

<400> SEQUENCE: 353
gucagggagc agggcuggct t                                                    21

<210> SEQ ID NO 354
<211> LENGTH: 21
<212> TYPE: DNA
<213> ORGANISM: Artificial Sequence
<220> FEATURE:
<223> OTHER INFORMATION: siRNA

<400> SEQUENCE: 354
accuuggcuu ugaauauugt t                                                    21

<210> SEQ ID NO 355
<211> LENGTH: 19
<212> TYPE: DNA
<213> ORGANISM: Artificial Sequence
<220> FEATURE:
<223> OTHER INFORMATION: siRNA

<400> SEQUENCE: 355
gggccagccu ucaccaucg                                                       19

<210> SEQ ID NO 356
<211> LENGTH: 19
<212> TYPE: DNA
<213> ORGANISM: Artificial Sequence
<220> FEATURE:
<223> OTHER INFORMATION: siRNA

<400> SEQUENCE: 356
auaaaucuga agcauuuaa                                                       19

<210> SEQ ID NO 357
<211> LENGTH: 21
<212> TYPE: DNA
<213> ORGANISM: Artificial Sequence
<220> FEATURE:
<223> OTHER INFORMATION: siRNA

<400> SEQUENCE: 357
ggcggcucgc gguuccucct t                                                    21

<210> SEQ ID NO 358
<211> LENGTH: 21
<212> TYPE: DNA
<213> ORGANISM: Artificial Sequence
<220> FEATURE:
<223> OTHER INFORMATION: siRNA

<400> SEQUENCE: 358
gacuucccgc aacauccact t                                                    21

<210> SEQ ID NO 359
<211> LENGTH: 21
<212> TYPE: DNA
<213> ORGANISM: Artificial Sequence

```
<220> FEATURE:
<223> OTHER INFORMATION: siRNA

<400> SEQUENCE: 359
cauccacucc uuggaccact t                                            21

<210> SEQ ID NO 360
<211> LENGTH: 21
<212> TYPE: DNA
<213> ORGANISM: Artificial Sequence
<220> FEATURE:
<223> OTHER INFORMATION: siRNA

<400> SEQUENCE: 360
guaucuguac cacguuuugt t                                            21

<210> SEQ ID NO 361
<211> LENGTH: 21
<212> TYPE: DNA
<213> ORGANISM: Artificial Sequence
<220> FEATURE:
<223> OTHER INFORMATION: siRNA

<400> SEQUENCE: 361
aaacaccaca gucacagaat t                                            21

<210> SEQ ID NO 362
<211> LENGTH: 21
<212> TYPE: DNA
<213> ORGANISM: Artificial Sequence
<220> FEATURE:
<223> OTHER INFORMATION: siRNA

<400> SEQUENCE: 362
cagaaccgga accugcuagt t                                            21

<210> SEQ ID NO 363
<211> LENGTH: 21
<212> TYPE: DNA
<213> ORGANISM: Artificial Sequence
<220> FEATURE:
<223> OTHER INFORMATION: siRNA

<400> SEQUENCE: 363
ccggaaccug cuaguggagt t                                            21

<210> SEQ ID NO 364
<211> LENGTH: 21
<212> TYPE: DNA
<213> ORGANISM: Artificial Sequence
<220> FEATURE:
<223> OTHER INFORMATION: siRNA

<400> SEQUENCE: 364
ccugcuagug gagaccauct t                                            21

<210> SEQ ID NO 365
<211> LENGTH: 21
<212> TYPE: DNA
<213> ORGANISM: Artificial Sequence
<220> FEATURE:
<223> OTHER INFORMATION: siRNA

<400> SEQUENCE: 365
aaugacagcu cuguauuugt t                                            21
```

```
<210> SEQ ID NO 366
<211> LENGTH: 21
<212> TYPE: DNA
<213> ORGANISM: Artificial Sequence
<220> FEATURE:
<223> OTHER INFORMATION: siRNA

<400> SEQUENCE: 366
ugacagcucu guauuugact t                                             21

<210> SEQ ID NO 367
<211> LENGTH: 21
<212> TYPE: DNA
<213> ORGANISM: Artificial Sequence
<220> FEATURE:
<223> OTHER INFORMATION: siRNA

<400> SEQUENCE: 367
gaauauguuu guuucuuct t                                              21

<210> SEQ ID NO 368
<211> LENGTH: 21
<212> TYPE: DNA
<213> ORGANISM: Artificial Sequence
<220> FEATURE:
<223> OTHER INFORMATION: siRNA

<400> SEQUENCE: 368
caucuugcgg caaaagucgt t                                             21

<210> SEQ ID NO 369
<211> LENGTH: 21
<212> TYPE: DNA
<213> ORGANISM: Artificial Sequence
<220> FEATURE:
<223> OTHER INFORMATION: siRNA

<400> SEQUENCE: 369
aagucgggcc guuacgugut t                                             21

<210> SEQ ID NO 370
<211> LENGTH: 21
<212> TYPE: DNA
<213> ORGANISM: Artificial Sequence
<220> FEATURE:
<223> OTHER INFORMATION: siRNA

<400> SEQUENCE: 370
gucgggccgu uacgugugct t                                             21

<210> SEQ ID NO 371
<211> LENGTH: 21
<212> TYPE: DNA
<213> ORGANISM: Artificial Sequence
<220> FEATURE:
<223> OTHER INFORMATION: siRNA

<400> SEQUENCE: 371
caucagucac gagaccucat t                                             21

<210> SEQ ID NO 372
<211> LENGTH: 21
<212> TYPE: DNA
<213> ORGANISM: Artificial Sequence
<220> FEATURE:
<223> OTHER INFORMATION: siRNA
```

```
<400> SEQUENCE: 372
auaacuacgu aaauucuaut t                                              21

<210> SEQ ID NO 373
<211> LENGTH: 21
<212> TYPE: DNA
<213> ORGANISM: Artificial Sequence
<220> FEATURE:
<223> OTHER INFORMATION: siRNA

<400> SEQUENCE: 373
cuacguaaau ucuaucauct t                                              21

<210> SEQ ID NO 374
<211> LENGTH: 21
<212> TYPE: DNA
<213> ORGANISM: Artificial Sequence
<220> FEATURE:
<223> OTHER INFORMATION: siRNA

<400> SEQUENCE: 374
auuugacuuu ucugaugagt t                                              21

<210> SEQ ID NO 375
<211> LENGTH: 19
<212> TYPE: DNA
<213> ORGANISM: Artificial Sequence
<220> FEATURE:
<223> OTHER INFORMATION: siRNA

<400> SEQUENCE: 375
aacacuuucg uuaaaacuc                                                 19

<210> SEQ ID NO 376
<211> LENGTH: 21
<212> TYPE: DNA
<213> ORGANISM: Artificial Sequence
<220> FEATURE:
<223> OTHER INFORMATION: siRNA

<400> SEQUENCE: 376
caaccacacu guccauuuct t                                              21

<210> SEQ ID NO 377
<211> LENGTH: 21
<212> TYPE: DNA
<213> ORGANISM: Artificial Sequence
<220> FEATURE:
<223> OTHER INFORMATION: siRNA

<400> SEQUENCE: 377
ccacacuguc cauuucuuut t                                              21

<210> SEQ ID NO 378
<211> LENGTH: 21
<212> TYPE: DNA
<213> ORGANISM: Artificial Sequence
<220> FEATURE:
<223> OTHER INFORMATION: siRNA

<400> SEQUENCE: 378
ugagcacacc aaugacuuut t                                              21

<210> SEQ ID NO 379
```

```
<211> LENGTH: 21
<212> TYPE: DNA
<213> ORGANISM: Artificial Sequence
<220> FEATURE:
<223> OTHER INFORMATION: siRNA

<400> SEQUENCE: 379
ugacuuugcc cguacacat t                                              21

<210> SEQ ID NO 380
<211> LENGTH: 21
<212> TYPE: DNA
<213> ORGANISM: Artificial Sequence
<220> FEATURE:
<223> OTHER INFORMATION: siRNA

<400> SEQUENCE: 380
gccaucaagu uuucaacct t                                              21

<210> SEQ ID NO 381
<211> LENGTH: 21
<212> TYPE: DNA
<213> ORGANISM: Artificial Sequence
<220> FEATURE:
<223> OTHER INFORMATION: siRNA

<400> SEQUENCE: 381
guuuuucaac cacccugaat t                                             21

<210> SEQ ID NO 382
<211> LENGTH: 21
<212> TYPE: DNA
<213> ORGANISM: Artificial Sequence
<220> FEATURE:
<223> OTHER INFORMATION: siRNA

<400> SEQUENCE: 382
ccacccugaa agcaugguut t                                             21

<210> SEQ ID NO 383
<211> LENGTH: 19
<212> TYPE: DNA
<213> ORGANISM: Artificial Sequence
<220> FEATURE:
<223> OTHER INFORMATION: siRNA

<400> SEQUENCE: 383
uugcuguaag aaccauaac                                                19

<210> SEQ ID NO 384
<211> LENGTH: 21
<212> TYPE: DNA
<213> ORGANISM: Artificial Sequence
<220> FEATURE:
<223> OTHER INFORMATION: siRNA

<400> SEQUENCE: 384
gaaccauaac uuugaaugut t                                             21

<210> SEQ ID NO 385
<211> LENGTH: 21
<212> TYPE: DNA
<213> ORGANISM: Artificial Sequence
<220> FEATURE:
<223> OTHER INFORMATION: siRNA

<400> SEQUENCE: 385
```

```
cuuugaaugu cuauaaagut t                                        21

<210> SEQ ID NO 386
<211> LENGTH: 21
<212> TYPE: DNA
<213> ORGANISM: Artificial Sequence
<220> FEATURE:
<223> OTHER INFORMATION: siRNA

<400> SEQUENCE: 386
ugucuauaaa gugcauugt t                                         21

<210> SEQ ID NO 387
<211> LENGTH: 21
<212> TYPE: DNA
<213> ORGANISM: Artificial Sequence
<220> FEATURE:
<223> OTHER INFORMATION: siRNA

<400> SEQUENCE: 387 agugcauug gauaaccagt t                                         21

<210> SEQ ID NO 388
<211> LENGTH: 21
<212> TYPE: DNA
<213> ORGANISM: Artificial Sequence
<220> FEATURE:
<223> OTHER INFORMATION: siRNA

<400> SEQUENCE: 388
ccaggccaug cugcacuact t                                        21

<210> SEQ ID NO 389
<211> LENGTH: 21
<212> TYPE: DNA
<213> ORGANISM: Artificial Sequence
<220> FEATURE:
<223> OTHER INFORMATION: siRNA

<400> SEQUENCE: 389
cugcuguucc uuacuucuct t                                        21

<210> SEQ ID NO 390
<211> LENGTH: 21
<212> TYPE: DNA
<213> ORGANISM: Artificial Sequence
<220> FEATURE:
<223> OTHER INFORMATION: siRNA

<400> SEQUENCE: 390
uuuggucugg uucauugggt t                                        21

<210> SEQ ID NO 391
<211> LENGTH: 21
<212> TYPE: DNA
<213> ORGANISM: Artificial Sequence
<220> FEATURE:
<223> OTHER INFORMATION: siRNA

<400> SEQUENCE: 391
cucgaugacu gcgugcagat t                                        21

<210> SEQ ID NO 392
<211> LENGTH: 21
<212> TYPE: DNA
```

```
<213> ORGANISM: Artificial Sequence
<220> FEATURE:
<223> OTHER INFORMATION: siRNA

<400> SEQUENCE: 392
ucgggguaaa cugagugaut t                                               21

<210> SEQ ID NO 393
<211> LENGTH: 21
<212> TYPE: DNA
<213> ORGANISM: Artificial Sequence
<220> FEATURE:
<223> OTHER INFORMATION: siRNA

<400> SEQUENCE: 393
acugagugau cugguggcat t                                               21

<210> SEQ ID NO 394
<211> LENGTH: 21
<212> TYPE: DNA
<213> ORGANISM: Artificial Sequence
<220> FEATURE:
<223> OTHER INFORMATION: siRNA

<400> SEQUENCE: 394
ugacauccug aucaucaact t                                               21

<210> SEQ ID NO 395
<211> LENGTH: 21
<212> TYPE: DNA
<213> ORGANISM: Artificial Sequence
<220> FEATURE:
<223> OTHER INFORMATION: siRNA

<400> SEQUENCE: 395
cugugaguuc cucaacgaut t                                               21

<210> SEQ ID NO 396
<211> LENGTH: 21
<212> TYPE: DNA
<213> ORGANISM: Artificial Sequence
<220> FEATURE:
<223> OTHER INFORMATION: siRNA

<400> SEQUENCE: 396
cgaugugcuc acugaccact t                                               21

<210> SEQ ID NO 397
<211> LENGTH: 21
<212> TYPE: DNA
<213> ORGANISM: Artificial Sequence
<220> FEATURE:
<223> OTHER INFORMATION: siRNA

<400> SEQUENCE: 397
caggcucuuc cugccccuct t                                               21

<210> SEQ ID NO 398
<211> LENGTH: 21
<212> TYPE: DNA
<213> ORGANISM: Artificial Sequence
<220> FEATURE:
<223> OTHER INFORMATION: siRNA

<400> SEQUENCE: 398
gggaggagaa cggccgaaat t                                               21
```

<210> SEQ ID NO 399
<211> LENGTH: 21
<212> TYPE: DNA
<213> ORGANISM: Artificial Sequence
<220> FEATURE:
<223> OTHER INFORMATION: siRNA

<400> SEQUENCE: 399
cggccgaaaa uuagccugct t                                              21

<210> SEQ ID NO 400
<211> LENGTH: 21
<212> TYPE: DNA
<213> ORGANISM: Artificial Sequence
<220> FEATURE:
<223> OTHER INFORMATION: siRNA

<400> SEQUENCE: 400
aauuagccug ccgugucut t                                               21

<210> SEQ ID NO 401
<211> LENGTH: 21
<212> TYPE: DNA
<213> ORGANISM: Artificial Sequence
<220> FEATURE:
<223> OTHER INFORMATION: siRNA

<400> SEQUENCE: 401
uuauacauca ugcaccgcut t                                              21

<210> SEQ ID NO 402
<211> LENGTH: 21
<212> TYPE: DNA
<213> ORGANISM: Artificial Sequence
<220> FEATURE:
<223> OTHER INFORMATION: siRNA

<400> SEQUENCE: 402
cucguuagcu gaagucauut t                                              21

<210> SEQ ID NO 403
<211> LENGTH: 21
<212> TYPE: DNA
<213> ORGANISM: Artificial Sequence
<220> FEATURE:
<223> OTHER INFORMATION: siRNA

<400> SEQUENCE: 403
gucauucuga auggugauct t                                              21

<210> SEQ ID NO 404
<211> LENGTH: 21
<212> TYPE: DNA
<213> ORGANISM: Artificial Sequence
<220> FEATURE:
<223> OTHER INFORMATION: siRNA

<400> SEQUENCE: 404
uggugaucug ucugagaugt t                                              21

<210> SEQ ID NO 405
<211> LENGTH: 21
<212> TYPE: DNA
<213> ORGANISM: Artificial Sequence
<220> FEATURE:

<223> OTHER INFORMATION: siRNA

<400> SEQUENCE: 405
gacugaacag gauauucagt t					21

<210> SEQ ID NO 406
<211> LENGTH: 21
<212> TYPE: DNA
<213> ORGANISM: Artificial Sequence
<220> FEATURE:
<223> OTHER INFORMATION: siRNA

<400> SEQUENCE: 406
caggauauuc agagaaguut t					21

<210> SEQ ID NO 407
<211> LENGTH: 21
<212> TYPE: DNA
<213> ORGANISM: Artificial Sequence
<220> FEATURE:
<223> OTHER INFORMATION: siRNA

<400> SEQUENCE: 407
guucugccaa gcccagcaut t					21

<210> SEQ ID NO 408
<211> LENGTH: 21
<212> TYPE: DNA
<213> ORGANISM: Artificial Sequence
<220> FEATURE:
<223> OTHER INFORMATION: siRNA

<400> SEQUENCE: 408
gcccagcauu cggugcuuct t					21

<210> SEQ ID NO 409
<211> LENGTH: 21
<212> TYPE: DNA
<213> ORGANISM: Artificial Sequence
<220> FEATURE:
<223> OTHER INFORMATION: siRNA

<400> SEQUENCE: 409
acccaccgag acacucgagt t					21

<210> SEQ ID NO 410
<211> LENGTH: 21
<212> TYPE: DNA
<213> ORGANISM: Artificial Sequence
<220> FEATURE:
<223> OTHER INFORMATION: siRNA

<400> SEQUENCE: 410
caagcacaag ggcaagaggt t					21

<210> SEQ ID NO 411
<211> LENGTH: 21
<212> TYPE: DNA
<213> ORGANISM: Artificial Sequence
<220> FEATURE:
<223> OTHER INFORMATION: siRNA

<400> SEQUENCE: 411
gcacaagggc aagaggcggt t					21

```
<210> SEQ ID NO 412
<211> LENGTH: 21
<212> TYPE: DNA
<213> ORGANISM: Artificial Sequence
<220> FEATURE:
<223> OTHER INFORMATION: siRNA

<400> SEQUENCE: 412
gggcaagagg cgggugcaat t                                              21

<210> SEQ ID NO 413
<211> LENGTH: 21
<212> TYPE: DNA
<213> ORGANISM: Artificial Sequence
<220> FEATURE:
<223> OTHER INFORMATION: siRNA

<400> SEQUENCE: 413
gagacccaac uacaaaaact t                                              21

<210> SEQ ID NO 414
<211> LENGTH: 21
<212> TYPE: DNA
<213> ORGANISM: Artificial Sequence
<220> FEATURE:
<223> OTHER INFORMATION: siRNA

<400> SEQUENCE: 414
cuacaaaaac guuggggaat t                                              21

<210> SEQ ID NO 415
<211> LENGTH: 21
<212> TYPE: DNA
<213> ORGANISM: Artificial Sequence
<220> FEATURE:
<223> OTHER INFORMATION: siRNA

<400> SEQUENCE: 415
aaacguuggg gaagaagaat t                                              21

<210> SEQ ID NO 416
<211> LENGTH: 21
<212> TYPE: DNA
<213> ORGANISM: Artificial Sequence
<220> FEATURE:
<223> OTHER INFORMATION: siRNA

<400> SEQUENCE: 416
acguugggga agaagaagat t                                              21

<210> SEQ ID NO 417
<211> LENGTH: 21
<212> TYPE: DNA
<213> ORGANISM: Artificial Sequence
<220> FEATURE:
<223> OTHER INFORMATION: siRNA

<400> SEQUENCE: 417
gaugaggaga aagggcccat t                                              21

<210> SEQ ID NO 418
<211> LENGTH: 21
<212> TYPE: DNA
<213> ORGANISM: Artificial Sequence
<220> FEATURE:
<223> OTHER INFORMATION: siRNA
```

<400> SEQUENCE: 418
agggcccacc gaggaugcct t                                              21

<210> SEQ ID NO 419
<211> LENGTH: 21
<212> TYPE: DNA
<213> ORGANISM: Artificial Sequence
<220> FEATURE:
<223> OTHER INFORMATION: siRNA

<400> SEQUENCE: 419
gaagacgccg agaaggcuat t                                              21

<210> SEQ ID NO 420
<211> LENGTH: 21
<212> TYPE: DNA
<213> ORGANISM: Artificial Sequence
<220> FEATURE:
<223> OTHER INFORMATION: siRNA

<400> SEQUENCE: 420
gacgccgaga aggcuaaagt t                                              21

<210> SEQ ID NO 421
<211> LENGTH: 21
<212> TYPE: DNA
<213> ORGANISM: Artificial Sequence
<220> FEATURE:
<223> OTHER INFORMATION: siRNA

<400> SEQUENCE: 421
aaggcaucaa gacgaguggt t                                              21

<210> SEQ ID NO 422
<211> LENGTH: 21
<212> TYPE: DNA
<213> ORGANISM: Artificial Sequence
<220> FEATURE:
<223> OTHER INFORMATION: siRNA

<400> SEQUENCE: 422
ggcaucaaga cgaguggggt t                                              21

<210> SEQ ID NO 423
<211> LENGTH: 21
<212> TYPE: DNA
<213> ORGANISM: Artificial Sequence
<220> FEATURE:
<223> OTHER INFORMATION: siRNA

<400> SEQUENCE: 423
gacgaguggg gagagugaat t                                              21

<210> SEQ ID NO 424
<211> LENGTH: 21
<212> TYPE: DNA
<213> ORGANISM: Artificial Sequence
<220> FEATURE:
<223> OTHER INFORMATION: siRNA

<400> SEQUENCE: 424
gcucucagag cuggccgcct t                                              21

<210> SEQ ID NO 425
<211> LENGTH: 21

```
<212> TYPE: DNA
<213> ORGANISM: Artificial Sequence
<220> FEATURE:
<223> OTHER INFORMATION: siRNA

<400> SEQUENCE: 425
caccacggac gaggagaaat t                                               21

<210> SEQ ID NO 426
<211> LENGTH: 21
<212> TYPE: DNA
<213> ORGANISM: Artificial Sequence
<220> FEATURE:
<223> OTHER INFORMATION: siRNA

<400> SEQUENCE: 426
aagcgccgcc gccaccugct t                                               21

<210> SEQ ID NO 427
<211> LENGTH: 21
<212> TYPE: DNA
<213> ORGANISM: Artificial Sequence
<220> FEATURE:
<223> OTHER INFORMATION: siRNA

<400> SEQUENCE: 427
gcgccgccgc caccugcuct t                                               21

<210> SEQ ID NO 428
<211> LENGTH: 21
<212> TYPE: DNA
<213> ORGANISM: Artificial Sequence
<220> FEATURE:
<223> OTHER INFORMATION: siRNA

<400> SEQUENCE: 428
uaaaggcaug gauccugaat t                                               21

<210> SEQ ID NO 429
<211> LENGTH: 21
<212> TYPE: DNA
<213> ORGANISM: Artificial Sequence
<220> FEATURE:
<223> OTHER INFORMATION: siRNA

<400> SEQUENCE: 429
aggcauggau ccugaaaaat t                                               21

<210> SEQ ID NO 430
<211> LENGTH: 21
<212> TYPE: DNA
<213> ORGANISM: Artificial Sequence
<220> FEATURE:
<223> OTHER INFORMATION: siRNA

<400> SEQUENCE: 430
aaauuagagc gaauccagct t                                               21

<210> SEQ ID NO 431
<211> LENGTH: 21
<212> TYPE: DNA
<213> ORGANISM: Artificial Sequence
<220> FEATURE:
<223> OTHER INFORMATION: siRNA

<400> SEQUENCE: 431
```
auuagagcga auccagcuct t                                              21

<210> SEQ ID NO 432
<211> LENGTH: 21
<212> TYPE: DNA
<213> ORGANISM: Artificial Sequence
<220> FEATURE:
<223> OTHER INFORMATION: siRNA

<400> SEQUENCE: 432
uccagcuccc cgugccaaat t                                              21

<210> SEQ ID NO 433
<211> LENGTH: 21
<212> TYPE: DNA
<213> ORGANISM: Artificial Sequence
<220> FEATURE:
<223> OTHER INFORMATION: siRNA

<400> SEQUENCE: 433
augcggccga gaagaccact t                                              21

<210> SEQ ID NO 434
<211> LENGTH: 21
<212> TYPE: DNA
<213> ORGANISM: Artificial Sequence
<220> FEATURE:
<223> OTHER INFORMATION: siRNA

<400> SEQUENCE: 434
gaccaccuac aaccacccgt t                                              21

<210> SEQ ID NO 435
<211> LENGTH: 21
<212> TYPE: DNA
<213> ORGANISM: Artificial Sequence
<220> FEATURE:
<223> OTHER INFORMATION: siRNA

<400> SEQUENCE: 435
ccacccgcua gcugaaagat t                                              21

<210> SEQ ID NO 436
<211> LENGTH: 21
<212> TYPE: DNA
<213> ORGANISM: Artificial Sequence
<220> FEATURE:
<223> OTHER INFORMATION: siRNA

<400> SEQUENCE: 436
cgcugcccag ccagaugggt t                                              21

<210> SEQ ID NO 437
<211> LENGTH: 21
<212> TYPE: DNA
<213> ORGANISM: Artificial Sequence
<220> FEATURE:
<223> OTHER INFORMATION: siRNA

<400> SEQUENCE: 437
gauccggcug gcgacgcugt t                                              21

<210> SEQ ID NO 438
<211> LENGTH: 21
<212> TYPE: DNA
<213> ORGANISM: Artificial Sequence

```
<220> FEATURE:
<223> OTHER INFORMATION: siRNA

<400> SEQUENCE: 438
gcagcaaguc cugaugagut t                                              21

<210> SEQ ID NO 439
<211> LENGTH: 21
<212> TYPE: DNA
<213> ORGANISM: Artificial Sequence
<220> FEATURE:
<223> OTHER INFORMATION: siRNA

<400> SEQUENCE: 439
guccugauga gugcuggcut t                                              21

<210> SEQ ID NO 440
<211> LENGTH: 21
<212> TYPE: DNA
<213> ORGANISM: Artificial Sequence
<220> FEATURE:
<223> OTHER INFORMATION: siRNA

<400> SEQUENCE: 440
ggacgugcac cuggccugct t                                              21

<210> SEQ ID NO 441
<211> LENGTH: 21
<212> TYPE: DNA
<213> ORGANISM: Artificial Sequence
<220> FEATURE:
<223> OTHER INFORMATION: siRNA

<400> SEQUENCE: 441
gaaaguguuc accuuguact t                                              21

<210> SEQ ID NO 442
<211> LENGTH: 21
<212> TYPE: DNA
<213> ORGANISM: Artificial Sequence
<220> FEATURE:
<223> OTHER INFORMATION: siRNA

<400> SEQUENCE: 442
aguguucacc uuguacgact t                                              21

<210> SEQ ID NO 443
<211> LENGTH: 21
<212> TYPE: DNA
<213> ORGANISM: Artificial Sequence
<220> FEATURE:
<223> OTHER INFORMATION: siRNA

<400> SEQUENCE: 443
gggagaagac auuuuuugt t                                               21

<210> SEQ ID NO 444
<211> LENGTH: 21
<212> TYPE: DNA
<213> ORGANISM: Artificial Sequence
<220> FEATURE:
<223> OTHER INFORMATION: siRNA

<400> SEQUENCE: 444
gacauuuuuu uggacaugt t                                               21
```

<210> SEQ ID NO 445
<211> LENGTH: 21
<212> TYPE: DNA
<213> ORGANISM: Artificial Sequence
<220> FEATURE:
<223> OTHER INFORMATION: siRNA

<400> SEQUENCE: 445
gaugaguaua ggagcaugat t                                              21

<210> SEQ ID NO 446
<211> LENGTH: 21
<212> TYPE: DNA
<213> ORGANISM: Artificial Sequence
<220> FEATURE:
<223> OTHER INFORMATION: siRNA

<400> SEQUENCE: 446
gcccaugaac guggaauaut t                                              21

<210> SEQ ID NO 447
<211> LENGTH: 21
<212> TYPE: DNA
<213> ORGANISM: Artificial Sequence
<220> FEATURE:
<223> OTHER INFORMATION: siRNA

<400> SEQUENCE: 447
uaucucauga uggacgccut t                                              21

<210> SEQ ID NO 448
<211> LENGTH: 21
<212> TYPE: DNA
<213> ORGANISM: Artificial Sequence
<220> FEATURE:
<223> OTHER INFORMATION: siRNA

<400> SEQUENCE: 448
gacugaugau guccuggaut t                                              21

<210> SEQ ID NO 449
<211> LENGTH: 21
<212> TYPE: DNA
<213> ORGANISM: Artificial Sequence
<220> FEATURE:
<223> OTHER INFORMATION: siRNA

<400> SEQUENCE: 449
uaacagcgac uugauugcat t                                              21

<210> SEQ ID NO 450
<211> LENGTH: 21
<212> TYPE: DNA
<213> ORGANISM: Artificial Sequence
<220> FEATURE:
<223> OTHER INFORMATION: siRNA

<400> SEQUENCE: 450
cagcgacuug auugcaugut t                                              21

<210> SEQ ID NO 451
<211> LENGTH: 21
<212> TYPE: DNA
<213> ORGANISM: Artificial Sequence
<220> FEATURE:
<223> OTHER INFORMATION: siRNA

```
<400> SEQUENCE: 451
ggauggcggc augguccagt t                                              21

<210> SEQ ID NO 452
<211> LENGTH: 21
<212> TYPE: DNA
<213> ORGANISM: Artificial Sequence
<220> FEATURE:
<223> OTHER INFORMATION: siRNA

<400> SEQUENCE: 452
guuugcaggc cuauugcagt t                                              21

<210> SEQ ID NO 453
<211> LENGTH: 21
<212> TYPE: DNA
<213> ORGANISM: Artificial Sequence
<220> FEATURE:
<223> OTHER INFORMATION: siRNA

<400> SEQUENCE: 453
caucaccauc cacaagccut t                                              21

<210> SEQ ID NO 454
<211> LENGTH: 21
<212> TYPE: DNA
<213> ORGANISM: Artificial Sequence
<220> FEATURE:
<223> OTHER INFORMATION: siRNA

<400> SEQUENCE: 454
gccugcgucc agcccccaut t                                              21

<210> SEQ ID NO 455
<211> LENGTH: 21
<212> TYPE: DNA
<213> ORGANISM: Artificial Sequence
<220> FEATURE:
<223> OTHER INFORMATION: siRNA

<400> SEQUENCE: 455
gcccuucccc auccuccagt t                                              21

<210> SEQ ID NO 456
<211> LENGTH: 21
<212> TYPE: DNA
<213> ORGANISM: Artificial Sequence
<220> FEATURE:
<223> OTHER INFORMATION: siRNA

<400> SEQUENCE: 456
gcagcgccug gccaaaggct t                                              21

<210> SEQ ID NO 457
<211> LENGTH: 21
<212> TYPE: DNA
<213> ORGANISM: Artificial Sequence
<220> FEATURE:
<223> OTHER INFORMATION: siRNA

<400> SEQUENCE: 457
aggccgcauc caggcaaggt t                                              21

<210> SEQ ID NO 458
```

```
<211> LENGTH: 21
<212> TYPE: DNA
<213> ORGANISM: Artificial Sequence
<220> FEATURE:
<223> OTHER INFORMATION: siRNA

<400> SEQUENCE: 458
ggcgcaugaa gaugcagagt t                                              21

<210> SEQ ID NO 459
<211> LENGTH: 21
<212> TYPE: DNA
<213> ORGANISM: Artificial Sequence
<220> FEATURE:
<223> OTHER INFORMATION: siRNA

<400> SEQUENCE: 459
gaugcagaga auagcugcct t                                              21

<210> SEQ ID NO 460
<211> LENGTH: 21
<212> TYPE: DNA
<213> ORGANISM: Artificial Sequence
<220> FEATURE:
<223> OTHER INFORMATION: siRNA

<400> SEQUENCE: 460
uagcugcccu ccuggaccut t                                              21

<210> SEQ ID NO 461
<211> LENGTH: 21
<212> TYPE: DNA
<213> ORGANISM: Artificial Sequence
<220> FEATURE:
<223> OTHER INFORMATION: siRNA

<400> SEQUENCE: 461
uccagcccac cacugaagut t                                              21

<210> SEQ ID NO 462
<211> LENGTH: 21
<212> TYPE: DNA
<213> ORGANISM: Artificial Sequence
<220> FEATURE:
<223> OTHER INFORMATION: siRNA

<400> SEQUENCE: 462
guccuggggu uuggacucgt t                                              21

<210> SEQ ID NO 463
<211> LENGTH: 21
<212> TYPE: DNA
<213> ORGANISM: Artificial Sequence
<220> FEATURE:
<223> OTHER INFORMATION: siRNA

<400> SEQUENCE: 463
ggugccaggc uucgccgugt t                                              21

<210> SEQ ID NO 464
<211> LENGTH: 21
<212> TYPE: DNA
<213> ORGANISM: Artificial Sequence
<220> FEATURE:
<223> OTHER INFORMATION: siRNA

<400> SEQUENCE: 464
```
accagcacag cuccccguct t                                              21

<210> SEQ ID NO 465
<211> LENGTH: 21
<212> TYPE: DNA
<213> ORGANISM: Artificial Sequence
<220> FEATURE:
<223> OTHER INFORMATION: siRNA

<400> SEQUENCE: 465
cugccuaagc cucaccuuct t                                              21

<210> SEQ ID NO 466
<211> LENGTH: 21
<212> TYPE: DNA
<213> ORGANISM: Artificial Sequence
<220> FEATURE:
<223> OTHER INFORMATION: siRNA

<400> SEQUENCE: 466
gccucaccuu ccugaccagt t                                              21

<210> SEQ ID NO 467
<211> LENGTH: 21
<212> TYPE: DNA
<213> ORGANISM: Artificial Sequence
<220> FEATURE:
<223> OTHER INFORMATION: siRNA

<400> SEQUENCE: 467
gcagacucua agcccagcat t                                              21

<210> SEQ ID NO 468
<211> LENGTH: 21
<212> TYPE: DNA
<213> ORGANISM: Artificial Sequence
<220> FEATURE:
<223> OTHER INFORMATION: siRNA

<400> SEQUENCE: 468
gcccagcaag aacguggcct t                                              21

<210> SEQ ID NO 469
<211> LENGTH: 21
<212> TYPE: DNA
<213> ORGANISM: Artificial Sequence
<220> FEATURE:
<223> OTHER INFORMATION: siRNA

<400> SEQUENCE: 469
gaacguggcc aggagcgcat t                                              21

<210> SEQ ID NO 470
<211> LENGTH: 21
<212> TYPE: DNA
<213> ORGANISM: Artificial Sequence
<220> FEATURE:
<223> OTHER INFORMATION: siRNA

<400> SEQUENCE: 470
ucgcugaccc uugucccect t                                              21

<210> SEQ ID NO 471
<211> LENGTH: 21
<212> TYPE: DNA

```
<213> ORGANISM: Artificial Sequence
<220> FEATURE:
<223> OTHER INFORMATION: siRNA

<400> SEQUENCE: 471
gacacacugg gagcacccat t                                              21

<210> SEQ ID NO 472
<211> LENGTH: 21
<212> TYPE: DNA
<213> ORGANISM: Artificial Sequence
<220> FEATURE:
<223> OTHER INFORMATION: siRNA

<400> SEQUENCE: 472
ccaccuaucc cugcgcucct t                                              21

<210> SEQ ID NO 473
<211> LENGTH: 21
<212> TYPE: DNA
<213> ORGANISM: Artificial Sequence
<220> FEATURE:
<223> OTHER INFORMATION: siRNA

<400> SEQUENCE: 473
ugggaagaag ccccacguut t                                              21

<210> SEQ ID NO 474
<211> LENGTH: 21
<212> TYPE: DNA
<213> ORGANISM: Artificial Sequence
<220> FEATURE:
<223> OTHER INFORMATION: siRNA

<400> SEQUENCE: 474
gaagccccac guuguccuut t                                              21

<210> SEQ ID NO 475
<211> LENGTH: 21
<212> TYPE: DNA
<213> ORGANISM: Artificial Sequence
<220> FEATURE:
<223> OTHER INFORMATION: siRNA

<400> SEQUENCE: 475
uuccuuuuuc acuuugcaut t                                              21

<210> SEQ ID NO 476
<211> LENGTH: 21
<212> TYPE: DNA
<213> ORGANISM: Artificial Sequence
<220> FEATURE:
<223> OTHER INFORMATION: siRNA

<400> SEQUENCE: 476
ugcagaugac ugcaccggct t                                              21

<210> SEQ ID NO 477
<211> LENGTH: 21
<212> TYPE: DNA
<213> ORGANISM: Artificial Sequence
<220> FEATURE:
<223> OTHER INFORMATION: siRNA

<400> SEQUENCE: 477
gaauuggacc aggucacugt t                                              21
```

<210> SEQ ID NO 478
<211> LENGTH: 21
<212> TYPE: DNA
<213> ORGANISM: Artificial Sequence
<220> FEATURE:
<223> OTHER INFORMATION: siRNA

<400> SEQUENCE: 478
uuggaccagg ucacuguact t                                              21

<210> SEQ ID NO 479
<211> LENGTH: 21
<212> TYPE: DNA
<213> ORGANISM: Artificial Sequence
<220> FEATURE:
<223> OTHER INFORMATION: siRNA

<400> SEQUENCE: 479
auuuguagaa aagcagacut t                                              21

<210> SEQ ID NO 480
<211> LENGTH: 21
<212> TYPE: DNA
<213> ORGANISM: Artificial Sequence
<220> FEATURE:
<223> OTHER INFORMATION: siRNA

<400> SEQUENCE: 480
aagcagacuu agauaaacat t                                              21

<210> SEQ ID NO 481
<211> LENGTH: 21
<212> TYPE: DNA
<213> ORGANISM: Artificial Sequence
<220> FEATURE:
<223> OTHER INFORMATION: siRNA

<400> SEQUENCE: 481
aagaagucca aaaacaucat t                                              21

<210> SEQ ID NO 482
<211> LENGTH: 21
<212> TYPE: DNA
<213> ORGANISM: Artificial Sequence
<220> FEATURE:
<223> OTHER INFORMATION: siRNA

<400> SEQUENCE: 482
gaaguccaaa aacaucaact t                                              21

<210> SEQ ID NO 483
<211> LENGTH: 21
<212> TYPE: DNA
<213> ORGANISM: Artificial Sequence
<220> FEATURE:
<223> OTHER INFORMATION: siRNA

<400> SEQUENCE: 483
aaacaucaac acuaagguut t                                              21

<210> SEQ ID NO 484
<211> LENGTH: 21
<212> TYPE: DNA
<213> ORGANISM: Artificial Sequence
<220> FEATURE:

```
<223> OTHER INFORMATION: siRNA

<400> SEQUENCE: 484
acaucaacac uaagguuugt t                                              21

<210> SEQ ID NO 485
<211> LENGTH: 21
<212> TYPE: DNA
<213> ORGANISM: Artificial Sequence
<220> FEATURE:
<223> OTHER INFORMATION: siRNA

<400> SEQUENCE: 485
cacuaagguu ugaugucaut t                                              21

<210> SEQ ID NO 486
<211> LENGTH: 21
<212> TYPE: DNA
<213> ORGANISM: Artificial Sequence
<220> FEATURE:
<223> OTHER INFORMATION: siRNA

<400> SEQUENCE: 486
gugauucuuu guuacucact t                                              21

<210> SEQ ID NO 487
<211> LENGTH: 21
<212> TYPE: DNA
<213> ORGANISM: Artificial Sequence
<220> FEATURE:
<223> OTHER INFORMATION: siRNA

<400> SEQUENCE: 487
cucugcaagc cuguggaaut t                                              21

<210> SEQ ID NO 488
<211> LENGTH: 21
<212> TYPE: DNA
<213> ORGANISM: Artificial Sequence
<220> FEATURE:
<223> OTHER INFORMATION: siRNA

<400> SEQUENCE: 488
gccuguggaa uaaugaagut t                                              21

<210> SEQ ID NO 489
<211> LENGTH: 21
<212> TYPE: DNA
<213> ORGANISM: Artificial Sequence
<220> FEATURE:
<223> OTHER INFORMATION: siRNA

<400> SEQUENCE: 489
uaaugaagua ccuuccuggt t                                              21

<210> SEQ ID NO 490
<211> LENGTH: 21
<212> TYPE: DNA
<213> ORGANISM: Artificial Sequence
<220> FEATURE:
<223> OTHER INFORMATION: siRNA

<400> SEQUENCE: 490
ugaaguaccu uccuggaaat t                                              21
```

```
<210> SEQ ID NO 491
<211> LENGTH: 21
<212> TYPE: DNA
<213> ORGANISM: Artificial Sequence
<220> FEATURE:
<223> OTHER INFORMATION: siRNA

<400> SEQUENCE: 491
aguuuggauu auuuuuaat t                                              21

<210> SEQ ID NO 492
<211> LENGTH: 21
<212> TYPE: DNA
<213> ORGANISM: Artificial Sequence
<220> FEATURE:
<223> OTHER INFORMATION: siRNA

<400> SEQUENCE: 492
acaaaaacaa gggagauact t                                             21

<210> SEQ ID NO 493
<211> LENGTH: 21
<212> TYPE: DNA
<213> ORGANISM: Artificial Sequence
<220> FEATURE:
<223> OTHER INFORMATION: siRNA

<400> SEQUENCE: 493
aaacaaggga gauacaugut t                                             21

<210> SEQ ID NO 494
<211> LENGTH: 21
<212> TYPE: DNA
<213> ORGANISM: Artificial Sequence
<220> FEATURE:
<223> OTHER INFORMATION: siRNA

<400> SEQUENCE: 494
acaagggaga uacauguaut t                                             21

<210> SEQ ID NO 495
<211> LENGTH: 21
<212> TYPE: DNA
<213> ORGANISM: Artificial Sequence
<220> FEATURE:
<223> OTHER INFORMATION: siRNA

<400> SEQUENCE: 495
gggagauaca uguauucuct t                                             21

<210> SEQ ID NO 496
<211> LENGTH: 21
<212> TYPE: DNA
<213> ORGANISM: Artificial Sequence
<220> FEATURE:
<223> OTHER INFORMATION: siRNA

<400> SEQUENCE: 496
ugguuuucug cuauagcagt t                                             21

<210> SEQ ID NO 497
<211> LENGTH: 19
<212> TYPE: DNA
<213> ORGANISM: Artificial Sequence
<220> FEATURE:
<223> OTHER INFORMATION: siRNA
```

<400> SEQUENCE: 497
gaaggaacca guugggacc						19

<210> SEQ ID NO 498
<211> LENGTH: 21
<212> TYPE: DNA
<213> ORGANISM: Artificial Sequence
<220> FEATURE:
<223> OTHER INFORMATION: siRNA

<400> SEQUENCE: 498
ggaaccaguu gggaccgugt t						21

<210> SEQ ID NO 499
<211> LENGTH: 21
<212> TYPE: DNA
<213> ORGANISM: Artificial Sequence
<220> FEATURE:
<223> OTHER INFORMATION: siRNA

<400> SEQUENCE: 499
ccaguuggga ccgugaagat t						21

<210> SEQ ID NO 500
<211> LENGTH: 21
<212> TYPE: DNA
<213> ORGANISM: Artificial Sequence
<220> FEATURE:
<223> OTHER INFORMATION: siRNA

<400> SEQUENCE: 500
gacucccgac ccuguggcct t						21

<210> SEQ ID NO 501
<211> LENGTH: 21
<212> TYPE: DNA
<213> ORGANISM: Artificial Sequence
<220> FEATURE:
<223> OTHER INFORMATION: siRNA

<400> SEQUENCE: 501
aggaagacac ccucuacgut t						21

<210> SEQ ID NO 502
<211> LENGTH: 21
<212> TYPE: DNA
<213> ORGANISM: Artificial Sequence
<220> FEATURE:
<223> OTHER INFORMATION: siRNA

<400> SEQUENCE: 502
gacacccucu acgucaccut t						21

<210> SEQ ID NO 503
<211> LENGTH: 21
<212> TYPE: DNA
<213> ORGANISM: Artificial Sequence
<220> FEATURE:
<223> OTHER INFORMATION: siRNA

<400> SEQUENCE: 503
gggcauggug uccccagagt t						21

<210> SEQ ID NO 504
<211> LENGTH: 21

```
<212> TYPE: DNA
<213> ORGANISM: Artificial Sequence
<220> FEATURE:
<223> OTHER INFORMATION: siRNA

<400> SEQUENCE: 504
uauggaaacc ccaugguuct t                                              21

<210> SEQ ID NO 505
<211> LENGTH: 21
<212> TYPE: DNA
<213> ORGANISM: Artificial Sequence
<220> FEATURE:
<223> OTHER INFORMATION: siRNA

<400> SEQUENCE: 505
accccauggu ucccuuccct t                                              21

<210> SEQ ID NO 506
<211> LENGTH: 21
<212> TYPE: DNA
<213> ORGANISM: Artificial Sequence
<220> FEATURE:
<223> OTHER INFORMATION: siRNA

<400> SEQUENCE: 506
gcaaggaccc agaugcauct t                                              21

<210> SEQ ID NO 507
<211> LENGTH: 21
<212> TYPE: DNA
<213> ORGANISM: Artificial Sequence
<220> FEATURE:
<223> OTHER INFORMATION: siRNA

<400> SEQUENCE: 507
ggacccagau gcaucagact t                                              21

<210> SEQ ID NO 508
<211> LENGTH: 21
<212> TYPE: DNA
<213> ORGANISM: Artificial Sequence
<220> FEATURE:
<223> OTHER INFORMATION: siRNA

<400> SEQUENCE: 508
gauguuccuu ucuacucggt t                                              21

<210> SEQ ID NO 509
<211> LENGTH: 21
<212> TYPE: DNA
<213> ORGANISM: Artificial Sequence
<220> FEATURE:
<223> OTHER INFORMATION: siRNA

<400> SEQUENCE: 509
guccaccagg gccagcggct t                                              21

<210> SEQ ID NO 510
<211> LENGTH: 21
<212> TYPE: DNA
<213> ORGANISM: Artificial Sequence
<220> FEATURE:
<223> OTHER INFORMATION: siRNA

<400> SEQUENCE: 510
```
cuuuccucca gaccugccat t    21

<210> SEQ ID NO 511
<211> LENGTH: 21
<212> TYPE: DNA
<213> ORGANISM: Artificial Sequence
<220> FEATURE:
<223> OTHER INFORMATION: siRNA

<400> SEQUENCE: 511
gaacaugguc ucugucucct t    21

<210> SEQ ID NO 512
<211> LENGTH: 21
<212> TYPE: DNA
<213> ORGANISM: Artificial Sequence
<220> FEATURE:
<223> OTHER INFORMATION: siRNA

<400> SEQUENCE: 512 caugguucucu gucccucgt t    21

<210> SEQ ID NO 513
<211> LENGTH: 21
<212> TYPE: DNA
<213> ORGANISM: Artificial Sequence
<220> FEATURE:
<223> OTHER INFORMATION: siRNA

<400> SEQUENCE: 513
ggccugccga gggcaguuut t    21

<210> SEQ ID NO 514
<211> LENGTH: 21
<212> TYPE: DNA
<213> ORGANISM: Artificial Sequence
<220> FEATURE:
<223> OTHER INFORMATION: siRNA

<400> SEQUENCE: 514
ccucaugaag gaaacacagt t    21

<210> SEQ ID NO 515
<211> LENGTH: 21
<212> TYPE: DNA
<213> ORGANISM: Artificial Sequence
<220> FEATURE:
<223> OTHER INFORMATION: siRNA

<400> SEQUENCE: 515
ggaaacacag uccugccaat t    21

<210> SEQ ID NO 516
<211> LENGTH: 21
<212> TYPE: DNA
<213> ORGANISM: Artificial Sequence
<220> FEATURE:
<223> OTHER INFORMATION: siRNA

<400> SEQUENCE: 516
acacaguccu gccaaggagt t    21

<210> SEQ ID NO 517
<211> LENGTH: 21
<212> TYPE: DNA
<213> ORGANISM: Artificial Sequence -continued

```
<220> FEATURE:
<223> OTHER INFORMATION: siRNA

<400> SEQUENCE: 517 ggaggggag uggcgcccat t                                            21

<210> SEQ ID NO 518
<211> LENGTH: 21
<212> TYPE: DNA
<213> ORGANISM: Artificial Sequence
<220> FEATURE:
<223> OTHER INFORMATION: siRNA

<400> SEQUENCE: 518
gcccucuggg uagcugugct t                                           21

<210> SEQ ID NO 519
<211> LENGTH: 21
<212> TYPE: DNA
<213> ORGANISM: Artificial Sequence
<220> FEATURE:
<223> OTHER INFORMATION: siRNA

<400> SEQUENCE: 519
ggaccuuugc uuccauagat t                                           21

<210> SEQ ID NO 520
<211> LENGTH: 21
<212> TYPE: DNA
<213> ORGANISM: Artificial Sequence
<220> FEATURE:
<223> OTHER INFORMATION: siRNA

<400> SEQUENCE: 520
aacgcacagc ucagaaaggt t                                           21

<210> SEQ ID NO 521
<211> LENGTH: 21
<212> TYPE: DNA
<213> ORGANISM: Artificial Sequence
<220> FEATURE:
<223> OTHER INFORMATION: siRNA

<400> SEQUENCE: 521
ucccuggaag agaaggaagt t                                           21

<210> SEQ ID NO 522
<211> LENGTH: 21
<212> TYPE: DNA
<213> ORGANISM: Artificial Sequence
<220> FEATURE:
<223> OTHER INFORMATION: siRNA

<400> SEQUENCE: 522
gagaaggaag gcaggguggt t                                           21

<210> SEQ ID NO 523
<211> LENGTH: 21
<212> TYPE: DNA
<213> ORGANISM: Artificial Sequence
<220> FEATURE:
<223> OTHER INFORMATION: siRNA

<400> SEQUENCE: 523
ggaaggcagg guggagcggt t                                           21
```

<210> SEQ ID NO 524
<211> LENGTH: 21
<212> TYPE: DNA
<213> ORGANISM: Artificial Sequence
<220> FEATURE:
<223> OTHER INFORMATION: siRNA

<400> SEQUENCE: 524
ggcagggugg agcgggggt t                                              21

<210> SEQ ID NO 525
<211> LENGTH: 21
<212> TYPE: DNA
<213> ORGANISM: Artificial Sequence
<220> FEATURE:
<223> OTHER INFORMATION: siRNA

<400> SEQUENCE: 525
gaccaucaug gagagaaggt t                                             21

<210> SEQ ID NO 526
<211> LENGTH: 21
<212> TYPE: DNA
<213> ORGANISM: Artificial Sequence
<220> FEATURE:
<223> OTHER INFORMATION: siRNA

<400> SEQUENCE: 526
ggaccacagc aucaggagat t                                             21

<210> SEQ ID NO 527
<211> LENGTH: 21
<212> TYPE: DNA
<213> ORGANISM: Artificial Sequence
<220> FEATURE:
<223> OTHER INFORMATION: siRNA

<400> SEQUENCE: 527
uuuuuuaaga gcaagagggt t                                             21

<210> SEQ ID NO 528
<211> LENGTH: 21
<212> TYPE: DNA
<213> ORGANISM: Artificial Sequence
<220> FEATURE:
<223> OTHER INFORMATION: siRNA

<400> SEQUENCE: 528
gagcaagagg gguagagagt t                                             21

<210> SEQ ID NO 529
<211> LENGTH: 21
<212> TYPE: DNA
<213> ORGANISM: Artificial Sequence
<220> FEATURE:
<223> OTHER INFORMATION: siRNA

<400> SEQUENCE: 529
gagggguaga gaggaucaat t                                             21

<210> SEQ ID NO 530
<211> LENGTH: 21
<212> TYPE: DNA
<213> ORGANISM: Artificial Sequence
<220> FEATURE:
<223> OTHER INFORMATION: siRNA

```
<400> SEQUENCE: 530
gcuggcccug gcuggagaut t                                              21

<210> SEQ ID NO 531
<211> LENGTH: 21
<212> TYPE: DNA
<213> ORGANISM: Artificial Sequence
<220> FEATURE:
<223> OTHER INFORMATION: siRNA

<400> SEQUENCE: 531
augacucugu cuguggggct t                                              21

<210> SEQ ID NO 532
<211> LENGTH: 21
<212> TYPE: DNA
<213> ORGANISM: Artificial Sequence
<220> FEATURE:
<223> OTHER INFORMATION: siRNA

<400> SEQUENCE: 532 ggcaagug gc ugccccacct t                                             21

<210> SEQ ID NO 533
<211> LENGTH: 21
<212> TYPE: DNA
<213> ORGANISM: Artificial Sequence
<220> FEATURE:
<223> OTHER INFORMATION: siRNA

<400> SEQUENCE: 533
guggcugccc caccccaagt t                                              21

<210> SEQ ID NO 534
<211> LENGTH: 21
<212> TYPE: DNA
<213> ORGANISM: Artificial Sequence
<220> FEATURE:
<223> OTHER INFORMATION: siRNA

<400> SEQUENCE: 534
cagccugcag cucacuccat t                                              21

<210> SEQ ID NO 535
<211> LENGTH: 21
<212> TYPE: DNA
<213> ORGANISM: Artificial Sequence
<220> FEATURE:
<223> OTHER INFORMATION: siRNA

<400> SEQUENCE: 535
gucucugggc uccaacuggt t                                              21

<210> SEQ ID NO 536
<211> LENGTH: 21
<212> TYPE: DNA
<213> ORGANISM: Artificial Sequence
<220> FEATURE:
<223> OTHER INFORMATION: siRNA

<400> SEQUENCE: 536
cuggucuugu aaccacugat t                                              21

<210> SEQ ID NO 537
```

```
<211> LENGTH: 21
<212> TYPE: DNA
<213> ORGANISM: Artificial Sequence
<220> FEATURE:
<223> OTHER INFORMATION: siRNA

<400> SEQUENCE: 537
ccacugagca cugaaggagt t                                              21

<210> SEQ ID NO 538
<211> LENGTH: 21
<212> TYPE: DNA
<213> ORGANISM: Artificial Sequence
<220> FEATURE:
<223> OTHER INFORMATION: siRNA

<400> SEQUENCE: 538
ggagagaggu cuuggucagt t                                              21

<210> SEQ ID NO 539
<211> LENGTH: 21
<212> TYPE: DNA
<213> ORGANISM: Artificial Sequence
<220> FEATURE:
<223> OTHER INFORMATION: siRNA

<400> SEQUENCE: 539
aggugacugg gaggaccagt t                                              21

<210> SEQ ID NO 540
<211> LENGTH: 21
<212> TYPE: DNA
<213> ORGANISM: Artificial Sequence
<220> FEATURE:
<223> OTHER INFORMATION: siRNA

<400> SEQUENCE: 540
aagacacugc ucagggcagt t                                              21

<210> SEQ ID NO 541
<211> LENGTH: 21
<212> TYPE: DNA
<213> ORGANISM: Artificial Sequence
<220> FEATURE:
<223> OTHER INFORMATION: siRNA

<400> SEQUENCE: 541
gacacugcuc agggcagggt t                                              21

<210> SEQ ID NO 542
<211> LENGTH: 21
<212> TYPE: DNA
<213> ORGANISM: Artificial Sequence
<220> FEATURE:
<223> OTHER INFORMATION: siRNA

<400> SEQUENCE: 542
gaaaagggca guccccaugt t                                              21

<210> SEQ ID NO 543
<211> LENGTH: 21
<212> TYPE: DNA
<213> ORGANISM: Artificial Sequence
<220> FEATURE:
<223> OTHER INFORMATION: siRNA

<400> SEQUENCE: 543
```
aagggcaguc cccauguggt t 21

<210> SEQ ID NO 544
<211> LENGTH: 21
<212> TYPE: DNA
<213> ORGANISM: Artificial Sequence
<220> FEATURE:
<223> OTHER INFORMATION: siRNA

<400> SEQUENCE: 544
gggcaguccc caugugggct t 21

<210> SEQ ID NO 545
<211> LENGTH: 21
<212> TYPE: DNA
<213> ORGANISM: Artificial Sequence
<220> FEATURE:
<223> OTHER INFORMATION: siRNA

<400> SEQUENCE: 545
cuugcgucug ggggacacct t 21

<210> SEQ ID NO 546
<211> LENGTH: 21
<212> TYPE: DNA
<213> ORGANISM: Artificial Sequence
<220> FEATURE:
<223> OTHER INFORMATION: siRNA

<400> SEQUENCE: 546
ccagggcucc cagaagcuut t 21

<210> SEQ ID NO 547
<211> LENGTH: 21
<212> TYPE: DNA
<213> ORGANISM: Artificial Sequence
<220> FEATURE:
<223> OTHER INFORMATION: siRNA

<400> SEQUENCE: 547
ggaggucugg gagccagcct t 21

<210> SEQ ID NO 548
<211> LENGTH: 21
<212> TYPE: DNA
<213> ORGANISM: Artificial Sequence
<220> FEATURE:
<223> OTHER INFORMATION: siRNA

<400> SEQUENCE: 548
aggacccacc cucacccagt t 21

<210> SEQ ID NO 549
<211> LENGTH: 21
<212> TYPE: DNA
<213> ORGANISM: Artificial Sequence
<220> FEATURE:
<223> OTHER INFORMATION: siRNA

<400> SEQUENCE: 549
accucauagc uggggcgcut t 21

<210> SEQ ID NO 550
<211> LENGTH: 21
<212> TYPE: DNA

```
<213> ORGANISM: Artificial Sequence
<220> FEATURE:
<223> OTHER INFORMATION: siRNA

<400> SEQUENCE: 550
gagccaggag ugugggaagt t                                              21

<210> SEQ ID NO 551
<211> LENGTH: 21
<212> TYPE: DNA
<213> ORGANISM: Artificial Sequence
<220> FEATURE:
<223> OTHER INFORMATION: siRNA

<400> SEQUENCE: 551
ggcccacagu gggggcugut t                                              21

<210> SEQ ID NO 552
<211> LENGTH: 21
<212> TYPE: DNA
<213> ORGANISM: Artificial Sequence
<220> FEATURE:
<223> OTHER INFORMATION: siRNA

<400> SEQUENCE: 552
gucccugcag agagcacuut t                                              21

<210> SEQ ID NO 553
<211> LENGTH: 21
<212> TYPE: DNA
<213> ORGANISM: Artificial Sequence
<220> FEATURE:
<223> OTHER INFORMATION: siRNA

<400> SEQUENCE: 553
cucccaaacc uuggcuuugt t                                              21

<210> SEQ ID NO 554
<211> LENGTH: 21
<212> TYPE: DNA
<213> ORGANISM: Artificial Sequence
<220> FEATURE:
<223> OTHER INFORMATION: siRNA

<400> SEQUENCE: 554
uauuguugug gaggugugct t                                              21

<210> SEQ ID NO 555
<211> LENGTH: 21
<212> TYPE: DNA
<213> ORGANISM: Artificial Sequence
<220> FEATURE:
<223> OTHER INFORMATION: siRNA

<400> SEQUENCE: 555
gguaccuguc ccagcaggut t                                              21

<210> SEQ ID NO 556
<211> LENGTH: 21
<212> TYPE: DNA
<213> ORGANISM: Artificial Sequence
<220> FEATURE:
<223> OTHER INFORMATION: siRNA

<400> SEQUENCE: 556
cccagacacu ugcguucact t                                              21
```

<210> SEQ ID NO 557
<211> LENGTH: 21
<212> TYPE: DNA
<213> ORGANISM: Artificial Sequence
<220> FEATURE:
<223> OTHER INFORMATION: siRNA

<400> SEQUENCE: 557
gcaaccuaag gggcaggugt t                                              21

<210> SEQ ID NO 558
<211> LENGTH: 19
<212> TYPE: DNA
<213> ORGANISM: Artificial Sequence
<220> FEATURE:
<223> OTHER INFORMATION: siRNA

<400> SEQUENCE: 558
ccuaaggggc aggugaaga                                                 19

<210> SEQ ID NO 559
<211> LENGTH: 21
<212> TYPE: DNA
<213> ORGANISM: Artificial Sequence
<220> FEATURE:
<223> OTHER INFORMATION: siRNA

<400> SEQUENCE: 559
ggggcaggug aagaagcgct t                                              21

<210> SEQ ID NO 560
<211> LENGTH: 21
<212> TYPE: DNA
<213> ORGANISM: Artificial Sequence
<220> FEATURE:
<223> OTHER INFORMATION: siRNA

<400> SEQUENCE: 560
gaagcgcagc ccugccagat t                                              21

<210> SEQ ID NO 561
<211> LENGTH: 21
<212> TYPE: DNA
<213> ORGANISM: Artificial Sequence
<220> FEATURE:
<223> OTHER INFORMATION: siRNA

<400> SEQUENCE: 561
gcgcagcccu gccagacgct t                                              21

<210> SEQ ID NO 562
<211> LENGTH: 21
<212> TYPE: DNA
<213> ORGANISM: Artificial Sequence
<220> FEATURE:
<223> OTHER INFORMATION: siRNA

<400> SEQUENCE: 562
ggucucugag augcaccgut t                                              21

<210> SEQ ID NO 563
<211> LENGTH: 21
<212> TYPE: DNA
<213> ORGANISM: Artificial Sequence
<220> FEATURE:

<223> OTHER INFORMATION: siRNA

<400> SEQUENCE: 563
aaaggcgugg ggugaacugt t                                          21

<210> SEQ ID NO 564
<211> LENGTH: 21
<212> TYPE: DNA
<213> ORGANISM: Artificial Sequence
<220> FEATURE:
<223> OTHER INFORMATION: siRNA

<400> SEQUENCE: 564
aggcgugggg ugaacugaut t                                          21

<210> SEQ ID NO 565
<211> LENGTH: 21
<212> TYPE: DNA
<213> ORGANISM: Artificial Sequence
<220> FEATURE:
<223> OTHER INFORMATION: siRNA

<400> SEQUENCE: 565
cugauuuuga ucuucuugut t                                          21

<210> SEQ ID NO 566
<211> LENGTH: 21
<212> TYPE: DNA
<213> ORGANISM: Artificial Sequence
<220> FEATURE:
<223> OTHER INFORMATION: siRNA

<400> SEQUENCE: 566
uaaauaaauc ugaagcauut t                                          21

<210> SEQ ID NO 567
<211> LENGTH: 21
<212> TYPE: DNA
<213> ORGANISM: Artificial Sequence
<220> FEATURE:
<223> OTHER INFORMATION: siRNA

<400> SEQUENCE: 567
aucugaagca uuuaauguat t                                          21

<210> SEQ ID NO 568
<211> LENGTH: 21
<212> TYPE: DNA
<213> ORGANISM: Artificial Sequence
<220> FEATURE:
<223> OTHER INFORMATION: siRNA

<400> SEQUENCE: 568
gcauuuaaug uagucaucut t                                          21

<210> SEQ ID NO 569
<211> LENGTH: 21
<212> TYPE: DNA
<213> ORGANISM: Artificial Sequence
<220> FEATURE:
<223> OTHER INFORMATION: siRNA

<400> SEQUENCE: 569
uguagucauc uugacauugt t                                          21

```
<210> SEQ ID NO 570
<211> LENGTH: 21
<212> TYPE: DNA
<213> ORGANISM: Artificial Sequence
<220> FEATURE:
<223> OTHER INFORMATION: siRNA

<400> SEQUENCE: 570
aaauauguaa auaauuuuut t                                              21

<210> SEQ ID NO 571
<211> LENGTH: 21
<212> TYPE: DNA
<213> ORGANISM: Artificial Sequence
<220> FEATURE:
<223> OTHER INFORMATION: siRNA

<400> SEQUENCE: 571
auauguaaau aauuuugut t                                               21

<210> SEQ ID NO 572
<211> LENGTH: 21
<212> TYPE: DNA
<213> ORGANISM: Artificial Sequence
<220> FEATURE:
<223> OTHER INFORMATION: siRNA

<400> SEQUENCE: 572
auaauuuuug ucccagugat t                                              21

<210> SEQ ID NO 573
<211> LENGTH: 21
<212> TYPE: DNA
<213> ORGANISM: Artificial Sequence
<220> FEATURE:
<223> OTHER INFORMATION: siRNA

<400> SEQUENCE: 573
uuuuuguccc agugagaact t                                              21

<210> SEQ ID NO 574
<211> LENGTH: 21
<212> TYPE: DNA
<213> ORGANISM: Artificial Sequence
<220> FEATURE:
<223> OTHER INFORMATION: siRNA

<400> SEQUENCE: 574
ccgaggguua gaaaaccuct t                                              21

<210> SEQ ID NO 575
<211> LENGTH: 21
<212> TYPE: DNA
<213> ORGANISM: Artificial Sequence
<220> FEATURE:
<223> OTHER INFORMATION: siRNA

<400> SEQUENCE: 575
aaccucgaug ccucugagct t                                              21

<210> SEQ ID NO 576
<211> LENGTH: 21
<212> TYPE: DNA
<213> ORGANISM: Artificial Sequence
<220> FEATURE:
<223> OTHER INFORMATION: siRNA
```

```
<400> SEQUENCE: 576
ccucgaugcc ucugagccut t                                              21

<210> SEQ ID NO 577
<211> LENGTH: 21
<212> TYPE: DNA
<213> ORGANISM: Artificial Sequence
<220> FEATURE:
<223> OTHER INFORMATION: siRNA

<400> SEQUENCE: 577
guaccugcuu ucgccagcat t                                              21

<210> SEQ ID NO 578
<211> LENGTH: 21
<212> TYPE: DNA
<213> ORGANISM: Artificial Sequence
<220> FEATURE:
<223> OTHER INFORMATION: siRNA

<400> SEQUENCE: 578
cacgagggug gaaaugaaat t                                              21

<210> SEQ ID NO 579
<211> LENGTH: 21
<212> TYPE: DNA
<213> ORGANISM: Artificial Sequence
<220> FEATURE:
<223> OTHER INFORMATION: siRNA

<400> SEQUENCE: 579
augaaaacug gaacuuccut t                                              21

<210> SEQ ID NO 580
<211> LENGTH: 21
<212> TYPE: DNA
<213> ORGANISM: Artificial Sequence
<220> FEATURE:
<223> OTHER INFORMATION: siRNA

<400> SEQUENCE: 580
aacuggaacu uccuuguaat t                                              21

<210> SEQ ID NO 581
<211> LENGTH: 21
<212> TYPE: DNA
<213> ORGANISM: Artificial Sequence
<220> FEATURE:
<223> OTHER INFORMATION: siRNA

<400> SEQUENCE: 581
cuggaacuuc cuuguaaaut t                                              21

<210> SEQ ID NO 582
<211> LENGTH: 21
<212> TYPE: DNA
<213> ORGANISM: Artificial Sequence
<220> FEATURE:
<223> OTHER INFORMATION: siRNA

<400> SEQUENCE: 582
cuuccuugua aauuuaaact t                                              21

<210> SEQ ID NO 583
<211> LENGTH: 6786
```

```
<212> TYPE: DNA
<213> ORGANISM: Homo sapiens

<400> SEQUENCE: 583
gaggaaggcg gctcgcggtt cctccaccgc ctccgccgcc gcatcctccg cttgtgctac      60
cgccgcgggc gctgggccgc tctgctggtc cggcatgaga ccgtgagacg agagacgggt     120
cggggccgcc gacatgtttg ccgctcgcg  gagctgggtg ggcgggggcc atggcaagac     180
ttcccgcaac atccactcct tggaccacct caagtatctg taccacgttt tgaccaaaaa     240
caccacagtc acagaacaga accggaacct gctagtggag accatccgtt ccatcactga     300
gatcctgatc tggggagatc aaaatgacag ctctgtattt gacttcttcc tggagaagaa     360
tatgtttgtt ttcttcttga acatcttgcg gcaaaagtcg ggccgttacg tgtgcgttca     420
gctgctgcag accttgaaca tcctctttga gaacatcagt cacgagacct cactttatta     480
tttgctctca ataactacg  taaattctat catcgttcat aaatttgact tttctgatga     540
ggagattatg gcctattata tatcgttcct gaaaacactt tcgttaaaac tcaacaacca     600
cactgtccat ttcttttata tgagcacac  caatgacttt gccctgtaca cagaagccat     660
caagttttc  aaccaccctg aaagcatggt tagaattgct gtaagaacca taactttgaa     720
tgtctataaa gtgtcattgg ataaccaggc catgctgcac tacatccgag ataaaactgc     780
tgttccttac ttctccaatt tggtctggtt cattgggagc catgtgatcg aactcgatga     840
ctgcgtgcag actgatgagg agcatcggaa tcggggtaaa ctgagtgatc tggtggcaga     900
gcacctagac cacctgcact atctcaatga catcctgatc atcaactgtg agttcctcaa     960
cgatgtgctc actgaccacc tgctcaacag gctcttcctg cccctctacg tgtactcact    1020
ggagaaccag gacaagggag gagaacggcc gaaaattagc ctgccggtgt ctctttatct    1080
tctgtcacag gtcttcttaa ttatacatca tgcaccgctg gtgaactcgt tagctgaagt    1140
cattctgaat ggtgatctgt ctgagatgta cgctaagact gaacaggata ttcagagaag    1200
ttctgccaag cccagcattc ggtgcttcat taaacccacc gagacactcg agcggtccct    1260
tgagatgaac aagcacaagg gcaagaggcg ggtgcaaaag agacccaact acaaaaacgt    1320
tggggaagaa gaagatgagg agaaagggcc caccgaggat gcccaagaag acgccgagaa    1380
ggctaaaggt acagagggtg gttcaaaagg catcaagacg agtggggaga gtgaagagat    1440
cgagatggtg atcatggagc gtagcaagct ctcagagctg gccgccagca cctccgtgca    1500
ggagcagaac accacggacg aggagaaaag cgccgccgcc acctgctctg agagcacgca    1560
atggagcaga cccttcctgg atatggtgta ccacgcgctg gacagcccgg atgatgatta    1620
ccatgccctg ttcgtgctct gcctcctcta tgccatgtct cataataaag gcatggatcc    1680
tgaaaaatta gagcgaatcc agctccccgt gccaaatgcg gccgagaaga ccacctacaa    1740
ccacccgcta gctgaaagac tcatcaggat catgaacaac gctgcccagc cagatgggaa    1800
gatccggctg gcgacgctgg agctgagctg cctgcttctg aagcagcaag tcctgatgag    1860
tgctggctgc atcatgaagg acgtgcacct ggcctgcctg gagggtgcga gagaagaaag    1920
tgttcacctt gtacgacatt tttataaggg agaagacatt ttttggaca  tgtttgaaga    1980
tgagtatagg agcatgacaa tgaagcccat gaacgtggaa tatctcatga tggacgcctc    2040
catcctgctg cccccaacag gcacgccact gacgggcatt gacttcgtga agcggctgcc    2100
gtgtggcgat gtgagaagaa cccggcggc  catccggggt tcttcatgc  tgcgttccct    2160
gtcactgcaa ttgcgagggg agcctgagac acagttgccg ctgactcggg aggaggacct    2220
```

```
gatcaagact gatgatgtcc tggatctgaa taacagcgac ttgattgcat gtacagtgat    2280
caccaaggat ggcggcatgg tccagcgatt cctggctgtg gatatttacc agatgagttt    2340
ggtggagcct gatgtgtcca ggcttggctg gggagtggtc aagtttgcag gcctattgca    2400
ggacatgcag gtgactggcg tggaggacga cagccgtgcc ctgaacatca ccatccacaa    2460
gcctgcgtcc agcccccatt ccaagccctt ccccatcctc caggccacct tcatcttctc    2520
agaccacatc cgctgcatca tcgccaagca gcgcctggcc aaaggccgca tccaggcaag    2580
gcgcatgaag atgcagagaa tagctgccct cctggacctc ccaatccagc ccaccactga    2640
agtcctgggg tttggactcg gctcctccac ctccactcag cacctgcctt ccgcttcta    2700 cgaccagggg cgccggggca gcagcgaccc cacagtgcag cgctccgtgt ttgcatcggt    2760
ggacaaggtg ccaggcttcg ccgtggccca gtgcataaac cagcacagct ccccgtccct    2820
gtcctcacag tcgccaccct ccgccagcgg gagcccagc ggcagcggga gcaccagcca    2880
ctgcgactct ggaggcacca gctcgtcctc cacccctcc acagcccaga gtccagcaga    2940
tgcccccatg agtccagaac tgcctaagcc tcaccttcct gaccagttgg taatcgtcaa    3000
cgaaacggaa gcagactcta agcccagcaa gaacgtggcc aggagcgcag ccgtggagac    3060
agccagcctg tccccagcc tcgtccctgc ccggcagccc accatttccc tgctctgcga    3120
ggacacggct gacacgctga gcgtcgaatc gctgacccct gtcccccag ttgaccccca    3180 cagcctccgc agcctcaccg gcatgccccc gctgtccacg ccggctgccg cctgcacaga    3240
gcccgtgggc gaagaggctg catgtgctga gcctgtgggc accgctgagg actgagtcag    3300
tgccggggcc tcccttttgtg tgtgtggccc cgctggtagg acccagtg ccgctgactg    3360 gcaagacaca ctgggagcac ccaccattct gtgcggcccc cagcagccat ctcaaccacc    3420
tatccctgcg ctcccttgaa tgggaagaag cccacgttg tccttgaatt cctttttcac    3480
tttgcatctc ttcacgtgca ggctgggacc agcggagaca ccgcggcgaa tgcagatgac    3540
tgcaccggcc actcagggag ctgcctgggc tccgtgtctc tgagccccgg gtggcaggac    3600
ccaccggcac ctcttcttc ctctgtcata tggctcctct gtcaccagcc cagtgtgca    3660 cagaagaatt ggaccaggtc actgtacgta gaaatttgta gaaagcaga cttagataaa    3720 catctccttt ggatatttat ttccgctttt ggcagcaggt gaacatttat ttttaaaact    3780
tctatttaaa agaagtccaa aaacatcaac actaaggttt gatgtcatgt gaaaagtgta    3840
ataataacag ttaagatttc atgatcattt tcactggacc tttcctgata ttttgtttca    3900
gagttcttag tgtggctttt tccatttatt taagtgattc tttgttactc actaactctg    3960
caagcctgtg gaataatgaa gtaccttcct ggaaagtttg gattatttt taaacaaaaa    4020 caagggagat acatgtattc tcaggtacac acagagctga gagggctgaa tggttttctg    4080
ctatagcagc cgagaggcct cccatcatgg aaagattcct ccaggaaaag gaggaatgta    4140
gccagctccc cactcaggac gcttcctcat ttctcttcac caaaaccaaa cagagacagc    4200
ttccagcacc ttcttcagtg ttaccatctc taagaaggaa ccagttggga ccgtgaagac    4260
tcccgaccct gtggccatga tggaaatcaa aggaagacac cctctacgtc acctgccctc    4320
gactgtgtgt gccacatgt gccgagagat ggcccgagc cagttcccct ccagctgcaa    4380
gggcatggtg tccccagagc tctgagtctg tcactctccc tctgctactg ctgctgatct    4440
gaatatggaa accccatggt tcccttcccc attcggactg ggtgtgtaca agcaaggacc    4500
cagatgcatc agacacagcc cccaagatgt tcctttctac tcggcagct cgggagccag    4560 acacagcact cacagcccag gccgtgatcc accctcccca agtccaccag gccagcggc    4620
```

```
cccctcacctc tctggtcact ggtgagacct tccacaactt tcctccagac ctgccagcag    4680
atgtgcccac caggggcatt aggtatccgc cggagcctgg ccatagggta gtctcgggag    4740
ccgcgctgag atcttttgcc acctgcattt tagaagaaca tggtctctgt ctcctcggcc    4800
cagccagctg tcccggcaag gcctgccgag ggcagttttc aacctcatga aggaaacaca    4860
gtcctgccaa ggaggggggag tggcgcccat ggggacaggc ctcagtcctt agaagccctc    4920
tgggtagctg tgcccaccca gccttcatgg ctgcaggtac aaggacctt gcttccatag     4980 agaaaacgca cagctcagaa agggggccac atgggcagaa acccaaagga aggacaaacc    5040
acgaccaccg tggccatctg cagaatccct ggaagagaag gaaggcaggg tggagcgggg    5100
ggaagaccat catggagaga aggaccacag catcaggaga cgggacacgc cacacccagc    5160
aggcagcctg tgtgttgctt aattttttaa gagcaagagg ggtagagagg atcaagctgg    5220
ccctggctgg agatggctag cccctgagac atgcacttct ggttttgaaa tgactctgtc    5280
tgtggggcag cagaaactag agaaggcaag tggctgcccc accccaaggc gtgaccagga    5340
ggaacagcct gcagctcact ccatgccaca cgggtgggcc accagcctgc tgtcagaagt    5400
ctctgggctc caactggtct tgtaaccact gagcactgaa ggagagaggt cttggtcagg    5460
gctggacagc atgcccggga ggaccagcag aggattaaag gtgactggga ggaccagcgg    5520
aggataaaag acactgctca gggcagggct tctaccctgc atccctggcc aagaaaaggg    5580
cagtccccat gtgggcttgc aggtcactc tcaggggcct ctttcagctg gggctggcaa     5640
cttgcgtctg ggggacacct ccaggtgtgt ggggtgagga tttcctataa ccagggctcc    5700
cagaagcttt gcttatgtaa ggaggtctgg gagccagccc attggaggcc accagccatt    5760
ttggcttcaa aggaccccac ctcacccagg tctcagcggc agtgggcaca gctatgtctt    5820
caggagctcc cgtcaaacct catagctggg gcgctcccag acaggccagt ccagacagga    5880
cacgctgggc ccctggcatc cagaggaaga gccaggagtg tgggaaggcc cacagtgggg    5940
gctgtggctt ctgacactca ggtcatagcc tcagaggtct gaggtcagcc cccacagacc    6000
catccggccc gccccccaag tccctgcaga gagcacttag agttatggcc caggccctgg    6060
tccacccttc ccctgtgcac ctccggctgg gtttgccaag tcaggagca gggctggccg     6120 caggaactcc caaaccttgg cttttgaatat tgttgtggag gtgtgctcgt cccttttctgg   6180 acgtgcaagg tacctgtccc agcaggtcag atggggccag ctgaggcgct cccccaggca    6240
ggaagggcca gccttcacca tcgcgtggga ttgggaggag gggcctccgt gagcagcccc    6300
tcctctgccg ctgtcccagc ccagtccctc tcccggagcc ttggcagcct cccacaaccc    6360
agacacttgc gttcacaagc aacctaaggg gcaggtgaag aagcgcagcc ctgccagacg    6420
cgctagattc ctctaaggtc tctgagatgc accgtttttt aaaaaggcgt ggggtgaact    6480
gattttgatc ttcttgtcta gatgcaataa ataaatctga agcatttaat gtagtcatct    6540
tgacattggg cctacactgt acgagttcct tatgtttcct tgagctaaaa atatgtaaat    6600 aattttttgtc ccagtgagaa ccgagggtta gaaaacctcg atgcctctga gcctcgggac   6660
cgctctaggg aagtacctgc tttcgccagc atgactcatg cttcgtgggt actgaacacg    6720
agggtggaaa tgaaaactgg aacttccttg taaatttaaa cttggcaata aagagaaaa     6780 aaagtt                                                               6786
```

<210> SEQ ID NO 584
<211> LENGTH: 1052
<212> TYPE: PRT

<213> ORGANISM: Homo Sapiens

<400> SEQUENCE: 584

```
Met Phe Gly Arg Ser Arg Ser Trp Val Gly Gly His Gly Lys Thr
1               5                   10                  15

Ser Arg Asn Ile His Ser Leu Asp His Leu Lys Tyr Leu Tyr His Val
            20                  25                  30

Leu Thr Lys Asn Thr Thr Val Thr Glu Gln Asn Arg Asn Leu Leu Val
            35                  40                  45

Glu Thr Ile Arg Ser Ile Thr Glu Ile Leu Ile Trp Gly Asp Gln Asn
50                  55                  60

Asp Ser Ser Val Phe Asp Phe Phe Leu Glu Lys Asn Met Phe Val Phe
65                  70                  75                  80

Phe Leu Asn Ile Leu Arg Gln Lys Ser Gly Arg Tyr Val Cys Val Gln
                85                  90                  95

Leu Leu Gln Thr Leu Asn Ile Leu Phe Glu Asn Ile Ser His Glu Thr
            100                 105                 110

Ser Leu Tyr Tyr Leu Leu Ser Asn Asn Tyr Val Asn Ser Ile Ile Val
            115                 120                 125

His Lys Phe Asp Phe Ser Asp Glu Glu Ile Met Ala Tyr Tyr Ile Ser
130                 135                 140

Phe Leu Lys Thr Leu Ser Leu Lys Leu Asn Asn His Thr Val His Phe
145                 150                 155                 160

Phe Tyr Asn Glu His Thr Asn Asp Phe Ala Leu Tyr Thr Glu Ala Ile
                165                 170                 175

Lys Phe Phe Asn His Pro Glu Ser Met Val Arg Ile Ala Val Arg Thr
            180                 185                 190

Ile Thr Leu Asn Val Tyr Lys Val Ser Leu Asp Asn Gln Ala Met Leu
            195                 200                 205

His Tyr Ile Arg Asp Lys Thr Ala Val Pro Tyr Phe Ser Asn Leu Val
210                 215                 220

Trp Phe Ile Gly Ser His Val Ile Glu Leu Asp Asp Cys Val Gln Thr
225                 230                 235                 240

Asp Glu Glu His Arg Asn Arg Gly Lys Leu Ser Asp Leu Val Ala Glu
                245                 250                 255

His Leu Asp His Leu His Tyr Leu Asn Asp Ile Leu Ile Ile Asn Cys
            260                 265                 270

Glu Phe Leu Asn Asp Val Leu Thr Asp His Leu Leu Asn Arg Leu Phe
            275                 280                 285

Leu Pro Leu Tyr Val Tyr Ser Leu Glu Asn Gln Asp Lys Gly Gly Glu
290                 295                 300

Arg Pro Lys Ile Ser Leu Pro Val Ser Leu Tyr Leu Leu Ser Gln Val
305                 310                 315                 320

Phe Leu Ile Ile His His Ala Pro Leu Val Asn Ser Leu Ala Glu Val
                325                 330                 335

Ile Leu Asn Gly Asp Leu Ser Glu Met Tyr Ala Lys Thr Glu Gln Asp
            340                 345                 350

Ile Gln Arg Ser Ser Ala Lys Pro Ser Ile Arg Cys Phe Ile Lys Pro
            355                 360                 365

Thr Glu Thr Leu Glu Arg Ser Leu Glu Met Asn Lys His Lys Gly Lys
370                 375                 380

Arg Arg Val Gln Lys Arg Pro Asn Tyr Lys Asn Val Gly Glu Glu Glu
385                 390                 395                 400
```

```
Asp Glu Glu Lys Gly Pro Thr Glu Asp Ala Gln Glu Asp Ala Glu Lys
                405             410             415

Ala Lys Gly Thr Glu Gly Gly Ser Lys Gly Ile Lys Thr Ser Gly Glu
    420             425             430

Ser Glu Glu Ile Glu Met Val Ile Met Glu Arg Ser Lys Leu Ser Glu
    435             440             445

Leu Ala Ala Ser Thr Ser Val Gln Glu Gln Asn Thr Thr Asp Glu Glu
    450             455             460

Lys Ser Ala Ala Ala Thr Cys Ser Glu Ser Thr Gln Trp Ser Arg Pro
465             470             475             480

Phe Leu Asp Met Val Tyr His Ala Leu Asp Ser Pro Asp Asp Asp Tyr
        485             490             495

His Ala Leu Phe Val Leu Cys Leu Leu Tyr Ala Met Ser His Asn Lys
    500             505             510

Gly Met Asp Pro Glu Lys Leu Glu Arg Ile Gln Leu Pro Val Pro Asn
    515             520             525

Ala Ala Glu Lys Thr Thr Tyr Asn His Pro Leu Ala Glu Arg Leu Ile
    530             535             540

Arg Ile Met Asn Asn Ala Ala Gln Pro Asp Gly Lys Ile Arg Leu Ala
545             550             555             560

Thr Leu Glu Leu Ser Cys Leu Leu Lys Gln Gln Val Leu Met Ser
        565             570             575

Ala Gly Cys Ile Met Lys Asp Val His Leu Ala Cys Leu Glu Gly Ala
        580             585             590

Arg Glu Glu Ser Val His Leu Val Arg His Phe Tyr Lys Gly Glu Asp
    595             600             605

Ile Phe Leu Asp Met Phe Glu Asp Glu Tyr Arg Ser Met Thr Met Lys
    610             615             620

Pro Met Asn Val Glu Tyr Leu Met Met Asp Ala Ser Ile Leu Leu Pro
625             630             635             640

Pro Thr Gly Thr Pro Leu Thr Gly Ile Asp Phe Val Lys Arg Leu Pro
        645             650             655

Cys Gly Asp Val Glu Lys Thr Arg Arg Ala Ile Arg Val Phe Phe Met
        660             665             670

Leu Arg Ser Leu Ser Leu Gln Leu Arg Gly Glu Pro Glu Thr Gln Leu
    675             680             685

Pro Leu Thr Arg Glu Glu Asp Leu Ile Lys Thr Asp Asp Val Leu Asp
    690             695             700

Leu Asn Asn Ser Asp Leu Ile Ala Cys Thr Val Ile Thr Lys Asp Gly
705             710             715             720

Gly Met Val Gln Arg Phe Leu Ala Val Asp Ile Tyr Gln Met Ser Leu
        725             730             735

Val Glu Pro Asp Val Ser Arg Leu Gly Trp Gly Val Val Lys Phe Ala
        740             745             750

Gly Leu Leu Gln Asp Met Gln Val Thr Gly Val Glu Asp Asp Ser Arg
    755             760             765

Ala Leu Asn Ile Thr Ile His Lys Pro Ala Ser Ser Pro His Ser Lys
    770             775             780

Pro Phe Pro Ile Leu Gln Ala Thr Phe Ile Phe Ser Asp His Ile Arg
785             790             795             800

Cys Ile Ile Ala Lys Gln Arg Leu Ala Lys Gly Arg Ile Gln Ala Arg
        805             810             815

Arg Met Lys Met Gln Arg Ile Ala Ala Leu Leu Asp Leu Pro Ile Gln
```

-continued

```
                820                 825                 830
Pro Thr Thr Glu Val Leu Gly Phe Gly Leu Gly Ser Ser Thr Ser Thr
            835                 840                 845
Gln His Leu Pro Phe Arg Phe Tyr Asp Gln Gly Arg Arg Gly Ser Ser
    850                 855                 860
Asp Pro Thr Val Gln Arg Ser Val Phe Ala Ser Val Asp Lys Val Pro
865                 870                 875                 880
Gly Phe Ala Val Ala Gln Cys Ile Asn Gln His Ser Ser Pro Ser Leu
                885                 890                 895
Ser Ser Gln Ser Pro Pro Ser Ala Ser Gly Ser Pro Ser Gly Ser Gly
            900                 905                 910
Ser Thr Ser His Cys Asp Ser Gly Gly Thr Ser Ser Ser Ser Thr Pro
        915                 920                 925
Ser Thr Ala Gln Ser Pro Ala Asp Ala Pro Met Ser Pro Glu Leu Pro
    930                 935                 940
Lys Pro His Leu Pro Asp Gln Leu Val Ile Val Asn Glu Thr Glu Ala
945                 950                 955                 960
Asp Ser Lys Pro Ser Lys Asn Val Ala Arg Ser Ala Ala Val Glu Thr
            965                 970                 975
Ala Ser Leu Ser Pro Ser Leu Val Pro Ala Arg Gln Pro Thr Ile Ser
        980                 985                 990
Leu Leu Cys Glu Asp Thr Ala Asp Thr Leu Ser Val Glu Ser Leu Thr
    995                 1000                1005
Leu Val Pro Pro Val Asp Pro His Ser Leu Arg Ser Leu Thr Gly Met
 1010                1015                1020
Pro Pro Leu Ser Thr Pro Ala Ala Cys Thr Glu Pro Val Gly Glu Glu
1025                1030                1035               1040
Ala Ala Cys Ala Glu Pro Val Gly Thr Ala Glu Asp
            1045                1050
```

GENETIC ALTERATIONS ON CHROMOSOME 16 AND METHODS OF USE THEREOF FOR THE DIAGNOSIS AND TREATMENT OF TYPE 1 DIABETES

This application is a continuation of U.S. application Ser. No. 12/531,272 filed May 19, 2011, which is a § 371 national phase entry of PCT/US2008/056869 filed Mar. 13, 2008, which claims priority to US Provisional Application Nos. 60/894,649 filed Mar. 13, 2007, 60/910,019 filed Apr. 4, 2007 and 60/940,274 filed May 25, 2007, the entire disclosure of each being incorporated by reference herein.

FIELD OF THE INVENTION

This invention relates to the fields of glucose metabolism, genetics and pathology associated with diabetes, particularly type I diabetes. More specifically, the invention provides a panel of genes containing single nucleotide polymorphisms which had heretofore not been associated with this disease. Methods and kits for using the sequences so identified for diagnostic and therapeutic treatment purposes are also provided, as are therapeutic compositions for management of diabetes.

BACKGROUND OF THE INVENTION

Several publications and patent documents are cited throughout the specification in order to describe the state of the art to which this invention pertains. Each of these citations is incorporated herein by reference as though set forth in full.

Type I diabetes (T1D) results from the autoimmune destruction of pancreatic beta cells, a process believed to be strongly influenced by multiple genes and environmental factors. The incidence of T1D has been increasing in Western countries and has more than doubled in the United States over the past 30 years. The disease shows a strong familial component, with first-degree relatives of cases being at 15 times greater risk of T1D than a randomly selected member of the general population and monozygotic twins being concordant for T1D at a frequency of approximately 50%. However, while the genetic evidence is strong, the latter data suggests that an interplay with environmental factors also plays a key role in influencing T1D outcome.

The familial clustering of T1D is influenced by multiple genes. Variation in four loci has already been established to account for a significant proportion of the familial aggregation of T1D. These include the major histocompatibility complex (MHC) region on 6p21 (including the HLA-DRB1, -DQA1 and -DRQ1 genes); the insulin/insulin-like growth factor 2 gene complex (INS-IGF2) on 11p15[2-4], the protein tyrosine phosphatase-22 (PTPN22) gene on 1p13[5,6] and the gene encoding cytotoxic T-lymphocyte-associated protein 4 (CTLA4) on 2q31[7,8]. The interleukin-2 receptor alpha (CD25) locus on 10p15[9] has also been implicated in the pathogenesis of T1D but remains to be replicated by independent studies. In addition, spontaneous mouse model studies of T1D have implicated numerous other regions that have been confirmed in replication studies[10]. Several other loci have also been implicated in human association studies with T1D but the effects of these implicated genes remain controversial and are subject to confirmation in independent studies utilizing sufficient sample sizes. Together, these studies suggest that many more T1D susceptibility genes remain to be discovered. It is also clear that there are differences in genetic susceptibility to T1D between populations. An explanation for this variation may be related to differing frequencies of T1D causative and protective variants between different populations and ethnic groups, a hypothesis that needs to be addressed in multi-center, multi-national studies that are truly trans-continental.

SUMMARY OF THE INVENTION

In accordance with the present invention, T1D-associated SNPs have been identified which are indicative of an increased or reduced risk of developing T1D. Thus, in one aspect, nucleic acids comprising at least one genetic alteration identified in Tables 1-3 are provided. Such nucleic acids and the proteins encoded thereby have utility in the diagnosis and management of type 1 diabetes (T1D).

In another aspect of the invention, methods for assessing susceptibility for developing T1D are provided. An exemplary method entails providing a target nucleic acid from a patient sample, said target nucleic acid having a predetermined sequence in the normal population, and assessing said target nucleic acid for the presence of a single nucleotide polymorphism which is indicative of an increased or decreased risk of developing T1D. Such genetic alterations include, without limitation, inversion, deletion, duplication, and insertion of at least one nucleotide in said sequence.

Preferably, the genetic alteration is a single nucleotide polymorphism at the KIAA0350 locus region of chromosome 16, and the SNP is selected from of an A at rs2903692, a C at rs725613, or a G at rs17673553 in the CLEC16A gene sequence and is associated with a decreased risk of developing T1D, or an A at rs7200786 which is associated with an increased risk of developing T1D.

The methods of the invention also include the detection of any of the T1D associated genetic alterations comprising the single nucleotide polymorphisms set forth in Tables 1-3 for the diagnosis of T1D. Kits and microarrays for practicing the foregoing methods are also provided.

In yet another embodiment, a method of managing T1D is provided which entails administering a therapeutic agent to a patient in need thereof. The therapeutic agent can be a small molecule, an antibody, a protein, an oligonucleotide, or a siRNA molecule.

In another aspect of the invention, a method for identifying agents that bind and/or modulate CLEC16A functional activity is provided, as well as pharmaceutical compositions comprising said agent in a biologically acceptable carrier.

BRIEF DESCRIPTION OF THE DRAWINGS

FIG. 2A-FIG. 2D: CLEC16A sequence of the KIAA0350 gene on chromosome 16. Both the nucleic acid sequence (SEQ ID NO: 583; FIG. 2A-FIG. 2C) and protein sequence (SEQ ID NO: 584; FIG. 2D) of CLEC16A corresponding to GenBank Accession number NM_015226.1 are shown.

DETAILED DESCRIPTION OF THE INVENTION

Figure 1:
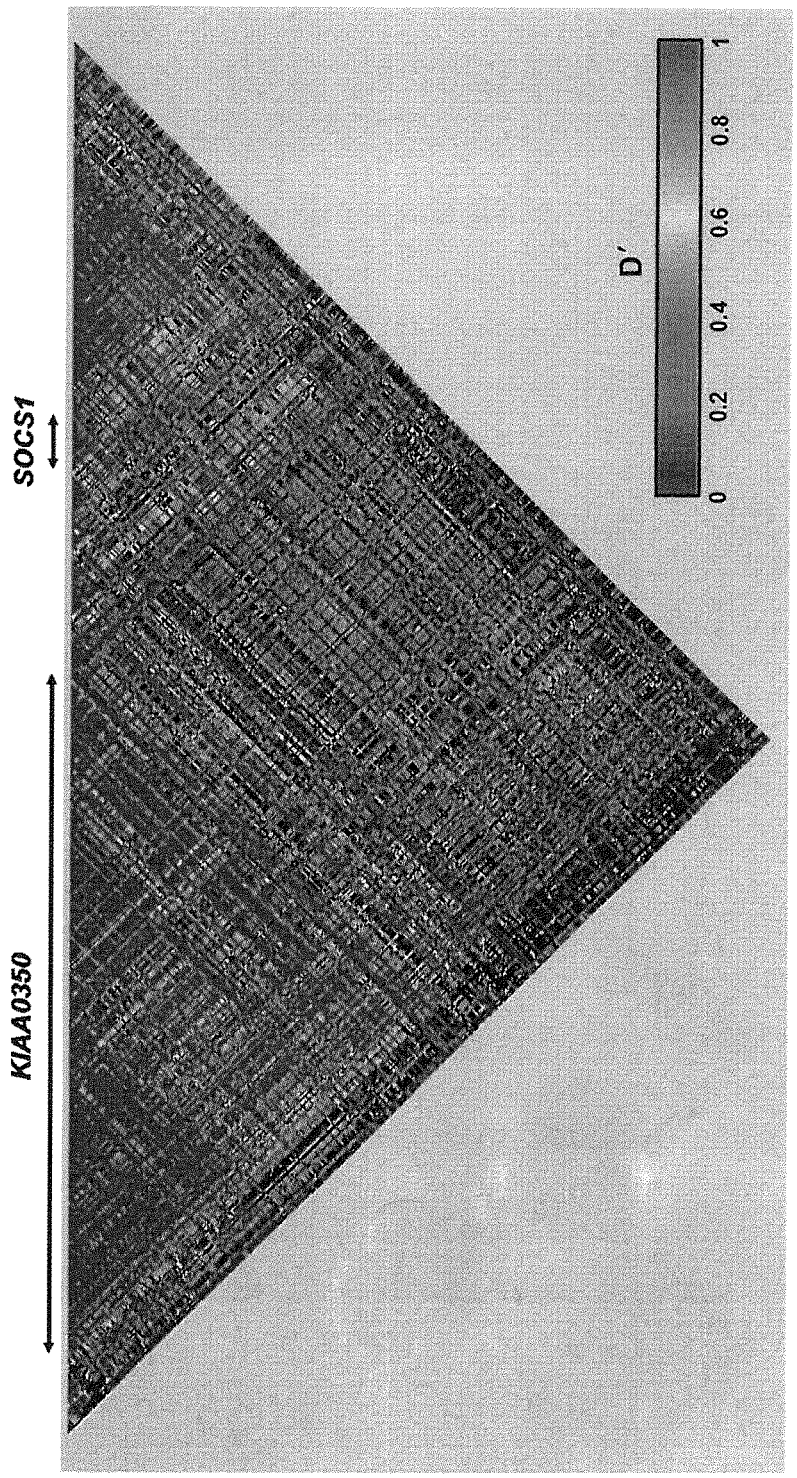
FIG. 1. Pairwise linkage disequilibrium diagram of the KIAA0350 locus on 16p13.13. This 'gold plot' is derived from HapMap CEU data corresponding to a region spanning from 10899122 (rs8063850) to 11395501 (rs12597032) base pairs on chromosome 16 (Build 35); intensity of shading is proportional to D'. The relative genomic location of the KIAA0350 gene is shown; it is contained within a single LD block; no other gene resides within this LD block of association. The most pertinent gene in the adjacent region is the SOCS1 gene (indicated).

A number of genetic determinants of T1D have already been established through candidate gene studies, primarily with the major histocompatibility complex (MHC) but also with other loci. To identify novel genetic factors that confer risk of T1D, a genome-wide association (GWA) study in a large pediatric study cohort of Western European decent was performed. In addition to confirming previously identified loci, a highly significant association with variation within the KIAA0350 locus on 16p13, the gene product of which appears to be a sugar binding C-type lectin, was observed. Three common non-coding variants (rs2903692 allele A, rs725613 allele C and rs17673553 allele G) in strong LD conferred strong protection against T1D (p-value range=$1.30 \times 10^{-6}$-$1.03 \times 10^{-10}$, OR range=0.65-0.72). These results provide evidence for a novel genetic factor that contributes substantially to the pathogenesis of T1D, including a common variant conferring a large protective effect, and thus providing a promising new T1D therapeutic and diagnostic target.

The following definitions are provided to facilitate an understanding of the present invention:

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, Aisolated@ and Abiologically pure@ do not necessarily reflect the extent to which the compound has been purified. An isolated compound of the present invention can be obtained from its natural source, can be produced using laboratory synthetic techniques or can be produced by any such chemical synthetic route.

A "single nucleotide polymorphism (SNP)" refers to a change in which a single base in the DNA differs from the usual base at that position. These single base changes are called SNPs or "snips." Millions of SNP's have been cataloged in the human genome. Some SNPs such as that which causes sickle cell are responsible for disease. Other SNPs are normal variations in the genome.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

The phrase "Type 1 diabetes (T1D)" refers to a chronic (lifelong) disease that occurs when the pancreas produces too little insulin to regulate blood sugar levels appropriately. T1D, often called juvenile or insulin-dependent diabetes results from altered metabolism of carbohydrates (including sugars such as glucose), proteins, and fats. In type 1 diabetes, the beta cells of the pancreas produce little or no insulin, the hormone that allows glucose to enter body cells. Once glucose enters a cell, it is used as fuel. Without adequate insulin, glucose builds up in the bloodstream instead of going into the cells. The body is unable to use this glucose for energy despite high levels in the bloodstream, leading to increased hunger. In addition, the high levels of glucose in the blood cause the patient to urinate more, which in turn causes excessive thirst. Within 5 to 10 years after diagnosis, the insulin-producing beta cells of the pancreas are completely destroyed, and no more insulin is produced.

"T1D-associated SNP or specific marker" is a SNP or marker which is associated with an increased or decreased risk of developing TID not found normal patients who do not have this disease. Such markers may include but are not limited to nucleic acids, proteins encoded thereby, or other small molecules. Type 1 diabetes can occur at any age, but it usually starts in people younger than 30. Symptoms are usually severe and occur rapidly. The exact cause of type 1 diabetes is not known. Type 1 diabetes accounts for 3% of all new cases of diabetes each year. There is 1 new case per every 7,000 children per year. New cases are less common among adults older than 20.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose. "Sample" or "patient sample" or "biological sample" generally refers to a sample which may be tested for a particular molecule, preferably an T1D specific marker molecule, such as a marker shown in the tables provided below. Samples may include but are not limited to cells, body fluids, including blood, serum, plasma, urine, saliva, tears, pleural fluid and the like.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

"Target nucleic acid" as used herein refers to a previously defined region of a nucleic acid present in a complex nucleic acid mixture wherein the defined wild-type region contains at least one known nucleotide variation which may or may not be associated with T1D. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form. By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. Thus, the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any T1D specific marker gene or nucleic acid, but does not hybridize to other human nucleotides. Also polynucleotide which Aspecifically hybridizes@ may hybridize only to a T1D specific marker, such a T1D-specific marker shown in Tables 1-3. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m = 81.5"C + 16.6 \text{ Log } [Na+] + 0.41(\% \ G+C) - 0.63(\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57" C. The $T_m$ of a DNA duplex decreases by 1-1.5" C with every 1% decrease in homology. Thus, targets with greater than about 75% sequence identity would be observed using a hybridization temperature of 42" C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide" or "oligo" as used herein means a short sequence of DNA or DNA derivatives typically 8 to 35 nucleotides in length, primers, or probes. An oligonucleotide can be derived synthetically, by cloning or by amplification. An oligo is defined as a nucleic acid molecule comprised of two or more ribo- or deoxyribonucleotides, preferably more than three. The exact size of the oligonucleotide will depend on various factors and on the particular application and use of the oligonucleotide. The term "derivative" is intended to include any of the above described variants when comprising an additional chemical moiety not normally a part of these molecules. These chemical moieties can have varying purposes including, improving solubility, absorption, biological half life, decreasing toxicity and eliminating or decreasing undesirable side effects.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting CLEC16A mRNA may be between 15-35 nucleotides in length, and more typically about 21 nucleotides in length. A list of candidate siRNAs directed to CLEC16A are provided in Table 4.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and Atransduction@ refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, peptide-tethering, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the T1D specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the T1D specific marker gene nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene@ refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms Arecombinant organism," or Atransgenic organism@ refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase Aa recombinant organism@ encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term Aspecific binding pair@ is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long. "Sample" or "patient sample" or "biological sample" generally refers to a sample which may be tested for a particular molecule, preferably a T1D specific marker molecule, such as a marker shown in Tables 1-3. Samples may include but are not limited to cells, body fluids, including blood, serum, plasma, urine, saliva, tears, pleural fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, small molecules, antibodies, peptides, peptide/DNA complexes, and any nucleic acid based molecule, for example an oligo, which exhibits the capacity to modulate the activity of the SNP containing nucleic acids described herein or their encoded proteins. Agents are evaluated for potential biological activity by inclusion in screening assays described herein below.

The term "modulate" as used herein refers increasing or decreasing. For example, the term modulate refers to the ability of a compound or test agent to interfere with signaling or activity of a gene or protein of the present invention. Therefore, modulating the signaling mediated by KIAA0350 means that an agent or compound inhibits or enhances the activity of the proteins encoded by the gene. This includes altering the activity of natural killer cells, and preventing autoimmune beta cell destruction.

Methods of Using T1D-Associated SNPS for T1D Detection Assays

T1D SNP containing nucleic acids, including but not limited to those listed in Tables 1-3, may be used for a variety of purposes in accordance with the present invention. T1D-associated SNP containing DNA, RNA, or fragments thereof may be used as probes to detect the presence of and/or expression of T1D specific markers. Methods in which T1D specific marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting T1D-associated SNPs may be conducted on any type of biological sample, including but not limited to body fluids (including blood, urine, serum, gastric lavage), any type of cell (such as white blood cells, mononuclear cells) or body tissue.

From the foregoing discussion, it can be seen that T1D associated SNP containing nucleic acids, vectors expressing the same, T1D SNP containing marker proteins and anti-T1D specific marker antibodies of the invention can be used to detect T1D associated SNPs in body tissue, cells, or fluid, and alter T1D SNP containing marker protein expression for purposes of assessing the genetic and protein interactions involved in T1D.

In most embodiments for screening for T1D-associated SNPs, the T1D-associated SNP containing nucleic acid in the sample will initially be amplified, e.g. using PCR, to increase the amount of the template as compared to other sequences present in the sample. This allows the target sequences to be detected with a high degree of sensitivity if they are present in the sample. This initial step may be avoided by using highly sensitive array techniques that are becoming increasingly important in the art.

Alternatively, new detection technologies can overcome this limitation and enable analysis of small samples containing as little as 1 μg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Thus, any of the aforementioned techniques may be used to detect or quantify T1D-associated SNP marker expression and accordingly, detect patient susceptibility for developing T1D.

Kits and Articles of Manufacture

Any of the aforementioned products can be incorporated into a kit which may contain an T1D-associated SNP specific marker polynucleotide or one or more such markers immobilized on a Gene Chip, an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof.

Methods of Using T1D-Associated SNPS for Development of Therapeutic Agents

Since the SNPs identified herein have been associated with the etiology of T1D, methods for identifying agents that modulate the activity of the genes and their encoded products containing such SNPs should result in the generation of efficacious therapeutic agents for the treatment of a variety of disorders associated with this condition.

Chromosome 16 contains regions which provide suitable targets for the rational design of therapeutic agents which modulate their activity. Small peptide molecules corresponding to these regions may be used to advantage in the design of therapeutic agents which effectively modulate the activity of the encoded proteins.

Molecular modeling should facilitate the identification of specific organic molecules with capacity to bind to the active site of the proteins encoded by the SNP containing nucleic acids based on conformation or key amino acid residues required for function. A combinatorial chemistry approach will be used to identify molecules with greatest activity and then iterations of these molecules will be developed for further cycles of screening.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered T1D associated gene. These host cell lines or cells are defective at the polypeptide level. The host cell lines or cells are grown in the presence of drug compound. The rate of cellular metabolism of the host cells is measured to determine if the compound is capable of regulating cellular metabolism in the defective cells. Host cells contemplated for use in the present invention include but are not limited to bacterial cells, fungal cells, insect cells, mammalian cells, and plant cells. The T1D-associated SNP encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

Cells and cell lines suitable for studying the effects of the SNP encoding nucleic acids on glucose metabolism and methods of use thereof for drug discovery are provided. Such cells and cell lines will be transfected with the SNP encoding nucleic acids described herein and the effects on glucagon secretion, insulin secretion and/or beta cell apoptosis can be determined. Such cells and cell lines will also be contacted with the siRNA molecules provided herein to assess the effects thereof on glucagon secretion, insulin secretion and/or beta cell apoptosis. The siRNA molecules will be tested alone and in combination of 2, 3, 4, and 5 siRNAs to identify the most efficacious combination for down regulating CLEC16A. Cells suitable for these purposes include, without limitation, INS cells (ATCC CRL 11605), PC12 cells (ATCC CRL 1721), MIN6 cells, alpha-TC6 cells and INS-1 832/13 cells (Fernandez et al., J. of Proteome Res. (2007). 7:400-411). Pancreatic islet cells can be isolated and cultured as described in Joseph, J. et al., (J. Biol. Chem. (2004) 279:51049). Diao et al. (J. Biol. Chem. (2005) 280:33487-33496), provide methodology for assessing the effects of the SNP encoding nucleic acids and/or the siRNAs provided herein on glucagon secretion and insulin secretion. Park, J. et al. (J. of Bioch. and Mol. Biol. (2007) 40:1058-68) provide methodology for assessing the effect of these nucleic acid molecules on glucosamine induced beta cell apoptosis in pancreatic islet cells.

A wide variety of expression vectors are available that can be modified to express the novel DNA or RNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in Saccharomyces are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/V5&His (Invitrogen); baculovirus vectors such as pVL1392, pVL1393, or pAC360 (Invitrogen); and yeast vectors such as YRP17, YIPS, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and Saccharomyces promoters such as the gal4 inducible promoter and the PGK constitutive promoter, as well as neuronal-specific platelet-derived growth factor promoter (PDGF), the Thy-1 promoter, the hamster and mouse Prion promoter (MoPrP), and the Glial fibrillar acidic protein (GFAP) for the expression of transgenes in glial cells.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the T1D-associated SNPs of the present invention or functional fragments thereof provide a system in which to screen potential compounds or agents for the ability to modulate the development of T1D. Thus, in one embodiment, the nucleic acid molecules of the invention may be used to create recombinant cell lines for use in assays to identify agents which modulate aspects of lectin binding. Also provided herein are methods to screen for compounds capable of modulating the function of proteins encoded by the SNP containing nucleic acids described below.

Another approach entails the use of phage display libraries engineered to express fragment of the polypeptides encoded by the SNP containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacophore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacophore.

Thus, one may design drugs which have, e.g., improved polypeptide activity or stability or which act as inhibitors, agonists, antagonists, etc. of polypeptide activity. By virtue of the availability of SNP containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of T1D-associated SNP containing nucleic acids enables the production of strains of laboratory mice carrying the T1D-associated SNPs of the invention. Transgenic mice expressing the T1D-associated SNP of the invention provide a model system in which to examine the role of the protein encoded by the SNP containing nucleic acid in the development and progression towards T1D. Methods of introducing transgenes in laboratory mice are known to those of skill in the art. Three common methods include: (1) integration of retroviral vectors encoding the foreign gene of interest into an early embryo; (2) injection of DNA into the pronucleus of a newly fertilized egg; and (3) the incorporation of genetically manipulated embryonic stem cells into an early embryo. Production of the transgenic mice described above will facilitate the molecular elucidation of the role that a target protein plays in various cellular metabolic processes, including: aberrant lipid deposition, altered cellular metabolism and glucose regulation. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extra-chromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of T1D-associated SNP containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated T1D-associated SNP genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extra-chromosomal recombination, which occurs at a frequency approaching 100%, homologous plasmid-chromosome recombination was originally reported to only be detected at frequencies between $10^{-6}$ and $10^{-3}$. Non-homologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabino-fluranosyl)-5-iodou-racil, (FIAU). By this counter selection, the number of homologous recombinants in the surviving transformants can be increased. Utilizing T1D-associated SNP containing nucleic acid as a targeted insertional cassette provides means to detect a successful insertion as visualized, for example, by acquisition of immunoreactivity to an antibody immunologically specific for the polypeptide encoded by T1D-associated SNP nucleic acid and, therefore, facilitates screening/selection of ES cells with the desired genotype.

As used herein, a knock-in animal is one in which the endogenous murine gene, for example, has been replaced with human T1D-associated SNP containing gene of the invention. Such knock-in animals provide an ideal model system for studying the development of T1D.

As used herein, the expression of a T1D-associated SNP containing nucleic acid, fragment thereof, or a T1D-associated SNP fusion protein can be targeted in a "tissue specific manner" or "cell type specific manner" using a vector in which nucleic acid sequences encoding all or a portion of T1D-associated SNP are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific expression of proteins are well known in the art and described herein.

The nucleic acid sequence encoding the T1D-associated SNP of the invention may be operably linked to a variety of different promoter sequences for expression in transgenic animals. Such promoters include, but are not limited to a prion gene promoter such as hamster and mouse Prion promoter (MoPrP), described in U.S. Pat. No. 5,877,399 and in Borchelt et al., Genet. Anal. 13(6) (1996) pages 159-163; a rat neuronal specific enolase promoter, described in U.S.

Pat. Nos. 5,612,486, and 5,387,742; a platelet-derived growth factor B gene promoter, described in U.S. Pat. No. 5,811,633; a brain specific dystrophin promoter, described in U.S. Pat. No. 5,849,999; a Thy-1 promoter; a PGK promoter; a CMV promoter; a neuronal-specific platelet-derived growth factor B gene promoter; and Glial fibrillar acidic protein (GFAP) promoter for the expression of transgenes in glial cells.

Methods of use for the transgenic mice of the invention are also provided herein. Transgenic mice into which a nucleic acid containing the T1D-associated SNP or its encoded protein have been introduced are useful, for example, to develop screening methods to screen therapeutic agents to identify those capable of modulating the development of T1D.

Pharmaceuticals and Peptide Therapies

The elucidation of the role played by the T1D associated SNPs described herein in cellular metabolism facilitates the development of pharmaceutical compositions useful for treatment and diagnosis of T1D. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

As it is presently understood, RNA interference involves a multi-step process. Double stranded RNAs are cleaved by the endonuclease Dicer to generate nucleotide fragments (siRNA). The siRNA duplex is resolved into 2 single stranded RNAs, one strand being incorporated into a protein-containing complex where it functions as guide RNA to direct cleavage of the target RNA (Schwarz et al, Mol. Cell. 10:537 548 (2002), Zamore et al, Cell 101:25 33 (2000)), thus silencing a specific genetic message (see also Zeng et al, Proc. Natl. Acad. Sci. 100:9779 (2003)).

The invention includes a method of treating T1D in a mammal. An exemplary method entails administering to the mammal a pharmaceutically effective amount of CLEC16A siRNA. The siRNA inhibits the expression of CLEC16A. Preferably, the mammal is a human. The term "patient" as used herein refers to a human.

Specific siRNA preparations directed at inhibiting the expression of CLEC16A, as well as delivery methods are provided as a novel therapy to treat T1D. SiRNA oligonucleotides directed to CLEC16A specifically hybridize with nucleic acids encoding CLEC16A and interfere with CLEC16A gene expression. The siRNA can be delivered to a patient in vivo either systemically or locally with carriers, as discussed below. The compositions of the invention may be used alone or in combination with other agents or genes encoding proteins to augment the efficacy of the compositions.

A "membrane permeant peptide sequence" refers to a peptide sequence which is able to facilitate penetration and entry of the CLEC16A inhibitor across the cell membrane. Exemplary peptides include with out limitation, the signal sequence from Karposi fibroblast growth factor exemplified herein, the HIV tat peptide (Vives et al., J Biol. Chem., 272:16010-16017, 1997), Nontoxic membrane translocation peptide from protamine (Park et al., FASEB J. 19(11):1555-7, 2005), CHARIOT® delivery reagent (Active Motif; U.S. Pat. No. 6,841,535) and the antimicrobial peptide Buforin 2.

In one embodiment of the invention siRNAs are delivered for therapeutic benefit. There are several ways to administer the siRNA of the invention to in vivo to treat T1D including, but not limited to, naked siRNA delivery, siRNA conjugation and delivery, liposome carrier-mediated delivery, polymer carrier delivery, nanoparticle compositions, plasmid-based methods, and the use of viruses.

siRNA composition of the invention can comprise a delivery vehicle, including liposomes, for administration to a subject, carriers and diluents and their salts, and/or can be present in pharmaceutically acceptable formulations. This can be necessary to allow the siRNA to cross the cell membrane and escape degradation. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192; Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule.

The frequency of administration of the siRNA to a patient will also vary depending on several factors including, but not limited to, the type and severity of the T1D to be treated, the route of administration, the age and overall health of the individual, the nature of the siRNA, and the like. It is contemplated that the frequency of administration of the siRNA to the patient may vary from about once every few months to about once a month, to about once a week, to about once per day, to about several times daily.

Pharmaceutical compositions that are useful in the methods of the invention may be administered systemically in parenteral, oral solid and liquid formulations, ophthalmic, suppository, aerosol, topical or other similar formulations. In addition to the appropriate siRNA, these pharmaceutical compositions may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate siRNA to a patient according to the methods of the invention. The use of nanoparticles to deliver siRNAs, as well as cell membrane permeable peptide carriers that can be used are described in Crombez et al., Biochemical Society Transactions v35:p44 (2007).

Methods of the invention directed to treating T1D involve the administration of CLEC16A siRNA in a pharmaceutical composition. CLEC16A siRNA is administered to an individual as a pharmaceutical composition comprising CLEC16A siRNA and a pharmaceutically acceptable carrier. Pharmaceutically acceptable carriers are well known in the art and include aqueous solutions such as physiologically buffered saline, other solvents or vehicles such as glycols, glycerol, oils such as olive oil or injectable organic esters.

A pharmaceutically acceptable carrier can contain physiologically acceptable compounds that act, for example, to stabilize the CLEC16A siRNA or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the CLEC16A siRNA.

One skilled in the art appreciates that a pharmaceutical composition comprising CLEC16A siRNA can be administered to a subject by various routes including, for example, orally or parenterally, such as intravenously (i.v.), intramuscularly, subcutaneously, intraorbitally, intranasally, intracapsularly, intraperitoneally (i.p.), intracisternally, intra-tracheally (it.), or intra-articularly or by passive or facilitated absorption. The same routes of administration can be used other pharmaceutically useful compounds, for example, small molecules, nucleic acid molecules, peptides, antibodies and polypeptides as discussed hereinabove.

A pharmaceutical composition comprising CLEC16A siRNA inhibitor also can be incorporated, if desired, into liposomes, microspheres, microbubbles, or other polymer matrices (Gregoriadis, Liposome Technology, Vols. I to III, 2nd ed., CRC Press, Boca Raton Fla. (1993)). Liposomes, for example, which consist of phospholipids or other lipids, are nontoxic, physiologically acceptable and metabolizable carriers that are relatively simple to make and administer.

The pharmaceutical preparation comprises a siRNA targeting CLEC16A or an expression vector encoding for an siRNA targeting CLEC16A. Such pharmaceutical preparations can be administered to a patient for treating T1D.

Expression vectors for the expression of siRNA molecules preferably employ a strong promoter which may be constitutive or regulated. Such promoters are well known in the art and include, but are not limited to, RNA polymerase II promoters, the T7 RNA polymerase promoter, and the RNA polymerase III promoters U6 and H1 (see, e.g., Myslinski et al. (2001) Nucl. Acids Res., 29:2502 09).

A formulated siRNA composition can be a composition comprising one or more siRNA molecules or a vector encoding one or more siRNA molecules independently or in combination with a cationic lipid, a neutral lipid, and/or a polyethyleneglycol-diacylglycerol (PEG-DAG) or PEG-cholesterol (PEG-Chol) conjugate. Non-limiting examples of expression vectors are described in Paul et al., 2002, Nature Biotechnology, 19, 505; Miyagishi and Taira, 2002, Nature Biotechnology, 19, 497; Lee et al., 2002, Nature Biotechnology, 19, 500-505.

A lipid nanoparticle composition is a composition comprising one or more biologically active molecules independently or in combination with a cationic lipid, a neutral lipid, and/or a polyethyleneglycol-diacylglycerol (i.e., polyethyleneglycol diacylglycerol (PEG-DAG), PEG-cholesterol, or PEG-DMB) conjugate. In one embodiment, the biologically active molecule is encapsulated in the lipid nanoparticle as a result of the process of providing and aqueous solution comprising a biologically active molecule of the invention (i.e., siRNA), providing an organic solution comprising lipid nanoparticle, mixing the two solutions, incubating the solutions, dilution, ultrafiltration, resulting in concentrations suitable to produce nanoparticle compositions.

Nucleic acid molecules can be administered to cells by incorporation into other vehicles, such as biodegradable polymers, hydrogels, cyclodextrins. (see for example Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722)

Cationic lipids and polymers are two classes of non-viral siRNA delivery which can form complexes with negatively charged siRNA. The self-assembly PEG-ylated polycation polyethylenimine (PEI) has also been used to condense and protect siRNAs (Schiffelers et al., 2004, Nuc. Acids Res. 32: 141-110). The siRNA complex can be condensed into a nanoparticle to allow efficient uptake of the siRNA through endocytosis. Also, the nucleic acid-condensing property of protamine has been combined with specific antibodies to deliver siRNAs and can be used in the invention (Song et al., 2005, Nat Biotech. 23:709-717).

In order to treat an individual having T1D, to alleviate a sign or symptom of the disease, CLEC16A siRNA should be administered in an effective dose. The total treatment dose can be administered to a subject as a single dose or can be administered using a fractionated treatment protocol, in which multiple doses are administered over a more prolonged period of time, for example, over the period of a day to allow administration of a daily dosage or over a longer period of time to administer a dose over a desired period of time. One skilled in the art would know that the amount of CLEC16A siRNA required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having T1D.

The effective dose of CLEC16A siRNA will depend on the mode of administration, and the weight of the individual being treated. The dosages described herein are generally those for an average adult but can be adjusted for the treatment of children. The dose will generally range from about 0.001 mg to about 1000 mg.

The concentration of CLEC16A siRNA in a particular formulation will depend on the mode and frequency of administration. A given daily dosage can be administered in a single dose or in multiple doses so long as the CLEC16A siRNA concentration in the formulation results in the desired daily dosage. One skilled in the art can adjust the amount of CLEC16A siRNA in the formulation to allow administration of a single dose or in multiple doses that provide the desired concentration of CLEC16A siRNA over a given period of time.

In an individual suffering from T1D, in particular a more severe form of the disease, administration of CLEC16A siRNA can be particularly useful when administered in combination, for example, with a conventional agent for treating such a disease. The skilled artisan would administer CLEC16A siRNA, alone or in combination and would monitor the effectiveness of such treatment using routine methods such as pulmonary function determination, radiologic, immunologic or, where indicated, histopathologic methods. Other conventional agents for the treatment of diabetes include insulin administration, glucagon administration or agents that alter levels of either of these two molecules. Glucophage®, Avandia®, Actos®, Januvia® and Glucovance® are examples of such agents.

Administration of the pharmaceutical preparation is preferably in an "effective amount" this being sufficient to show benefit to the individual. This amount prevents, alleviates, abates, or otherwise reduces the severity of T1D symptoms in a patient.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

As mentioned previously, a preferred embodiment of the invention comprises delivery of the CLEC16A siRNA to a patient in need thereof, and candidate siRNA compositions for use in the invention are provided in Table 4. The sequences in Table 4 include several siRNA duplexes (i.e., sense and antisense sequences for a CLEC16A target region), as well as several sequences of 'sense' strand alone. Those of skill in the art can determine the sequence of an antisense siRNA strand based on the disclosure of the sense strand, and will appreciate the difference between "U" and "T" designations in the sequences which correspond to RNA and DNA molecules, respectively.

The following examples are provided to illustrate certain embodiments of the invention. They are not intended to limit the invention in any way.

EXAMPLE I 550,000 single nucleotide polymorphisms (SNPs) were genotyped with the Illumina Human Hap550 Genotyping BeadChip[11] on the study population of 563 T1D probands of European ancestry and 1,146 controls without T1D and with matching ancestry (based on self report) plus 483 complete T1D family trios of the same ancestry. Following this process, 16 trios, 2 cases and 3 controls were removed due to genotyping yields <90%. All patients had clinically proven T1D.

In the case-control analysis, single-marker allele frequencies were compared using $\chi^2$ statistics for all markers while the transmission disequilibrium test (TDT) was used to calculate P-values of transmission distortion from heterozygous parents in affected parent-child trios. The resulting P-values from the case-control and family-based analyses were then combined using Fisher's method[12] to quantify the overall evidence for association. As anticipated, the MHC region was strongly positive, with 392 markers above the threshold for Bonferroni correction, the full breakdown of which is found in Table 2. As this locus is well established, and since a much denser marker coverage is needed to deal with the particularities of this region, this locus was not addressed further in these experiments; however, corresponding data is included in Table 1B, and it should be noted that allele A of the most significant MHC associated SNP, rs2647044, tags DRB1 equally efficiently as a previously identified SNP[13] and was observed to be in epistasis (P)<10⁻¹⁰ with rs3117098, also showing association to T1D, at the BTNL2 locus within the MHC. No other significant epistasis with significantly associated SNPs was observed.

Eleven non-MHC SNPs were the next most significant markers, and remained significant at the 0.05 level after Bonferroni correction (Table 1A). One of these eleven markers, rs2476601 (P=1.11×10⁻¹²) and another five markers, rs1004446, rs6356, rs10770141, rs7111341 and rs10743152 (P-value range=7.53×10⁻⁸-6.75×10⁻¹¹), are in two known T1D susceptibility loci, PTPN22 and INS, respectively. A novel locus was identified by three of the eleven markers, which are common non-coding variants (rs2903692 allele A, rs725613 allele C and rs17673553 allele G) in strong LD in the KIAA0350 gene on chromosome 16p13.13 (P-value range=6.12×10⁻⁸-1.03×10⁻¹⁰, case-control OR range=0.65-0.66). The minor allele is protective with a frequency of 0.28 to 0.39 in controls. This novel T1D locus resides in a 233 kb block of linkage disequilibrium (LD) that contains only KIAA0350 and no other gene. It is separated by two recombination hot spots from a neighboring LD block that includes the suppressor of cytokine signaling 1 (SOCS1) gene, which modulates β-cell response to inflammatory signaling. In addition to these three markers, eleven other markers in the KIAA0350, LD block, showed association P-values<0.00001 in the family trios and case-control cohort combined (See Table 1C). Two other novel loci, namely COL1A2 (rs10255021) and the other in the vicinity of LPHN2 (rs672797), were also significantly associated following Bonferroni correction. Thus, there is a confirmed association with the three known and abundantly replicated T1D loci, and three potentially novel T1D loci of genome-wide significance in Stage 1 were uncovered which were subjected to further analysis in Stage 2.

Many reported associations with common variants have not been replicated due to factors, such as population stratification, inadequate statistical power and genotyping errors[14]. Therefore, it was of interest to confirm the association between T1D and the three novel loci in an additional unrelated sample of affected parent-offspring trios, an approach resistant to population stratification. A transmission disequilibrium test (TDT) was used to calculate the level of significance on differences between transmitted and untransmitted allele counts in 1333 affected offspring from 549 nuclear families available from the Type 1 Diabetes Genetics Consortium (T1DGC) plus an additional 390 Canadian trios. Using the SNPlex platform from Sequenom, the association of three markers in KIAA0350, rs17673553, rs725613 and rs2903692 was confirmed (P=0.023-0.0022) and it was found that several other markers in the LD block also showed association (Table 1B and 1C). All of these SNPs were in LD, where the minor alleles of these SNPs were shown to confer protection of T1D (Table 1C), except for the minor A allele of rs7200786, which conferred risk, yielding an OR=1.33 and PAR=12.6% (combined P for all three cohorts=9.12×10⁻⁷). These SNPs have frequencies in the control cohort very close to those observed in the International HapMap CEU set; they are in Hardy Weinberg equilibrium and survive all QC measures for high quality SNPs.

It should also be noted that when limited to the 839 nuclear families that self-report as Caucasian, the results remain significant (see Tables 1B and 1C). In an analysis combining all three independent cohorts (563 cases vs 1,146 controls; 483 Stage 1 trios and Stage 2 1333 T1D offspring from 939 nuclear families) for these three intragenic KIAA0350 markers, the combined P values for their association with T1D ranged from $2.74 \times 10^{-9}$-$6.7 \times 10^{-11}$.

The location of KIAA0350 within a large LD block, (FIG. 1) containing no other gene, suggests this region harbors the causative variant. The genomic location of KIAA0350 is next to SOCS1; its almost exclusive expression specificity for antigen-presenting cells and natural-killer T-cells (see the world wide web at (symatlas.gnf.org/SymAtlas)) indicate potential importance in immune regulation. The protein product of KIAA0350 bears similarities to a subset of adhesion and immune function signaling molecules. Pfam[15] prediction suggests that this gene encodes a protein with a calcium-dependent, or C-type, lectin binding domain structure, a protein family known to be involved with calcium current flux, and its predicted function includes sugar binding, according to the Gene Ontology project (GO: 0005529—"interacting selectively with any mono-, di- or trisaccharide carbohydrate") (see the world wide web at (geneontology.org)). The C-type lectins are known for their recognition of a diversity of carbohydrates and are critical for a variety of processes ranging from cell adhesion to pathogen recognition[16]. More specifically, the protein product of KIAA0350 is identified as CLEC 16A (GenBank Accession No. NM 015226.1) as shown in FIG. 2.

The gene is expressed in B lymphocytes, dendritic antigen presenting cells and T cells, including NK-cells, which is in keeping with a function relevant to an immune-mediated disease such as T1D. Thus, the discovery of association at that locus points to a previously unknown pathway in the etiology of T1D, and is consistent with current understanding of common complex disease, where the predisposing allele is often the more common, as its deleterious effect may be counterbalanced by advantage in other contexts, e.g. better protection against infection at an autoimmunity locus (antagonistic pleiotropism).

In summary, a T1D associated variation in a gene that is expressed in immune cells, including dendritic, natural killer (NK) and B-cells, and contains a C-type lectin-binding domain involved with binding of sugar moieties has been discovered. In light of the critical role of the MHC genetic repertoire in antigen presentation, that typically involves a sugar moiety, such as lectin, a genetic variant in the binding site for such a molecule on the activating cytotoxic T-cell could trigger an autoimmune response that results in destruction of the islet cells of the pancreas, as seen in T1D.

EXAMPLE II

Standard convention for presenting the risk conferred by a given SNP is to describe the risk numerically for the less frequent allele in the population i.e. the minor allele. On occasions, the minor allele is less frequent in the cases than in the controls and therefore yields a risk of less than 1 (i.e. it is termed "protective"). In this event, it is the major, or more common, allele that confers risk. SNPs that show association are not necessarily causative themselves, rather they tag the mutation which must reside on a nearby region (i.e. within a few kilobases). The causative mutation itself may confer higher risk and be rarer. Thus, the SNP association essentially indicates that there is a causative mutation nearby and that this SNP-containing gene is involved in the pathogenesis of the disease and therefore can be utilized to detect susceptibility thereto. Many surrogate SNPs can be employed to capture the same signal, and here they have been categorized into three parts: CATEGORY 1: $r2>0.9$; CATEGORY 2: $r2=0.8$-$0.9$; CATEGORY 3: $r2<0.8$-$0.7$; see Table 3. Surrogates for the markers described in Example I have also been identified and are provided in Table 3.

As described briefly above, the KIAA0350 gene encodes a transmembrane protein molecule that is expressed by inflammatory cells and the pancreas. The KIAA0350 signaling pathway is activated through exposures of the targeted cell type to sugar moieties. In Natural Killer (NK) cells, exposures to sugars such as lectin can trigger either activation or depression of the cells. In T1D, the activation of NK cells is dysregulated causing the NK cell under certain circumstances to attack its own cells and destroy them (i.e., the beta insulin producing cells of the pancreas in the case of T1D). It is known that this is more prone to occur in subjects who are carriers of the at-risk variant in the KIAA0350 gene.

Down regulation of KIAA0350 mRNA expression levels is desirable to inhibit production of the CLEC16A gene product. Reduction in the expression level of this protein should impede or prevent the development of T1D. siRNA can be employed to regulate this locus, irrespective of the genetic status of the individual. Accordingly, candidate siRNA molecules to be delivered to patients are listed in Table 4. The genetic status is useful to predict who will develop the disease so it can be determined who will particularly benefit from therapeutic intervention. Yet those individuals who do not have this specific genetic predisposition of T1D, but have a family history of the disease or have another type of genetic predisposition, could also benefit.

EXAMPLE III

The information herein above can be applied clinically to patients for diagnosing an increased susceptibility for developing T1D, and therapeutic intervention. A preferred embodiment of the invention comprises clinical application of the information described herein to a patient. Diagnostic compositions, including microarrays, and methods can be designed to identify the genetic alterations described herein in nucleic acids from a patient to assess susceptibility for developing T1D. This can occur after a patient arrives in the clinic; the patient has blood drawn, and using the diagnostic methods described herein, a clinician can detect a SNP in the KIAA0350 region of chromosome 16. The typical age range for a patient to be screened is between 9 and 12 years of age. The information obtained from the patient sample, which can optionally be amplified prior to assessment, will be used to diagnose a patient with an increased or decreased susceptibility for developing T1D. Kits for performing the diagnostic method of the invention are also provided herein. Such kits comprise a microarray comprising at least one of the SNPs provided herein in and the necessary reagents for assessing the patient samples as described above.

The identity of T1D-involved genes and the patient results will indicate which variants are present, and will identify those that possess an altered risk for developing T1D. The information provided herein allows for therapeutic intervention at earlier times in disease progression that previously possible. Also as described herein above, CLEC16A provides a novel target for the development of new therapeutic agents efficacious for the treatment of T1D. In particular, it would be desirable to block expression of KIAA0350 in those patients that are more prone to develop the disease. In this regard, the therapeutic siRNAs described herein can be used to block expression of the gene product based on the patient signal, thereby inhibiting the pancreatic β-cell destruction that occurs in T1D.

REFERENCES

1. Cucca F, Lampis R, Congia M, et al. A correlation between the relative predisposition of MHC class II alleles to type 1 diabetes and the structure of their proteins. Human molecular genetics 2001; 10(19):2025-37.
2. Julier C, Hyer R N, Davies J, et al. Insulin-IGF2 region on chromosome 11p encodes a gene implicated in HLA-DR4-dependent diabetes susceptibility. Nature 1991; 354 (6349):155-9.
3. Barratt B J, Payne F, Lowe C E, et al. Remapping the insulin gene/IDDM2 locus in type 1 diabetes. Diabetes 2004; 53(7):1884-9.
4. Bell G I, Horita S, Karam J H. A polymorphic locus near the human insulin gene is associated with insulin-dependent diabetes mellitus. Diabetes 1984; 33(2):176-83.
5. Bottini N, Musumeci L, Alonso A, et al. A functional variant of lymphoid tyrosine phosphatase is associated with type I diabetes. Nature genetics 2004; 36(4):337-8.
6. Smyth D, Cooper J D, Collins J E, et al. Replication of an association between the lymphoid tyrosine phosphatase locus (LYP/PTPN22) with type 1 diabetes, and evidence for its role as a general autoimmunity locus. Diabetes 2004; 53(11):3020-3.
7. Nistico L, Buzzetti R, Pritchard L E, et al. The CTLA-4 gene region of chromosome 2q33 is linked to, and associated with, type 1 diabetes. Belgian Diabetes Registry. Human molecular genetics 1996; 5(7):1075-80.
8. Ueda H, Howson J M, Esposito L, et al. Association of the T-cell regulatory gene CTLA4 with susceptibility to autoimmune disease. Nature 2003; 423(6939):506-11.
9. Vella A, Cooper J D, Lowe C E, et al. Localization of a type 1 diabetes locus in the IL2RA/CD25 region by use of tag single-nucleotide polymorphisms. American journal of human genetics 2005; 76(5):773-9.
10. Leiter E H, Lee C H. Mouse models and the genetics of diabetes: is there evidence for genetic overlap between type 1 and type 2 diabetes? Diabetes 2005; 54 Suppl 2:S151-8.
11. Gunderson K L, Steemers F J, Lee G, Mendoza L G, Chee M S. A genome-wide scalable SNP genotyping assay using microarray technology. Nature genetics 2005; 37(5):549-54.
12. Fisher R A. Statistical Methods for Research Workers. 1958; Hafner, N.Y., ed. 13.
13. de Bakker P I, McVean G, Sabeti P C, et al. A high-resolution HLA and SNP haplotype map for disease association studies in the extended human MHC. Nature genetics 2006; 38(10):1166-72.
14. Hirschhorn J N, Lohmueller K, Byrne E, Hirschhorn K. A comprehensive review of genetic association studies. Genet Med 2002; 4(2):45-61.
15. Finn R D, Mistry J, Schuster-Bockler B, et al. Pfam: clans, web tools and services. Nucleic acids research 2006; 34(Database issue):D247-51.
16. Cambi A, Figdor C G. Levels of complexity in pathogen recognition by C-type lectins. Current opinion in immunology 2005; 17(4):345-51.

TABLE 1A

TDT and case-control association study results for markers residing in the LD block harboring KIAA0350, and for the other GW significant loci. Minor allele frequencies (MAF), P-values and odds ratios (OR) are shown. The ORs shown are for the minor alleles (as observed in the controls). Combined P-values are also shown, together with the gene in which the markers reside or are nearest to. P-values are two-sided in each instance.

| | | | Case-control cohort | | | | Triad cohort (n = 467) | | | | |
|---|---|---|---|---|---|---|---|---|---|---|---|
| | | | Aff allele | Ctrl Allele | | | | | | | |
| Chr | SNP | Allele | freq (n = 561) | Freq (n = 1,143) | OR [95% CI] | P-value | Alleles | Trans:untrans | TDT P-value | P-value combined | Locus |
| 1 | rs2476601 | A | 0.1471 | 0.08757 | 1.80 [1.44, 2.24] | $1.32 \times 10^{-7}$ | A:G | 137:64 | $2.62 \times 10^{-7}$ | $1.11 \times 10^{-12}$ | PTPN22 |
| 11 | rs1004446 | T | 0.254 | 0.3539 | 0.62 [0.53, 0.73] | $4.38 \times 10^{-9}$ | T:C | 160:228 | $5.56 \times 10^{-4}$ | $6.75 \times 10^{-11}$ | INS |
| 16 | rs2903692 | A | 0.2834 | 0.3782 | 0.65 [0.56, 0.76] | $4.77 \times 10^{-8}$ | A:G | 170:251 | $7.89 \times 10^{-5}$ | $1.03 \times 10^{-10}$ | KIAA0350 |
| 11 | rs6356 | A | 0.4602 | 0.3593 | 1.52 [1.31, 1.76] | $1.78 \times 10^{-8}$ | A:G | 255:197 | 0.00637 | $2.70 \times 10^{-9}$ | INS |
| 16 | rs725613 | C | 0.3004 | 0.3898 | 0.67 [0.58, 0.78] | $3.24 \times 10^{-7}$ | C:A | 178:248 | $6.95 \times 10^{-4}$ | $5.23 \times 10^{-9}$ | KIAA0350 |
| 7 | rs10255021 | A | 0.06667 | 0.1095 | 0.58 [0.44, 0.77] | $1.16 \times 10^{-4}$ | A:G | 18:57 | $6.69 \times 10^{-6}$ | $1.71 \times 10^{-8}$ | COL1A2 |
| 11 | rs10770141 | A | 0.2799 | 0.373 | 0.65 [0.56, 0.76] | $7.20 \times 10^{-8}$ | A:G | 186:234 | 0.01917 | $2.95 \times 10^{-8}$ | INS |
| 1 | rs672797 | T | 0.2257 | 0.1589 | 1.54 [1.29, 1.85] | $2.67 \times 10^{-6}$ | T:G | 177:119 | $7.49 \times 10^{-4}$ | $4.20 \times 10^{-8}$ | LPHN2 |
| 16 | rs17673553 | G | 0.2023 | 0.2791 | 0.66 [0.55, 0.78] | $1.30 \times 10^{-6}$ | G:A | 146:203 | 0.00228 | $6.12 \times 10^{-8}$ | KIAA0350 |
| 11 | rs7111341 | T | 0.1843 | 0.2631 | 0.63 [0.53, 0.76] | $3.77 \times 10^{-7}$ | T:C | 138:185 | 0.008919 | $6.90 \times 10^{-8}$ | INS |
| 11 | rs10743152 | T | 0.271 | 0.3574 | 0.67 [0.57, 0.78] | $4.73 \times 10^{-7}$ | T:C | 179:233 | 0.007805 | $7.53 \times 10^{-8}$ | INS |

TABLE 1B

Replication of stage 1 results in a family-based analysis of an independent cohort of 1333 affected offspring derived from 939 nuclear families. Family-based association P-values were computed using TDT. The ORs shown are for the minor alleles (as observed in the controls). P-values are also shown, together with the gene in which the markers reside or are nearest to. P-values are two-sided in each instance.

| | | | All trios (939 nuclear families) | | Caucasians only (839 nuclear families) | | Stage 1 and replication |
|---|---|---|---|---|---|---|---|
| Chr | SNP | Alleles | Trans:untrans | TDT P-value | Trans:untrans | TDT P-value | Combined P-value |
| 16 | rs2903692 | A:G | 466:538 | 0.023 | 438:504 | 0.032 | $6.70 \times 10^{-11}$ |
| 16 | rs725613 | C:A | 461:559 | $2.15 \times 10^{-3}$ | 435:520 | $5.95 \times 10^{-3}$ | $8.86 \times 10^{-11}$ |
| 16 | rs17673553 | G:A | 371:448 | $7.13 \times 10^{-3}$ | 348:422 | $7.66 \times 10^{-3}$ | $2.74 \times 10^{-9}$ |

TABLE 1C

All associated SNPs in the KIAA0350 LD block with combined $P < 10^{-5}$ in Stage 1 and genotyped in the replication cohort. Data are shown separately for the case-control, initial TDT and replication TDT (including presenting total and Caucasians only separately). P-values are two-sided in each instance. Note that rs12103174 failed on the Sequenom iPLEX platform.

| | | Stage 1 Case-control cohort | | | | Stage 1 Trio cohort | | |
|---|---|---|---|---|---|---|---|---|
| | | Aff | Ctrl | | | | | |
| SNP | Allele | Allele Freq | Allele Freq | OR [95% CI] | P-val | Alleles | Trans:Untrans | TDT P-val |
| rs12931878 | G | 0.16 | 0.225 | 0.66 [0.54, 0.79] | $1.01 \times 10^{-5}$ | G:A | 128:162 | 0.046 |
| rs12923849 | A | 0.137 | 0.202 | 0.63 [0.52, 0.77] | $4.12 \times 10^{-6}$ | A:G | 119:153 | 0.039 |
| rs17229044 | T | 0.171 | 0.24 | 0.65 [0.54, 0.79] | $4.72 \times 10^{-6}$ | T:C | 141:181 | 0.026 |
| rs13330041 | A | 0.172 | 0.246 | 0.64 [0.53, 0.76] | $1.01 \times 10^{-6}$ | A:G | 145:183 | 0.036 |
| rs725613 | C | 0.3 | 0.39 | 0.67 [0.58, 0.78] | $3.24 \times 10^{-7}$ | C:A | 178:248 | $6.95 \times 10^{-4}$ |
| rs2041670 | T | 0.265 | 0.345 | 0.68 [0.58, 0.80] | $2.01 \times 10^{-6}$ | T:C | 172:233 | 0.0024 |
| rs7200786 | A | 0.507 | 0.436 | 1.33 [1.15, 1.54] | $9.30 \times 10^{-5}$ | A:G | 258:199 | 0.0058 |
| rs12924729 | A | 0.273 | 0.349 | 0.70 [0.60, 0.82] | $1.44 \times 10^{-5}$ | A:G | 139:194 | 0.0026 |
| rs12599402 | C | 0.383 | 0.47 | 0.70 [0.60, 0.81] | $1.40 \times 10^{-6}$ | C:T | 198:250 | 0.014 |
| rs998592 | A | 0.366 | 0.447 | 0.72 [0.62, 0.83] | $7.29 \times 10^{-6}$ | A:G | 194:250 | 0.0079 |
| rs9933507 | C | 0.38 | 0.462 | 0.71 [0.62, 0.82] | $4.74 \times 10^{-6}$ | C:T | 195:252 | 0.007 |
| rs12103174 | G | 0.382 | 0.464 | 0.71 [0.62, 0.83] | $6.09 \times 10^{-6}$ | G:A | 200:251 | 0.016 |
| rs2903692 | A | 0.283 | 0.378 | 0.65 [0.56, 0.76] | $4.77 \times 10^{-8}$ | A:G | 170:251 | $7.89 \times 10^{-5}$ |
| rs17673553 | G | 0.202 | 0.279 | 0.66 [0.55, 0.78] | $1.30 \times 10^{-6}$ | G:A | 146:203 | 0.0023 |

| | Replication Trio cohort | | Replication Trio cohort (Caucasians only) | | All |
|---|---|---|---|---|---|
| SNP | Trans:Untrans | TDT P-val | Trans:Untrans | TDT P-val | P-val Combined |
| rs12931878 | 300:364 | 0.013 | 284:339 | 0.028 | $2.90 \times 10^{-7}$ |
| rs12923849 | 275:347 | 0.0039 | 260:327 | 0.0057 | $3.43 \times 10^{-8}$ |
| rs17229044 | 322:393 | 0.0079 | 303:369 | 0.011 | $5.55 \times 10^{-8}$ |
| rs13330041 | 327:407 | 0.0031 | 306:380 | 0.0047 | $6.80 \times 10^{-9}$ |
| rs725613 | 461:559 | 0.0021 | 435:520 | 0.006 | $8.86 \times 10^{-11}$ |
| rs2041670 | 430:530 | 0.0012 | 407:493 | 0.0041 | $6.70 \times 10^{-10}$ |
| rs7200786 | 621:541 | 0.019 | 569:504 | 0.047 | $9.12 \times 10^{-7}$ |
| rs12924729 | 438:530 | 0.0031 | 416:495 | 0.0089 | $1.46 \times 10^{-8}$ |
| rs12599402 | 476:575 | 0.0023 | 435:531 | 0.002 | $3.19 \times 10^{-9}$ |

TABLE 1C-continued

All associated SNPs in the KIAA0350 LD block with combined P < 10$^{-5}$ in Stage 1 and genotyped in the replication cohort. Data are shown separately for the case-control, initial TDT and replication TDT (including presenting total and Caucasians only separately). P-values are two-sided in each instance. Note that rs12103174 failed on the Sequenom iPLEX platform.

| | | | | | |
|---|---|---|---|---|---|
| rs998592 | 494:602 | 0.0011 | 459:559 | 0.0017 | 4.96 × 10$^{-9}$ |
| rs9933507 | 501:611 | 9.7 × 10$^{-4}$ | 465:562 | 0.0025 | 2.66 × 10$^{-9}$ |
| rs12103174 | — | — | — | — | — |
| rs2903692 | 466:538 | 0.023 | 438:504 | 0.032 | 6.69 × 10$^{-11}$ |
| rs17673553 | 371:448 | 0.0071 | 348:422 | 0.0077 | 2.74 × 10$^{-9}$ |

TABLE 2

All 392 associated SNPs in the MHC region that survived Bonferroni correction. P-values are two-sided in each instance.

| | | | Case-control cohort | | | | Triad cohort (n = 467) | | | |
|---|---|---|---|---|---|---|---|---|---|---|
| | | | Aff Allele | Ctrl Allele | | | | | | |
| Chr | SNP | Allele | Freq (n = 561) | Freq (n = 1,143) | OR [95% CI] | P-val | Alleles | Trans:Un-trans | TDT P-val | P-val combined |
| 6 | rs2647044 | A | 0.5443 | 0.1258 | 8.30 [6.97, 9.89] | 5.18 × 10$^{-142}$ | A:G | 134:20 | 4.06 × 10$^{-20}$ | <1.00 × 10$^{-16}$ |
| 6 | rs9275184 | C | 0.3403 | 0.09054 | 5.18 [4.28, 6.27] | 4.50 × 10$^{-72}$ | C:T | 260:42 | 4.26 × 10$^{-36}$ | <1.00 × 10$^{-16}$ |
| 6 | rs9275383 | T | 0.3482 | 0.1005 | 4.78 [3.98, 5.43] | 3.28 × 10$^{-69}$ | T:G | 239:45 | 1.15 × 10$^{-30}$ | <1.00 × 10$^{-16}$ |
| 6 | rs9275313 | T | 0.3624 | 0.1114 | 4.55 [3.79, 5.43] | 7.06 × 10$^{-67}$ | T:G | 213:42 | 9.29 × 10$^{-27}$ | <1.00 × 10$^{-16}$ |
| 6 | rs3957148 | G | 0.3402 | 0.0993 | 4.68 [3.89, 5.62] | 1.20 × 10$^{-66}$ | G:A | 264:48 | 2.19 × 10$^{-34}$ | <1.00 × 10$^{-16}$ |
| 6 | rs9275312 | G | 0.3743 | 0.1317 | 3.95 [3.33, 4.68] | 9.90 × 10$^{-60}$ | G:A | 289:65 | 1.11 × 10$^{-32}$ | <1.00 × 10$^{-16}$ |
| 6 | rs9275328 | T | 0.3741 | 0.1312 | 3.96 [3.34, 4.70] | 1.02 × 10$^{-59}$ | T:C | 288:65 | 1.71 × 10$^{-32}$ | <1.00 × 10$^{-16}$ |
| 6 | rs601945 | G | 0.3681 | 0.1239 | 4.12 [3.44, 4.93] | 1.53 × 10$^{-57}$ | G:A | 251:65 | 1.27 × 10$^{-25}$ | <1.00 × 10$^{-16}$ |
| 6 | rs3129871 | A | 0.09302 | 0.3507 | 0.19 [0.15, 0.24] | 1.87 × 10$^{-57}$ | A:C | 71:316 | 1.33 × 10$^{-35}$ | <1.00 × 10$^{-16}$ |
| 6 | rs2647050 | C | 0.1518 | 0.4221 | 0.25 [0.20, 0.29] | 1.02 × 10$^{-55}$ | C:T | 76:338 | 6.10 × 10$^{-38}$ | <1.00 × 10$^{-16}$ |
| 6 | rs2856718 | A | 0.1524 | 0.4221 | 0.25 [0.21, 0.30] | 1.59 × 10$^{-55}$ | A:G | 76:337 | 9.42 × 10$^{-38}$ | <1.00 × 10$^{-16}$ |
| 6 | rs2187668 | A | 0.3342 | 0.1122 | 3.97 [3.32, 4.76] | 2.39 × 10$^{-55}$ | A:G | 267:54 | 1.36 × 10$^{-32}$ | <1.00 × 10$^{-16}$ |
| 6 | rs16898264 | A | 0.1518 | 0.4209 | 0.25 [0.21, 0.30] | 3.06 × 10$^{-55}$ | A:G | 76:334 | 3.47 × 10$^{-37}$ | <1.00 × 10$^{-16}$ |
| 6 | rs2395173 | A | 0.09107 | 0.3326 | 0.20 [0.16, 0.25] | 2.35 × 10$^{-52}$ | A:G | 65:292 | 3.00 × 10$^{-33}$ | <1.00 × 10$^{-16}$ |
| 6 | rs3135338 | G | 0.08993 | 0.3173 | 0.21 [0.17, 0.27] | 5.55 × 10$^{-47}$ | G:A | 51:259 | 3.32 × 10$^{-32}$ | <1.00 × 10$^{-16}$ |
| 6 | rs2858331 | C | 0.2094 | 0.458 | 0.31 [0.27, 0.37] | 5.32 × 10$^{-45}$ | C:T | 105:350 | 1.56 × 10$^{-30}$ | <1.00 × 10$^{-16}$ |
| 6 | rs7745656 | T | 0.1176 | 0.3432 | 0.26 [0.21, 0.31] | 3.60 × 10$^{-44}$ | T:G | 62:275 | 3.99 × 10$^{-31}$ | <1.00 × 10$^{-16}$ |
| 6 | rs660895 | G | 0.4064 | 0.1855 | 3.01 [2.57, 3.53] | 1.28 × 10$^{-43}$ | G:A | 293:87 | 4.21 × 10$^{-26}$ | <1.00 × 10$^{-16}$ |
| 6 | rs9275555 | T | 0.4402 | 0.2147 | 2.88 [2.46, 3.36] | 2.54 × 10$^{-42}$ | T:C | 306:107 | 1.22 × 10$^{-22}$ | <1.00 × 10$^{-16}$ |
| 6 | rs9275595 | C | 0.4332 | 0.2113 | 2.85 [2.44, 3.33] | 1.72 × 10$^{-41}$ | C:T | 293:103 | 1.32 × 10$^{-21}$ | <1.00 × 10$^{-16}$ |
| 6 | rs9275371 | C | 0.47 | 0.2456 | 2.72 [2.34, 3.17] | 3.07 × 10$^{-41}$ | C:T | 288:104 | 1.49 × 10$^{-20}$ | <1.00 × 10$^{-16}$ |
| 6 | rs9275408 | C | 0.4642 | 0.2425 | 2.71 [2.33, 3.15] | 5.47 × 10$^{-39}$ | C:T | 316:119 | 3.54 × 10$^{-21}$ | <1.00 × 10$^{-16}$ |
| 6 | rs9275388 | C | 0.4661 | 0.2443 | 2.70 [2.32, 3.14] | 6.04 × 10$^{-39}$ | C:T | 317:122 | 1.32 × 10$^{-20}$ | <1.00 × 10$^{-16}$ |
| 6 | rs9275424 | G | 0.4651 | 0.2436 | 2.70 [2.32, 3.14] | 7.25 × 10$^{-39}$ | G:A | 320:122 | 4.60 × 10$^{-21}$ | <1.00 × 10$^{-16}$ |
| 6 | rs9275374 | T | 0.4652 | 0.2445 | 2.69 [2.31, 3.13] | 1.07 × 10$^{-38}$ | T:C | 319:122 | 6.54 × 10$^{-21}$ | <1.00 × 10$^{-16}$ |
| 6 | rs9275390 | C | 0.4652 | 0.2445 | 2.69 [2.31, 3.13] | 1.07 × 10$^{-38}$ | C:T | 320:121 | 2.64 × 10$^{-21}$ | <1.00 × 10$^{-16}$ |
| 6 | rs9275393 | A | 0.4652 | 0.2445 | 2.69 [2.31, 3.13] | 1.07 × 10$^{-38}$ | A:G | 321:122 | 3.24 × 10$^{-21}$ | <1.00 × 10$^{-16}$ |
| 6 | rs9275418 | G | 0.4652 | 0.2445 | 2.69 [2.31, 3.13] | 1.07 × 10$^{-38}$ | G:A | 321:122 | 3.24 × 10$^{-21}$ | <1.00 × 10$^{-16}$ |
| 6 | rs9275428 | G | 0.4652 | 0.2445 | 2.69 [2.31, 3.13] | 1.07 × 10$^{-38}$ | G:A | 321:122 | 3.24 × 10$^{-21}$ | <1.00 × 10$^{-16}$ |
| 6 | rs9275439 | C | 0.4652 | 0.2445 | 2.69 [2.31, 3.13] | 1.07 × 10$^{-38}$ | C:T | 321:122 | 3.24 × 10$^{-21}$ | <1.00 × 10$^{-16}$ |
| 6 | rs9275425 | A | 0.4651 | 0.2443 | 2.69 [2.31, 3.13] | 1.19 × 10$^{-38}$ | A:C | 321:122 | 3.24 × 10$^{-21}$ | <1.00 × 10$^{-16}$ |
| 6 | rs9275406 | T | 0.4652 | 0.2445 | 2.69 [2.31, 3.13] | 1.22 × 10$^{-38}$ | T:G | 318:121 | 5.34 × 10$^{-21}$ | <1.00 × 10$^{-16}$ |
| 6 | rs9275427 | T | 0.4652 | 0.2447 | 2.69 [2.31, 3.12] | 1.33 × 10$^{-38}$ | T:C | 321:122 | 3.24 × 10$^{-21}$ | <1.00 × 10$^{-16}$ |
| 6 | rs9275407 | T | 0.4676 | 0.2469 | 2.68 [2.30, 3.12] | 3.70 × 10$^{-38}$ | T:G | 305:117 | 5.61 × 10$^{-20}$ | <1.00 × 10$^{-16}$ |
| 6 | rs556025 | T | 0.4194 | 0.21 | 2.72 [2.32, 3.18] | 1.20 × 10$^{-36}$ | T:C | 211:86 | 4.07 × 10$^{-13}$ | <1.00 × 10$^{-16}$ |
| 6 | rs1063355 | A | 0.1649 | 0.3745 | 0.33 [0.28, 0.39] | 9.35 × 10$^{-36}$ | A:C | 101:308 | 1.38 × 10$^{-24}$ | <1.00 × 10$^{-16}$ |
| 6 | rs9357152 | G | 0.1062 | 0.2992 | 0.28 [0.23, 0.34] | 1.18 × 10$^{-35}$ | G:A | 66:263 | 1.77 × 10$^{-27}$ | <1.00 × 10$^{-16}$ |
| 6 | rs1046089 | A | 0.5196 | 0.3011 | 2.51 [2.16, 2.91] | 2.99 × 10$^{-34}$ | A:G | 311:137 | 2.02 × 10$^{-16}$ | <1.00 × 10$^{-16}$ |
| 6 | rs2395163 | C | 0.3904 | 0.1974 | 2.60 [2.22, 3.05] | 1.92 × 10$^{-33}$ | C:T | 263:90 | 3.33 × 10$^{-20}$ | <1.00 × 10$^{-16}$ |
| 6 | rs2242660 | T | 0.5507 | 0.3362 | 2.42 [2.09, 2.81] | 2.46 × 10$^{-32}$ | T:C | 284:119 | 2.05 × 10$^{-16}$ | <1.00 × 10$^{-16}$ |
| 6 | rs805303 | T | 0.5411 | 0.3338 | 2.35 [2.03, 2.73] | 4.64 × 10$^{-31}$ | T:C | 300:133 | 1.01 × 10$^{-15}$ | <1.00 × 10$^{-16}$ |
| 6 | rs3104404 | A | 0.07961 | 0.2428 | 0.27 [0.21, 0.34] | 3.58 × 10$^{-30}$ | A:C | 57:226 | 9.57 × 10$^{-24}$ | <1.00 × 10$^{-16}$ |
| 6 | rs3916765 | A | 0.2576 | 0.108 | 2.86 [2.37, 3.46] | 1.90 × 10$^{-29}$ | A:G | 218:63 | 2.32 × 10$^{-20}$ | <1.00 × 10$^{-16}$ |
| 6 | rs3129882 | G | 0.2647 | 0.4654 | 0.41 [0.35, 0.48] | 2.48 × 10$^{-29}$ | G:A | 123:334 | 5.61 × 10$^{-23}$ | <1.00 × 10$^{-16}$ |
| 6 | rs9275614 | G | 0.2629 | 0.1129 | 2.80 [2.33, 3.38] | 5.99 × 10$^{-29}$ | G:A | 219:64 | 3.15 × 10$^{-20}$ | <1.00 × 10$^{-16}$ |
| 6 | rs3763309 | A | 0.3832 | 0.2043 | 2.42 [2.07, 2.83] | 7.29 × 10$^{-29}$ | A:C | 277:105 | 1.37 × 10$^{-18}$ | <1.00 × 10$^{-16}$ |
| 6 | rs3763312 | A | 0.383 | 0.2043 | 2.42 [2.07, 2.83] | 8.90 × 10$^{-29}$ | A:G | 260:101 | 5.84 × 10$^{-17}$ | <1.00 × 10$^{-16}$ |
| 6 | rs9271366 | G | 0.0107 | 0.1247 | 0.08 [0.04, 0.14] | 1.47 × 10$^{-28}$ | G:A | 11:118 | 4.48 × 10$^{-21}$ | <1.00 × 10$^{-16}$ |
| 6 | rs3129941 | A | 0.07754 | 0.2316 | 0.28 [0.22, 0.35] | 4.78 × 10$^{-28}$ | A:G | 56:214 | 6.87 × 10$^{-22}$ | <1.00 × 10$^{-16}$ |
| 6 | rs2395182 | G | 0.05526 | 0.198 | 0.24 [0.18, 0.31] | 8.86 × 10$^{-28}$ | G:T | 46:175 | 4.05 × 10$^{-18}$ | <1.00 × 10$^{-16}$ |
| 6 | rs2596560 | G | 0.3734 | 0.2009 | 2.37 [2.02, 2.78] | 2.83 × 10$^{-27}$ | G:A | 264:104 | 7.39 × 10$^{-17}$ | <1.00 × 10$^{-16}$ |
| 6 | rs910049 | A | 0.0814 | 0.2335 | 0.29 [0.23, 0.37] | 5.42 × 10$^{-27}$ | A:G | 58:210 | 1.62 × 10$^{-20}$ | <1.00 × 10$^{-16}$ |
| 6 | rs926070 | C | 0.1364 | 0.3056 | 0.36 [0.30, 0.43] | 7.95 × 10$^{-27}$ | C:T | 91:252 | 3.52 × 10$^{-18}$ | <1.00 × 10$^{-16}$ |
| 6 | rs9268005 | C | 0.1384 | 0.306 | 0.36 [0.30, 0.44] | 8.73 × 10$^{-26}$ | C:A | 86:226 | 2.26 × 10$^{-15}$ | <1.00 × 10$^{-16}$ |
| 6 | rs377763 | T | 0.3685 | 0.2018 | 2.31 [1.97, 2.71] | 1.36 × 10$^{-25}$ | T:G | 281:111 | 8.98 × 10$^{-18}$ | <1.00 × 10$^{-16}$ |

TABLE 2-continued

All 392 associated SNPs in the MHC region that survived Bonferroni correction. P-values are two-sided in each instance.

| | | | Case-control cohort | | | | Triad cohort (n = 467) | | | |
|---|---|---|---|---|---|---|---|---|---|---|
| | | | Aff Allele | Ctrl Allele | | | | | | |
| Chr | SNP | Allele | Freq (n = 561) | Freq (n = 1,143) | OR [95% CI] | P-val | Alleles | Trans:Un-trans | TDT P-val | P-val combined |
| 6 | rs9267522 | G | 0.3209 | 0.1654 | 2.39 [2.02, 2.82] | $3.89 \times 10^{-25}$ | G:A | 258:101 | $1.17 \times 10^{-16}$ | $<1.00 \times 10^{-16}$ |
| 6 | rs3129860 | A | 0.01526 | 0.1219 | 0.11 [0.07, 0.18] | $3.84 \times 10^{-25}$ | A:G | 13:116 | $1.21 \times 10^{-19}$ | $<1.00 \times 10^{-16}$ |
| 6 | rs3115663 | G | 0.3209 | 0.1658 | 2.38 [2.01, 2.81] | $5.56 \times 10^{-25}$ | G:A | 256:102 | $3.98 \times 10^{-16}$ | $<1.00 \times 10^{-16}$ |
| 6 | rs805294 | C | 0.5205 | 0.3368 | 2.14 [1.85, 2.47] | $7.28 \times 10^{-25}$ | C:T | 305:151 | $5.53 \times 10^{-13}$ | $<1.00 \times 10^{-16}$ |
| 6 | rs3117583 | C | 0.3191 | 0.1654 | 2.37 [2.00, 2.80] | $1.20 \times 10^{-24}$ | C:T | 257:101 | $1.65 \times 10^{-16}$ | $<1.00 \times 10^{-16}$ |
| 6 | rs3130618 | A | 0.3187 | 0.1654 | 2.36 [2.00, 2.79] | $1.56 \times 10^{-24}$ | A:C | 258:102 | $2.00 \times 10^{-16}$ | $<1.00 \times 10^{-16}$ |
| 6 | rs2763979 | T | 0.5089 | 0.3341 | 2.07 [1.79, 2.39] | $8.74 \times 10^{-23}$ | T:C | 280:154 | $1.47 \times 10^{-9}$ | $<1.00 \times 10^{-16}$ |
| 6 | rs707928 | C | 0.4875 | 0.3146 | 2.07 [1.79, 2.39] | $1.00 \times 10^{-22}$ | C:T | 302:141 | $2.02 \times 10^{-14}$ | $<1.00 \times 10^{-16}$ |
| 6 | rs2856683 | C | 0.4113 | 0.2469 | 2.13 [1.83, 2.48] | $1.24 \times 10^{-22}$ | C:A | 274:125 | $8.70 \times 10^{-14}$ | $<1.00 \times 10^{-16}$ |
| 6 | rs3129934 | T | 0.04278 | 0.1575 | 0.24 [0.18, 0.33] | $3.23 \times 10^{-22}$ | T:C | 33:151 | $3.35 \times 10^{-18}$ | $<1.00 \times 10^{-16}$ |
| 6 | rs9268615 | A | 0.5998 | 0.4252 | 2.03 [1.75, 2.34] | $9.07 \times 10^{-22}$ | A:G | 306:175 | $2.33 \times 10^{-9}$ | $<1.00 \times 10^{-16}$ |
| 6 | rs9267649 | A | 0.04545 | 0.1566 | 0.26 [0.19, 0.35] | $6.41 \times 10^{-21}$ | A:G | 43:129 | $5.47 \times 10^{-11}$ | $<1.00 \times 10^{-16}$ |
| 6 | rs2071550 | T | 0.1747 | 0.3269 | 0.44 [0.37, 0.52] | $1.05 \times 10^{-20}$ | T:G | 100:244 | $8.23 \times 10^{-15}$ | $<1.00 \times 10^{-16}$ |
| 6 | rs9368741 | A | 0.1756 | 0.3272 | 0.44 [0.37, 0.52] | $1.51 \times 10^{-20}$ | A:G | 99:243 | $6.88 \times 10^{-15}$ | $<1.00 \times 10^{-16}$ |
| 6 | rs7755852 | A | 0.2731 | 0.4388 | 0.48 [0.41, 0.56] | $1.98 \times 10^{-20}$ | A:G | 125:229 | $3.25 \times 10^{-8}$ | $<1.00 \times 10^{-16}$ |
| 6 | rs17423968 | A | 0.04545 | 0.1527 | 0.26 [0.20, 0.36] | $6.34 \times 10^{-20}$ | A:G | 29:144 | $2.26 \times 10^{-18}$ | $<1.00 \times 10^{-16}$ |
| 6 | rs9267992 | G | 0.02585 | 0.1207 | 0.19 [0.13, 0.29] | $7.57 \times 10^{-20}$ | G:A | 23:109 | $7.14 \times 10^{-14}$ | $<1.00 \times 10^{-16}$ |
| 6 | rs1150754 | A | 0.2487 | 0.1251 | 2.31 [1.93, 2.78] | $7.91 \times 10^{-20}$ | A:G | 212:62 | $1.28 \times 10^{-19}$ | $<1.00 \times 10^{-16}$ |
| 6 | rs3134954 | G | 0.02852 | 0.1242 | 0.21 [0.14, 0.30] | $1.39 \times 10^{-19}$ | G:A | 32:101 | $2.19 \times 10^{-9}$ | $<1.00 \times 10^{-16}$ |
| 6 | rs2395175 | A | 0.2536 | 0.1309 | 2.26 [1.88, 2.70] | $4.82 \times 10^{-19}$ | A:G | 204:76 | $2.02 \times 10^{-14}$ | $<1.00 \times 10^{-16}$ |
| 6 | rs9268528 | G | 0.5777 | 0.4164 | 1.92 [1.66, 2.22] | $8.18 \times 10^{-19}$ | G:A | 310:174 | $6.34 \times 10^{-10}$ | $<1.00 \times 10^{-16}$ |
| 6 | rs1794282 | A | 0.1961 | 0.08968 | 2.48 [2.02, 3.04] | $1.00 \times 10^{-18}$ | A:G | 177:43 | $1.65 \times 10^{-19}$ | $<1.00 \times 10^{-16}$ |
| 6 | rs241425 | T | 0.2611 | 0.4159 | 0.50 [0.42, 0.58] | $1.15 \times 10^{-18}$ | T:C | 116:301 | $1.31 \times 10^{-19}$ | $<1.00 \times 10^{-16}$ |
| 6 | rs3129962 | A | 0.1955 | 0.09011 | 2.45 [2.00, 3.02] | $2.20 \times 10^{-18}$ | A:G | 131:41 | $6.77 \times 10^{-12}$ | $<1.00 \times 10^{-16}$ |
| 6 | rs3132946 | A | 0.02406 | 0.112 | 0.20 [0.13, 0.29] | $2.31 \times 10^{-18}$ | A:G | 32:92 | $7.12 \times 10^{-8}$ | $<1.00 \times 10^{-16}$ |
| 6 | rs12192104 | G | 0.04375 | 0.1435 | 0.27 [0.20, 0.37] | $2.90 \times 10^{-18}$ | G:T | 42:123 | $2.87 \times 10^{-10}$ | $<1.00 \times 10^{-16}$ |
| 6 | rs2858870 | G | 0.04456 | 0.1435 | 0.28 [0.20, 0.38] | $5.54 \times 10^{-18}$ | G:A | 41:125 | $7.05 \times 10^{-11}$ | $<1.00 \times 10^{-16}$ |
| 6 | rs9268542 | G | 0.5775 | 0.4208 | 1.88 [1.63, 2.17] | $7.19 \times 10^{-18}$ | G:A | 306:174 | $1.69 \times 10^{-9}$ | $<1.00 \times 10^{-16}$ |
| 6 | rs2227956 | C | 0.05348 | 0.1562 | 0.31 [0.23, 0.41] | $8.19 \times 10^{-18}$ | C:T | 55:130 | $3.51 \times 10^{-8}$ | $<1.00 \times 10^{-16}$ |
| 6 | rs7775397 | G | 0.1952 | 0.09143 | 2.41 [1.96, 2.96] | $8.70 \times 10^{-18}$ | G:T | 176:41 | $4.98 \times 10^{-20}$ | $<1.00 \times 10^{-16}$ |
| 6 | rs6903608 | C | 0.1996 | 0.3412 | 0.48 [0.41, 0.57] | $1.61 \times 10^{-17}$ | C:T | 105:257 | $1.36 \times 10^{-15}$ | $<1.00 \times 10^{-16}$ |
| 6 | rs3134603 | T | 0.03209 | 0.1218 | 0.24 [0.17, 0.34] | $1.82 \times 10^{-17}$ | T:C | 35:109 | $6.97 \times 10^{-10}$ | $<1.00 \times 10^{-16}$ |
| 6 | rs1015166 | T | 0.4332 | 0.2883 | 1.89 [1.63, 2.19] | $3.94 \times 10^{-17}$ | T:C | 286:167 | $2.26 \times 10^{-8}$ | $<1.00 \times 10^{-16}$ |
| 6 | rs3130299 | G | 0.1786 | 0.312 | 0.48 [0.40, 0.57] | $1.50 \times 10^{-16}$ | G:A | 105:217 | $4.33 \times 10^{-10}$ | $<1.00 \times 10^{-16}$ |
| 6 | rs1077393 | C | 0.3936 | 0.5424 | 0.55 [0.47, 0.63] | $3.78 \times 10^{-16}$ | C:T | 156:259 | $4.28 \times 10^{-7}$ | $<1.00 \times 10^{-16}$ |
| 6 | rs2395157 | G | 0.4162 | 0.2773 | 1.86 [1.60, 2.16] | $5.42 \times 10^{-16}$ | G:A | 267:139 | $2.12 \times 10^{-10}$ | $<1.00 \times 10^{-16}$ |
| 6 | rs241427 | T | 0.208 | 0.3428 | 0.50 [0.43, 0.60] | $6.77 \times 10^{-16}$ | T:C | 107:253 | $1.42 \times 10^{-14}$ | $<1.00 \times 10^{-16}$ |
| 6 | rs13199787 | T | 0.287 | 0.4296 | 0.53 [0.46, 0.62] | $8.41 \times 10^{-16}$ | T:C | 128:290 | $2.31 \times 10^{-15}$ | $<1.00 \times 10^{-16}$ |
| 6 | rs1980495 | G | 0.416 | 0.2749 | 1.88 [1.61, 2.19] | $9.31 \times 10^{-16}$ | G:T | 232:121 | $3.46 \times 10^{-9}$ | $<1.00 \times 10^{-16}$ |
| 6 | rs3793126 | G | 0.4337 | 0.295 | 1.83 [1.58, 2.12] | $1.20 \times 10^{-15}$ | G:A | 226:133 | $9.18 \times 10^{-7}$ | $<1.00 \times 10^{-16}$ |
| 6 | rs3117098 | C | 0.2023 | 0.3338 | 0.51 [0.43, 0.60] | $1.97 \times 10^{-15}$ | C:T | 116:258 | $2.09 \times 10^{-13}$ | $<1.00 \times 10^{-16}$ |
| 6 | rs1052486 | C | 0.3993 | 0.5449 | 0.56 [0.48, 0.64] | $2.34 \times 10^{-15}$ | C:T | 106:191 | $8.13 \times 10^{-7}$ | $<1.00 \times 10^{-16}$ |
| 6 | rs1270942 | C | 0.1898 | 0.09493 | 2.23 [1.82, 2.74] | $4.44 \times 10^{-15}$ | C:T | 178:51 | $4.76 \times 10^{-17}$ | $<1.00 \times 10^{-16}$ |
| 6 | rs2844697 | A | 0.4795 | 0.3419 | 1.77 [1.53, 2.05] | $9.99 \times 10^{-15}$ | A:G | 279:178 | $2.31 \times 10^{-6}$ | $<1.00 \times 10^{-16}$ |
| 6 | rs558702 | T | 0.1907 | 0.09684 | 2.20 [1.79, 2.69] | $1.23 \times 10^{-14}$ | T:C | 173:51 | $3.60 \times 10^{-16}$ | $<1.00 \times 10^{-16}$ |
| 6 | rs3134943 | A | 0.03743 | 0.1185 | 0.29 [0.21, 0.40] | $1.31 \times 10^{-14}$ | A:G | 42:101 | $8.06 \times 10^{-7}$ | $<1.00 \times 10^{-16}$ |
| 6 | rs3130617 | C | 0.1266 | 0.239 | 0.46 [0.38, 0.56] | $1.56 \times 10^{-14}$ | C:T | 81:191 | $2.56 \times 10^{-11}$ | $<1.00 \times 10^{-16}$ |
| 6 | rs389884 | C | 0.1881 | 0.09536 | 2.20 [1.79, 2.70] | $1.77 \times 10^{-14}$ | C:T | 175:50 | $7.86 \times 10^{-17}$ | $<1.00 \times 10^{-16}$ |
| 6 | rs9267658 | T | 0.03214 | 0.1098 | 0.27 [0.19, 0.38] | $1.79 \times 10^{-14}$ | T:C | 33:92 | $1.31 \times 10^{-7}$ | $<1.00 \times 10^{-16}$ |
| 6 | rs13206011 | C | 0.2923 | 0.4282 | 0.55 [0.47, 0.64] | $1.80 \times 10^{-14}$ | C:T | 129:288 | $6.90 \times 10^{-15}$ | $<1.00 \times 10^{-16}$ |
| 6 | rs7756516 | T | 0.3824 | 0.5219 | 0.57 [0.49, 0.66] | $1.80 \times 10^{-14}$ | T:C | 139:313 | $2.74 \times 10^{-16}$ | $<1.00 \times 10^{-16}$ |
| 6 | rs1480380 | T | 0.1702 | 0.08268 | 2.28 [1.84, 2.82] | $2.33 \times 10^{-14}$ | T:C | 151:54 | $1.25 \times 10^{-11}$ | $<1.00 \times 10^{-16}$ |
| 6 | rs10807113 | A | 0.3846 | 0.5237 | 0.57 [0.49, 0.66] | $2.43 \times 10^{-14}$ | A:C | 139:312 | $3.75 \times 10^{-16}$ | $<1.00 \times 10^{-16}$ |
| 6 | rs3817963 | G | 0.4198 | 0.2892 | 1.78 [1.53, 2.05] | $2.76 \times 10^{-14}$ | G:A | 271:151 | $5.17 \times 10^{-9}$ | $<1.00 \times 10^{-16}$ |
| 6 | rs492899 | G | 0.1756 | 0.08713 | 2.23 [1.81, 2.76] | $3.76 \times 10^{-14}$ | G:A | 131:57 | $6.78 \times 10^{-8}$ | $<1.00 \times 10^{-16}$ |
| 6 | rs3134942 | A | 0.2214 | 0.1219 | 2.05 [1.70, 2.47] | $4.68 \times 10^{-14}$ | A:C | 168:65 | $1.50 \times 10^{-11}$ | $<1.00 \times 10^{-16}$ |
| 6 | rs2855812 | T | 0.3455 | 0.2246 | 1.82 [1.56, 2.13] | $5.60 \times 10^{-14}$ | T:G | 241:126 | $1.94 \times 10^{-9}$ | $<1.00 \times 10^{-16}$ |
| 6 | rs652888 | C | 0.3152 | 0.199 | 1.85 [1.57, 2.18] | $7.12 \times 10^{-14}$ | C:T | 244:108 | $4.20 \times 10^{-13}$ | $<1.00 \times 10^{-16}$ |
| 6 | rs1265759 | G | 0.2812 | 0.4129 | 0.56 [0.48, 0.65] | $7.41 \times 10^{-14}$ | G:A | 160:288 | $1.47 \times 10^{-9}$ | $<1.00 \times 10^{-16}$ |
| 6 | rs2734583 | C | 0.1962 | 0.1034 | 2.12 [1.73, 2.59] | $8.54 \times 10^{-14}$ | C:T | 168:60 | $8.52 \times 10^{-13}$ | $<1.00 \times 10^{-16}$ |
| 6 | rs241448 | C | 0.157 | 0.2731 | 0.50 [0.41, 0.60] | $8.73 \times 10^{-14}$ | C:T | 108:207 | $2.43 \times 10^{-8}$ | $<1.00 \times 10^{-16}$ |
| 6 | rs9271568 | A | 0.4383 | 0.3088 | 1.75 [1.51, 2.03] | $1.23 \times 10^{-13}$ | A:G | 273:147 | $7.84 \times 10^{-10}$ | $<1.00 \times 10^{-16}$ |
| 6 | rs241424 | C | 0.3913 | 0.5263 | 0.58 [0.50, 0.67] | $1.25 \times 10^{-13}$ | C:T | 151:307 | $3.11 \times 10^{-13}$ | $<1.00 \times 10^{-16}$ |
| 6 | rs3131296 | A | 0.2196 | 0.1219 | 2.03 [1.68, 2.45] | $1.76 \times 10^{-13}$ | A:G | 193:66 | $2.99 \times 10^{-15}$ | $<1.00 \times 10^{-16}$ |
| 6 | rs7762279 | C | 0.1774 | 0.09055 | 2.17 [1.76, 2.67] | $1.96 \times 10^{-13}$ | C:T | 159:50 | $4.71 \times 10^{-14}$ | $<1.00 \times 10^{-16}$ |
| 6 | rs3135353 | A | 0.2193 | 0.1226 | 2.01 [1.66, 2.44] | $2.18 \times 10^{-13}$ | A:G | 190:68 | $3.07 \times 10^{-13}$ | $<1.00 \times 10^{-16}$ |
| 6 | rs3117582 | C | 0.1845 | 0.09632 | 2.12 [1.73, 2.61] | $2.80 \times 10^{-13}$ | C:A | 163:52 | $3.73 \times 10^{-14}$ | $<1.00 \times 10^{-16}$ |
| 6 | rs3099844 | A | 0.205 | 0.112 | 2.05 [1.68, 2.48] | $2.95 \times 10^{-13}$ | A:C | 179:72 | $1.44 \times 10^{-11}$ | $<1.00 \times 10^{-16}$ |
| 6 | rs241440 | A | 0.1586 | 0.271 | 1.77 [1.53, 2.05] | $3.33 \times 10^{-13}$ | A:G | 108:216 | $1.97 \times 10^{-9}$ | $<1.00 \times 10^{-16}$ |
| 6 | rs1265758 | T | 0.2773 | 0.4048 | 2.20 [1.79, 2.69] | $3.72 \times 10^{-13}$ | T:C | 160:287 | $1.89 \times 10^{-9}$ | $<1.00 \times 10^{-16}$ |
| 6 | rs9461799 | C | 0.2914 | 0.4195 | 0.29 [0.21, 0.40] | $4.23 \times 10^{-13}$ | C:T | 132:280 | $3.07 \times 10^{-13}$ | $<1.00 \times 10^{-16}$ |

TABLE 2-continued

All 392 associated SNPs in the MHC region that survived Bonferroni correction. P-values are two-sided in each instance.

| | | | Case-control cohort | | | | Triad cohort (n = 467) | | | |
|---|---|---|---|---|---|---|---|---|---|---|
| | | | Aff Allele | Ctrl Allele | | | | | | |
| Chr | SNP | Allele | Freq (n = 561) | Freq (n = 1,143) | OR [95% CI] | P-val | Alleles | Trans:Un-trans | TDT P-val | P-val combined |
| 6 | rs241452 | G | 0.1607 | 0.2728 | 0.46 [0.38, 0.56] | $4.65 \times 10^{-13}$ | G:A | 111:212 | $1.91 \times 10^{-8}$ | $<1.00 \times 10^{-16}$ |
| 6 | rs2395150 | G | 0.2781 | 0.4046 | 2.20 [1.79, 2.70] | $5.39 \times 10^{-13}$ | G:A | 162:288 | $2.86 \times 10^{-9}$ | $<1.00 \times 10^{-16}$ |
| 6 | rs3131379 | T | 0.1872 | 0.09939 | 0.27 [0.19, 0.38] | $6.04 \times 10^{-13}$ | T:C | 178:55 | $7.76 \times 10^{-16}$ | $<1.00 \times 10^{-16}$ |
| 6 | rs1003878 | T | 0.31 | 0.1984 | 0.55 [0.47, 0.64] | $6.13 \times 10^{-13}$ | T:C | 238:114 | $3.86 \times 10^{-11}$ | $<1.00 \times 10^{-16}$ |
| 6 | rs241453 | T | 0.1604 | 0.2717 | 0.57 [0.49, 0.66] | $6.19 \times 10^{-13}$ | T:C | 107:210 | $7.25 \times 10^{-9}$ | $<1.00 \times 10^{-16}$ |
| 6 | rs1894406 | A | 0.2158 | 0.3361 | 2.28 [1.84, 2.82] | $6.44 \times 10^{-13}$ | A:G | 130:248 | $1.29 \times 10^{-9}$ | $<1.00 \times 10^{-16}$ |
| 6 | rs241447 | G | 0.1616 | 0.273 | 0.57 [0.49, 0.66] | $6.61 \times 10^{-13}$ | G:A | 110:209 | $2.97 \times 10^{-8}$ | $<1.00 \times 10^{-16}$ |
| 6 | rs12177980 | A | 0.2923 | 0.4189 | 1.78 [1.51, 2.07] | $7.87 \times 10^{-13}$ | A:G | 132:280 | $3.07 \times 10^{-13}$ | $<1.00 \times 10^{-16}$ |
| 6 | rs434841 | A | 0.434 | 0.311 | 2.23 [1.81, 2.76] | $1.56 \times 10^{-12}$ | A:G | 282:146 | $4.90 \times 10^{-11}$ | $<1.00 \times 10^{-16}$ |
| 6 | rs2858308 | A | 0.04635 | 0.1226 | 2.05 [1.70, 2.47] | $1.77 \times 10^{-12}$ | A:C | 44:108 | $2.09 \times 10^{-7}$ | $<1.00 \times 10^{-16}$ |
| 6 | rs3130048 | C | 0.3663 | 0.2511 | 1.82 [1.56, 2.13] | $3.11 \times 10^{-12}$ | C:T | 275:144 | $1.56 \times 10^{-10}$ | $<1.00 \times 10^{-16}$ |
| 6 | rs6901084 | T | 0.3458 | 0.4715 | 1.85 [1.57, 2.18] | $3.26 \times 10^{-12}$ | T:C | 136:279 | $2.23 \times 10^{-12}$ | $<1.00 \times 10^{-16}$ |
| 6 | rs3104402 | T | 0.006239 | 0.05512 | 0.56 [0.48, 0.65] | $4.38 \times 10^{-12}$ | T:G | 0:53 | $3.34 \times 10^{-13}$ | $<1.00 \times 10^{-16}$ |
| 6 | rs2395185 | T | 0.4483 | 0.3275 | 2.12 [1.73, 2.59] | $6.24 \times 10^{-12}$ | T:G | 276:161 | $3.77 \times 10^{-8}$ | $<1.00 \times 10^{-16}$ |
| 6 | rs2051549 | C | 0.5125 | 0.3883 | 0.50 [0.41, 0.60] | $6.26 \times 10^{-12}$ | C:T | 268:121 | $9.11 \times 10^{-14}$ | $<1.00 \times 10^{-16}$ |
| 6 | rs1150752 | G | 0.1617 | 0.08304 | 1.75 [1.51, 2.03] | $7.99 \times 10^{-12}$ | G:A | 150:50 | $1.54 \times 10^{-10}$ | $<1.00 \times 10^{-16}$ |
| 6 | rs7775228 | C | 0.06798 | 0.1499 | 0.58 [0.50, 0.67] | $8.41 \times 10^{-12}$ | C:T | 52:126 | $2.91 \times 10^{-8}$ | $<1.00 \times 10^{-16}$ |
| 6 | rs2251396 | T | 0.3708 | 0.2575 | 2.03 [1.68, 2.45] | $9.46 \times 10^{-12}$ | T:C | 250:135 | $4.60 \times 10^{-9}$ | $<1.00 \times 10^{-16}$ |
| 6 | rs7453920 | A | 0.5125 | 0.3898 | 2.17 [1.76, 2.67] | $1.07 \times 10^{-11}$ | A:G | 287:131 | $2.34 \times 10^{-14}$ | $<1.00 \times 10^{-16}$ |
| 6 | rs477515 | T | 0.426 | 0.3086 | 2.01 [1.66, 2.43] | $1.36 \times 10^{-11}$ | T:C | 257:149 | $8.32 \times 10^{-8}$ | $<1.00 \times 10^{-16}$ |
| 6 | rs2301271 | T | 0.5116 | 0.3897 | 2.12 [1.73, 2.61] | $1.43 \times 10^{-11}$ | T:C | 288:131 | $1.72 \times 10^{-14}$ | $<1.00 \times 10^{-16}$ |
| 6 | rs2071469 | A | 0.2437 | 0.3587 | 2.05 [1.68, 2.48] | $1.52 \times 10^{-11}$ | A:G | 137:253 | $4.26 \times 10^{-9}$ | $<1.00 \times 10^{-16}$ |
| 6 | rs2516049 | G | 0.426 | 0.3093 | 1.66 [1.43, 1.92] | $1.75 \times 10^{-11}$ | G:A | 271:153 | $1.00 \times 10^{-8}$ | $<1.00 \times 10^{-16}$ |
| 6 | rs2442749 | G | 0.41 | 0.2948 | 1.66 [1.43, 1.92] | $2.03 \times 10^{-11}$ | G:A | 273:157 | $2.22 \times 10^{-8}$ | $<1.00 \times 10^{-16}$ |
| 6 | rs1980493 | G | 0.2228 | 0.1331 | 1.87 [1.55, 2.25] | $2.59 \times 10^{-11}$ | G:A | 187:79 | $3.55 \times 10^{-11}$ | $<1.00 \times 10^{-16}$ |
| 6 | rs3134792 | C | 0.176 | 0.0952 | 2.03 [1.64, 2.51] | $2.67 \times 10^{-11}$ | C:A | 139:61 | $3.48 \times 10^{-8}$ | $<1.00 \times 10^{-16}$ |
| 6 | rs17500468 | G | 0.05348 | 0.1269 | 0.39 [0.29, 0.52] | $3.32 \times 10^{-11}$ | G:A | 38:116 | $3.27 \times 10^{-10}$ | $<1.00 \times 10^{-16}$ |
| 6 | rs3129943 | G | 0.3394 | 0.2315 | 1.71 [1.46, 2.00] | $3.38 \times 10^{-11}$ | G:A | 259:117 | $2.42 \times 10^{-13}$ | $<1.00 \times 10^{-16}$ |
| 6 | rs2284178 | T | 0.3788 | 0.4987 | 0.61 [0.50, 0.71] | $4.26 \times 10^{-11}$ | T:C | 169:294 | $6.28 \times 10^{-9}$ | $<1.00 \times 10^{-16}$ |
| 6 | rs7750641 | T | 0.1887 | 0.1069 | 1.94 [1.59, 2.37] | $4.64 \times 10^{-11}$ | T:C | 161:69 | $1.31 \times 10^{-9}$ | $<1.00 \times 10^{-16}$ |
| 6 | rs3101942 | C | 0.269 | 0.3807 | 0.60 [0.51, 0.70] | $1.55 \times 10^{-10}$ | C:T | 109:273 | $4.82 \times 10^{-17}$ | $<1.00 \times 10^{-16}$ |
| 6 | rs3892710 | T | 0.2482 | 0.1575 | 1.77 [1.48, 2.11] | $1.82 \times 10^{-10}$ | T:C | 210:95 | $4.55 \times 10^{-11}$ | $<1.00 \times 10^{-16}$ |
| 6 | rs2233956 | G | 0.2549 | 0.1649 | 1.73 [1.46, 2.06] | $4.48 \times 10^{-10}$ | G:A | 204:99 | $1.62 \times 10^{-9}$ | $<1.00 \times 10^{-16}$ |
| 6 | rs3130544 | A | 0.1845 | 0.1077 | 1.87 [1.53, 2.29] | $5.56 \times 10^{-10}$ | A:C | 166:71 | $6.79 \times 10^{-10}$ | $<1.00 \times 10^{-16}$ |
| 6 | rs9268530 | C | 0.2228 | 0.141 | 1.75 [1.45, 2.10] | $1.91 \times 10^{-9}$ | C:T | 184:82 | $4.00 \times 10^{-10}$ | $<1.00 \times 10^{-16}$ |
| 6 | rs2395162 | T | 0.2228 | 0.141 | 1.75 [1.45, 2.10] | $1.91 \times 10^{-9}$ | T:G | 185:82 | $2.91 \times 10^{-10}$ | $<1.00 \times 10^{-16}$ |
| 6 | rs9501660 | G | 0.5348 | 0.4287 | 1.53 [1.33, 1.77] | $5.39 \times 10^{-9}$ | G:T | 292:137 | $7.24 \times 10^{-14}$ | $<1.00 \times 10^{-16}$ |
| 6 | rs2596472 | G | 0.1455 | 0.2559 | 0.50 [0.41, 0.60] | $3.34 \times 10^{-13}$ | G:A | 99:172 | $9.23 \times 10^{-6}$ | $1.11 \times 10^{-16}$ |
| 6 | rs3132486 | C | 0.3798 | 0.5136 | 0.58 [0.50, 0.67] | $1.21 \times 10^{-12}$ | C:T | 165:261 | $3.30 \times 10^{-6}$ | $1.11 \times 10^{-16}$ |
| 6 | rs3132630 | A | 0.1889 | 0.1061 | 1.96 [1.61, 2.40] | $2.43 \times 10^{-11}$ | A:G | 149:69 | $6.02 \times 10^{-8}$ | $1.11 \times 10^{-16}$ |
| 6 | rs2071474 | A | 0.1938 | 0.3008 | 0.56 [0.47, 0.66] | $3.05 \times 10^{-11}$ | A:G | 120:219 | $7.58 \times 10^{-9}$ | $1.11 \times 10^{-16}$ |
| 6 | rs2228397 | T | 0.1555 | 0.2414 | 0.58 [0.48, 0.70] | $2.64 \times 10^{-8}$ | T:G | 72:175 | $5.61 \times 10^{-11}$ | $1.11 \times 10^{-16}$ |
| 6 | rs154981 | G | 0.408 | 0.4926 | 0.71 [0.61, 0.82] | $3.41 \times 10^{-6}$ | G:A | 151:304 | $7.35 \times 10^{-13}$ | $1.11 \times 10^{-16}$ |
| 6 | rs2856705 | A | 0.04635 | 0.1227 | 0.35 [0.26, 0.47] | $1.72 \times 10^{-12}$ | A:G | 44:100 | $3.06 \times 10^{-6}$ | $2.22 \times 10^{-16}$ |
| 6 | rs3132131 | A | 0.2335 | 0.3056 | 0.69 [0.58, 0.81] | $1.11 \times 10^{-5}$ | A:G | 117:257 | $4.51 \times 10^{-13}$ | $2.22 \times 10^{-16}$ |
| 6 | rs7774434 | C | 0.5045 | 0.3835 | 1.64 [1.42, 1.89] | $1.97 \times 10^{-11}$ | C:T | 295:184 | $3.94 \times 10^{-7}$ | $3.33 \times 10^{-16}$ |
| 6 | rs2071472 | A | 0.1952 | 0.3004 | 0.56 [0.48, 0.67] | $6.55 \times 10^{-11}$ | A:G | 120:217 | $1.26 \times 10^{-7}$ | $3.33 \times 10^{-16}$ |
| 6 | rs2523454 | T | 0.3654 | 0.2581 | 1.66 [1.42, 1.93] | $1.02 \times 10^{-10}$ | T:C | 238:134 | $6.96 \times 10^{-8}$ | $3.33 \times 10^{-16}$ |
| 6 | rs2516424 | C | 0.4774 | 0.3604 | 1.62 [1.40, 1.88] | $7.14 \times 10^{-11}$ | C:T | 256:150 | $1.44 \times 10^{-7}$ | $4.44 \times 10^{-16}$ |
| 6 | rs2248617 | A | 0.4742 | 0.3596 | 1.61 [1.39, 1.86] | $1.33 \times 10^{-10}$ | A:G | 265:157 | $1.46 \times 10^{-7}$ | $7.77 \times 10^{-16}$ |
| 6 | rs2219893 | G | 0.2186 | 0.3268 | 0.58 [0.49, 0.68] | $7.32 \times 10^{-11}$ | G:A | 137:236 | $2.96 \times 10^{-7}$ | $8.88 \times 10^{-16}$ |
| 6 | rs7356880 | T | 0.008913 | 0.05302 | 0.16 [0.08, 0.31] | $3.19 \times 10^{-10}$ | T:C | 8:48 | $9.03 \times 10^{-8}$ | $1.11 \times 10^{-15}$ |
| 6 | rs2395488 | G | 0.4733 | 0.3596 | 1.60 [1.38, 1.85] | $1.93 \times 10^{-10}$ | G:A | 264:157 | $1.84 \times 10^{-7}$ | $1.33 \times 10^{-15}$ |
| 6 | rs3132244 | A | 0.1884 | 0.1044 | 1.99 [1.62, 2.44] | $1.05 \times 10^{-10}$ | A:G | 138:71 | $3.58 \times 10^{-6}$ | $1.44 \times 10^{-15}$ |
| 6 | rs2621373 | G | 0.2103 | 0.315 | 0.58 [0.49, 0.69] | $1.67 \times 10^{-10}$ | G:A | 131:229 | $2.40 \times 10^{-7}$ | $1.55 \times 10^{-15}$ |
| 6 | rs9267444 | A | 0.4385 | 0.3358 | 1.55 [1.33, 1.79] | $5.37 \times 10^{-9}$ | A:G | 280:159 | $7.70 \times 10^{-9}$ | $1.55 \times 10^{-15}$ |
| 6 | rs17842183 | A | 0.1337 | 0.2268 | 0.53 [0.43, 0.64] | $1.26 \times 10^{-10}$ | A:C | 110:199 | $4.13 \times 10^{-7}$ | $2.00 \times 10^{-15}$ |
| 6 | rs9391838 | A | 0.443 | 0.3208 | 1.68 [1.45, 1.95] | $3.02 \times 10^{-10}$ | A:G | 260:171 | $1.81 \times 10^{-5}$ | $2.11 \times 10^{-15}$ |
| 6 | rs6906662 | A | 0.008913 | 0.05517 | 0.15 [0.08, 0.29] | $9.18 \times 10^{-11}$ | A:G | 14:55 | $7.98 \times 10^{-7}$ | $2.78 \times 10^{-15}$ |
| 6 | rs6910071 | G | 0.2692 | 0.1759 | 1.73 [1.46, 2.05] | $2.57 \times 10^{-10}$ | G:A | 205:114 | $3.49 \times 10^{-7}$ | $3.44 \times 10^{-15}$ |
| 6 | rs2516400 | T | 0.4375 | 0.3323 | 1.56 [1.35, 1.81] | $2.23 \times 10^{-9}$ | T:C | 261:150 | $4.37 \times 10^{-8}$ | $3.66 \times 10^{-15}$ |
| 6 | rs2267644 | A | 0.1016 | 0.03937 | 2.76 [2.07, 3.67] | $6.16 \times 10^{-10}$ | A:G | 74:35 | $1.87 \times 10^{-4}$ | $4.33 \times 10^{-15}$ |
| 6 | rs3132453 | A | 0.01007 | 0.05979 | 0.16 [0.09, 0.30] | $3.94 \times 10^{-11}$ | A:C | 17:57 | $3.32 \times 10^{-6}$ | $4.89 \times 10^{-15}$ |
| 6 | rs2395471 | A | 0.3422 | 0.4614 | 0.61 [0.52, 0.70] | $3.76 \times 10^{-11}$ | A:G | 169:265 | $4.06 \times 10^{-6}$ | $5.77 \times 10^{-15}$ |
| 6 | rs154978 | G | 0.4002 | 0.4742 | 0.74 [0.64, 0.86] | $4.51 \times 10^{-5}$ | G:A | 150:297 | $3.58 \times 10^{-12}$ | $6.00 \times 10^{-15}$ |
| 6 | rs2596501 | G | 0.5268 | 0.4265 | 1.50 [1.30, 1.73] | $3.45 \times 10^{-8}$ | G:A | 279:157 | $5.14 \times 10^{-9}$ | $6.66 \times 10^{-15}$ |
| 6 | rs2253907 | G | 0.4143 | 0.5285 | 0.63 [0.55, 0.73] | $3.80 \times 10^{-10}$ | G:A | 168:273 | $5.73 \times 10^{-7}$ | $8.10 \times 10^{-15}$ |
| 6 | rs2523864 | G | 0.4064 | 0.5316 | 0.60 [0.52, 0.70] | $6.64 \times 10^{-12}$ | T:G | 277:193 | $1.07 \times 10^{-4}$ | $2.54 \times 10^{-14}$ |
| 6 | rs3094127 | C | 0.3226 | 0.2148 | 1.74 [1.48, 2.04] | $8.47 \times 10^{-12}$ | C:T | 209:136 | $8.49 \times 10^{-5}$ | $2.58 \times 10^{-14}$ |
| 6 | rs2050189 | G | 0.3021 | 0.2145 | 1.59 [1.35, 1.86] | $2.15 \times 10^{-8}$ | G:A | 218:117 | $3.43 \times 10^{-8}$ | $2.64 \times 10^{-14}$ |
| 6 | rs9261661 | C | 0.1676 | 0.09764 | 1.86 [1.51, 2.29] | $3.91 \times 10^{-9}$ | C:T | 139:65 | $2.21 \times 10^{-7}$ | $3.08 \times 10^{-14}$ |

TABLE 2-continued

All 392 associated SNPs in the MHC region that survived Bonferroni correction. P-values are two-sided in each instance.

| | | | Case-control cohort | | | | Triad cohort (n = 467) | | | |
| | | | Aff Allele | Ctrl Allele | | | | | | |
| Chr | SNP | Allele | Freq (n = 561) | Freq (n = 1,143) | OR [95% CI] | P-val | Alleles | Trans:Un-trans | TDT P-val | P-val combined |
| --- | --- | --- | --- | --- | --- | --- | --- | --- | --- | --- |
| 6 | rs886424 | A | 0.1881 | 0.1121 | 1.84 [1.51, 2.24] | $1.37 \times 10^{-9}$ | A:G | 155:79 | $6.76 \times 10^{-7}$ | $3.31 \times 10^{-14}$ |
| 6 | rs3129963 | G | 0.2255 | 0.1509 | 1.64 [1.37, 1.96] | $7.52 \times 10^{-8}$ | G:A | 184:91 | $2.05 \times 10^{-8}$ | $5.40 \times 10^{-14}$ |
| 6 | rs2239800 | C | 0.05804 | 0.1216 | 0.45 [0.34, 0.59] | $6.96 \times 10^{-9}$ | C:T | 39:100 | $2.29 \times 10^{-7}$ | $5.60 \times 10^{-14}$ |
| 6 | rs549182 | A | 0.07616 | 0.02641 | 3.04 [2.17, 4.26] | $1.76 \times 10^{-11}$ | A:G | 65:28 | $1.25 \times 10^{-4}$ | $7.61 \times 10^{-14}$ |
| 6 | rs6903496 | A | 0.06875 | 0.02318 | 3.11 [2.18, 4.45] | $7.02 \times 10^{-11}$ | A:G | 58:21 | $3.14 \times 10^{-5}$ | $7.67 \times 10^{-14}$ |
| 6 | rs3115673 | A | 0.1989 | 0.1096 | 2.02 [1.65, 2.46] | $2.36 \times 10^{-12}$ | A:C | 168:113 | 0.001034 | $8.46 \times 10^{-14}$ |
| 6 | rs2246618 | T | 0.4396 | 0.332 | 1.58 [1.36, 1.83] | $1.86 \times 10^{-9}$ | T:C | 207:120 | $1.50 \times 10^{-6}$ | $9.61 \times 10^{-14}$ |
| 6 | rs3130380 | A | 0.1533 | 0.09019 | 1.83 [1.47, 2.27] | $3.57 \times 10^{-8}$ | A:G | 126:54 | $8.03 \times 10^{-8}$ | $9.89 \times 10^{-14}$ |
| 6 | rs2071540 | A | 0.3316 | 0.4011 | 0.74 [0.64, 0.86] | $8.27 \times 10^{-5}$ | A:G | 144:279 | $5.24 \times 10^{-11}$ | $1.48 \times 10^{-13}$ |
| 6 | rs805274 | G | 0.3616 | 0.2419 | 1.78 [1.52, 2.07] | $2.90 \times 10^{-13}$ | G:A | 217:171 | 0.01953 | $1.91 \times 10^{-13}$ |
| 6 | rs507778 | A | 0.5382 | 0.4193 | 1.61 [1.40, 1.87] | $8.40 \times 10^{-11}$ | A:G | 262:179 | $7.74 \times 10^{-5}$ | $2.19 \times 10^{-13}$ |
| 6 | rs3129939 | G | 0.2112 | 0.1496 | 1.52 [1.29, 1.80] | $6.74 \times 10^{-6}$ | G:A | 187:86 | $9.79 \times 10^{-10}$ | $2.22 \times 10^{-13}$ |
| 6 | rs9501626 | A | 0.06194 | 0.1295 | 0.44 [0.34, 0.58] | $2.38 \times 10^{-9}$ | A:C | 60:123 | $3.21 \times 10^{-6}$ | $2.56 \times 10^{-13}$ |
| 6 | rs2516390 | G | 0.3084 | 0.4085 | 0.65 [0.55, 0.75] | $1.42 \times 10^{-8}$ | G:A | 160:263 | $5.50 \times 10^{-7}$ | $2.62 \times 10^{-13}$ |
| 6 | rs2508015 | T | 0.5223 | 0.4032 | 1.62 [1.40, 1.87] | $4.95 \times 10^{-11}$ | T:C | 266:186 | $1.68 \times 10^{-4}$ | $2.78 \times 10^{-13}$ |
| 6 | rs2844484 | T | 0.3089 | 0.4089 | 0.65 [0.56, 0.75] | $1.52 \times 10^{-8}$ | T:C | 162:265 | $6.21 \times 10^{-7}$ | $3.14 \times 10^{-13}$ |
| 6 | rs2027856 | T | 0.0625 | 0.1327 | 0.44 [0.33, 0.57] | $7.39 \times 10^{-10}$ | T:C | 50:104 | $1.35 \times 10^{-5}$ | $3.32 \times 10^{-13}$ |
| 6 | rs2269426 | T | 0.3253 | 0.4335 | 0.63 [0.54, 0.73] | $1.33 \times 10^{-9}$ | T:C | 158:248 | $7.95 \times 10^{-6}$ | $3.50 \times 10^{-13}$ |
| 6 | rs3095329 | C | 0.3107 | 0.2087 | 1.71 [1.45, 2.01] | $6.54 \times 10^{-11}$ | C:T | 206:137 | $1.95 \times 10^{-4}$ | $4.20 \times 10^{-13}$ |
| 6 | rs928815 | A | 0.3089 | 0.4086 | 0.65 [0.56, 0.75] | $1.69 \times 10^{-8}$ | A:C | 162:264 | $7.74 \times 10^{-7}$ | $4.32 \times 10^{-13}$ |
| 6 | rs408359 | T | 0.1741 | 0.09361 | 2.04 [1.66, 2.52] | $1.13 \times 10^{-11}$ | T:C | 107:65 | 0.001363 | $5.04 \times 10^{-13}$ |
| 6 | rs6903130 | G | 0.5598 | 0.4698 | 1.44 [1.24, 1.66] | $7.94 \times 10^{-7}$ | A:G | 154:269 | $2.25 \times 10^{-8}$ | $5.84 \times 10^{-13}$ |
| 6 | rs2256594 | C | 0.09447 | 0.1728 | 0.50 [0.40, 0.63] | $1.30 \times 10^{-9}$ | C:T | 98:169 | $1.39 \times 10^{-5}$ | $5.91 \times 10^{-13}$ |
| 6 | rs1573649 | C | 0.5597 | 0.4693 | 1.44 [1.24, 1.66] | $7.12 \times 10^{-7}$ | T:C | 155:268 | $3.92 \times 10^{-8}$ | $9.00 \times 10^{-13}$ |
| 6 | rs480092 | G | 0.2148 | 0.1261 | 1.90 [1.57, 2.29] | $1.85 \times 10^{-11}$ | G:A | 184:129 | 0.001879 | $1.11 \times 10^{-12}$ |
| 6 | rs1634747 | T | 0.5146 | 0.4195 | 1.47 [1.27, 1.70] | $2.25 \times 10^{-7}$ | T:C | 212:117 | $1.63 \times 10^{-7}$ | $1.17 \times 10^{-12}$ |
| 6 | rs9261290 | C | 0.148 | 0.08749 | 1.81 [1.45, 2.26] | $8.45 \times 10^{-8}$ | C:T | 128:59 | $4.52 \times 10^{-7}$ | $1.22 \times 10^{-12}$ |
| 6 | rs3132580 | T | 0.1979 | 0.1273 | 1.69 [1.40, 2.05] | $6.18 \times 10^{-8}$ | T:C | 162:85 | $9.61 \times 10^{-7}$ | $1.87 \times 10^{-12}$ |
| 6 | rs2076537 | T | 0.4091 | 0.3272 | 1.42 [1.23, 1.65] | $2.64 \times 10^{-6}$ | T:C | 287:168 | $2.42 \times 10^{-8}$ | $2.01 \times 10^{-12}$ |
| 6 | rs206777 | C | 0.3048 | 0.3993 | 0.66 [0.57, 0.77] | $7.72 \times 10^{-8}$ | C:T | 176:281 | $9.03 \times 10^{-7}$ | $2.18 \times 10^{-12}$ |
| 6 | rs12663103 | C | 0.01693 | 0.06255 | 0.26 [0.16, 0.42] | $4.06 \times 10^{-9}$ | C:T | 22:61 | $1.86 \times 10^{-5}$ | $2.36 \times 10^{-12}$ |
| 6 | rs3095340 | G | 0.2143 | 0.1409 | 1.66 [1.38, 2.00] | $5.84 \times 10^{-8}$ | G:T | 175:96 | $1.60 \times 10^{-6}$ | $2.89 \times 10^{-12}$ |
| 6 | rs8192591 | A | 0.00361 | 0.03384 | 0.10 [0.04, 0.28] | $6.81 \times 10^{-8}$ | A:G | 1:26 | $1.50 \times 10^{-6}$ | $3.16 \times 10^{-12}$ |
| 6 | rs3132610 | C | 0.1604 | 0.09886 | 1.74 [1.41, 2.15] | $1.85 \times 10^{-7}$ | C:T | 143:70 | $5.68 \times 10^{-7}$ | $3.25 \times 10^{-12}$ |
| 6 | rs3129763 | A | 0.367 | 0.2789 | 1.50 [1.29, 1.75] | $1.70 \times 10^{-7}$ | A:G | 243:145 | $6.52 \times 10^{-7}$ | $3.41 \times 10^{-12}$ |
| 6 | rs2857595 | T | 0.2665 | 0.1805 | 1.65 [1.39, 1.96] | $6.69 \times 10^{-9}$ | T:C | 208:129 | $1.68 \times 10^{-5}$ | $3.47 \times 10^{-12}$ |
| 6 | rs3094061 | G | 0.1774 | 0.112 | 1.71 [1.40, 2.09] | $1.34 \times 10^{-7}$ | G:T | 147:74 | $9.08 \times 10^{-7}$ | $3.75 \times 10^{-12}$ |
| 6 | rs9276831 | G | 0.07308 | 0.1578 | 0.42 [0.33, 0.54] | $4.90 \times 10^{-12}$ | G:A | 82:112 | 0.03125 | $4.67 \times 10^{-12}$ |
| 6 | rs3806156 | T | 0.4562 | 0.3548 | 1.53 [1.32, 1.77] | $1.19 \times 10^{-8}$ | T:G | 276:183 | $1.42 \times 10^{-5}$ | $5.12 \times 10^{-12}$ |
| 6 | rs3997987 | C | 0.2946 | 0.4115 | 0.60 [0.51, 0.70] | $3.71 \times 10^{-11}$ | C:A | 167:223 | 0.004573 | $5.16 \times 10^{-12}$ |
| 6 | rs1264622 | A | 0.2308 | 0.1619 | 1.55 [1.30, 1.86] | $1.07 \times 10^{-6}$ | A:G | 200:108 | $1.59 \times 10^{-7}$ | $5.17 \times 10^{-12}$ |
| 6 | rs9275602 | A | 0.2222 | 0.1455 | 1.68 [1.40, 2.02] | $2.88 \times 10^{-8}$ | A:C | 140:74 | $6.43 \times 10^{-6}$ | $5.62 \times 10^{-12}$ |
| 6 | rs2239804 | A | 0.367 | 0.479 | 0.63 [0.54, 0.73] | $6.21 \times 10^{-10}$ | A:G | 194:272 | $3.02 \times 10^{-4}$ | $5.69 \times 10^{-12}$ |
| 6 | rs376510 | A | 0.1257 | 0.05993 | 2.26 [1.76, 2.89] | $4.79 \times 10^{-11}$ | A:G | 95:60 | 0.004935 | $7.11 \times 10^{-12}$ |
| 6 | rs404860 | C | 0.09804 | 0.1745 | 0.51 [0.40, 0.64] | $3.91 \times 10^{-9}$ | C:T | 103:168 | $7.87 \times 10^{-5}$ | $9.16 \times 10^{-12}$ |
| 6 | rs12153855 | C | 0.06506 | 0.1229 | 0.50 [0.38, 0.65] | $1.97 \times 10^{-7}$ | C:T | 48:107 | $2.15 \times 10^{-6}$ | $1.24 \times 10^{-11}$ |
| 6 | rs2844773 | T | 0.2023 | 0.1347 | 1.63 [1.35, 1.97] | $3.46 \times 10^{-7}$ | T:G | 162:86 | $1.39 \times 10^{-6}$ | $1.41 \times 10^{-11}$ |
| 6 | rs580962 | G | 0.3209 | 0.4138 | 0.67 [0.58, 0.78] | $1.55 \times 10^{-7}$ | G:A | 186:287 | $3.42 \times 10^{-6}$ | $1.55 \times 10^{-11}$ |
| 6 | rs3094067 | T | 0.2068 | 0.1365 | 1.65 [1.39, 1.99] | $1.40 \times 10^{-7}$ | T:C | 162:89 | $4.07 \times 10^{-6}$ | $1.67 \times 10^{-11}$ |
| 6 | rs1053924 | A | 0.1756 | 0.2765 | 0.56 [0.47, 0.67] | $1.11 \times 10^{-10}$ | A:G | 158:211 | 0.005797 | $1.88 \times 10^{-11}$ |
| 6 | rs2516415 | T | 0.4328 | 0.3451 | 1.45 [1.25, 1.68] | $7.02 \times 10^{-7}$ | T:C | 244:147 | $9.32 \times 10^{-7}$ | $1.90 \times 10^{-11}$ |
| 6 | rs2071538 | T | 0.1328 | 0.1957 | 0.63 [0.51, 0.77] | $5.58 \times 10^{-6}$ | T:C | 90:176 | $1.34 \times 10^{-7}$ | $2.17 \times 10^{-11}$ |
| 6 | rs3132571 | C | 0.4848 | 0.378 | 1.55 [1.34, 1.79] | $2.67 \times 10^{-9}$ | C:T | 272:194 | $3.02 \times 10^{-4}$ | $2.33 \times 10^{-11}$ |
| 6 | rs3130050 | G | 0.06328 | 0.1203 | 0.49 [0.38, 0.65] | $2.23 \times 10^{-7}$ | G:A | 40:93 | $4.31 \times 10^{-6}$ | $2.76 \times 10^{-11}$ |
| 6 | rs2248372 | A | 0.2383 | 0.3399 | 0.61 [0.52, 0.72] | $1.87 \times 10^{-9}$ | A:G | 148:214 | $5.23 \times 10^{-4}$ | $2.79 \times 10^{-11}$ |
| 6 | rs406936 | T | 0.08021 | 0.1315 | 0.58 [0.45, 0.74] | $1.02 \times 10^{-5}$ | T:C | 69:147 | $1.11 \times 10^{-7}$ | $3.23 \times 10^{-11}$ |
| 6 | rs8321 | G | 0.1462 | 0.08772 | 1.78 [1.43, 2.22] | $2.16 \times 10^{-7}$ | G:T | 109:52 | $7.05 \times 10^{-6}$ | $4.29 \times 10^{-11}$ |
| 6 | rs2857106 | G | 0.1275 | 0.1933 | 0.61 [0.50, 0.74] | $1.69 \times 10^{-6}$ | G:A | 85:162 | $9.61 \times 10^{-7}$ | $4.58 \times 10^{-11}$ |
| 6 | rs9267532 | T | 0.1248 | 0.06212 | 2.15 [1.68, 2.75] | $4.39 \times 10^{-10}$ | T:C | 96:60 | 0.003948 | $4.86 \times 10^{-11}$ |
| 6 | rs454212 | A | 0.08152 | 0.1307 | 0.59 [0.46, 0.76] | $2.56 \times 10^{-5}$ | A:G | 68:147 | $7.13 \times 10^{-8}$ | $5.12 \times 10^{-11}$ |
| 6 | rs3130564 | T | 0.2527 | 0.1811 | 1.53 [1.29, 1.82] | $1.15 \times 10^{-6}$ | T:C | 196:112 | $1.70 \times 10^{-6}$ | $5.46 \times 10^{-11}$ |
| 6 | rs2523989 | A | 0.1946 | 0.1255 | 1.68 [1.39, 2.04] | $9.77 \times 10^{-8}$ | A:G | 158:92 | $2.99 \times 10^{-5}$ | $8.05 \times 10^{-11}$ |
| 6 | rs3130350 | T | 0.1569 | 0.08932 | 1.90 [1.53, 2.35] | $3.98 \times 10^{-9}$ | T:G | 79:42 | $7.69 \times 10^{-4}$ | $8.43 \times 10^{-11}$ |
| 6 | rs6924102 | G | 0.508 | 0.4462 | 1.28 [1.11, 1.48] | $6.74 \times 10^{-4}$ | G:A | 275:154 | $5.16 \times 10^{-9}$ | $9.53 \times 10^{-11}$ |
| 6 | rs1264350 | G | 0.1863 | 0.1238 | 1.62 [1.33, 1.97] | $1.08 \times 10^{-6}$ | G:A | 160:87 | $3.40 \times 10^{-6}$ | $1.00 \times 10^{-10}$ |
| 6 | rs2156875 | G | 0.4073 | 0.4969 | 0.70 [0.60, 0.80] | $8.34 \times 10^{-6}$ | G:A | 188:288 | $4.57 \times 10^{-6}$ | $1.04 \times 10^{-10}$ |
| 6 | rs3830041 | A | 0.04991 | 0.1006 | 0.47 [0.35, 0.63] | $5.26 \times 10^{-7}$ | A:G | 44:97 | $8.07 \times 10^{-6}$ | $1.15 \times 10^{-10}$ |
| 6 | rs6906846 | A | 0.2121 | 0.3074 | 0.61 [0.51, 0.72] | $5.10 \times 10^{-9}$ | A:G | 147:210 | $8.55 \times 10^{-4}$ | $1.18 \times 10^{-10}$ |
| 6 | rs2107202 | A | 0.1812 | 0.2662 | 0.61 [0.51, 0.73] | $4.59 \times 10^{-8}$ | A:G | 135:207 | $9.89 \times 10^{-5}$ | $1.23 \times 10^{-10}$ |
| 6 | rs2517532 | T | 0.2888 | 0.3753 | 0.68 [0.58, 0.79] | $7.24 \times 10^{-7}$ | T:C | 159:250 | $6.81 \times 10^{-6}$ | $1.33 \times 10^{-10}$ |
| 6 | rs387608 | T | 0.082 | 0.133 | 0.58 [0.46, 0.74] | $1.27 \times 10^{-5}$ | T:C | 72:147 | $4.02 \times 10^{-7}$ | $1.38 \times 10^{-10}$ |

TABLE 2-continued

All 392 associated SNPs in the MHC region that survived Bonferroni correction. P-values are two-sided in each instance.

| | | | Case-control cohort | | | | Triad cohort (n = 467) | | | |
|---|---|---|---|---|---|---|---|---|---|---|
| Chr | SNP | Allele | Aff Allele Freq (n = 561) | Ctrl Allele Freq (n = 1,143) | OR [95% CI] | P-val | Alleles | Trans:Un-trans | TDT P-val | P-val combined |
| 6 | rs2516398 | C | 0.2322 | 0.3088 | 0.68 [0.57, 0.80] | $3.97 \times 10^{-6}$ | C:A | 112:197 | $1.33 \times 10^{-6}$ | $1.42 \times 10^{-10}$ |
| 6 | rs9267665 | T | 0.09537 | 0.04243 | 2.38 [1.79, 3.16] | $9.28 \times 10^{-10}$ | T:C | 79:48 | 0.005945 | $1.48 \times 10^{-10}$ |
| 6 | rs204991 | G | 0.2509 | 0.1864 | 1.46 [1.23, 1.74] | $1.28 \times 10^{-5}$ | G:A | 212:120 | $4.44 \times 10^{-7}$ | $1.53 \times 10^{-10}$ |
| 6 | rs479536 | T | 0.02679 | 0.06955 | 0.37 [0.25, 0.55] | $3.02 \times 10^{-7}$ | T:C | 31:75 | $1.92 \times 10^{-5}$ | $1.56 \times 10^{-10}$ |
| 6 | rs3763349 | T | 0.4036 | 0.4536 | 0.82 [0.71, 0.94] | 0.005659 | T:C | 154:281 | $1.14 \times 10^{-9}$ | $1.72 \times 10^{-10}$ |
| 6 | rs4959089 | G | 0.1141 | 0.1859 | 0.56 [0.46, 0.70] | $9.05 \times 10^{-8}$ | G:A | 98:162 | $7.21 \times 10^{-5}$ | $1.75 \times 10^{-10}$ |
| 6 | rs385306 | T | 0.3021 | 0.2043 | 1.69 [1.43, 1.99] | $2.66 \times 10^{-10}$ | T:C | 201:159 | 0.02686 | $1.91 \times 10^{-10}$ |
| 6 | rs2395174 | G | 0.3107 | 0.2421 | 1.41 [1.20, 1.65] | $2.03 \times 10^{-5}$ | G:T | 235:137 | $3.75 \times 10^{-7}$ | $2.02 \times 10^{-10}$ |
| 6 | rs1419675 | C | 0.181 | 0.2677 | 0.60 [0.51, 0.72] | $2.61 \times 10^{-8}$ | C:A | 138:205 | $2.97 \times 10^{-4}$ | $2.06 \times 10^{-10}$ |
| 6 | rs4424066 | G | 0.4964 | 0.3998 | 1.48 [1.28, 1.71] | $8.75 \times 10^{-8}$ | G:A | 279:194 | $9.30 \times 10^{-5}$ | $2.16 \times 10^{-10}$ |
| 6 | rs3134940 | G | 0.2326 | 0.1728 | 1.45 [1.22, 1.73] | $3.14 \times 10^{-5}$ | G:A | 198:108 | $2.68 \times 10^{-7}$ | $2.23 \times 10^{-10}$ |
| 6 | rs415929 | G | 0.2888 | 0.3692 | 0.69 [0.59, 0.81] | $3.33 \times 10^{-6}$ | G:A | 142:233 | $2.61 \times 10^{-6}$ | $2.30 \times 10^{-10}$ |
| 6 | rs6911628 | T | 0.3625 | 0.2693 | 1.54 [1.32, 1.80] | $2.44 \times 10^{-8}$ | T:C | 228:158 | $3.67 \times 10^{-4}$ | $2.36 \times 10^{-10}$ |
| 6 | rs241407 | A | 0.1658 | 0.1072 | 1.66 [1.35, 2.03] | $1.32 \times 10^{-6}$ | A:G | 126:64 | $6.86 \times 10^{-6}$ | $2.39 \times 10^{-10}$ |
| 6 | rs9275653 | G | 0.4697 | 0.3723 | 1.49 [1.29, 1.73] | $5.14 \times 10^{-8}$ | G:A | 257:179 | $1.87 \times 10^{-4}$ | $2.54 \times 10^{-10}$ |
| 6 | rs1065356 | T | 0.2852 | 0.1935 | 1.66 [1.41, 1.96] | $1.59 \times 10^{-9}$ | T:C | 213:160 | 0.006065 | $2.55 \times 10^{-10}$ |
| 6 | rs3094694 | G | 0.2428 | 0.1617 | 1.66 [1.39, 1.98] | $1.37 \times 10^{-8}$ | G:A | 176:118 | $7.18 \times 10^{-4}$ | $2.60 \times 10^{-10}$ |
| 6 | rs241409 | C | 0.164 | 0.1072 | 1.63 [1.33, 2.01] | $2.61 \times 10^{-6}$ | C:T | 128:64 | $3.86 \times 10^{-6}$ | $2.65 \times 10^{-10}$ |
| 6 | rs3817973 | A | 0.4964 | 0.4005 | 1.48 [1.28, 1.70] | $1.12 \times 10^{-7}$ | A:G | 279:194 | $9.30 \times 10^{-5}$ | $2.73 \times 10^{-10}$ |
| 6 | rs9266722 | T | 0.1625 | 0.09624 | 1.82 [1.48, 2.25] | $1.79 \times 10^{-8}$ | T:C | 127:78 | $6.21 \times 10^{-4}$ | $2.92 \times 10^{-10}$ |
| 6 | rs7773694 | A | 0.2843 | 0.2103 | 1.49 [1.27, 1.76] | $1.70 \times 10^{-6}$ | A:G | 198:118 | $6.78 \times 10^{-4}$ | $3.01 \times 10^{-10}$ |
| 6 | rs204990 | T | 0.2482 | 0.1867 | 1.44 [1.21, 1.71] | $3.13 \times 10^{-5}$ | T:G | 214:121 | $3.75 \times 10^{-7}$ | $3.08 \times 10^{-10}$ |
| 6 | rs9257809 | G | 0.1355 | 0.08231 | 1.75 [1.39, 2.19] | $1.15 \times 10^{-6}$ | G:A | 112:55 | $1.03 \times 10^{-5}$ | $3.09 \times 10^{-10}$ |
| 6 | rs2076530 | G | 0.5027 | 0.4085 | 1.46 [1.27, 1.69] | $1.94 \times 10^{-7}$ | G:A | 280:193 | $6.33 \times 10^{-5}$ | $3.21 \times 10^{-10}$ |
| 6 | rs2523987 | G | 0.1809 | 0.115 | 1.70 [1.39, 2.07] | $1.44 \times 10^{-7}$ | G:T | 143:84 | $9.00 \times 10^{-5}$ | $3.38 \times 10^{-10}$ |
| 6 | rs7755596 | C | 0.2848 | 0.2106 | 1.49 [1.27, 1.76] | $1.60 \times 10^{-6}$ | C:T | 197:118 | $8.54 \times 10^{-6}$ | $3.54 \times 10^{-10}$ |
| 6 | rs9262143 | T | 0.1578 | 0.09711 | 1.74 [1.41, 2.15] | $2.29 \times 10^{-7}$ | T:C | 79:36 | $6.08 \times 10^{-5}$ | $3.61 \times 10^{-10}$ |
| 6 | rs9378200 | C | 0.02763 | 0.07568 | 0.35 [0.24, 0.51] | $2.75 \times 10^{-8}$ | C:T | 36:72 | $5.32 \times 10^{-4}$ | $3.80 \times 10^{-10}$ |
| 6 | rs3130361 | A | 0.1375 | 0.2122 | 0.59 [0.49, 0.72] | $1.58 \times 10^{-7}$ | A:G | 122:191 | $9.62 \times 10^{-5}$ | $3.93 \times 10^{-10}$ |
| 6 | rs412657 | A | 0.4189 | 0.5166 | 0.67 [0.58, 0.78] | $8.11 \times 10^{-8}$ | A:C | 195:275 | $2.24 \times 10^{-4}$ | $4.68 \times 10^{-10}$ |
| 6 | rs9276162 | G | 0.2941 | 0.2215 | 1.46 [1.25, 1.72] | $3.73 \times 10^{-6}$ | G:A | 202:120 | $4.89 \times 10^{-6}$ | $4.69 \times 10^{-10}$ |
| 6 | rs1634731 | G | 0.09982 | 0.1649 | 0.56 [0.45, 0.70] | $3.51 \times 10^{-7}$ | G:A | 78:136 | $7.35 \times 10^{-5}$ | $6.54 \times 10^{-10}$ |
| 6 | rs9276291 | T | 0.2905 | 0.2177 | 1.47 [1.25, 1.74] | $3.81 \times 10^{-6}$ | T:C | 195:116 | $7.48 \times 10^{-6}$ | $7.21 \times 10^{-10}$ |
| 6 | rs2254556 | A | 0.08913 | 0.1461 | 0.57 [0.45, 0.72] | $2.74 \times 10^{-6}$ | A:G | 69:131 | $1.17 \times 10^{-5}$ | $8.05 \times 10^{-10}$ |
| 6 | rs2534678 | A | 0.09034 | 0.1504 | 0.56 [0.44, 0.71] | $1.04 \times 10^{-6}$ | A:C | 57:111 | $3.10 \times 10^{-5}$ | $8.10 \times 10^{-10}$ |
| 6 | rs9296015 | A | 0.1138 | 0.1796 | 0.59 [0.47, 0.73] | $8.29 \times 10^{-7}$ | A:G | 96:162 | $3.97 \times 10^{-5}$ | $8.28 \times 10^{-10}$ |
| 6 | rs3819715 | T | 0.2932 | 0.3723 | 0.70 [0.60, 0.82] | $5.18 \times 10^{-6}$ | T:G | 157:247 | $7.55 \times 10^{-6}$ | $9.75 \times 10^{-10}$ |
| 6 | rs2523535 | C | 0.458 | 0.3633 | 1.48 [1.28, 1.71] | $1.12 \times 10^{-7}$ | C:T | 252:178 | $3.59 \times 10^{-4}$ | $9.98 \times 10^{-10}$ |
| 6 | rs9501239 | G | 0.07728 | 0.03853 | 2.09 [1.53, 2.86] | $2.47 \times 10^{-6}$ | G:A | 75:31 | $1.92 \times 10^{-5}$ | $1.18 \times 10^{-9}$ |
| 6 | rs188245 | C | 0.5304 | 0.443 | 1.42 [1.23, 1.64] | $1.63 \times 10^{-6}$ | C:T | 277:187 | $2.94 \times 10^{-5}$ | $1.18 \times 10^{-9}$ |
| 6 | rs1012471 | C | 0.3939 | 0.3027 | 1.50 [1.29, 1.74] | $1.09 \times 10^{-7}$ | C:A | 253:180 | $4.51 \times 10^{-4}$ | $1.21 \times 10^{-9}$ |
| 6 | rs13215135 | G | 0.006239 | 0.03196 | 0.19 [0.09, 0.41] | $3.18 \times 10^{-6}$ | G:A | 7:35 | $1.56 \times 10^{-6}$ | $1.22 \times 10^{-9}$ |
| 6 | rs2844635 | C | 0.4679 | 0.3864 | 1.40 [1.21, 1.61] | $5.65 \times 10^{-6}$ | C:T | 274:180 | $1.03 \times 10^{-5}$ | $1.42 \times 10^{-9}$ |
| 6 | rs2844746 | A | 0.2718 | 0.3591 | 0.67 [0.57, 0.78] | $3.65 \times 10^{-7}$ | A:G | 175:253 | $1.63 \times 10^{-4}$ | $1.46 \times 10^{-9}$ |
| 6 | rs7758736 | A | 0.2112 | 0.1633 | 1.37 [1.15, 1.63] | $6.08 \times 10^{-4}$ | A:G | 170:85 | $1.02 \times 10^{-7}$ | $1.52 \times 10^{-9}$ |
| 6 | rs6457536 | G | 0.246 | 0.1957 | 1.34 [1.13, 1.59] | $7.44 \times 10^{-4}$ | G:A | 209:113 | $8.80 \times 10^{-8}$ | $1.60 \times 10^{-9}$ |
| 6 | rs3117230 | C | 0.2825 | 0.2143 | 1.44 [1.23, 1.70] | $1.08 \times 10^{-5}$ | C:T | 219:134 | $6.07 \times 10^{-6}$ | $1.60 \times 10^{-9}$ |
| 6 | rs2064478 | A | 0.2825 | 0.2145 | 1.44 [1.22, 1.70] | $1.15 \times 10^{-5}$ | A:G | 219:134 | $6.07 \times 10^{-6}$ | $1.71 \times 10^{-9}$ |
| 6 | rs1058026 | G | 0.134 | 0.2121 | 0.57 [0.47, 0.70] | $4.19 \times 10^{-8}$ | G:T | 97:146 | 0.00167 | $1.71 \times 10^{-9}$ |
| 6 | rs4678 | T | 0.2703 | 0.1889 | 1.59 [1.34, 1.88] | $6.59 \times 10^{-8}$ | T:C | 175:119 | 0.001091 | $1.75 \times 10^{-9}$ |
| 6 | rs2746150 | T | 0.1301 | 0.08005 | 1.72 [1.37, 2.16] | $3.30 \times 10^{-6}$ | T:C | 108:54 | $2.21 \times 10^{-5}$ | $1.77 \times 10^{-9}$ |
| 6 | rs6457374 | C | 0.2914 | 0.2172 | 1.48 [1.26, 1.75] | $1.94 \times 10^{-6}$ | C:T | 213:136 | $3.76 \times 10^{-5}$ | $1.78 \times 10^{-9}$ |
| 6 | rs204999 | G | 0.361 | 0.2878 | 1.40 [1.20, 1.63] | $1.49 \times 10^{-5}$ | G:A | 265:170 | $5.24 \times 10^{-6}$ | $1.90 \times 10^{-9}$ |
| 6 | rs1265761 | C | 0.1052 | 0.05468 | 2.03 [1.56, 2.64] | $7.34 \times 10^{-8}$ | C:T | 95:55 | 0.001091 | $1.94 \times 10^{-9}$ |
| 6 | rs719654 | T | 0.1604 | 0.2259 | 0.65 [0.54, 0.79] | $8.38 \times 10^{-6}$ | T:C | 103:177 | $9.76 \times 10^{-6}$ | $1.98 \times 10^{-9}$ |
| 6 | rs2905722 | T | 0.05804 | 0.1121 | 0.49 [0.37, 0.65] | $3.98 \times 10^{-7}$ | T:C | 54:100 | $2.10 \times 10^{-4}$ | $2.02 \times 10^{-9}$ |
| 6 | rs2517403 | G | 0.4676 | 0.3861 | 1.40 [1.21, 1.61] | $6.07 \times 10^{-6}$ | G:A | 276:183 | $1.42 \times 10^{-5}$ | $2.08 \times 10^{-9}$ |
| 6 | rs3128918 | C | 0.1417 | 0.2005 | 0.66 [0.54, 0.80] | $2.81 \times 10^{-5}$ | C:T | 76:145 | $3.46 \times 10^{-6}$ | $2.33 \times 10^{-9}$ |
| 6 | rs209473 | A | 0.3696 | 0.45 | 0.72 [0.62, 0.83] | $8.20 \times 10^{-6}$ | A:C | 193:289 | $1.23 \times 10^{-5}$ | $2.42 \times 10^{-9}$ |
| 6 | rs2844494 | G | 0.2303 | 0.3091 | 0.67 [0.57, 0.79] | $2.14 \times 10^{-6}$ | G:T | 131:205 | $5.41 \times 10^{-5}$ | $2.76 \times 10^{-9}$ |
| 6 | rs3094691 | T | 0.3923 | 0.4936 | 0.66 [0.57, 0.77] | $4.34 \times 10^{-8}$ | T:C | 153:210 | 0.002774 | $2.87 \times 10^{-9}$ |
| 6 | rs2281390 | A | 0.1417 | 0.1996 | 0.66 [0.54, 0.81] | $3.60 \times 10^{-5}$ | A:C | 76:145 | $3.46 \times 10^{-6}$ | $2.97 \times 10^{-9}$ |
| 6 | rs3094054 | A | 0.156 | 0.09413 | 1.78 [1.44, 2.20] | $9.99 \times 10^{-8}$ | A:C | 81:45 | 0.001341 | $3.18 \times 10^{-9}$ |
| 6 | rs200968 | G | 0.205 | 0.1401 | 1.58 [1.31, 1.91] | $1.32 \times 10^{-6}$ | G:A | 159:97 | $1.07 \times 10^{-4}$ | $3.33 \times 10^{-9}$ |
| 6 | rs2249742 | T | 0.4231 | 0.5163 | 0.69 [0.59, 0.79] | $3.31 \times 10^{-7}$ | T:C | 185:259 | $4.45 \times 10^{-4}$ | $3.48 \times 10^{-9}$ |
| 6 | rs2517598 | T | 0.2032 | 0.137 | 1.61 [1.33, 1.94] | $6.86 \times 10^{-7}$ | T:C | 162:102 | $2.22 \times 10^{-4}$ | $3.59 \times 10^{-9}$ |
| 6 | rs206015 | T | 0.0615 | 0.1172 | 0.49 [0.37, 0.65] | $3.02 \times 10^{-7}$ | T:C | 72:120 | $5.32 \times 10^{-4}$ | $3.78 \times 10^{-9}$ |
| 6 | rs4386816 | C | 0.09002 | 0.1601 | 0.52 [0.41, 0.66] | $2.25 \times 10^{-8}$ | C:T | 72:108 | 0.00729 | $3.86 \times 10^{-9}$ |
| 6 | rs3132685 | T | 0.1491 | 0.09843 | 1.61 [1.30, 1.99] | $1.34 \times 10^{-5}$ | T:C | 121:62 | $1.29 \times 10^{-5}$ | $4.05 \times 10^{-9}$ |
| 6 | rs2844657 | C | 0.2602 | 0.19 | 1.50 [1.27, 1.78] | $2.55 \times 10^{-6}$ | C:T | 190:120 | $7.02 \times 10^{-5}$ | $4.20 \times 10^{-9}$ |
| 6 | rs2247056 | T | 0.2914 | 0.2187 | 1.47 [1.25, 1.73] | $3.26 \times 10^{-6}$ | T:C | 212:137 | $5.95 \times 10^{-5}$ | $4.53 \times 10^{-9}$ |

TABLE 2-continued

All 392 associated SNPs in the MHC region that survived Bonferroni correction. P-values are two-sided in each instance.

| | | | Case-control cohort | | | | Triad cohort (n = 467) | | | |
|---|---|---|---|---|---|---|---|---|---|---|
| | | | Aff Allele | Ctrl Allele | | | | | | |
| Chr | SNP | Allele | Freq (n = 561) | Freq (n = 1,143) | OR [95% CI] | P-val | Alleles | Trans:Un-trans | TDT P-val | P-val combined |
| 6 | rs3095089 | A | 0.2339 | 0.1649 | 1.55 [1.30, 1.85] | $1.28 \times 10^{-6}$ | A:C | 165:103 | $1.52 \times 10^{-4}$ | $4.56 \times 10^{-9}$ |
| 6 | rs423639 | T | 0.131 | 0.08574 | 1.61 [1.28, 2.02] | $3.65 \times 10^{-5}$ | T:C | 124:62 | $5.47 \times 10^{-6}$ | $4.66 \times 10^{-9}$ |
| 6 | rs3094122 | C | 0.2843 | 0.2113 | 1.48 [1.26, 1.75] | $2.33 \times 10^{-6}$ | C:A | 194:124 | $8.66 \times 10^{-5}$ | $4.70 \times 10^{-9}$ |
| 6 | rs2856997 | T | 0.3276 | 0.4131 | 0.69 [0.60, 0.80] | $1.61 \times 10^{-6}$ | T:G | 167:244 | $1.46 \times 10^{-4}$ | $5.43 \times 10^{-9}$ |
| 6 | rs2844659 | A | 0.2598 | 0.1907 | 1.49 [1.26, 1.77] | $3.77 \times 10^{-6}$ | A:G | 195:124 | $7.03 \times 10^{-5}$ | $6.12 \times 10^{-9}$ |
| 6 | rs3131063 | A | 0.5285 | 0.4353 | 1.45 [1.26, 1.68] | $2.91 \times 10^{-7}$ | A:G | 263:193 | 0.001045 | $6.97 \times 10^{-9}$ |
| 6 | rs1367728 | A | 0.06328 | 0.1146 | 0.52 [0.40, 0.69] | $2.11 \times 10^{-6}$ | A:G | 48:93 | $1.51 \times 10^{-4}$ | $7.28 \times 10^{-9}$ |
| 6 | rs1977090 | A | 0.06774 | 0.1185 | 0.54 [0.41, 0.70] | $4.04 \times 10^{-6}$ | A:G | 45:91 | $8.00 \times 10^{-5}$ | $7.38 \times 10^{-9}$ |
| 6 | rs1235162 | C | 0.1329 | 0.08341 | 1.68 [1.34, 2.12] | $6.32 \times 10^{-6}$ | C:T | 102:52 | $5.60 \times 10^{-5}$ | $8.05 \times 10^{-9}$ |
| 6 | rs2516440 | T | 0.2991 | 0.3836 | 0.69 [0.59, 0.80] | $1.29 \times 10^{-6}$ | T:C | 170:243 | $3.28 \times 10^{-4}$ | $9.58 \times 10^{-9}$ |
| 6 | rs2621330 | A | 0.08125 | 0.03907 | 2.18 [1.61, 2.94] | $2.47 \times 10^{-7}$ | A:G | 73:40 | 0.001907 | $1.06 \times 10^{-8}$ |
| 6 | rs12660382 | T | 0.1562 | 0.2373 | 0.60 [0.49, 0.72] | $5.06 \times 10^{-8}$ | T:C | 111:153 | 0.00974 | $1.11 \times 10^{-8}$ |
| 6 | rs9264779 | A | 0.08824 | 0.1475 | 0.56 [0.44, 0.71] | $1.12 \times 10^{-6}$ | A:C | 80:131 | $4.46 \times 10^{-4}$ | $1.12 \times 10^{-8}$ |
| 6 | rs2244839 | A | 0.2291 | 0.3071 | 0.67 [0.57, 0.79] | $1.93 \times 10^{-6}$ | A:G | 148:217 | $3.04 \times 10^{-4}$ | $1.31 \times 10^{-8}$ |
| 6 | rs185819 | T | 0.508 | 0.4413 | 1.31 [1.13, 1.51] | $2.44 \times 10^{-4}$ | C:T | 178:278 | $2.83 \times 10^{-6}$ | $1.52 \times 10^{-8}$ |
| 6 | rs602875 | G | 0.3521 | 0.2813 | 1.39 [1.19, 1.62] | $2.71 \times 10^{-5}$ | G:A | 226:145 | $2.61 \times 10^{-5}$ | $1.56 \times 10^{-8}$ |
| 6 | rs206769 | A | 0.1639 | 0.2299 | 0.66 [0.54, 0.79] | $9.59 \times 10^{-6}$ | A:G | 95:158 | $7.47 \times 10^{-5}$ | $1.58 \times 10^{-8}$ |
| 6 | rs3130933 | A | 0.05526 | 0.1006 | 0.52 [0.39, 0.70] | $8.77 \times 10^{-6}$ | A:G | 53:102 | $8.29 \times 10^{-5}$ | $1.60 \times 10^{-8}$ |
| 6 | rs13199524 | T | 0.05268 | 0.09632 | 0.52 [0.39, 0.70] | $1.29 \times 10^{-5}$ | T:C | 36:79 | $6.08 \times 10^{-5}$ | $1.72 \times 10^{-8}$ |
| 6 | rs2844539 | C | 0.1863 | 0.2351 | 0.74 [0.62, 0.89] | 0.001209 | C:T | 107:193 | $6.86 \times 10^{-7}$ | $1.82 \times 10^{-8}$ |
| 6 | rs9275596 | C | 0.3802 | 0.3099 | 1.37 [1.18, 1.59] | $5.00 \times 10^{-5}$ | C:T | 210:131 | $1.89 \times 10^{-5}$ | $2.05 \times 10^{-8}$ |
| 6 | rs757256 | A | 0.4777 | 0.4299 | 1.21 [1.05, 1.40] | 0.008475 | A:G | 280:168 | $1.21 \times 10^{-7}$ | $2.23 \times 10^{-8}$ |
| 6 | rs2280800 | T | 0.1533 | 0.09055 | 1.82 [1.47, 2.26] | $4.37 \times 10^{-8}$ | T:G | 131:97 | 0.02434 | $2.30 \times 10^{-8}$ |
| 6 | rs1383265 | G | 0.1221 | 0.1899 | 0.59 [0.48, 0.73] | $6.47 \times 10^{-7}$ | G:A | 107:158 | 0.001731 | $2.42 \times 10^{-8}$ |
| 6 | rs3130340 | C | 0.25 | 0.2038 | 1.30 [1.10, 1.54] | 0.002218 | C:T | 218:125 | $5.13 \times 10^{-7}$ | $2.46 \times 10^{-8}$ |
| 6 | rs1055569 | T | 0.2961 | 0.38 | 0.69 [0.59, 0.80] | $1.47 \times 10^{-6}$ | T:C | 171:239 | $7.84 \times 10^{-4}$ | $2.48 \times 10^{-8}$ |
| 6 | rs3115553 | A | 0.2496 | 0.2038 | 1.30 [1.10, 1.54] | 0.002427 | A:G | 218:125 | $5.13 \times 10^{-7}$ | $2.68 \times 10^{-8}$ |
| 6 | rs2442719 | G | 0.3426 | 0.4217 | 0.71 [0.62, 0.83] | $9.27 \times 10^{-6}$ | G:A | 165:242 | $1.35 \times 10^{-4}$ | $2.69 \times 10^{-8}$ |
| 6 | rs2260000 | C | 0.3295 | 0.4204 | 0.68 [0.58, 0.79] | $3.23 \times 10^{-7}$ | C:T | 174:231 | 0.004621 | $3.18 \times 10^{-8}$ |
| 6 | rs12207951 | T | 0.08945 | 0.1489 | 0.56 [0.44, 0.71] | $1.21 \times 10^{-6}$ | T:C | 69:112 | 0.001393 | $3.56 \times 10^{-8}$ |
| 6 | rs10484566 | G | 0.08125 | 0.04549 | 1.86 [1.39, 2.48] | $2.45 \times 10^{-5}$ | G:T | 74:33 | $7.38 \times 10^{-5}$ | $3.82 \times 10^{-8}$ |
| 6 | rs1041981 | A | 0.4016 | 0.3271 | 1.38 [1.19, 1.60] | $1.89 \times 10^{-5}$ | A:C | 241:163 | $1.04 \times 10^{-4}$ | $4.14 \times 10^{-8}$ |
| 6 | rs2517485 | A | 0.4724 | 0.3971 | 1.36 [1.18, 1.57] | $2.95 \times 10^{-5}$ | A:G | 270:185 | $6.75 \times 10^{-5}$ | $4.18 \times 10^{-8}$ |
| 6 | rs2248462 | A | 0.1426 | 0.2145 | 0.61 [0.50, 0.74] | $5.14 \times 10^{-7}$ | A:G | 110:157 | 0.004023 | $4.34 \times 10^{-8}$ |
| 6 | rs2256965 | T | 0.3449 | 0.4369 | 0.68 [0.59, 0.79] | $2.81 \times 10^{-7}$ | T:C | 193:249 | 0.00773 | $4.55 \times 10^{-8}$ |
| 6 | rs3130837 | T | 0.1232 | 0.07881 | 1.64 [1.30, 2.08] | $2.88 \times 10^{-5}$ | T:G | 98:50 | $7.96 \times 10^{-5}$ | $4.79 \times 10^{-8}$ |
| 6 | rs2071554 | A | 0.08645 | 0.04816 | 1.87 [1.41, 2.48] | $1.10 \times 10^{-5}$ | A:G | 75:36 | $2.14 \times 10^{-4}$ | $4.92 \times 10^{-8}$ |
| 6 | rs175597 | G | 0.1527 | 0.09772 | 1.66 [1.34, 2.06] | $2.51 \times 10^{-6}$ | G:A | 121:75 | 0.001017 | $5.31 \times 10^{-8}$ |
| 6 | rs7765379 | G | 0.05982 | 0.106 | 0.54 [0.41, 0.71] | $1.07 \times 10^{-5}$ | G:T | 47:90 | $2.39 \times 10^{-4}$ | $5.32 \times 10^{-8}$ |
| 6 | rs9276991 | G | 0.08913 | 0.05862 | 1.57 [1.20, 2.06] | $9.34 \times 10^{-4}$ | G:A | 97:42 | $3.09 \times 10^{-6}$ | $5.95 \times 10^{-8}$ |
| 6 | rs3763313 | C | 0.1292 | 0.1859 | 0.65 [0.53, 0.80] | $3.09 \times 10^{-5}$ | C:A | 106:171 | $9.40 \times 10^{-5}$ | $6.01 \times 10^{-8}$ |
| 6 | rs2516509 | G | 0.142 | 0.2128 | 0.61 [0.50, 0.74] | $7.25 \times 10^{-7}$ | G:A | 110:157 | 0.004023 | $6.02 \times 10^{-8}$ |
| 6 | rs9784758 | C | 0.1078 | 0.06349 | 1.78 [1.39, 2.30] | $5.77 \times 10^{-6}$ | C:T | 91:50 | $5.55 \times 10^{-4}$ | $6.58 \times 10^{-8}$ |
| 6 | rs12198173 | A | 0.05882 | 0.101 | 0.56 [0.42, 0.74] | $4.01 \times 10^{-5}$ | A:G | 38:81 | $8.09 \times 10^{-5}$ | $6.66 \times 10^{-8}$ |
| 6 | rs17533090 | T | 0.09893 | 0.1489 | 0.63 [0.50, 0.79] | $5.33 \times 10^{-5}$ | T:G | 79:138 | $6.20 \times 10^{-5}$ | $6.78 \times 10^{-8}$ |
| 6 | rs3129791 | A | 0.1248 | 0.08005 | 1.64 [1.30, 2.07] | $2.80 \times 10^{-5}$ | A:G | 102:54 | $1.22 \times 10^{-4}$ | $6.98 \times 10^{-8}$ |
| 6 | rs9368699 | C | 0.01337 | 0.04374 | 0.30 [0.17, 0.51] | $3.93 \times 10^{-6}$ | C:T | 14:38 | $8.74 \times 10^{-4}$ | $7.04 \times 10^{-8}$ |
| 6 | rs887464 | A | 0.5 | 0.4172 | 1.40 [1.21, 1.61] | $4.85 \times 10^{-6}$ | A:G | 256:185 | $7.22 \times 10^{-4}$ | $7.17 \times 10^{-8}$ |
| 6 | rs3130819 | G | 0.2505 | 0.1819 | 1.50 [1.26, 1.79] | $4.38 \times 10^{-6}$ | G:T | 147:95 | $8.30 \times 10^{-4}$ | $7.42 \times 10^{-8}$ |
| 6 | rs3117326 | A | 0.1239 | 0.07962 | 1.64 [1.29, 2.06] | $3.21 \times 10^{-5}$ | A:G | 102:54 | $1.22 \times 10^{-4}$ | $7.94 \times 10^{-8}$ |
| 6 | rs11244 | T | 0.3717 | 0.2955 | 1.41 [1.21, 1.64] | $7.68 \times 10^{-6}$ | T:C | 238:168 | $5.13 \times 10^{-4}$ | $8.01 \times 10^{-8}$ |
| 6 | rs9277554 | T | 0.3455 | 0.2839 | 1.33 [1.14, 1.55] | $2.40 \times 10^{-4}$ | T:C | 253:165 | $1.68 \times 10^{-5}$ | $8.17 \times 10^{-8}$ |
| 6 | rs2071481 | G | 0.1453 | 0.0923 | 1.67 [1.34, 2.08] | $3.33 \times 10^{-6}$ | G:A | 125:79 | 0.001279 | $8.63 \times 10^{-8}$ |

TABLE 3

All HapMap SNPs in the KIAA0350 linkage disequilibrium block that have $r^2 > 0.7$ in CEPH Utah Caucasians (CEU) to the three most protective variants (rs2903692, rs725613, rs17673553) or to the at-risk variant rs7200786.

| B35 pos1 | B35 pos2 | Key SNP | Other SNP | D' | $r^2$ |
|---|---|---|---|---|---|
| 11149407 | 11151695 | rs17673553 | rs11864680 | 1 | 1 |
| 11149407 | 11126542 | rs17673553 | rs12935657 | 1 | 1 |
| 11149407 | 11132565 | rs17673553 | rs2241099 | 1 | 0.954 |
| 11149407 | 11138204 | rs17673553 | rs7203459 | 1 | 0.899 |
| 11149407 | 11068467 | rs17673553 | rs8062923 | 0.95 | 0.859 |
| 11149407 | 11100000 | rs17673553 | rs17806056 | 0.948 | 0.814 |
| 11149407 | 10971822 | rs17673553 | rs12921922 | 1 | 0.773 |
| 11149407 | 10996309 | rs17673553 | rs13330041 | 1 | 0.773 |
| 11149407 | 10970437 | rs17673553 | rs17229044 | 1 | 0.773 |
| 11149407 | 11049638 | rs17673553 | rs17230818 | 1 | 0.773 |

TABLE 3-continued

All HapMap SNPs in the KIAA0350 linkage disequilibrium block that have $r^2 > 0.7$ in CEPH Utah Caucasians (CEU) to the three most protective variants (rs2903692, rs725613, rs17673553) or to the at-risk variant rs7200786.

| B35 pos1 | B35 pos2 | Key SNP | Other SNP | D' | $r^2$ |
|---|---|---|---|---|---|
| 11149407 | 10985839 | rs17673553 | rs7201845 | 0.943 | 0.727 |
| 11149407 | 10986662 | rs17673553 | rs9652599 | 0.943 | 0.726 |
| 11149407 | 10992204 | rs17673553 | rs8055968 | 0.941 | 0.718 |
| 11149407 | 11120182 | rs17673553 | rs9927527 | 1 | 0.7 |
| 11146284 | 11120182 | rs2903692 | rs9927527 | 1 | 1 |
| 11146284 | 11147479 | rs2903692 | rs12917893 | 1 | 0.959 |
| 11146284 | 11139358 | rs2903692 | rs2867880 | 1 | 0.959 |
| 11146284 | 11087374 | rs2903692 | rs12708716 | 1 | 0.958 |
| 11146284 | 11117948 | rs2903692 | rs12935413 | 1 | 0.958 |
| 11146284 | 11077184 | rs2903692 | rs725613 | 1 | 0.958 |
| 11146284 | 11089257 | rs2903692 | rs7204099 | 1 | 0.958 |
| 11146284 | 11111231 | rs2903692 | rs12103174 | 1 | 0.957 |
| 11146284 | 11085746 | rs2903692 | rs9929994 | 1 | 0.955 |
| 11146284 | 11066386 | rs2903692 | rs887864 | 0.956 | 0.876 |
| 11146284 | 11111066 | rs2903692 | rs9926078 | 0.955 | 0.874 |
| 11146284 | 10993469 | rs2903692 | rs7403919 | 0.913 | 0.799 |
| 11146284 | 11108929 | rs2903692 | rs9933507 | 1 | 0.786 |
| 11146284 | 11000680 | rs2903692 | rs9926367 | 1 | 0.777 |
| 11146284 | 11115118 | rs2903692 | rs7198004 | 0.954 | 0.772 |
| 11146284 | 11090394 | rs2903692 | rs11642009 | 0.951 | 0.758 |
| 11146284 | 11096649 | rs2903692 | rs12917716 | 0.954 | 0.743 |
| 11146284 | 11101431 | rs2903692 | rs3893660 | 0.954 | 0.743 |
| 11146284 | 11115223 | rs2903692 | rs7203150 | 0.954 | 0.743 |
| 11146284 | 11111722 | rs2903692 | rs767448 | 0.954 | 0.743 |
| 11146284 | 11100288 | rs2903692 | rs8061826 | 0.954 | 0.743 |
| 11146284 | 11103542 | rs2903692 | rs9941107 | 0.954 | 0.743 |
| 11146284 | 11107179 | rs2903692 | rs998592 | 0.954 | 0.743 |
| 11146284 | 11072518 | rs2903692 | rs11860603 | 1 | 0.738 |
| 11146284 | 11097389 | rs2903692 | rs12599402 | 0.953 | 0.737 |
| 11146284 | 11093374 | rs2903692 | rs17805769 | 0.953 | 0.737 |
| 11146284 | 11091127 | rs2903692 | rs11861236 | 0.952 | 0.735 |
| 11146284 | 11101519 | rs2903692 | rs3862468 | 0.952 | 0.733 |
| 11146284 | 11096431 | rs2903692 | rs12919083 | 1 | 0.727 |
| 11146284 | 11082153 | rs2903692 | rs2041670 | 1 | 0.727 |
| 11146284 | 11074959 | rs2903692 | rs7198621 | 1 | 0.727 |
| 11146284 | 10999820 | rs2903692 | rs8062322 | 1 | 0.727 |
| 11146284 | 11115395 | rs2903692 | rs9746695 | 1 | 0.727 |
| 11146284 | 11088745 | rs2903692 | rs9888908 | 1 | 0.727 |
| 11146284 | 11115823 | rs2903692 | rs12924985 | 0.951 | 0.727 |
| 11146284 | 11074189 | rs2903692 | rs11865121 | 1 | 0.72 |
| 11146284 | 11081866 | rs2903692 | rs9652601 | 1 | 0.72 |
| 11146284 | 11101381 | rs2903692 | rs3893661 | 0.94 | 0.717 |
| 11146284 | 11098901 | rs2903692 | rs12928537 | 1 | 0.714 |
| 11146284 | 11102272 | rs2903692 | rs12927355 | 1 | 0.711 |
| 11146284 | 11082065 | rs2903692 | rs9652582 | 1 | 0.711 |
| 11146284 | 11095363 | rs2903692 | rs12917656 | 0.945 | 0.706 |
| 11146284 | 11079103 | rs2903692 | rs12925642 | 1 | 0.703 |
| 11077184 | 11087374 | rs725613 | rs12708716 | 1 | 1 |
| 11077184 | 11117948 | rs725613 | rs12935413 | 1 | 1 |
| 11077184 | 11089257 | rs725613 | rs7204099 | 1 | 1 |
| 11077184 | 11085746 | rs725613 | rs9929994 | 1 | 1 |
| 11077184 | 11111231 | rs725613 | rs12103174 | 1 | 0.959 |
| 11077184 | 11120182 | rs725613 | rs9927527 | 1 | 0.959 |
| 11077184 | 11147479 | rs725613 | rs12917893 | 1 | 0.922 |
| 11077184 | 11139358 | rs725613 | rs2867880 | 1 | 0.922 |
| 11077184 | 11111066 | rs725613 | rs9926078 | 1 | 0.92 |
| 11077184 | 11066386 | rs725613 | rs887864 | 0.959 | 0.919 |
| 11077184 | 10993469 | rs725613 | rs7403919 | 0.957 | 0.845 |
| 11077184 | 11115118 | rs725613 | rs7198004 | 1 | 0.82 |
| 11077184 | 11090394 | rs725613 | rs11642009 | 0.954 | 0.802 |
| 11077184 | 11096649 | rs725613 | rs12917716 | 1 | 0.791 |
| 11077184 | 11101431 | rs725613 | rs3893660 | 1 | 0.791 |
| 11077184 | 11115223 | rs725613 | rs7203150 | 1 | 0.791 |
| 11077184 | 11111722 | rs725613 | rs767448 | 1 | 0.791 |
| 11077184 | 11100288 | rs725613 | rs8061826 | 1 | 0.791 |
| 11077184 | 11108929 | rs725613 | rs9933507 | 1 | 0.791 |
| 11077184 | 11103542 | rs725613 | rs9941107 | 1 | 0.791 |
| 11077184 | 11107179 | rs725613 | rs998592 | 1 | 0.791 |
| 11077184 | 11097389 | rs725613 | rs12599402 | 1 | 0.786 |
| 11077184 | 11093374 | rs725613 | rs17805769 | 1 | 0.786 |
| 11077184 | 11091127 | rs725613 | rs11861236 | 1 | 0.785 |
| 11077184 | 11101519 | rs725613 | rs3862468 | 1 | 0.783 |
| 11077184 | 11115823 | rs725613 | rs12924985 | 1 | 0.779 |
| 11077184 | 11101381 | rs725613 | rs3893661 | 1 | 0.779 |
| 11077184 | 11000680 | rs725613 | rs9926367 | 1 | 0.778 |
| 11077184 | 11095363 | rs725613 | rs12917656 | 1 | 0.763 |
| 11077184 | 11067186 | rs725613 | rs741175 | 0.954 | 0.744 |
| 11077184 | 11072518 | rs725613 | rs11860603 | 1 | 0.74 |
| 11077184 | 11096431 | rs725613 | rs12919083 | 1 | 0.734 |
| 11077184 | 11082153 | rs725613 | rs2041670 | 1 | 0.734 |
| 11077184 | 11074959 | rs725613 | rs7198621 | 1 | 0.734 |
| 11077184 | 10999820 | rs725613 | rs8062322 | 1 | 0.734 |
| 11077184 | 11115395 | rs725613 | rs9746695 | 1 | 0.734 |
| 11077184 | 11088745 | rs725613 | rs9888908 | 1 | 0.734 |
| 11077184 | 11074189 | rs725613 | rs11865121 | 1 | 0.728 |
| 11077184 | 11081866 | rs725613 | rs9652601 | 1 | 0.728 |
| 11077184 | 11098901 | rs725613 | rs12928537 | 1 | 0.722 |
| 11077184 | 11022124 | rs725613 | rs1003603 | 0.955 | 0.721 |
| 11077184 | 11062271 | rs725613 | rs2286973 | 0.955 | 0.721 |
| 11077184 | 11050221 | rs725613 | rs3901386 | 0.955 | 0.721 |
| 11077184 | 11067420 | rs725613 | rs741173 | 0.955 | 0.721 |
| 11077184 | 11027154 | rs725613 | rs8045749 | 0.955 | 0.721 |
| 11077184 | 11102272 | rs725613 | rs12927355 | 1 | 0.72 |
| 11077184 | 11082065 | rs725613 | rs9652582 | 1 | 0.72 |
| 11077184 | 11022340 | rs725613 | rs1985372 | 0.954 | 0.715 |
| 11077184 | 11018848 | rs725613 | rs9935174 | 0.954 | 0.715 |
| 11077184 | 11026001 | rs725613 | rs1861548 | 0.953 | 0.715 |
| 11077184 | 11007208 | rs725613 | rs7194305 | 0.953 | 0.715 |
| 11077184 | 11079103 | rs725613 | rs12925642 | 1 | 0.712 |
| 11077184 | 11007469 | rs725613 | rs17804470 | 0.952 | 0.708 |
| 11085302 | 10997588 | rs7200786 | rs8050144 | 1 | 0.815 |
| 11085302 | 10999062 | rs7200786 | rs8055544 | 1 | 0.815 |
| 11085302 | 10954327 | rs7200786 | rs12443971 | 1 | 0.808 |
| 11085302 | 10964119 | rs7200786 | rs1700820 | 1 | 0.783 |
| 11085302 | 10960425 | rs7200786 | rs7404554 | 1 | 0.783 |
| 11085302 | 10964770 | rs7200786 | rs1700818 | 1 | 0.77 |
| 11085302 | 10959949 | rs7200786 | rs4781027 | 1 | 0.742 |
| 11085302 | 11164093 | rs7200786 | rs8063318 | 1 | 0.71 |
| 11085302 | 11108929 | rs7200786 | rs9933507 | 1 | 0.704 |
| 11085302 | 11042887 | rs7200786 | rs7184431 | 0.908 | 0.7 |

TABLE 4

Candidate siRNA constructs for CLEC16A
Corresponding GenBank Accession number: NM_015226

SEQ ID NO: 1    CAAAAAAAUGUCUUCUCCCtt

SEQ ID NO: 2    AAAUAUCCAAAGGAGAUGUtt

SEQ ID NO: 3    CUGCUAUAGCAGAAAACCAtt

SEQ ID NO: 4    UUCUCUUUUAUUGCCAAGUtt

SEQ ID NO: 5    GAGGUUUUCUAACCCUCGGtt

SEQ ID NO: 6    CAAAACGUGGUACAGAUACtt

SEQ ID NO: 7    UUCUGUGACUGUGGUGUUUtt

SEQ ID NO: 8    CUAGCAGGUUCCGGUUCUGtt

SEQ ID NO: 9    CUCCACUAGCAGGUUCCGGtt

SEQ ID NO: 10   GAUGGUCUCCACUAGCAGGtt

SEQ ID NO: 11   CAAGAAGAAAACAAACAUAtt

SEQ ID NO: 12   ACACGUAACGGCCCGACUUtt

SEQ ID NO: 13   UGAGGUCUCGUGACUGAUGtt

SEQ ID NO: 14   CUCAUCAGAAAGUCAAAUtt

TABLE 4-continued

Candidate siRNA constructs for CLEC16A
Corresponding GenBank Accession number: NM_015226

| | |
|---|---|
| SEQ ID NO: 15 | GAGUUUUAACGAAAGUGUU~~ |
| SEQ ID NO: 16 | AAAGAAAUGGACAGUGUGGtt |
| SEQ ID NO: 17 | UGUGUACAGGGCAAAGUCAtt |
| SEQ ID NO: 18 | GGUUGAAAAACUUGAUGGCtt |
| SEQ ID NO: 19 | UUCAGGGUGGUUGAAAAACtt |
| SEQ ID NO: 20 | ACUUUAUAGACAUUCAAAGtt |
| SEQ ID NO: 21 | CCCAAUGAACCAGACCAAAtt |
| SEQ ID NO: 22 | UCUGCACGCAGUCAUCGAGtt |
| SEQ ID NO: 23 | GUUGAUGAUCAGGAUGUCAtt |
| SEQ ID NO: 24 | AUCGUUGAGGAACUCACAGtt |
| SEQ ID NO: 25 | GUGGUCAGUGAGCACAUCGtt |
| SEQ ID NO: 26 | AGCGGUGCAUGAUGUAUAAtt |
| SEQ ID NO: 27 | AAUGACUUCAGCUAACGAGtt |
| SEQ ID NO: 28 | GAUCACCAUUCAGAAUGACtt |
| SEQ ID NO: 29 | CAUCUCAGACAGAUCACCAtt |
| SEQ ID NO: 30 | CUGAAUAUCCUGUUCAGUCtt |
| SEQ ID NO: 31 | AACUUCUCUGAAUAUCCUGtt |
| SEQ ID NO: 32 | CCUCUUGCCCUUGUGCUUGtt |
| SEQ ID NO: 33 | UGGGCCCUUUCUCCUCAUCtt |
| SEQ ID NO: 34 | GGCAUCCUCGGUGGGCCCUtt |
| SEQ ID NO: 35 | GCUGGAUUCGCUCUAAUUUtt |
| SEQ ID NO: 36 | AUCUGGCUGGGCAGCGUUGtt |
| SEQ ID NO: 37 | CAGCGUCGCCAGCCGGAUCtt |
| SEQ ID NO: 38 | ACUCAUCAGGACUUGCUGCtt |
| SEQ ID NO: 39 | AGCCAGCACUCAUCAGGACtt |
| SEQ ID NO: 40 | GCAGGCCAGGUGCACGuCCtt |
| SEQ ID NO: 41 | ACAUGUCCAAAAAAAUGUC~~ |
| SEQ ID NO: 42 | UCAUGCUCCUAUACUCAUCtt |
| SEQ ID NO: 43 | AGGCUUGUGGAUGGUGAUGtt |
| SEQ ID NO: 44 | CUGGUCAGGAAGGUGAGGCtt |
| SEQ ID NO: 45 | UGCGCUCCUGGCCACGUUCtt |
| SEQ ID NO: 46 | GGCUGCGCUCCUGGCCACGtt |
| SEQ ID NO: 47 | UGGGUGCUCCCAGUGUGUCtt |
| SEQ ID NO: 48 | GGAGCGCAGGGAUAGGUGGtt |
| SEQ ID NO: 49 | UGAUGUUUUUGGACUUCUUtt |
| SEQ ID NO: 50 | GUUGAUGUUUUUGGACUUCtt |
| SEQ ID NO: 51 | AGUGUUGAUGUUUUUGGACtt |
| SEQ ID NO: 52 | AACCUUAGUGUUGAUGUUUtt |
| SEQ ID NO: 53 | CAAACCUUAGUGUUGAUGUtt |
| SEQ ID NO: 54 | ACUUCAUUAUUCCACAGGCtt |
| SEQ ID NO: 55 | UUUCCAGGAAGGUACUUCAtt |
| SEQ ID NO: 56 | GUAUCUCCCUUGUUUUUGU~~ |
| SEQ ID NO: 57 | GGAAGCUGUCUCUGUUUGGtt |
| SEQ ID NO: 58 | UCUUCACGGUCCCAACUGGtt |
| SEQ ID NO: 59 | GGCCACAGGGUCGGGAGUCtt |
| SEQ ID NO: 60 | GUCUGAUGCAUCUGGGUCCtt |
| SEQ ID NO: 61 | CCGAGUAGAAAGGAACAUCtt |
| SEQ ID NO: 62 | UGGCAGGUCUGGAGGAAAGtt |
| SEQ ID NO: 63 | GGAGACAGAGACCAUGUUCtt |
| SEQ ID NO: 64 | CGAGGAGACAGAGACCAUGtt |
| SEQ ID NO: 65 | AAACUGCCCUCGGCAGGCCtt |
| SEQ ID NO: 66 | UUGGCAGGACUGUGUUUCCtt |
| SEQ ID NO: 67 | CUCCUUGGCAGGACUGUGU~~ |
| SEQ ID NO: 68 | UGGGCGCCACUCCCCCUCCtt |
| SEQ ID NO: 69 | CCUUUCUGAGCUGUGCGUU~~ |
| SEQ ID NO: 70 | GUUUGUCCUUCCUUUGGGUtt |
| SEQ ID NO: 71 | CUUGGGGUGGGGCAGCCACtt |
| SEQ ID NO: 72 | CUGGGUGAGGUGGGGUCCUtt |
| SEQ ID NO: 73 | ACAAAAAUUAUUUACAUAUtt |
| SEQ ID NO: 74 | UCACUGGGACAAAAAUUAUtt |
| SEQ ID NO: 75 | GUUCUCACUGGGACAAAAAtt |
| SEQ ID NO: 76 | GCUCAGAGGCAUCGAGGUUtt |
| SEQ ID NO: 77 | AGGCUCAGAGGCAUCGAGGtt |
| SEQ ID NO: 78 | UCACUCAGUUUACCCCGAtt |
| SEQ ID NO: 79 | GGAGGAACCGCGAGCCGCCtt |
| SEQ ID NO: 80 | GUGGAUGUUGCGGGAAGUCtt |
| SEQ ID NO: 81 | GUGGUCCAAGGAGUGGAUGtt |
| SEQ ID NO: 82 | UGUUCUGUGACUGUGGUGUtt |
| SEQ ID NO: 83 | CAAAUACAGAGCUGUCAUUtt |
| SEQ ID NO: 84 | GUCAAAUACAGAGCUGUCAtt |
| SEQ ID NO: 85 | GAAGAAAACAAACAUAUUCtt |
| SEQ ID NO: 86 | CGACUUUGCCGCAAGAUGtt |
| SEQ ID NO: 87 | GCACACGUAACGGCCCGACtt |
| SEQ ID NO: 88 | GAUGUUCUCAAAGAGGAUGtt |
| SEQ ID NO: 89 | AUAGAAUUUACGUAGUUAUtt |
| SEQ ID NO: 90 | GAUGAUAGAAUUUACGUAG~~ |
| SEQ ID NO: 91 | UUAUGAACGAUGAUAGAAUtt |

TABLE 4-continued

Candidate siRNA constructs for CLEC16A
Corresponding GenBank Accession number: NM_015226

| SEQ ID NO: 92 | UUGAGUUUUAACGAAAGUG~~ |
|---|---|
| SEQ ID NO: 93 | GGACAGUGUGGUUGUUGAGtt |
| SEQ ID NO: 94 | GAAAUGGACAGUGUGGUUGtt |
| SEQ ID NO: 95 | AAAGUCAUUGGUGUGCUCAtt |
| SEQ ID NO: 96 | AACCAUGCUUUCAGGGUGG~~ |
| SEQ ID NO: 97 | CAGCAAUUCUAACCAUGCUtt |
| SEQ ID NO: 98 | GUUAUGGUUCUUACAGCAAtt |
| SEQ ID NO: 99 | ACAUUCAAAGUUAUGGUUCtt |
| SEQ ID NO: 100 | UAGACAUUCAAAGUUAUGGtt |
| SEQ ID NO: 101 | CAAUGACACUUUAUAGACAtt |
| SEQ ID NO: 102 | CUGGUUAUCCAAUGACACUtt |
| SEQ ID NO: 103 | GUAGUGCAGCAUGGCCUGG~~ |
| SEQ ID NO: 104 | GAAGUAAGGAACAGCAGUUtt |
| SEQ ID NO: 105 | GAGAAGUAAGGAACAGCAGtt |
| SEQ ID NO: 106 | UGCCACCAGAUCACUCAGUtt |
| SEQ ID NO: 107 | GAGGGGCAGGAAGAGCCUGtt |
| SEQ ID NO: 108 | UUCUCCUCCCUUGUCCUGGtt |
| SEQ ID NO: 109 | UUUCGGCCGUUCUCCUCCCtt |
| SEQ ID NO: 110 | GCAGGCUAAUUUUCGGCCG~~ |
| SEQ ID NO: 111 | AGACACCGGCAGGCUAAUU~~ |
| SEQ ID NO: 112 | AGAGACACCGGCAGGCUAAtt |
| SEQ ID NO: 113 | AUGCUGGGCUUGGCAGAACtt |
| SEQ ID NO: 114 | GAAGCACCGAAUGCUGGGCtt |
| SEQ ID NO: 115 | CUCGAGUGUCUCGGUGGGUtt |
| SEQ ID NO: 116 | CCGCCUCUUGCCCUUGUGCtt |
| SEQ ID NO: 117 | UUGCACCCGCCUCUUGCCCtt |
| SEQ ID NO: 118 | UCUCUUUUGCACCCGCCUCtt |
| SEQ ID NO: 119 | UUUUGUAGUUGGGUCUCUUtt |
| SEQ ID NO: 120 | GUUUUUGUAGUUGGGUCUCtt |
| SEQ ID NO: 121 | UUCCCCAACGUUUUUGUAGtt |
| SEQ ID NO: 122 | UUCUUCUUCCCCAACGUUUtt |
| SEQ ID NO: 123 | UCUUCUUCUUCCCCAACGUtt |
| SEQ ID NO: 124 | CUUUCUCCUCAUCUUCUUCtt |
| SEQ ID NO: 125 | GCCCUUUCUCCUCAUCUUCtt |
| SEQ ID NO: 126 | UAGCCUUCUCGGCGUCUUCtt |
| SEQ ID NO: 127 | CUUUAGCCUUCUCGGCGUCtt |
| SEQ ID NO: 128 | ACCCUCUGUACCUUUAGCCtt |
| SEQ ID NO: 129 | UGAACCACCCUCUGUACCUtt |
| SEQ ID NO: 130 | CCACUCGUCUUGAUGCCUUtt |
| SEQ ID NO: 131 | CCCCACUCGUCUUGAUGCCtt |
| SEQ ID NO: 132 | UUCACUCUCCCCACUCGUCtt |
| SEQ ID NO: 133 | UGAUCACCAUCUCGAUCUCtt |
| SEQ ID NO: 134 | GGCGGCCAGCUCUGAGAGCtt |
| SEQ ID NO: 135 | UUUCUCCUCGUCCGUGGUGtt |
| SEQ ID NO: 136 | GCAGGUGGCGGCGGCGCUUtt |
| SEQ ID NO: 137 | GAGCAGGUGGCGGCGGCGCtt |
| SEQ ID NO: 138 | CCAGGAAGGGUCUGCUCCAtt |
| SEQ ID NO: 139 | UUCAGGAUCCAUGCCUUUAtt |
| SEQ ID NO: 140 | UUUUUCAGGAUCCAUGCCU~~ |
| SEQ ID NO: 141 | GAGCUGGAUUCGCUCUAAUtt |
| SEQ ID NO: 142 | UUUGGCACGGGGAGCUGGAtt |
| SEQ ID NO: 143 | GUGGUCUUCUCGGCCGCAUtt |
| SEQ ID NO: 144 | CGGGUGGUUGUAGGUGGUCtt |
| SEQ ID NO: 145 | UCUUUCAGCUAGCGGGUGGtt |
| SEQ ID NO: 146 | UCAUGAUCCUGAUGAGUCUtt |
| SEQ ID NO: 147 | GUACAAGGUGAACACUUUCtt |
| SEQ ID NO: 148 | GUCGUACAAGGUGAACACU~~ |
| SEQ ID NO: 149 | UCCACGUUCAUGGGCUUCAtt |
| SEQ ID NO: 150 | AUAUUCCACGUUCAUGGGCtt |
| SEQ ID NO: 151 | CAUCAUGAGAUAUUCCACGtt |
| SEQ ID NO: 152 | AGGCGUCCAUCAUGAGAUA~~ |
| SEQ ID NO: 153 | CCCGUCAGUGGCGUGCCUGtt |
| SEQ ID NO: 154 | AUCGCCACACGGCAGCCGCtt |
| SEQ ID NO: 155 | CCGGAUGGCCCGCCGGGUCtt |
| SEQ ID NO: 156 | UCUCAGGCUCCCCUCGCAAtt |
| SEQ ID NO: 157 | AUCCAGGACAUCAUCAGUCtt |
| SEQ ID NO: 158 | UGCAAUCAAGUCGCUGUUAtt |
| SEQ ID NO: 159 | ACAUGCAAUCAAGUCGCUGtt |
| SEQ ID NO: 160 | CUGGACCAUGCCGCCAUCCtt |
| SEQ ID NO: 161 | CUGCAAUAGGCCUGCAAACtt |
| SEQ ID NO: 162 | CUGGAGGAUGGGAAGGGCtt |
| SEQ ID NO: 163 | GCCUUUGGCCAGGCGCUGCtt |
| SEQ ID NO: 164 | CCUUGCCUGGAUGCGGCCUtt |
| SEQ ID NO: 165 | CUCUGCAUCUUCAUGCGCCtt |
| SEQ ID NO: 166 | GGCAGCUAUUCUCUGCAUCtt |
| SEQ ID NO: 167 | AGGUCCAGGAGGGCAGCUAtt |
| SEQ ID NO: 168 | ACUUCAGUGGUGGGCUGGAtt |

TABLE 4-continued

Candidate siRNA constructs for CLEC16A
Corresponding GenBank Accession number: NM_015226

| SEQ ID NO: | Sequence |
|---|---|
| SEQ ID NO: 169 | CGAGUCCAAACCCCAGGACtt |
| SEQ ID NO: 170 | CACGGCGAAGCCUGGCACCtt |
| SEQ ID NO: 171 | GACGGGGAGCUGUGCUGGU~~ |
| SEQ ID NO: 172 | GAAGGUGAGGCUUAGGCAGtt |
| SEQ ID NO: 173 | GCUUCCGUUUCGUUGACGAtt |
| SEQ ID NO: 174 | AGAGUCUGCUUCCGUUUCGtt |
| SEQ ID NO: 175 | GCUUAGAGUCUGCUUCCGUtt |
| SEQ ID NO: 176 | UGCUGGGCUUAGAGUCUGCtt |
| SEQ ID NO: 177 | GGCCACGUUCUUGCUGGGCtt |
| SEQ ID NO: 178 | GGGGGACAAGGGUCAGCGAtt |
| SEQ ID NO: 179 | GCUCAGCACAUGCAGCCUCtt |
| SEQ ID NO: 180 | AACGUGGGGCUUCUUCCCAtt |
| SEQ ID NO: 181 | UUCAAGGACAACGUGGGGCtt |
| SEQ ID NO: 182 | AUGCAAAGUGAAAAGGAAtt |
| SEQ ID NO: 183 | GCCGGUGCAGUCAUCUGCAtt |
| SEQ ID NO: 184 | CAGUGACCUGGUCCAAUUCtt |
| SEQ ID NO: 185 | AGUCUGCUUUUCUACAAAUtt |
| SEQ ID NO: 186 | UGUUUAUCUAAGUCUGCUUtt |
| SEQ ID NO: 187 | GAUGUUUAUCUAAGUCUGCtt |
| SEQ ID NO: 188 | GAAGUUUAAAAAUAAAUGtt |
| SEQ ID NO: 189 | CUUCUUUUAAAUAGAAGUUtt |
| SEQ ID NO: 190 | GACUUCUUUUAAAUAGAAGtt |
| SEQ ID NO: 191 | AUGACAUCAAACCUUAGUGtt |
| SEQ ID NO: 192 | UUUCACAUGACAUCAAACCtt |
| SEQ ID NO: 193 | AACUGUUAUUAUUACACUUtt |
| SEQ ID NO: 194 | UUAACUGUUAUUAUUACACtt |
| SEQ ID NO: 195 | GAAAUCUUAACUGUUAUUAtt |
| SEQ ID NO: 196 | CAUGAAAUCUUAACUGUUAtt |
| SEQ ID NO: 197 | GAUCAUGAAAUCUUAACUGtt |
| SEQ ID NO: 198 | UGAAAAUGAUCAUGAAAUC~~ |
| SEQ ID NO: 199 | GUGAGUAACAAAGAAUCACtt |
| SEQ ID NO: 200 | AUUCCACAGGCUUGCAGAGtt |
| SEQ ID NO: 201 | CCAGGAAGGUACUUCAUUAtt |
| SEQ ID NO: 202 | AAACUUCCAGGAAGGUACtt |
| SEQ ID NO: 203 | UUAAAAAAUAAUCCAAACUtt |
| SEQ ID NO: 204 | ACAUGUAUCUCCCUUGUUUtt |
| SEQ ID NO: 205 | AUACAUGUAUCUCCCUUGUtt |
| SEQ ID NO: 206 | GAGAAUACAUGUAUCUCCC~~ |
| SEQ ID NO: 207 | CCUUUUCCUGGAGAAAUCUtt |
| SEQ ID NO: 208 | GCUGGCUACAUUCCUCCUU~~ |
| SEQ ID NO: 209 | GAGCUGGCUACAUUCCUCCtt |
| SEQ ID NO: 210 | GAGUGGGAGCUGGCUACAtt |
| SEQ ID NO: 211 | AAGCUGUCUCUGUUUGGUUtt |
| SEQ ID NO: 212 | UGCUGGAAGCUGUCUCUGU~~ |
| SEQ ID NO: 213 | GGUCCCAACUGGUUCCUUCtt |
| SEQ ID NO: 214 | CACGGUCCCAACUGGUUCCtt |
| SEQ ID NO: 215 | GAGGGUGUCUUCCUUUGAUtt |
| SEQ ID NO: 216 | ACGUAGAGGGUGUCUUCCUtt |
| SEQ ID NO: 217 | AGGUGACGUAGAGGGUGUCtt |
| SEQ ID NO: 218 | CUCUGGGGACACCAUGCCCtt |
| SEQ ID NO: 219 | GAACCAUGGGGUUUCCAUAtt |
| SEQ ID NO: 220 | GAUGCAUCUGGGUCCUUGCtt |
| SEQ ID NO: 221 | CUGUGUUUCCUUCAUGAGGtt |
| SEQ ID NO: 222 | GCACAGCUACCCAGAGGGC~~ |
| SEQ ID NO: 223 | UCUAUGGAAGCAAAGGUCC~~ |
| SEQ ID NO: 224 | CCCCUUUCUGAGCUGUGCGtt |
| SEQ ID NO: 225 | UCUGCCCAUGUGGCCCCUtt |
| SEQ ID NO: 226 | GUCGUGGUUUGUCCUUCCUtt |
| SEQ ID NO: 227 | CGGUGGUCGUGGUUUGUCC~~ |
| SEQ ID NO: 228 | UGGCCACGGUGGUCGUGGUtt |
| SEQ ID NO: 229 | CUUCCUUCUCUUCCAGGGAtt |
| SEQ ID NO: 230 | CCACCCUGCCUUCCUUCUCtt |
| SEQ ID NO: 231 | CCGCUCCACCCUGCCUUCCtt |
| SEQ ID NO: 232 | CCCCCCGCUCCACCCUGCCtt |
| SEQ ID NO: 233 | CCUUCUCUCCAUGAUGGUCtt |
| SEQ ID NO: 234 | UCUCCUGAUGCUGUGGUCCtt |
| SEQ ID NO: 235 | CCCUCUUGCUCUUAAAAAAtt |
| SEQ ID NO: 236 | CUCUCUACCCCUCUUGCUCtt |
| SEQ ID NO: 237 | UUGAUCCUCUCUACCCCUCtt |
| SEQ ID NO: 238 | AUCUCCAGCCAGGGCCAGC~~ |
| SEQ ID NO: 239 | GCCCCACAGACAGAGUCAUtt |
| SEQ ID NO: 240 | GCCACUUGCCUUCUCUAGUtt |
| SEQ ID NO: 241 | GGUGGGGCAGCCACUUGCCtt |
| SEQ ID NO: 242 | UGUUCCUCCUGGUCACGCCtt |
| SEQ ID NO: 243 | UGGAGUGAGCUGCAGGCUGtt |
| SEQ ID NO: 244 | CCAGUUGGAGCCCAGAGACtt |
| SEQ ID NO: 245 | UCAGUGGUUACAAGACCAGtt |

TABLE 4-continued

Candidate siRNA constructs for CLEC16A
Corresponding GenBank Accession number: NM_015226

| | |
|---|---|
| SEQ ID NO: 246 | CUCCUUCAGUGCUCAGUGGtt |
| SEQ ID NO: 247 | CUGACCAAGACCUCUCUCCtt |
| SEQ ID NO: 248 | CUGGUCCUCCCAGUCACCUtt |
| SEQ ID NO: 249 | CUGCCCUGAGCAGUGUCUUtt |
| SEQ ID NO: 250 | CCCUGCCCUGAGCAGUGUCtt |
| SEQ ID NO: 251 | CAUGGGGACUGCCCUUUUCtt |
| SEQ ID NO: 252 | CCACAUGGGGACUGCCCUUtt |
| SEQ ID NO: 253 | GCCCACAUGGGGACUGCCC~~ |
| SEQ ID NO: 254 | GGUGUCCCCAGACGCAAGtt |
| SEQ ID NO: 255 | CUCCUUACAUAAGCAAAGCtt |
| SEQ ID NO: 256 | GGCUGGCUCCCAGACCUCCtt |
| SEQ ID NO: 257 | AGCGCCCAGCUAUGAGGUtt |
| SEQ ID NO: 258 | CUUCCCACACUCCUGGCUCtt |
| SEQ ID NO: 259 | ACAGCCCCACUGUGGGCCtt |
| SEQ ID NO: 260 | AAGUGCUCUCUGCAGGGACtt |
| SEQ ID NO: 261 | GCCAGCCCUGCUCCCUGACtt |
| SEQ ID NO: 262 | CAAAGCCAAGGUUUGGGAGtt |
| SEQ ID NO: 263 | CAAUAUUCAAAGCCAAGGUtt |
| SEQ ID NO: 264 | GCACACCUCCACAACAAUA~~ |
| SEQ ID NO: 265 | ACCUGCUGGGACAGGUACCtt |
| SEQ ID NO: 266 | CGAUGGUGAAGGCUGGCCCtt |
| SEQ ID NO: 267 | GUGAACGCAAGUGUCUGGG~~ |
| SEQ ID NO: 268 | CACCUGCCCCUUAGGUUGCtt |
| SEQ ID NO: 269 | UCUUCACCUGCCCCUUAGGtt |
| SEQ ID NO: 270 | GCGUCUGGCAGGGCUGCGCtt |
| SEQ ID NO: 271 | ACGGUGCAUCUCAGAGACCtt |
| SEQ ID NO: 272 | AUCAGUUCACCCCACGCCUtt |
| SEQ ID NO: 273 | ACAAGAAGAUCAAAAUCAGtt |
| SEQ ID NO: 274 | AAUGCUUCAGAUUUAUUAtt |
| SEQ ID NO: 275 | UUAAAUGCUUCAGAUUUAtt |
| SEQ ID NO: 276 | UACAUUAAAUGCUUCAGAUtt |
| SEQ ID NO: 277 | AGAUGACUACAUUAAAUGCtt |
| SEQ ID NO: 278 | CAAUGUCAAGAUGACUACAtt |
| SEQ ID NO: 279 | AAAAAUUAUUUACAUAUUUtt |
| SEQ ID NO: 280 | UGCUGGCAAAGCAGGUACtt |
| SEQ ID NO: 281 | UUUCAUUCCACCCUCGUGtt |
| SEQ ID NO: 282 | AGGAAGUUCCAGUUUUCAUtt |
| SEQ ID NO: 283 | UUACAAGGAAGUUCCAGUUtt |
| SEQ ID NO: 284 | AUUUACAAGGAAGUUCCAGtt |
| SEQ ID NO: 285 | GUUUAAAUUUACAAGGAAGtt |
| SEQ ID NO: 286 | AUUUAAACUUGGCAAUAAAtt |
| SEQ ID NO: 287 | ACUUGGCAAUAAAAGAGAAtt |
| SEQ ID NO: 288 | CUUCUAUUUAAAAGAAGUCtt |
| SEQ ID NO: 289 | ACACCACAGUCACAGAACAtt |
| SEQ ID NO: 290 | UAUGUUUGUUUUCUUCUUGtt |
| SEQ ID NO: 291 | CAUCCUCUUUGAGAACAUCtt |
| SEQ ID NO: 292 | AUUCUAUCAUCGUUCAUAA~~ |
| SEQ ID NO: 293 | CACUUUCGUUAAAACUCAA~~ |
| SEQ ID NO: 294 | AACUCAACAACCACACUGUtt |
| SEQ ID NO: 295 | CUCAACAACCACACUGUCCtt |
| SEQ ID NO: 296 | AGCAUGGUUAGAAUUGCUGtt |
| SEQ ID NO: 297 | CCAUAACUUUGAAUGUCUAtt |
| SEQ ID NO: 298 | AACUGCUGUUCCUUACUUCtt |
| SEQ ID NO: 299 | CCAGGACAAGGGAGGAGAAtt |
| SEQ ID NO: 300 | UUAGCCUGCCGGUGUCUCU~~ |
| SEQ ID NO: 301 | GAGGCGGGUGCAAAAGAGAtt |
| SEQ ID NO: 302 | AAGAGACCCAACUACAAAAtt |
| SEQ ID NO: 303 | GAAGAAGAUGAGGAGAAAGtt |
| SEQ ID NO: 304 | GAAGAUGAGGAGAAAGGGCtt |
| SEQ ID NO: 305 | GGCUAAAGGUACAGAGGGUtt |
| SEQ ID NO: 306 | AGGUACAGAGGGUGGUUCAtt |
| SEQ ID NO: 307 | GAGAUCGAGAUGGUGAUCAtt |
| SEQ ID NO: 308 | UGGAGCAGACCCUUCCUGGtt |
| SEQ ID NO: 309 | AGACUCAUCAGGAUCAUGAtt |
| SEQ ID NO: 310 | CAACGCUGCCCAGCCAGAUtt |
| SEQ ID NO: 311 | UGAAGCCCAUGAACGUGGAtt |
| SEQ ID NO: 312 | CGUGGAAUAUCUCAUGAUGtt |
| SEQ ID NO: 313 | CAGGCACGCCACUGACGGGtt |
| SEQ ID NO: 314 | GCGGCUGCCGUGUGGCGAUtt |
| SEQ ID NO: 315 | GACCCGGCGGGCCAUCCGGtt |
| SEQ ID NO: 316 | UUGCGAGGGGAGCCUGAGAtt |
| SEQ ID NO: 317 | UCGUCAACGAAACGGAAGCtt |
| SEQ ID NO: 318 | CGAAACGGAAGCAGACUCUtt |
| SEQ ID NO: 319 | ACGGAAGCAGACUCUAAGCtt |
| SEQ ID NO: 320 | CGUGGCCAGGAGCGCAGCC~~ |
| SEQ ID NO: 321 | GAGGCUGCAUGUGCUGAGCtt |
| SEQ ID NO: 322 | GCCCCACGUUGUCCUUGAAtt |

TABLE 4-continued

Candidate siRNA constructs for CLEC16A
Corresponding GenBank Accession number: NM_015226

| | |
|---|---|
| SEQ ID NO: 323 | GCAGACUUAGAUAAACAUCtt |
| SEQ ID NO: 324 | ACAUCUCCUUUGGAUAUUUtt |
| SEQ ID NO: 325 | CAUUUAUUUUAAAACUUC~~ |
| SEQ ID NO: 326 | AACUUCUAUUUAAAAGAAGtt |
| SEQ ID NO: 327 | GUCCAAAAACAUCAACACUtt |
| SEQ ID NO: 328 | GGUUUGAUGUCAUGUGAAAtt |
| SEQ ID NO: 329 | AAGUGUAAUAAUAACAGUU~~ |
| SEQ ID NO: 330 | GUGUAAUAAUAACAGUUAAtt |
| SEQ ID NO: 331 | UAAUAACAGUUAAGAUUUCtt |
| SEQ ID NO: 332 | UAACAGUUAAGAUUUCAUGtt |
| SEQ ID NO: 333 | CAGUUAAGAUUUCAUGAUCtt |
| SEQ ID NO: 334 | GAUUUCAUGAUCAUUUUCAtt |
| SEQ ID NO: 335 | GUACCUUCCUGGAAAGUUUtt |
| SEQ ID NO: 336 | AGAUUUCUCCAGGAAAAGG~~ |
| SEQ ID NO: 337 | AAGGAGGAAUGUAGCCAGCtt |
| SEQ ID NO: 338 | GGAGGAAUGUAGCCAGCUCtt |
| SEQ ID NO: 339 | UGUAGCCAGCUCCCCACUCtt |
| SEQ ID NO: 340 | AACCAAACAGAGACAGCUUtt |
| SEQ ID NO: 341 | CCAAAC4GAGACAGCUUCCtt |
| SEQ ID NO: 342 | ACAGAGACAGCUUCCAGCAtt |
| SEQ ID NO: 343 | AUCAAAGGAAGACACCCUCtt |
| SEQ ID NO: 344 | CGCACAGCUCAGAAAGGGGtt |
| SEQ ID NO: 345 | AGGGGGCCACAUGGGCAGAtt |
| SEQ ID NO: 346 | ACCCAAAGGAAGGACAAACtt |
| SEQ ID NO: 347 | AGGAAGGACAAACCACGAC~~ |
| SEQ ID NO: 348 | GGACAAACCACGACCACCG~~ |
| SEQ ID NO: 349 | ACCACGACCACCGUGGCCAtt |
| SEQ ID NO: 350 | ACUAGAGAAGGCAAGUGGCtt |
| SEQ ID NO: 351 | GGCGUGACCAGGAGGAACAtt |
| SEQ ID NO: 352 | GCUUUGCUUAUGUAAGGAGtt |
| SEQ ID NO: 353 | GUCAGGGAGCAGGGCUGGCtt |
| SEQ ID NO: 354 | ACCUUGGCUUUGAAUAUUGtt |
| SEQ ID NO: 355 | GGGCCAGCCUUCACCAUCG~~ |
| SEQ ID NO: 356 | AUAAAUCUGAAGCAUUUAA~~ |
| SEQ ID NO: 357 | GGCGGCUCGCGGUUCCUCCtt |
| SEQ ID NO: 358 | GACUUCCCGCAACAUCCACtt |
| SEQ ID NO: 359 | CAUCCACUCCUUGGACCACtt |
| SEQ ID NO: 360 | GUAUCUGUACCACGUUUUGtt |
| SEQ ID NO: 361 | AAACACCACAGUCACAGAAtt |
| SEQ ID NO: 362 | CAGAACCGGAACCUGCUAGtt |
| SEQ ID NO: 363 | CCGGAACCUGCUAGUGGAGtt |
| SEQ ID NO: 364 | CCUGCUAGUGGAGACCAUCtt |
| SEQ ID NO: 365 | AAUGACAGCUCUGUAUUUGtt |
| SEQ ID NO: 366 | UGACAGCUCUGUAUUUGACtt |
| SEQ ID NO: 367 | GAAUAUGUUUGUUUUCUUCtt |
| SEQ ID NO: 368 | CAUCUUGCGGCAAAAGUCGtt |
| SEQ ID NO: 369 | AAGUCGGGCCGUUACGUGUtt |
| SEQ ID NO: 370 | GUCGGGCCGUUACGUGUGCtt |
| SEQ ID NO: 371 | CAUCAGUCACGAGACCUCAtt |
| SEQ ID NO: 372 | AUAACUACGUAAAUUCUAUtt |
| SEQ ID NO: 373 | CUACGUAAAUUCUAUCAUCtt |
| SEQ ID NO: 374 | AUUUGACUUUUCUGAUGAGtt |
| SEQ ID NO: 375 | AACACUUUCGUUAAAACUC~~ |
| SEQ ID NO: 376 | CAACCACACUGUCCAUUUCtt |
| SEQ ID NO: 377 | CCACACUGUCCAUUUCUUUtt |
| SEQ ID NO: 378 | UGAGCACACCAAUGACUUUtt |
| SEQ ID NO: 379 | UGACUUUGCCCUGUACACAtt |
| SEQ ID NO: 380 | GCCAUCAAGUUUUUCAACCtt |
| SEQ ID NO: 381 | GUUUUUCAACCACCCUGAAtt |
| SEQ ID NO: 382 | CCACCCUGAAAGCAUGGUUtt |
| SEQ ID NO: 383 | UUGCUGUAAGAACCAUAAC~~ |
| SEQ ID NO: 384 | GAACCAUAACUUUGAAUGUtt |
| SEQ ID NO: 385 | CUUUGAAUGUCUAUAAAGUtt |
| SEQ ID NO: 386 | UGUCUAUAAAGUGUCAUUGtt |
| SEQ ID NO: 387 | AGUGUCAUUGGAUAACCAGtt |
| SEQ ID NO: 388 | CCAGGCCAUGCUGCACUACtt |
| SEQ ID NO: 389 | CUGCUGUUCCUUACUUCUCtt |
| SEQ ID NO: 390 | UUUGGUCUGGUUCAUUGGGtt |
| SEQ ID NO: 391 | CUCGAUGACUGCGUGCAGAtt |
| SEQ ID NO: 392 | UCGGGUAAACUGAGUGAUtt |
| SEQ ID NO: 393 | ACUGAGUGAUCUGGUGGCAtt |
| SEQ ID NO: 394 | UGACAUCCUGAUCAUCAACtt |
| SEQ ID NO: 395 | CUGUGAGUUCCUCAACGAUtt |
| SEQ ID NO: 396 | CGAUGUGCUCACUGACCACtt |
| SEQ ID NO: 397 | CAGGCUCUUCCUGCCCCUCtt |
| SEQ ID NO: 398 | GGGAGGAGAACGGCCGAAAtt |
| SEQ ID NO: 399 | CGGCCGAAAAUUAGCCUGCtt |

TABLE 4-continued

Candidate siRNA constructs for CLEC16A
Corresponding GenBank Accession number: NM_015226

| | |
|---|---|
| SEQ ID NO: 400 | AAUUAGCCUGCCGGUGUCUtt |
| SEQ ID NO: 401 | UUAUACAUCAUGCACCGCUtt |
| SEQ ID NO: 402 | CUCGUUAGCUGAAGUCAUUtt |
| SEQ ID NO: 403 | GUCAUUCUGAAUGGUGAUCtt |
| SEQ ID NO: 404 | UGGUGAUCUGUCUGAGAUGtt |
| SEQ ID NO: 405 | GACUGAACAGGAUAUUCAGtt |
| SEQ ID NO: 406 | CAGGAUAUUCAGAGAAGUUtt |
| SEQ ID NO: 407 | GUUCUGCCAAGCCCAGCAUtt |
| SEQ ID NO: 408 | GCCCAGCAUUCGGUGCUUCtt |
| SEQ ID NO: 409 | ACCCACCGAGACACUCGAGtt |
| SEQ ID NO: 410 | CAAGCACAAGGGCAAGAGGtt |
| SEQ ID NO: 411 | GCACAAGGGCAAGAGGCGGtt |
| SEQ ID NO: 412 | GGGCAAGAGGCGGGUGCAAtt |
| SEQ ID NO: 413 | GAGACCCAACUACAAAAACtt |
| SEQ ID NO: 414 | CUACAAAAACGUUGGGGAAtt |
| SEQ ID NO: 415 | AAACGUUGGGGAAGAAGAAtt |
| SEQ ID NO: 416 | ACGUUGGGGAAGAAGAAGAtt |
| SEQ ID NO: 417 | GAUGAGGAGAAAGGGCCCAtt |
| SEQ ID NO: 418 | AGGGCCCACCGAGGAUGCCtt |
| SEQ ID NO: 419 | GAAGACGCCGAGAAGGCUAtt |
| SEQ ID NO: 420 | GACGCCGAGAAGGCUAAAGtt |
| SEQ ID NO: 421 | AAGGCAUCAAGACGAGUGGtt |
| SEQ ID NO: 422 | GGCAUCAAGACGAGUGGGGtt |
| SEQ ID NO: 423 | GACGAGUGGGGAGAGUGAAtt |
| SEQ ID NO: 424 | GCUCUCAGAGCUGGCCGCCtt |
| SEQ ID NO: 425 | CACCACGGACGAGGAGAAAtt |
| SEQ ID NO: 426 | AAGCGCCGCCGCCACCUGCtt |
| SEQ ID NO: 427 | GCGCCGCCGCCACCUGCUCtt |
| SEQ ID NO: 428 | UAAAGGCAUGGAUCCUGAAtt |
| SEQ ID NO: 429 | AGGCAUGGAUCCUGAAAAtt |
| SEQ ID NO: 430 | AAAUUAGAGCGAAUCCAGCtt |
| SEQ ID NO: 431 | AUUAGAGCGAAUCCAGCUCtt |
| SEQ ID NO: 432 | UCCAGCUCCCCGUGCCAAAtt |
| SEQ ID NO: 433 | AUGCGGCCGAGAAGACCACtt |
| SEQ ID NO: 434 | GACCACCUACAACCACCCGtt |
| SEQ ID NO: 435 | CCACCCGCUAGCUGAAAGAtt |
| SEQ ID NO: 436 | CGCUGCCCAGCCAGAUGGGtt |
| SEQ ID NO: 437 | GAUCCGGCUGGCGACGCUGtt |
| SEQ ID NO: 438 | GCAGCAAGUCCUGAUGAGUtt |
| SEQ ID NO: 439 | GUCCUGAUGAGUGCUGGCUtt |
| SEQ ID NO: 440 | GGACGUGCACCUGGCCUGCtt |
| SEQ ID NO: 441 | GAAAGUGUUCACCUUGUACtt |
| SEQ ID NO: 442 | AGUGUUCACCUUGUACGACtt |
| SEQ ID NO: 443 | GGGAGAAGACAUUUUUUUGtt |
| SEQ ID NO: 444 | GACAUUUUUUUGGACAUGUtt |
| SEQ ID NO: 445 | GAUGAGUAUAGGAGCAUGAtt |
| SEQ ID NO: 446 | GCCCAUGAACGUGGAAUAUtt |
| SEQ ID NO: 447 | UAUCUCAUGAUGGACGCCUtt |
| SEQ ID NO: 448 | GACUGAUGAUGUCCUGGAUtt |
| SEQ ID NO: 449 | UAACAGCGACUUGAUUGCAtt |
| SEQ ID NO: 450 | CAGCGACUUGAUUGCAUGUtt |
| SEQ ID NO: 451 | GGAUGGCGGCAUGGUCCAGtt |
| SEQ ID NO: 452 | GUUUGCAGGCCUAUUGCAGtt |
| SEQ ID NO: 453 | CAUCACCAUCCACAAGCCUtt |
| SEQ ID NO: 454 | GCCUGCGUCCAGCCCCCAUtt |
| SEQ ID NO: 455 | GCCCUUCCCCAUCCUCCAGtt |
| SEQ ID NO: 456 | GCAGCGCCUGGCCAAAGGCtt |
| SEQ ID NO: 457 | AGGCCGCAUCCAGGCAAGGtt |
| SEQ ID NO: 458 | GGCGCAUGAAGAUGCAGAGtt |
| SEQ ID NO: 459 | GAUGCAGAGAAUAGCUGCCtt |
| SEQ ID NO: 460 | UAGCUGCCCUCCUGGACCUtt |
| SEQ ID NO: 461 | UCCAGCCCACCACUGAAGUtt |
| SEQ ID NO: 462 | GUCCUGGGGUUUGGACUCGtt |
| SEQ ID NO: 463 | GGUGCCAGGCUUCGCCGUGtt |
| SEQ ID NO: 464 | ACCAGCACAGCUCCCCGUCtt |
| SEQ ID NO: 465 | CUGCCUAAGCCUCACCUUCtt |
| SEQ ID NO: 466 | GCCUCACCUUCCUGACCAGtt |
| SEQ ID NO: 467 | GCAGACUCUAAGCCCAGCAtt |
| SEQ ID NO: 468 | GCCCAGCAAGAACGUGGCCtt |
| SEQ ID NO: 469 | GAACGUGGCCAGGAGCGCAtt |
| SEQ ID NO: 470 | UCGCUGACCCUUGUCCCCCtt |
| SEQ ID NO: 471 | GACACACUGGGAGCACCCAtt |
| SEQ ID NO: 472 | CCACCUAUCCCUGCGCUCCtt |
| SEQ ID NO: 473 | UGGGAAGAAGCCCCACGUUtt |
| SEQ ID NO: 474 | GAAGCCCCACGUUGUCCUUtt |
| SEQ ID NO: 475 | UUCCUUUUUCACUUUGCAUtt |
| SEQ ID NO: 476 | UGCAGAUGACUGCACCGGCtt |

TABLE 4-continued

Candidate siRNA constructs for CLEC16A
Corresponding GenBank Accession number: NM_015226

| | |
|---|---|
| SEQ ID NO: 477 | GAAUUGGACCAGGUCACUGtt |
| SEQ ID NO: 478 | UUGGACCAGGUCACUGUACtt |
| SEQ ID NO: 479 | AUUUGUAGAAAAGCAGACUtt |
| SEQ ID NO: 480 | AAGCAGACUUAGAUAAACAtt |
| SEQ ID NO: 481 | AAGAAGUCCAAAAACAUCAtt |
| SEQ ID NO: 482 | GAAGUCCAAAAACAUCAACtt |
| SEQ ID NO: 483 | AAACAUCAACACUAAGGUUtt |
| SEQ ID NO: 484 | ACAUCAACACUAAGGUUUGtt |
| SEQ ID NO: 485 | CACUAAGGUUUGAUGUCAUtt |
| SEQ ID NO: 486 | GUGAUUCUUUGUUACUCACtt |
| SEQ ID NO: 487 | CUCUGCAAGCCUGUGGAAUtt |
| SEQ ID NO: 488 | GCCUGUGGAAUAAUGAAGUtt |
| SEQ ID NO: 489 | UAAUGAAGUACCUUCCUGGtt |
| SEQ ID NO: 490 | UGAAGUACCUUCCUGGAAAtt |
| SEQ ID NO: 491 | AGUUUGGAUUAUUUUUUAAtt |
| SEQ ID NO: 492 | ACAAAACAAGGGAGAUACtt |
| SEQ ID NO: 493 | AAACAAGGGAGAUACAUGUtt |
| SEQ ID NO: 494 | ACAAGGGAGAUACAUGUAUtt |
| SEQ ID NO: 495 | GGGAGAUACAUGUAUUCUCtt |
| SEQ ID NO: 496 | UGGUUUUCUGCUAUAGCAGtt |
| SEQ ID NO: 497 | GAAGGAACCAGUUGGGACC~~ |
| SEQ ID NO: 498 | GGAACCAGUUGGGACCGUGtt |
| SEQ ID NO: 499 | CCAGUUGGGACCGUGAAGAtt |
| SEQ ID NO: 500 | GACUCCCGACCCUGUGGCCtt |
| SEQ ID NO: 501 | AGGAAGACACCCUCUACGUtt |
| SEQ ID NO: 502 | GACACCCUCUACGUCACCUtt |
| SEQ ID NO: 503 | GGGCAUGGUGUCCCCAGAGtt |
| SEQ ID NO: 504 | UAUGGAAACCCCAUGGUUCtt |
| SEQ ID NO: 505 | ACCCCAUGGUUCCCUUCCCtt |
| SEQ ID NO: 506 | GCAAGGACCCAGAUGCAUCtt |
| SEQ ID NO: 507 | GGACCCAGAUGCAUCAGACtt |
| SEQ ID NO: 508 | GAUGUUCCUUUCUACUCGGtt |
| SEQ ID NO: 509 | GUCCACCAGGGCCAGCGGCtt |
| SEQ ID NO: 510 | CUUUCCUCCAGACCUGCCAtt |
| SEQ ID NO: 511 | GAACAUGGUCUCUGUCUCCtt |
| SEQ ID NO: 512 | CAUGGUCUCUGUCUCCUCGtt |
| SEQ ID NO: 513 | GGCCUGCCGAGGGCAGUUUtt |
| SEQ ID NO: 514 | CCUCAUGAAGGAAACACAGtt |
| SEQ ID NO: 515 | GGAAACACAGUCCUGCCAAtt |
| SEQ ID NO: 516 | ACACAGUCCUGCCAAGGAGtt |
| SEQ ID NO: 517 | GGAGGGGGAGUGGCGCCCAtt |
| SEQ ID NO: 518 | GCCCUCUGGGUAGCUGUGCtt |
| SEQ ID NO: 519 | GGACCUUUGCUUCCAUAGAtt |
| SEQ ID NO: 520 | AACGCACAGCUCAGAAAGGtt |
| SEQ ID NO: 521 | UCCCUGGAAGAGAAGGAAGtt |
| SEQ ID NO: 522 | GAGAAGGAAGGCAGGGUGGtt |
| SEQ ID NO: 523 | GGAAGGCAGGGUGGAGCGGtt |
| SEQ ID NO: 524 | GGCAGGGUGGAGCGGGGGGtt |
| SEQ ID NO: 525 | GACCAUCAUGGAGAGAAGGtt |
| SEQ ID NO: 526 | GGACCACAGCAUCAGGAGAtt |
| SEQ ID NO: 527 | UUUUUUAAGAGCAAGAGGGtt |
| SEQ ID NO: 528 | GAGCAAGAGGGGUAGAGAGtt |
| SEQ ID NO: 529 | GAGGGGUAGAGAGGAUCAAtt |
| SEQ ID NO: 530 | GCUGGCCCUGGCUGGAGAUtt |
| SEQ ID NO: 531 | AUGACUCUGUCUGUGGGGCtt |
| SEQ ID NO: 532 | GGCAAGUGGCUGCCCCACCtt |
| SEQ ID NO: 533 | GUGGCUGCCCCACCCCAAGtt |
| SEQ ID NO: 534 | CAGCCUGCAGCUCACUCCAtt |
| SEQ ID NO: 535 | GUCUCUGGGCUCCAACUGGtt |
| SEQ ID NO: 536 | CUGGUCUUGUAACCACUGAtt |
| SEQ ID NO: 537 | CCACUGAGCACUGAAGGAGtt |
| SEQ ID NO: 538 | GGAGAGAGGUCUUGGUCAGtt |
| SEQ ID NO: 539 | AGGUGACUGGGAGGACCAGtt |
| SEQ ID NO: 540 | AAGACACUGCUCAGGGCAGtt |
| SEQ ID NO: 541 | GACACUGCUCAGGGCAGGGtt |
| SEQ ID NO: 542 | GAAAAGGGCAGUCCCCAUGtt |
| SEQ ID NO: 543 | AAGGGCAGUCCCCAUGUGGtt |
| SEQ ID NO: 544 | GGGCAGUCCCCAUGUGGGCtt |
| SEQ ID NO: 545 | CUUGCGUCUGGGGGACACCtt |
| SEQ ID NO: 546 | CCAGGGCUCCCAGAAGCUUtt |
| SEQ ID NO: 547 | GGAGGUCUGGGAGCCAGCCtt |
| SEQ ID NO: 548 | AGGACCCCACCUCACCCAGtt |
| SEQ ID NO: 549 | ACCUCAUAGCUGGGGCGCUtt |
| SEQ ID NO: 550 | GAGCCAGGAGUGUGGGAAGtt |
| SEQ ID NO: 551 | GGCCCACAGUGGGGCUGUtt |
| SEQ ID NO: 552 | GUCCCUGCAGAGAGCACUUtt |
| SEQ ID NO: 553 | CUCCCAAACCUUGGCUUUGtt |

TABLE 4-continued

Candidate siRNA constructs for CLEC16A
Corresponding GenBank Accession number: NM_015226

| | |
|---|---|
| SEQ ID NO: 554 | UAUUGUUGUGGAGGUGUGCtt |
| SEQ ID NO: 555 | GGUACCUGUCCCAGCAGGUtt |
| SEQ ID NO: 556 | CCCAGACACUUGCGUUCACtt |
| SEQ ID NO: 557 | GCAACCUAAGGGGCAGGUGtt |
| SEQ ID NO: 558 | CCUAAGGGGCAGGUGAAGA~~ |
| SEQ ID NO: 559 | GGGGCAGGUGAAGAAGCGCtt |
| SEQ ID NO: 560 | GAAGCGCAGCCCUGCCAGAtt |
| SEQ ID NO: 561 | GCGCAGCCCUGCCAGACGCtt |
| SEQ ID NO: 562 | GGUCUCUGAGAUGCACCGUtt |
| SEQ ID NO: 563 | AAAGGCGUGGGGUGAACUGtt |
| SEQ ID NO: 564 | AGGCGUGGGGUGAACUGAUtt |
| SEQ ID NO: 565 | CUGAUUUGAUCUUCUUGUtt |
| SEQ ID NO: 566 | UAAAUAAAUCUGAAGCAUUtt |
| SEQ ID NO: 567 | AUCUGAAGCAUUUAAUGUAtt |
| SEQ ID NO: 568 | GCAUUUAAUGUAGUCAUCUtt |
| SEQ ID NO: 569 | UGUAGUCAUCUUGACAUUGtt |
| SEQ ID NO: 570 | AAAUAUGUAAAUAAUUUUtt |
| SEQ ID NO: 571 | AUAUGUAAAUAAUUUUUGUtt |
| SEQ ID NO: 572 | AUAAUUUUGUCCCAGUGAtt |
| SEQ ID NO: 573 | UUUUUGUCCCAGUGAGAACtt |
| SEQ ID NO: 574 | CCGAGGGUUAGAAAACCUCtt |
| SEQ ID NO: 575 | AACCUCGAUGCCUCUGAGCtt |
| SEQ ID NO: 576 | CCUCGAUGCCUCUGAGCCUtt |
| SEQ ID NO: 577 | GUACCUGCUUUCGCCAGCAtt |
| SEQ ID NO: 578 | CACGAGGGUGGAAAUGAAAtt |
| SEQ ID NO: 579 | AUGAAAACUGGAACUUCCUtt |
| SEQ ID NO: 580 | AACUGGAACUUCCUUGUAAtt |
| SEQ ID NO: 581 | CUGGAACUUCCUUGUAAAUtt |
| SEQ ID NO: 582 | CUUCCUUGUAAAUUUAAACtt |

While certain of the preferred embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

What is claimed is:

1. A method for detecting the presence of at least one nucleic acid harboring a single nucleotide polymorphism (SNP) at the 16p13 region of chromosome 16 associated with an altered risk of Type 1 diabetes, comprising
   a) obtaining a nucleic acid from a human patient sample; and
   b) detecting said at least one T1D associated SNP allele selected from the group consisting of an A at rs2903692, a G at rs17673553, or an A at rs7200786 in the sample by contacting said sample with a probe or primer and detecting hybridization or amplification of said at least one nucleic acid harboring said SNP, wherein said single nucleotide polymorphism is an A at rs7200786.

2. The method as claimed in claim 1, wherein said single nucleotide polymorphism is an A at rs2903692.

3. The method as claimed in claim 1, wherein said single nucleotide polymorphism is a G at rs17673553.

* * * * *